(12) United States Patent
Ellsworth et al.

(10) Patent No.: US 8,288,404 B2
(45) Date of Patent: Oct. 16, 2012

(54) PYRROLIDINE GPR40 MODULATORS

(75) Inventors: Bruce A. Ellsworth, Princeton, NJ (US); William R. Ewing, Yardley, PA (US); Elizabeth Jurica, Robbinsville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 115 days.

(21) Appl. No.: 12/897,913

(22) Filed: Oct. 5, 2010

(65) Prior Publication Data
US 2011/0082165 A1    Apr. 7, 2011

Related U.S. Application Data

(60) Provisional application No. 61/248,896, filed on Oct. 6, 2009.

(51) Int. Cl.
*A01N 43/54* (2006.01)
*A61K 31/505* (2006.01)

(52) U.S. Cl. ..... 514/275; 514/343; 544/298; 546/276.4; 548/556; 548/572

(58) Field of Classification Search ............... 514/275, 514/343; 544/298; 546/276.4; 548/556; 548/572
See application file for complete search history.

(56) References Cited

U.S. PATENT DOCUMENTS

| | | | |
|---|---|---|---|
| 7,279,485 | B2 | 10/2007 | Cheng et al. |
| 7,501,440 | B2 | 3/2009 | Schoenafinger et al. |
| 2008/0090840 | A1 | 4/2008 | Beck et al. |

OTHER PUBLICATIONS

Edfalk, S. et al., "*Gpr40* is Expressed in Enteroendocrine Cells and Mediates Free Fatty Acid Stimulation of Incretin Secretion", Diabetes, vol. 57, pp. 2280-2287 (2008).

Itoh, Y. et al., "Free fatty acids regulate insulin secretion from pancreatic β cells through GPR40", Nature, vol. 422, pp. 173-176 (2003).

Tan, C. et al., "Selective Small-Molecule Agonists of G Protein-Coupled Receptor 40 Promote Glucose-Dependent Insulin Secretion and Reduce Blood Glucose in Mice", Diabetes, vol. 57, pp. 2211-2219 (2008).

Yamashima, T., "A putative link of PUFA, GPR40 and adult-born hippocampal neurons for memory", Progress in Neurobiology, vol. 84, pp. 105-115 (2008).

*Primary Examiner* — Yong Chu
*Assistant Examiner* — Valerie Rodriguez-Garcia
(74) *Attorney, Agent, or Firm* — Jing G. Sun

(57) ABSTRACT

The present invention provides compounds of Formula (I):

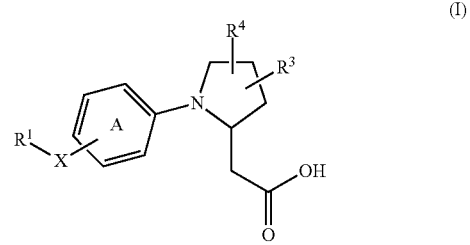

or a stereoisomer, or a pharmaceutically acceptable salt thereof, wherein all of the variables are as defined herein. These compounds are GPR40 G protein-coupled receptor modulators which may be used as medicaments.

18 Claims, No Drawings

PYRROLIDINE GPR40 MODULATORS

CROSS-REFERENCE TO RELATED APPLICATIONS

This application claims the priority benefit of U.S. Provisional Application No. 61/248,896, filed Oct. 6, 2009, which is incorporated fully herein by reference.

FIELD OF THE INVENTION

The present invention provides novel carboxylic acid substituted pyrrolidine compounds, and their analogues thereof, which are GPR40 G protein-coupled receptor modulators, compositions containing them, and methods of using them, for example, for the treatment or prophylaxis of diabetes and related conditions.

BACKGROUND OF THE INVENTION

Diabetes mellitus is a progressively debilitating disorder of epidemic proportions leading to various micro- and macrovascular complications and morbidity. The most common type of diabetes, type 2 diabetes, is characterized by increasing insulin resistance associated with inadequate insulin secretion after a period of compensatory hyperinsulinemia. Free fatty acids (FFAs) are evidenced to influence insulin secretion from β cells primarily by enhancing glucose-stimulated insulin secretion (GSIS). G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells and mediates medium to long chain fatty acid induced insulin secretion. To decrease medical burden of type 2 diabetes through enhanced glycemic control, GPR40 modulator compounds hold the promise of exerting an incretin effect to promote GSIS as well as potential combination with a broad range of antidiabetic drugs.

The present invention relates to novel substituted pyrrolidine compounds which have the ability to modulate GPR40. Such compounds are therefore potentially useful for the treatment or prophylaxis of diabetes and related conditions.

SUMMARY OF THE INVENTION

The present invention provides substituted pyrrolidine compounds, and their analogues thereof, which are useful as GPR40 modulators, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with GPR40, such as diabetes and related conditions, microvascular complications associated with diabetes, the macrovascular complications associated with diabetes, cardiovascular diseases, Metabolic Syndrome and its component conditions, disorders of glucose metabolism, obesity and other maladies.

The compounds of the invention may be used in therapy.

The compounds of the invention may be used for the manufacture of a medicament for the treatment and/or prophylaxis of multiple diseases or disorders associated with GPR40.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

or a stereoisomer, a tautomer, a pharmaceutically acceptable salt, or a solvate thereof, wherein:

X is selected from the group consisting of: O, S, $CH_2$, $CH(C_{1-4}$ alkyl$)$, $C(C_{1-4}$ alkyl$)_2$, $CH(C_{1-4}$ alkoxy-phenyl$)$, and $C(O)$;

ring A is phenyl substituted with 0-2 $R^5$, pyridinyl substituted with 0-2 $R^5$, or pyrimidyl substituted with 0-2 $R^5$;

$R^1$ is —$(CH_2)_n$-phenyl substituted with 0-3 $R^2$, —$(CH_2)_n$-naphthyl substituted with 0-3 $R^2$, or —$(CH_2)_n$-5- to 6-membered heteroaryl containing carbon atoms and 1-4 heteroatoms selected from the group consisting of N, O, and $S(O)_p$; wherein said heteroaryl is substituted with 0-3 $R^2$;

$R^2$, at each occurrence, is independently selected from the group consisting of: halo, $CF_3$, CN, $NO_2$, $OCF_3$, $SCF_3$, $C_{1-6}$ alkyl, $C_{1-6}$ alkoxy, $C_{1-6}$ alkylthio, $NH_2$, $NH(C_{1-4}$ alkyl$)$, $N(C_{1-4}$ alkyl$)_2$, —$(CH_2)_n$—$C_{3-10}$ carbocycle, —$(CH_2)_n$—O—$C_{3-10}$ carbocycle, and —$(CH_2)_n$-3- to 10-membered heterocycle containing carbon atoms and 1-4 heteroatoms selected from the group consisting of N, O, and $S(O)_p$; wherein said carbocycle and heterocycle are substituted with 0-3 $R^6$;

$R^3$ and $R^4$, at each occurrence, are independently selected from the group consisting of: H, OH, halo, $CF_3$, $C_{1-4}$ alkyl, and $C_{1-4}$ alkoxy;

$R^5$, at each occurrence, is independently selected from the group consisting of: halo and $C_{1-4}$ alkyl;

$R^6$, at each occurrence, is independently selected from the group consisting of: halo, $CF_3$, $C_{1-4}$ alkyl, and $C_{1-4}$ alkoxy;

n, at each occurrence, is independently 0, 1, 2 or 3; and p, at each occurrence, is independently 0, 1 or 2.

In a second aspect, the present invention includes compounds of Formula (I), or a stereoisomer, a tautomer, a pharmaceutically acceptable salt, or a solvate thereof, within the scope of the first aspect wherein:

X is selected from the group consisting of: O, S, $CH_2$, $CH(C_{1-4}$ alkyl$)$, $CH(C_{1-4}$ alkoxy-phenyl$)$, and $C(O)$;

$R^1$ is —$(CH_2)_n$-phenyl substituted with 0-3 $R^2$, —$(CH_2)_n$-naphthyl substituted with 0-3 $R^2$, or —$(CH_2)_n$-pyridyl substituted with 0-3 $R^2$;

$R^2$, at each occurrence, is independently selected from the group consisting of: halo, $CF_3$, CN, $NO_2$, $OCF_3$, $SCF_3$, $C_{1-6}$ alkyl, $C_{1-6}$ alkoxy, $C_{1-6}$ alkylthio, $NH_2$, $NH(C_{1-4}$ alkyl), $N(C_{1-4}$ alkyl$)_2$, —$(CH_2)_n$—$C_{3-6}$ cycloalkyl, —$(CH_2)_n$—$C_{4-6}$ cycloalkenyl, —$(CH_2)_n$-phenyl, —$(CH_2)_n$—O-phenyl, and —$(CH_2)_n$-5- to 6-membered heteroaryl containing carbon atoms and 1-4 heteroatoms selected from the group consisting of N, O, and $S(O)_p$; wherein said cycloalkyl, cycloalkenyl, phenyl and heteroaryl are substituted with 0-2 $R^6$; and n, at each occurrence, is independently 0, 1 or 2.

In another aspect, the present invention includes compounds of Formula (I), or a stereoisomer, a tautomer, a pharmaceutically acceptable salt, or a solvate thereof, within the scope of the first or second aspect wherein:

$R^1$ is —$(CH_2)_n$-phenyl substituted with 0-3 $R^2$ or —$(CH_2)_n$-pyridyl substituted with 0-3 $R^2$; and n, at each occurrence, is independently 0 or 1.

In another aspect, the present invention includes compounds of Formula (I), or a stereoisomer, a tautomer, a pharmaceutically acceptable salt, or a solvate thereof, within the scope of the first aspect or second wherein:

$R^1$ is —$(CH_2)_n$-phenyl substituted with 0-2 $R^2$; and n, at each occurrence, is independently 0 or 1.

In a third aspect, the present invention includes compounds of Formula (II):

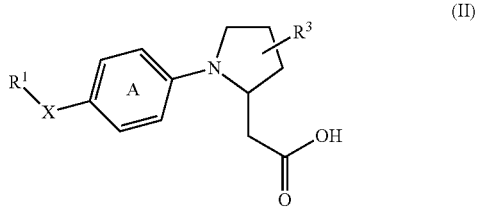

(II)

or a stereoisomer, a tautomer, a pharmaceutically acceptable salt, or a solvate thereof, within the scope of the first aspect or second wherein:

X is selected from the group consisting of: O, S, $CH_2$, $CH(C_{1-4}$ alkyl), CH(2-(methoxy)-phenyl), and C(O);

ring A is selected from the group consisting of:

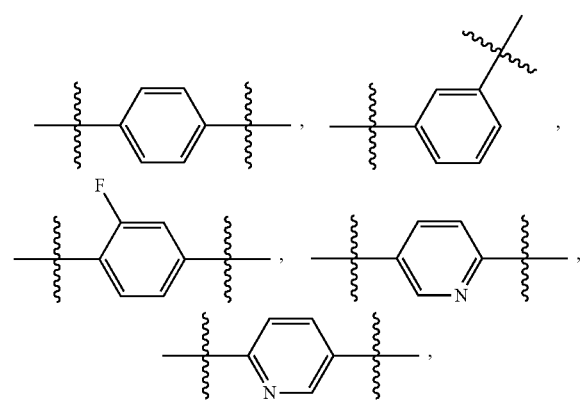

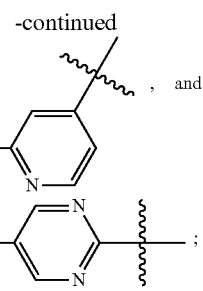, and $R^2$, at each occurrence, is independently selected from the group consisting of: halo, $CF_3$, CN, $NO_2$, $OCF_3$, $SCF_3$, $C_{1-6}$ alkyl, $C_{1-6}$ alkoxy, $C_{1-6}$ alkylthio, NH, $NH(C_{1-4}$ alkyl), $N(C_{1-4}$ alkyl$)_2$, cyclopentenyl substituted with 0-2 $R^6$, phenyl substituted with 0-2 $R^6$, benzyl substituted with 0-2 $R^6$, phenoxy substituted with 0-2 $R^6$, benzoxy substituted with 0-2 $R^6$, and pyrazol-1-yl; and $R^3$ is selected from the group consisting of: H, OH, halo, $CF_3$, $C_{1-4}$ alkyl, and $C_{1-4}$ alkoxy.

In a fourth aspect, the present invention includes compounds of Formula (I) or Formula (II), or a stereoisomer, a tautomer, a pharmaceutically acceptable salt, or a solvate thereof, within the scope of any of the above aspects wherein:

$R^1$ is selected from the group consisting of: phenyl, 2-halophenyl, 3-halophenyl, 4-halophenyl, 2-($C_{1-4}$ alkyl)phenyl, 3-($C_{1-4}$ alkyl)phenyl, 4-($C_{1-4}$ alkyl)phenyl, 2-($C_{1-4}$ alkoxy)phenyl, 4-($C_{1-4}$ alkoxy)phenyl, 2-trifluoromethylphenyl, 3-trifluoromethylphenyl, 4-trifluoromethylphenyl, 2-trifluoromethoxyphenyl, 3-trifluoromethoxyphenyl, 4-cyanophenyl, 3-(N,N-dimethylamino)-phenyl, 4-phenoxyphenyl, 3-(2-halophenyl)phenyl, 3-(4-halophenoxy)phenyl, 3-(2-halobenzyl)phenyl, 3-(2-($C_{1-4}$ alkyl)benzyl)phenyl, 4-(2-halobenzoxy)phenyl, 3-(2-halo-5-($C_{1-4}$ alkoxy)-phenyl)phenyl, 2-biphenyl, 2-benzylphenyl, 4-benzylphenyl, 3-benzoxyphenyl, 4-benzoxyphenyl, 2-($C_{1-4}$ alkyl)-3-($C_{1-4}$ alkyl)-phenyl, 2-($C_{1-4}$ alkyl)-4-($C_{1-4}$ alkyl)-phenyl, 2-($C_{1-4}$ alkyl)-6-($C_{1-4}$ alkyl)-phenyl, 2-halo-3-halophenyl, 2-halo-4-halo-phenyl, 3-halo-4-halophenyl, 3-halo-5-halophenyl, 2-halo-6-halophenyl, 2-($C_{1-4}$ alkyl)-4-($C_{1-4}$ alkoxy)-phenyl, 2-($C_{1-4}$ alkyl)-3-halo-phenyl, 2-($C_{1-4}$ alkyl)-4-halo-phenyl, 2-halo-3-($C_{1-4}$ alkyl)-phenyl, 3-halo-4-($C_{1-4}$ alkyl)-phenyl, 2,4-ditrifluoromethyl-phenyl, 2-halo-3-trifluoromethyl-phenyl, 2-halo-4-trifluoromethyl-phenyl, 2-($C_{1-4}$ alkyl)-4-benzoxy-phenyl, 2-trifluoromethyl-4-cyano-phenyl, 2-cyano-4-trifluoromethyl-phenyl, 3-cyano-4-trifluoromethyl-phenyl, 3-trifluoromethyl-4-cyano-phenyl, 2-halo-4-cyano-phenyl, 2-($C_{1-4}$ alkyl)-3-(2-halo-5-($C_{1-4}$ alkoxy)-phenyl)-phenyl, benzyl, 2-halobenzyl, 3-halobenzyl, 4-halobenzyl, 2-($C_{1-4}$ alkyl)benzyl, 4-($C_{1-4}$ alkyl)benzyl, 4-($C_{1-4}$ alkylthio)benzyl, 2-trifluoromethyl-benzyl, 3-trifluoromethyl-benzyl, 4-trifluoromethyl-benzyl, 2-trifluoromethoxy-benzyl, 3-trifluoromethoxy-benzyl, 4-trifluoromethoxy-benzyl, 2-trifluoromeththio-benzyl, 2-cyanobenzyl, 2-phenylbenzyl, 3-phenylbenzyl, 4-phenylbenzyl, 2-halo-3-halo-benzyl, 2-halo-4-halo-benzyl, 2-halo-5-halo-benzyl, 3-halo-4-halo-benzyl, 2-halo-3-($C_{1-4}$ alkyl)-benzyl, 3-($C_{1-4}$ alkyl)-4-halo-benzyl, 3-(2-halophenoxy)-benzyl, 3-($C_{1-4}$ alkyl)-4-(2-halophenyl)-benzyl, 4-(pyrazol-1-yl)-benzyl, 3-($C_{1-4}$ alkyl)-5-($C_{1-4}$ alkyl)-benzyl, 3-($C_{1-4}$ alkyl)-4-(2-halo-5-($C_{1-4}$ alkoxy)-phenyl)-benzyl, 3-(2-halo-5-($C_{1-4}$ alkoxy)-phenyl)-4-($C_{1-4}$ alkyl)-benzyl, 3-(5,5-dimethylcyclopent-1-enyl)-4-(2-halo-5-($C_{1-4}$ alkoxy)-phenyl)benzyl, 3-halo-5-trifluoromethylpyrid-3-yl, (2-($C_{1-4}$ alkyl)-6-trifluoromethyl-pyrid-3-yl)methyl, and (2-($C_{1-4}$ alkylthio)-pyrid-3-yl)methyl, and 2-naphthyl.

In a fifth aspect, the present invention includes a compound of Formula (III):

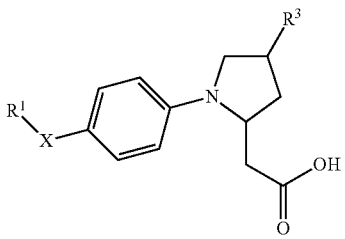

(III)

or a stereoisomer, a tautomer, a pharmaceutically acceptable salt, or a solvate thereof, wherein:

X is selected from the group consisting of: O, S, CH₂, CH(CH₃), CH(CH₂CH₃), CH(2-methoxyphenyl), and C(O);

R¹ is selected from the group consisting of: phenyl, 2-methylphenyl, 3-methylphenyl, 4-methylphenyl, 4-(t-butyl)phenyl, 2-methoxyphenyl, 4-methoxyphenyl, 2-ethoxyphenyl, 2-fluorophenyl, 3-fluorophenyl, 2-chlorophenyl, 3-chlorophenyl, 4-chlorophenyl, 3-bromophenyl, 2-trifluoromethylphenyl, 3-trifluoromethylphenyl, 4-trifluoromethylphenyl, 2-trifluoromethoxyphenyl, 3-trifluoromethoxyphenyl, 4-cyanophenyl, 3-(N,N-dimethylamino)phenyl, 4-phenoxyphenyl, 3-(4-fluorophenoxy)-phenyl, 2-biphenyl, 2-benzylphenyl, 4-benzylphenyl, 3-benzoxyphenyl, 4-benzoxyphenyl, 3-(2-fluorophenyl)phenyl, 3-(2-fluorobenzyl)phenyl, 3-(2-methylbenzyl)phenyl, 4-(2-fluorobenzoxy)phenyl, 3-(2-fluoro-5-methoxy-phenyl)phenyl, 2,3-dimethylphenyl, 2,4-dimethylphenyl, 2,6-dimethylphenyl, 2,4-difluorophenyl, 2,6-difluorophenyl, 3,4-difluorophenyl, 3,5-difluorophenyl, 2,3-dichlorophenyl, 2,4-dichlorophenyl, 3,4-dichlorophenyl, 3,5-dichlorophenyl, 2,4-ditrifluoromethylphenyl, 3-fluoro-4-methyl-phenyl, 2-methyl-4-methoxy-phenyl, 2-methyl-3-chloro-phenyl, 2-methyl-4-chloro-phenyl, 2-fluoro-4-chloro-phenyl, 2-chloro-3-trifluoromethyl-phenyl, 2-chloro-4-trifluoromethyl-phenyl, 2-methyl-4-benzoxy-phenyl, 2-fluoro-4-cyano-phenyl, 2-chloro-4-cyano-phenyl, 2-cyano-4-trifluoromethyl-phenyl, 3-cyano-4-trifluoromethyl-phenyl, 2-trifluoromethyl-4-cyano-phenyl, 3-trifluoromethyl-4-cyano-phenyl, 2-methyl-3-(2-fluoro-5-methoxy-phenyl)-phenyl, benzyl, 2-methylbenzyl, 3-methylbenzyl, 4-methylbenzyl, 4-(n-butyl)benzyl, 4-(t-butyl)benzyl, 2-fluorobenzyl, 3-fluorobenzyl, 4-fluorobenzyl, 3-chlorobenzyl, 4-chlorobenzyl, 4-methylthiobenzyl, 2-trifluoromethylbenzyl, 3-trifluoromethylbenzyl, 4-trifluoromethylbenzyl, 2-trifluoromethoxybenzyl, 3-trifluoromethoxybenzyl, 2-trifluoromethylthiobenzyl, 2-cyanobenzyl, 2-phenylbenzyl, 3-phenylbenzyl, 4-phenylbenzyl, 3-(2-fluorophenoxy)benzyl, 4-(pyrazol-1-yl)benzyl, 3,5-dimethylbenzyl, 2,4-difluorobenzyl, 3,4-difluorobenzyl, 2,3-dichlorobenzyl, 2,4-dichlorobenzyl, 2,5-dichlorobenzyl, 3,4-dichlorobenzyl, 2-fluoro-3-methyl-benzyl, 3-methyl-4-bromo-benzyl, 3-methyl-4-(2-fluorophenyl)-benzyl, 3-methyl-4-(2-fluoro-5-methoxy-phenyl)-benzyl, 3-(2-fluoro-5-methoxy-phenyl)-4-(t-butyl)-benzyl, 3-(5,5-dimethylcyclopent-1-enyl)-4-(2-fluoro-5-methoxy-phenyl)benzyl, 3-chloro-5-trifluoromethylpyrid-2-yl, (2-(isopropylthio)-pyrid-3-yl)methyl, (2-methyl-6-trifluoromethylpyrid-3-yl)methyl, and 2-naphthyl; and R³ is selected from the group consisting of: H, F, OH, CH₃, CH₂CH₃, OCH₃, and CF₃.

In a sixth aspect, the present invention includes a compound of Formula (III), or a stereoisomer, a tautomer, a pharmaceutically acceptable salt, or a solvate thereof, within the scope of the fifth wherein:

X is selected from the group consisting of: O, S and CH₂;

R¹ is selected from the group consisting of: phenyl, 2-methylphenyl, 3-methylphenyl, 4-methylphenyl, 4-methoxyphenyl, 2-fluorophenyl, 2-chlorophenyl, 3-chlorophenyl, 4-chlorophenyl, 3-bromophenyl, 2-trifluoromethylphenyl, 3-trifluoromethylphenyl, 4-trifluoromethylphenyl, 2-trifluoromethoxyphenyl, 3-trifluoromethoxyphenyl, 4-phenoxyphenyl, 2-benzylphenyl, 3-benzoxyphenyl, 4-benzoxyphenyl, 3-(2-fluorophenyl)phenyl, 3-(2-fluorobenzyl)phenyl, 4-(2-fluorobenzoxy)phenyl, 3-(2-fluoro-5-methoxy-phenyl)phenyl, 2,3-dimethylphenyl, 2,4-dimethylphenyl, 2,6-dimethylphenyl, 2,4-difluorophenyl, 2,6-difluorophenyl, 3,5-difluorophenyl, 2,4-dichlorophenyl, 3,5-dichlorophenyl, 2,4-ditrifluoromethylphenyl, 3-fluoro-4-methyl-phenyl, 2-methyl-4-methoxy-phenyl, 2-methyl-3-chloro-phenyl, 2-methyl-4-chloro-phenyl, 2-fluoro-4-chloro-phenyl, 2-chloro-3-trifluoromethyl-phenyl, 2-chloro-4-trifluoromethyl-phenyl, 2-methyl-4-benzoxy-phenyl, 2-chloro-4-cyano-phenyl, 2-cyano-4-trifluoromethyl-phenyl, 2-trifluoromethyl-4-cyano-phenyl, 3-trifluoromethyl-4-cyano-phenyl, 2-methyl-3-(2-fluoro-5-methoxy-phenyl)-phenyl, benzyl, 2-methylbenzyl, 4-methylbenzyl, 2-fluorobenzyl, 3-fluorobenzyl, 3-chlorobenzyl, 4-chlorobenzyl, 4-methylthiobenzyl, 2-trifluoromethylbenzyl, 3-trifluoromethylbenzyl, 2-trifluoromethoxybenzyl, 3-trifluoromethoxybenzyl, 2-trifluoromethylthiobenzyl, 2-cyanobenzyl, 2-phenylbenzyl, 4-phenylbenzyl, 3-(2-fluorophenoxy)benzyl, 3,5-dimethylbenzyl, 2,3-dichlorobenzyl, 2,4-dichlorobenzyl, 3,4-dichlorobenzyl, 2-fluoro-3-methyl-benzyl, 3-methyl-4-bromo-benzyl, 3-(5,5-dimethylcyclopent-1-enyl)-4-(2-fluoro-5-methoxy-phenyl)benzyl, (2-(isopropylthio)-pyrid-3-yl)methyl, (2-methyl-6-trifluoromethylpyrid-3-yl)methyl, and 2-naphthyl; and R³ is selected from the group consisting of: H, F, CH₃, CH₂CH₃, and CF₃.

In a seventh aspect, the present invention includes a compound of Formula (III), or a stereoisomer, a tautomer, a pharmaceutically acceptable salt, or a solvate thereof, within the scope of the fifth or sixth wherein:

X is selected from the group consisting of: O, S and CH₂;

R¹ is selected from the group consisting of: phenyl, 2-methylphenyl, 3-methylphenyl, 4-methylphenyl, 2-fluorophenyl, 4-chlorophenyl, 3-bromophenyl, 2-trifluoromethylphenyl, 2-trifluoromethoxyphenyl, 3-trifluoromethoxyphenyl, 4-phenoxyphenyl, 4-benzoxyphenyl, 3-(2-fluorophenyl)phenyl, 4-(2-fluorobenzoxy)phenyl, 2,3-dimethylphenyl, 2,4-dimethylphenyl, 2,6-dimethylphenyl, 2,6-difluorophenyl, 2,4-dichlorophenyl, 3,5-dichlorophenyl, 2-methyl-4-methoxy-phenyl, 2-methyl-3-chloro-phenyl, 2-methyl-4-chloro-phenyl, 2-methyl-4-benzoxy-phenyl, 3-cyano-4-trifluoromethyl-phenyl, 2-chloro-4-trifluoromethyl-phenyl, 2-methyl-3-(2-fluoro-5-methoxy-phenyl)-phenyl, 2-methylbenzyl, 2-chlorobenzyl, 2-trifluoromethylbenzyl, 2-trifluoromethoxybenzyl, 2-trifluoromethylthiobenzyl, 2-phenylbenzyl, 3-(2-fluorophenoxy)benzyl, 2,3-dichlorobenzyl, 2,4-dichlorobenzyl, 3,4-dichlorobenzyl, 2-methyl-4-chlorobenzyl, 2-methyl-3-trifluoromethyl-benzyl, and (2-(isopropylthio)-pyrid-3-yl)methyl; and R³ is selected from the group consisting of: H, F, CH₃, CH₂CH₃, and CF₃.

In another aspect, the present invention includes a compound of Formula (III), or a stereoisomer, a tautomer, a pharmaceutically acceptable salt, or a solvate thereof, within the scope of any of the above aspects wherein:

X is selected from the group consisting of: O and $CH_2$;

$R^1$ is selected from the group consisting of: 2-methylphenyl, 2-fluorophenyl, 2-trifluoromethoxyphenyl, 3-trifluoromethoxyphenyl, 4-benzoxyphenyl, 2,3-dimethylphenyl, 2,4-dimethylphenyl, 2,6-dimethylphenyl, 2-methyl-4-methoxy-phenyl, 2-methyl-3-chloro-phenyl, 2-methyl-4-benzoxy-phenyl, 2-methylbenzyl, 2-chlorobenzyl, 2-trifluoromethylbenzyl, 2-trifluoromethoxybenzyl, 2-trifluoromethylthiobenzyl, 2,3-dichlorobenzyl, and 2-methyl-4-chloro-benzyl; and $R^3$ is selected from the group consisting of: H, F, $CH_3$, and $CF_3$.

In another aspect, the present invention includes a compound of Formula (III), or a stereoisomer, a tautomer, a pharmaceutically acceptable salt, or a solvate thereof, within the scope of any of the above aspects wherein:

X is selected from the group consisting of: O and $CH_2$;

$R^1$ is selected from the group consisting of: 2-methylphenyl, 2-fluorophenyl, 2,3-dimethylphenyl, 2,4-dimethylphenyl, 2,6-dimethylphenyl, 2-methyl-4-methoxy-phenyl, 2-methyl-3-chloro-phenyl, 2-trifluoromethoxy-benzyl, and 2-methyl-4-chloro-benzyl; and $R^3$ is selected from the group consisting of: H, F and $CF_3$.

In an eighth aspect, the present invention includes a compound of Formula (III):

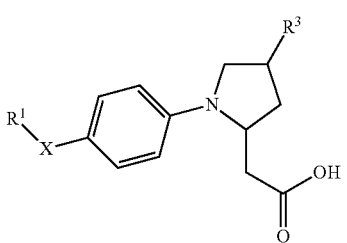

(III)

or a stereoisomer, a tautomer, a pharmaceutically acceptable salt, or a solvate thereof, within the scope of any of the above aspects wherein:

X, $R^1$ and $R^3$ are selected in concert from the group consisting of:

| X | $R^1$ | $R^3$ |
|---|---|---|
| O | 2-methyl-4-methoxy-phenyl | $CF_3$ |
| O | 2-methylphenyl | $CF_3$ |
| $CH_2$ | 2-methylphenyl | $CF_3$ |
| O | 2-trifluoromethoxybenzyl | H |
| O | 2-methylphenyl | H |
| O | 2,3-dimethylphenyl | $CF_3$ |
| $CH_2$ | 2-methylphenyl | F |
| O | 2-methyl-3-chloro-phenyl | $CF_3$ |
| O | 2-fluorophenyl | $CF_3$ |
| O | 2,6-dimethylphenyl | H |
| O | 2,4-dimethylphenyl | H |
| O | 2-methylphenyl | F |
| O | 2-fluorophenyl | F |
| O | 2-methylbenzyl | $CF_3$ |
| O | 2-trifluoromethylthiobenzyl | H |
| O | 2,3-dimethylphenyl | H |
| O | 2-methylphenyl | F |
| O | 2-methyl-4-benzoxy-phenyl | $CF_3$ |
| $CH_2$ | 2-methylphenyl | H |
| O | 2-methyl-4-methoxy-phenyl | H |
| $CH_2$ | 2-methylphenyl | $CH_3$ |
| O | 2-fluorophenyl | H |
| O | 2-methylbenzyl | F |
| O | 4-benzoxyphenyl | H |
| O | 2-trifluoromethoxybenzyl | $CF_3$ |
| O | 2-trifluoromethoxyphenyl | $CF_3$ |
| O | 2-methylphenyl | $CH_3$ |
| O | 2-methylbenzyl | H |
| O | 2-trifluoromethylbenzyl | H |
| O | 2-trifluoromethylbenzyl | $CH_3$ |
| O | 3-trifluoromethoxyphenyl | H |
| O | 4-benzoxyphenyl | H |
| O | 2,4-dichlorobenzyl | H |
| $CH_2$ | 4-chlorophenyl | H |
| $CH_2$ | 3-methylphenyl | H |
| O | 3,4-dichlorobenzyl | H |
| O | 3-methylphenyl | H |
| O | (2-(isopropylthio)-pyrid-3-yl)methyl | H |
| $CH_2$ | 2-fluorophenyl | H |
| $CH_2$ | 2,6-difluorophenyl | H |
| O | 4-chlorophenyl | H |
| O | 2-phenylbenzyl | H |
| O | 2-chloro-4-trifluoromethyl-phenyl | $CF_3$ |
| O | 2-trifluoromethoxyphenyl | $CF_3$ |
| $CH_2$ | 4-methylphenyl | H |
| O | 3,5-dichlorophenyl | H |
| O | 2-methyl-3-(2-fluoro-5-methoxy-phenyl)-phenyl | H |
| O | 3-(2-fluorophenyl)phenyl | H |
| O | 4-phenoxyphenyl | H |
| $CH_2$ | 2-trifluoromethylphenyl | H |
| O | 3-bromophenyl | H |
| $CH_2$ | 4-benzoxyphenyl | H |
| O | 3-(2-fluorophenoxy)benzyl | H |
| O | 2,3-dichlorobenzyl | H |
| S | 2-methylphenyl | H |
| O | 2-trifluoromethylbenzyl | H |
| O | 2-methylphenyl | Et |
| O | 2,4-dichlorobenzyl | H |
| $CH_2$ | 2,4-dimethylphenyl | H |
| $CH_2$ | 2-methyl-4-chloro-phenyl | H |
| O | 3-cyano-4-trifluoromethyl-phenyl | H |
| O | 4-methylphenyl | H |
| $CH_2$ | 3-fluoro-4-methyl-phenyl | H |
| O | 4-methoxyphenyl | H |
| $CH_2$ | 2-naphthyl | H |
| O | 4-methylthiobenzyl | H |
| O | (2-methyl-6-trifluoromethylpyrid-3-yl)methyl | H |
| O | phenyl | H |
| O | 4-methylbenzyl | H |
| $CH_2$ | 2,4-difluorophenyl | H |
| O | 2-chloro-4-cyano-phenyl | H |
| O | 2-trifluoromethyl-4-cyano-phenyl | H |
| $CH_2$ | 2-chlorophenyl | H |
| $CH_2$ | 2-fluoro-4-chloro-phenyl | H |
| O | 2-fluoro-3-methyl-benzyl | H |
| O | 3-(2-fluorobenzyl)phenyl | H |
| O | 3-chlorophenyl | H |
| $CH_2$ | phenyl | H |
| O | 2-fluorobenzyl | H |
| O | 3-trifluoromethyl-4-cyano-phenyl | H |
| $CH_2$ | 2-chloro-3-trifluoromethyl-phenyl | H |
| O | 2-benzylphenyl | H |
| O | 3-(5,5-dimethylcyclopent-1-enyl)-4-(2-fluoro-5-methoxy-phenyl)benzyl | H |
| O | benzyl | H |
| O | 3-fluorobenzyl | H |
| $CH_2$ | 3,5-difluorophenyl | H |
| O | 3-benzoxyphenyl | H |
| $CH_2$ | 4-trifluoromethylphenyl | H |
| $CH_2$ | 2,4-ditrifluoromethylphenyl | H |
| O | 3-(2-fluoro-5-methoxy-phenyl)phenyl | H |
| $CH_2$ | 3-trifluoromethylphenyl | H |
| O | 3-methyl-4-bromo-benzyl | H |
| O | 4-phenylbenzyl | H |
| O | 3-trifluoromethoxybenzyl | H |
| O | 2-cyanobenzyl | H |

In a ninth aspect, the present invention includes a compound of Formula (III), or a stereoisomer, a tautomer, a pharmaceutically acceptable salt, or a solvate thereof, within the scope of any of the above aspects wherein:

X, $R^1$ and $R^3$ are selected in concert from the group consisting of:

| X | $R^1$ | $R^3$ |
|---|---|---|
| O | 2-methyl-4-methoxy-phenyl | $CF_3$ |
| O | 2-methylphenyl | $CF_3$ |
| $CH_2$ | 2-methylphenyl | $CF_3$ |
| O | 2-trifluoromethoxybenzyl | H |
| O | 2-methylphenyl | H |
| O | 2,3-dimethylphenyl | $CF_3$ |
| $CH_2$ | 2-methylphenyl | F |
| O | 2-methyl-3-chloro-phenyl | $CF_3$ |
| O | 2-fluorophenyl | $CF_3$ |
| O | 2,6-dimethylphenyl | H |
| O | 2,4-dimethylphenyl | H |
| O | 2-methylphenyl | F |
| O | 2-fluorophenyl | F |
| O | 2-methylbenzyl | $CF_3$ |
| O | 2-trifluoromethylthiobenzyl | H |
| O | 2,3-dimethylphenyl | H |
| O | 2-methylphenyl | F |
| O | 2-methyl-4-benzoxy-phenyl | $CF_3$ |
| $CH_2$ | 2-methylphenyl | H |
| O | 2-methyl-4-methoxy-phenyl | H |
| $CH_2$ | 2-methylphenyl | $CH_3$ |
| O | 2-fluorophenyl | H |
| O | 2-methylbenzyl | F |
| O | 4-benzoxyphenyl | H |
| O | 2-trifluoromethoxybenzyl | $CF_3$ |
| O | 2-trifluoromethoxyphenyl | $CF_3$ |
| O | 2-methylphenyl | $CH_3$ |
| O | 2-methylbenzyl | H |
| O | 2-trifluoromethylbenzyl | H |
| O | 2-trifluoromethylbenzyl | $CH_3$ |
| O | 3-trifluoromethoxyphenyl | H |
| O | 4-benzoxyphenyl | H |
| O | 2,4-dichlorobenzyl | H |
| $CH_2$ | 4-chlorophenyl | H |
| $CH_2$ | 3-methylphenyl | H |
| O | 3,4-dichlorobenzyl | H |
| O | 3-methylphenyl | H |
| O | (2-(isopropylthio)-pyrid-3-yl)methyl | H |
| $CH_2$ | 2-fluorophenyl | H |
| $CH_2$ | 2,6-difluorophenyl | H |
| O | 4-chlorophenyl | H |
| O | 2-phenylbenzyl | H |
| O | 2-chloro-4-trifluoromethyl-phenyl | $CF_3$ |
| O | 2-trifluoromethylphenyl | $CF_3$ |
| $CH_2$ | 4-methylphenyl | H |
| O | 3,5-dichlorophenyl | H |
| O | 2-methyl-3-(2-fluoro-5-methoxy-phenyl)-phenyl | H |
| O | 3-(2-fluorophenyl)phenyl | H |
| O | 4-phenoxyphenyl | H |
| $CH_2$ | 2-trifluoromethylphenyl | H |
| O | 3-bromophenyl | H |
| $CH_2$ | 4-benzoxyphenyl | H |
| O | 3-(2-fluorophenoxy)benzyl | H |
| O | 2,3-dichlorobenzyl | H |
| S | 2-methylphenyl | H |
| O | 2-trifluoromethylbenzyl | H |
| O | 2-methylphenyl | Et |
| O | 2,4-dichlorophenyl | H |
| $CH_2$ | 2,4-dimethylphenyl | H |
| $CH_2$ | 2-methyl-4-chloro-phenyl | H |
| O | 3-cyano-4-trifluoromethyl-phenyl | H |
| O | 4-methylphenyl | H |

In a tenth aspect, the present invention includes a compound of Formula (III), or a stereoisomer, a tautomer, a pharmaceutically acceptable salt, or a solvate thereof, within the scope of any of the above aspects wherein:

X, $R^1$ and $R^3$ are selected in concert from the group consisting of:

| X | $R^1$ | $R^3$ |
|---|---|---|
| O | 2-methyl-4-methoxy-phenyl | $CF_3$ |
| O | 2-methylphenyl | $CF_3$ |
| $CH_2$ | 2-methylphenyl | $CF_3$ |
| O | 2-trifluoromethoxybenzyl | H |
| O | 2-methylphenyl | H |
| O | 2,3-dimethylphenyl | $CF_3$ |
| $CH_2$ | 2-methylphenyl | F |
| O | 2-methyl-3-chloro-phenyl | $CF_3$ |
| O | 2-fluorophenyl | $CF_3$ |
| O | 2,6-dimethylphenyl | H |
| O | 2,4-dimethylphenyl | H |
| O | 2-methylphenyl | F |
| O | 2-fluorophenyl | F |
| O | 2-methylbenzyl | $CF_3$ |
| O | 2-trifluoromethylthiobenzyl | H |
| O | 2,3-dimethylphenyl | H |
| O | 2-methylphenyl | F |
| O | 2-methyl-4-benzoxy-phenyl | $CF_3$ |
| $CH_2$ | 2-methylphenyl | H |
| O | 2-methyl-4-methoxy-phenyl | H |
| $CH_2$ | 2-methylphenyl | $CH_3$ |
| O | 2-fluorophenyl | H |
| O | 2-methylbenzyl | F |
| O | 4-benzoxyphenyl | H |
| O | 2-trifluoromethoxybenzyl | $CF_3$ |
| O | 2-trifluoromethoxyphenyl | $CF_3$ |
| O | 2-methylphenyl | $CH_3$ |
| O | 2-methylbenzyl | H |
| O | 2-trifluoromethylbenzyl | H |
| O | 2-trifluoromethylbenzyl | $CH_3$ |
| O | 3-trifluoromethoxyphenyl | H |

In an eleventh aspect, the present invention includes a compound of Formula (III), or a stereoisomer, a tautomer, a pharmaceutically acceptable salt, or a solvate thereof, within the scope of any of the above aspects wherein:

X, $R^1$ and $R^3$ are selected in concert from the group consisting of:

| X | $R^1$ | $R^3$ |
|---|---|---|
| O | 2-methyl-4-methoxy-phenyl | $CF_3$ |
| O | 2-methylphenyl | $CF_3$ |
| $CH_2$ | 2-methylphenyl | $CF_3$ |
| O | 2-trifluoromethoxybenzyl | H |
| O | 2-methylphenyl | H |
| O | 2,3-dimethylphenyl | $CF_3$ |
| $CH_2$ | 2-methylphenyl | F |
| O | 2-methyl-3-chloro-phenyl | $CF_3$ |
| O | 2-fluorophenyl | $CF_3$ |
| O | 2,6-dimethylphenyl | H |
| O | 2,4-dimethylphenyl | H |
| O | 2-methylphenyl | F |
| O | 2-fluorophenyl | F |

In another aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of any of the above aspects.

In another embodiment, the present invention provides a compound of Formula (Ia), (IIa) or (IIIa):

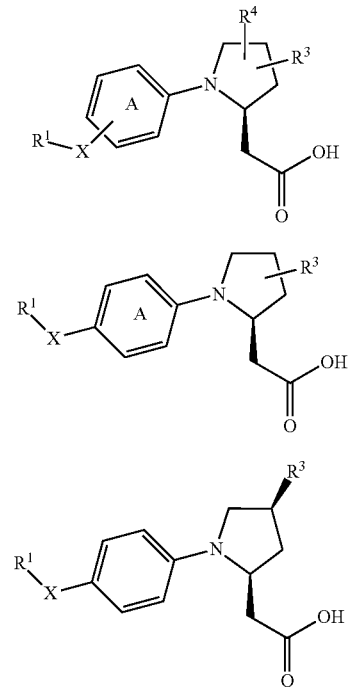

wherein: the variables in each formula are the same as defined in the above respective aspects.

In another embodiment, X is O, S, CH$_2$, CH(C$_{1-4}$ alkyl), CH(C$_{1-4}$ alkoxy-phenyl), or C(O).

In another embodiment, X is O, S or CH$_2$.
In another embodiment, X is O or CH$_2$.
In another embodiment, X is O.
In another embodiment, X is CH$_2$.

In another embodiment, ring A is selected from the group consisting of:

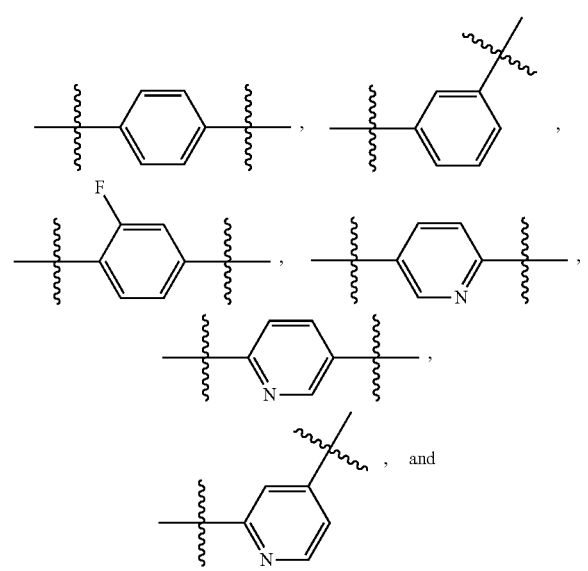

-continued

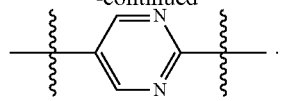

In another embodiment, ring A is selected from the group consisting of:

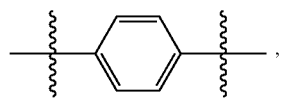

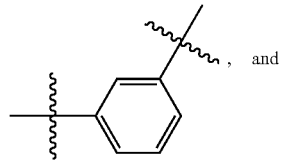

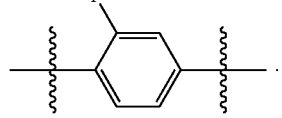

In another embodiment, ring A is

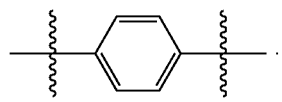

In another embodiment, ring A is selected from the group consisting of:

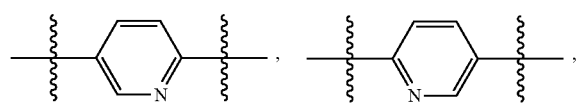

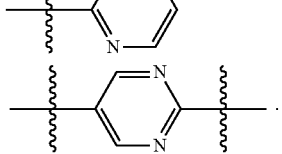

In another embodiment, ring A is selected from the group consisting of:

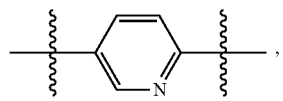

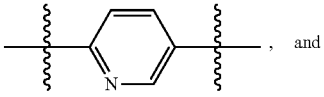

-continued

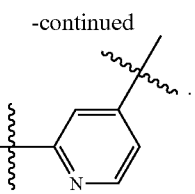

In another embodiment, ring A is

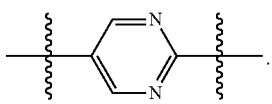

In another embodiment, $R^1$ is —$(CH_2)_n$-phenyl substituted with 0-3 $R^2$, —$(CH_2)_n$-naphthyl substituted with 0-3 $R^2$, or —$(CH_2)_n$-pyridyl substituted with 0-3 $R^2$.

In another embodiment, $R^1$ is —$(CH_2)_n$-phenyl substituted with 0-3 $R^2$ or —$(CH_2)_n$-pyridyl substituted with 0-3 $R^2$.

In another embodiment, $R^1$ is —$(CH_2)_n$-phenyl substituted with 0-2 $R^2$.

In another embodiment, $R^2$, at each occurrence, is independently selected from the group consisting of: halo, $CF_3$, CN, $NO_2$, $OCF_3$, $SCF_3$, $C_{1-6}$ alkyl, $C_{1-6}$ alkoxy, $C_{1-6}$ alkylthio, $NH_2$, $NH(C_{1-4}$ alkyl), $N(C_{1-4}$ alkyl$)_2$, —$(CH_2)_n$—$C_{3-6}$ cycloalkyl, —$(CH_2)_n$-phenyl, —$(CH_2)_n$—O-phenyl, and —$(CH_2)_n$-5- to 6-membered heteroaryl containing carbon atoms and 1-4 heteroatoms selected from the group consisting of N, O, and $S(O)_p$; wherein said cycloalkyl, phenyl and heteroaryl are substituted with 0-2 $R^6$.

In another embodiment, $R^2$, at each occurrence, is independently selected from the group consisting of: halo, $CF_3$, CN, $NO_2$, $OCF_3$, $SCF_3$, $C_{1-6}$ alkyl, $C_{1-6}$ alkoxy, $C_{1-6}$ alkylthio, NH, $NH(C_{1-4}$ alkyl), $N(C_{1-4}$ alkyl$)_2$, cyclopentenyl substituted with 0-2 $R^6$, phenyl substituted with 0-2 $R^6$, benzyl substituted with 0-2 $R^6$, phenoxy substituted with 0-2 $R^6$, benzoxy substituted with 0-2 $R^6$, and pyrazol-1-yl.

In another embodiment, $R^3$ is selected from the group consisting of: H, halo, $CF_3$, and $C_{1-4}$ alkyl.

In another embodiment, $R^3$ is selected from the group consisting of: H, F, $CH_3$, and $CF_3$.

In another embodiment, $R^3$ is selected from the group consisting of: H, F, and $CF_3$.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). In a preferred embodiment, the present invention provides pharmaceutical composition, wherein the additional therapeutic agent is, for example, a dipeptidyl peptidase-IV (DPP4) inhibitor (for example a member selected from saxagliptin, sitagliptin, vildagliptin and alogliptin).

In another embodiment, the present invention provides a method for the treatment and/or prophylaxis of multiple diseases or disorders associated with GPR40, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the GPR40 that can be prevented, modulated, or treated according to the present invention include, but are not limited to, diabetes, hyperglycemia, impaired glucose tolerance, gestational diabetes, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In another embodiment, the present invention provides a method for the treatment and/or prophylaxis of diabetes, hyperglycemia, gestational diabetes, obesity, dyslipidemia, hypertension and cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of diabetes, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hyperglycemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with GPR40.

In another embodiment, the present invention also provides the use of a compound of the present invention for the manufacture of a medicament for the treatment and/or prophylaxis of multiple diseases or disorders associated with GPR40.

In another embodiment, the present invention provides a method for the treatment and/or prophylaxis of multiple diseases or disorders associated with GPR40, comprising: administering to a patient in need thereof a therapeutically effective amount of a first and second therapeutic agent, wherein the first therapeutic agent is a compound of the present invention. Preferably, the second therapeutic agent, for example, dipeptidyl peptidase-IV (DPP4) inhibitor (for example a member selected from saxagliptin, sitagliptin, vildagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with GPR40.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle" or "carbocyclic residue" is intended to mean any stable 3-, 4-, 5-, 6-, 7-, or 8-membered monocyclic or bicyclic or 7-, 8-, 9-, or 10-membered bicyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, and adamantyl. Preferred carbocycles, unless otherwise specified, are cyclopropyl, cyclobutyl, cyclopentyl, cyclohexyl, phenyl, and naphthyl. When the term "carbocycle" is used, it is intended to include "aryl".

As used herein, the term "bicyclic carbocycle" or "bicyclic carbocyclic group" is intended to mean a stable 9 or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in *Hawley's Condensed Chemical Dictionary* (13th ed.), R. J. Lewis, ed., J. Wiley & Sons, Inc., New York, 1997. "$C_{6-10}$ aryl" refers to phenyl and naphthyl.

As used herein, the term "heterocycle" or "heterocyclic group" is intended to mean a stable 3-, 4-, 5-, 6-, or 7-membered monocyclic or 7-, 8-, 9-, 10-membered or bicyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. When the term "heterocycle" is used, it is intended to include "heteroaryl".

Examples of heterocycles include, but are not limited to, acridinyl, azetidinyl, aziridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2 H,6H-1,5,2-dithiazinyl, dihydrofuro[2,3-b]tetrahydrofuran, furanyl, furazanyl, imidazolidinyl, imidazolinyl, imidazolyl, 1 H-indazolyl, imidazolopyridinyl, indolenyl, indolinyl, indolizinyl, indolyl, 3 H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylpyrimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2 H-pyrrolyl, pyrrolyl, quinazolinyl, quinolinyl, 4 H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1 H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteraryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

The term "counter ion" is used to represent a negatively charged species such as chloride, bromide, hydroxide, acetate, and sulfate or a positively charged species such as sodium (Na+), potassium (K+), ammonium ($R_nNH_m$+where n=0-4 and m=0-4) and the like.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and *Methods in Enzymology,* 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry Principles and Practice*, King, F. D., ed., The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); *The Practice of Medicinal Chemistry*, Wermuth, C. G., ed., Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
$CDCl_3$ deutero-chloroform
$CHCl_3$ chloroform
cDNA complimentary DNA
DMF dimethyl formamide
DMSO dimethyl sulfoxide
EDTA ethylenediaminetetraacetic acid
EtOAc ethyl acetate
$Et_2O$ diethyl ether
$AlCl_3$ aluminum chloride
Boc tert-butyloxycarbonyl
$CH_2Cl_2$ dichloromethane
$CH_3CN$ or ACN acetonitrile
$Cs_2CO_3$ cesium carbonate
HCl hydrochloric acid
$H_2SO_4$ sulfuric acid
$K_2CO_3$ potassium carbonate
mCPBA or m-CPBA meta-chloroperbenzoic acid
Pd/C palladium on carbon
PS polystyrene
$SiO_2$ silica oxide
$SnCl_2$ tin(II) chloride
TEA triethylamine
TFA trifluoroacetic acid
THF tetrahydrofuran
KOAc potassium acetate
$MgSO_4$ magnesium sulfate
MsOH or MSA methylsulfonic acid
NaCl sodium chloride
NaH sodium hydride
$NaHCO_3$ sodium bicarbonate
NaOH sodium hydroxide
$Na_2SO_3$ sodium sulfite
$Na_2SO_4$ sodium sulfate
$NH_3$ ammonia
$NH_4Cl$ ammonium chloride
$NH_4OH$ ammonium hydroxide
L.G. leaving group The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The Compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and de-protection in the processes below may be carried out by procedures generally known in the art (see, for example, Greene, T. W. et al., *Protecting Groups in Organic Synthesis*, 3rd Edition, Wiley (1999)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Chemistry: Reactions, Mechanisms, and Structure.* 4th Edition, Wiley & Sons, New York, N.Y. (1992); Katritzky, A. R. et al., eds., *Comprehensive Organic Functional Groups Transformations*, 1st Edition, Elsevier Science Inc., Tarrytown, N.Y. (1995); Larock, R. C., *Comprehensive Organic Transformations*, VCH Publishers, Inc., New York, N.Y. (1989), and references therein.

Methods for synthesis of a large variety of substituted pyrrolidine compounds useful as starting materials for the preparation of compounds of the present invention are well known in the art. For examples of methods useful for the preparation of pyrrolidine materials see the following references and citations therein: Katritzky et al., eds., *Comprehensive Heterocyclic Chemistry*, Pergamon Press Inc., New York (1996); Bellina, F. et al., *Tetrahedron*, 62:7213 (2006); Wolfe, J. P., *Eur. J. Org. Chem.*, 571 (2007); Deng, Q.-H. et al., *Organic Letters*, 10:1529 (2008); Pisaneschi, F. et al., *Synlett*, 18:2882 (2007); Najera, C. et al., *Angewandte Chemie, International Edition*, 44(39):6272 (2005); Sasaki, N. A., *Methods in Molecular Medicine*, 23(*Peptidomimetics Protocols*):489 (1999); Zhou, J.-Q. et al., *Journal of Organic Chemistry*, 57(12):3328 (1992); Coldham, I. et al., *Tetrahedron Letters*, 38(43):7621 (1997); Schlummer, B. et al., *Organic Letters*, 4(9):1471 (2002); Larock, R. C. et al., *Journal of Organic Chemistry*, 59(15):4172 (1994); Galliford, C. V. et al., *Organic Letters*, 5(19):3487 (2003); Kimura, M. et al., *Angewandte Chemie, International Edition*, 47(31):5803 (2008); Ney, J. E. et al., *Adv. Synth. Catal.*, 347:1614 (2005); Paderes, M. C. et al., *Organic Letters*, 11(9):1915 (2009); Wang, Y.-G. et al. *Organic Letters*, 11(9):2027 (2009); Cordero, F. M. et al., *Journal of Organic Chemistry*, 74(11):4225 (2009); Hoang, C. T. et al., *Journal of Organic Chemistry*, 74(11):4177 (2009). Luly, J. R. et al., *Journal of the American Chemical Society*, 105:2859 (1983); Kimball, F. S. et al., *Bioorganic and Medicinal Chemistry*, 16:4367 (2008); Bertrand, M. B. et al., *Journal of Organic Chemistry*, 73(22):8851 (2008); Browning, R. G. et al., *Tetrahedron*, 60:359 (2004); Ray, J. K. et al., *Bioorganic and Medicinal Chemistry*, 2(12):1417 (1994); Evans, G. L. et al., *Journal of the American Chemical Society*, 72:2727 (1950); Stephens, B. E. et al., *Journal of Organic Chemistry*, 74(1):254 (2009); Spangenberg, T. et al., *Organic Letters*, 11(2):261 (2008).

Compounds of Formula (I) can be prepared as shown in Scheme 1.

Nucleophilic aromatic substitution of intermediate A wherein L.G. is a leaving group such as =F, Cl, Br and the like with $R_1$—X—H, followed by reduction of the nitro group with, for example, zinc, or hydrogenation, or other methods known in the art, results in aniline C. Aniline C can be converted to pyrrolidine E via reaction with bis-electrophile D. Optional chiral separation and hydrolysis of the ester gives compounds of Formula (I).

Scheme 1

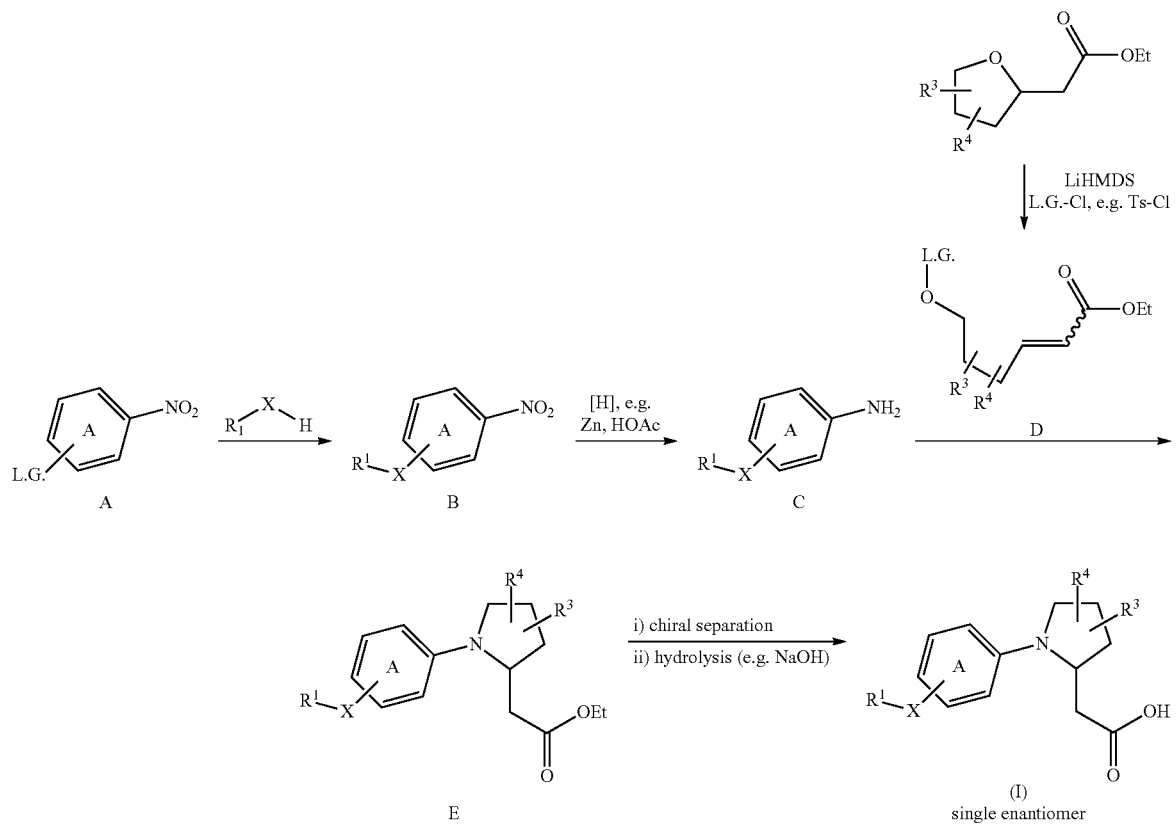

Alternatively, compounds of Formula (I) can be synthesized via reaction of intermediate G with R¹-L.G. to give intermediate H, that can be converted to compounds of Formula (I) according to the sequence depicted in Scheme 2.

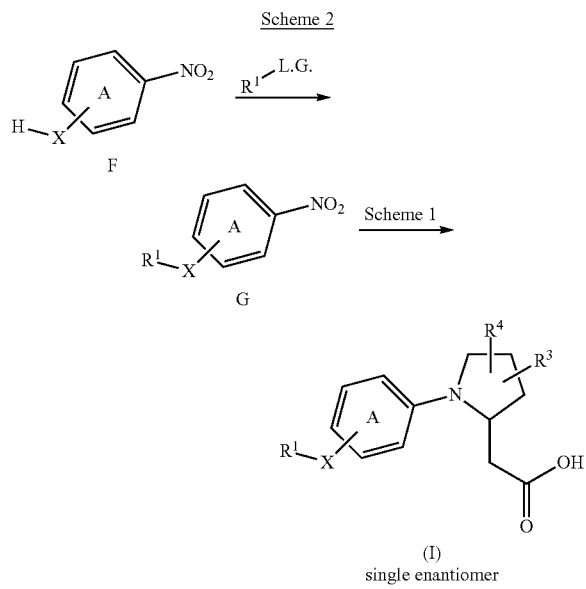

Compounds of Formula (I) may be synthesized starting with pyrrolidines J via coupling to Intermediate K to give pyrrolidine L as depicted in Scheme 3. Activation of the hydroxyl L, via methane sulfonyl chloride, for example, and displacement with sodium cyanide, leads to nitrile M. Nitrile M could be synthesized with an intact R¹—X group, or R¹ itself could be a protecting group that is deprotected to reveal intermediate N. Intermediate N can be converted to compounds of Formula (I) employing the methods depicted in Schemes 1 and 2.

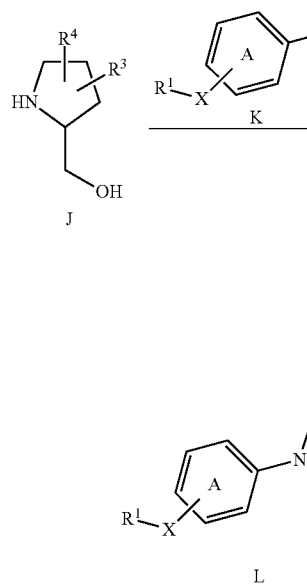

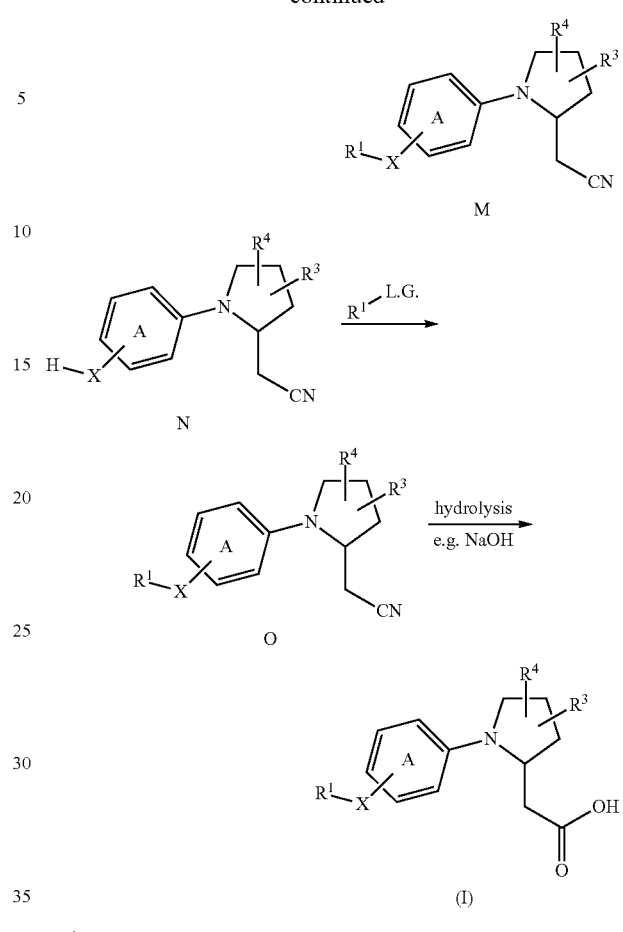

if R¹ = Bn, deprotect via H₂, Pd/C

Alternatively, pyrrolidine J can be coupled to intermediate P that contains a group Y, such as bromine and the like, that can later be converted to other functionality, such as —B(OH)₂, to enable coupling to R¹—X-functionality, resulting in compounds of Formula (I).

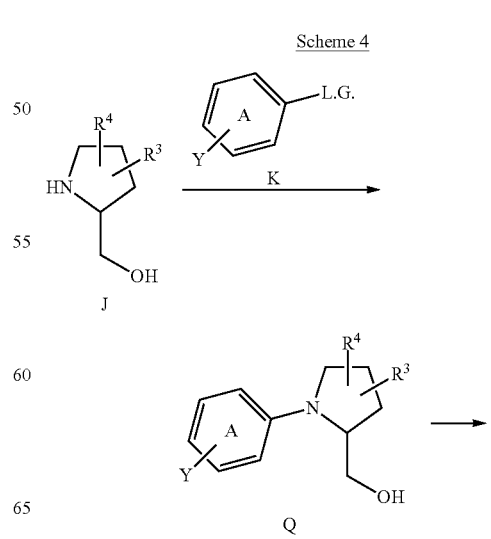

-continued

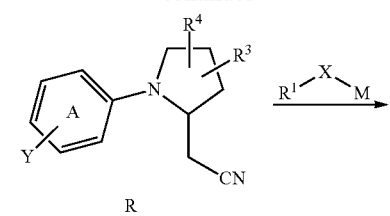

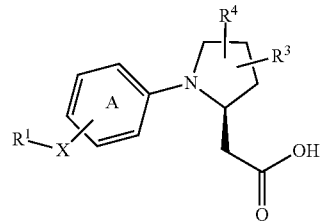

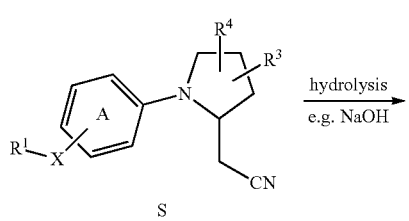

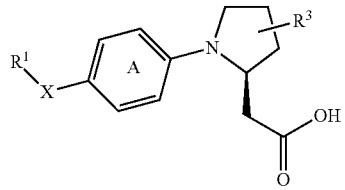

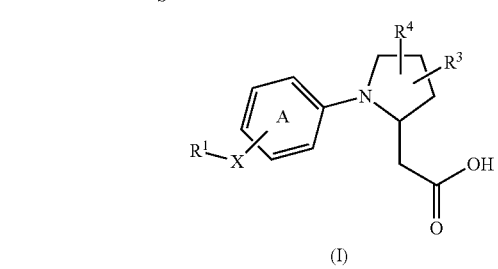

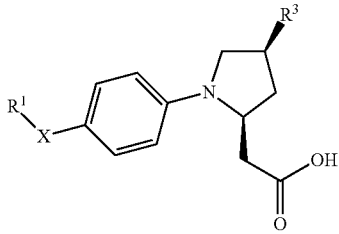

The compound of the instant invention herein described may have asymmetric centers. For example, the chiral carbon atoms in Formula (I), (II) or (III) as indicated below, exist in either as S or R configuration.

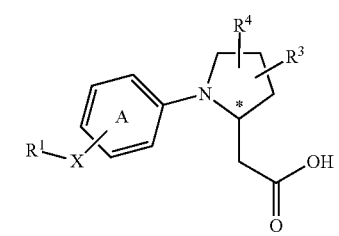

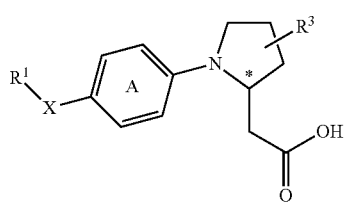

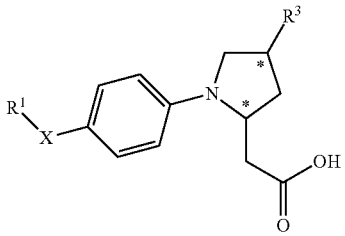

In a preferred embodiment, the present invention provides a stereoisomeric configuration of Formula (Ia), (IIa) or (IIIa):

IV. Biology

Diabetes mellitus is a serious disease afflicting over 100 million people worldwide. It is diagnosed as a group of disorders characterized by abnormal glucose homeostasis resulting in elevated blood glucose. Diabetes is a syndrome with interrelated metabolic, vascular, and neuropathic components. The metabolic abnormality is generally characterized by hyperglycemia and alterations in carbohydrate, fat and protein metabolism caused by absent or reduced insulin secretion and/or ineffective insulin secretion. The vascular syndrome consists of abnormalities in the blood vessels leading to cardiovascular, retinal and renal complications. Abnormalities in the peripheral and autonomic nervous systems are also part of diabetic syndrome. Strikingly, diabetes is the fourth leading cause of global death by disease, the largest cause of kidney failure in developed countries, the leading cause of vision loss in industrialized countries and has the greatest prevalence increase in developing countries.

Type 2 diabetes, which accounts for 90% of diabetes cases, is characterized by increasing insulin resistance associated with inadequate insulin secretion after a period of compensatory hyperinsulinemia. The reasons for β cell secondary failure are not completely understood. Acquired pancreatic islet damage or exhaustion and/or genetic factors causing susceptibility to islet secretory insufficiency have been hypothesized.

Free fatty acids (FFAs) are evidenced to influence insulin secretion from β cells primarily by enhancing glucose-stimulated insulin secretion (GSIS). Although glucose is recognized as the major stimulator of insulin secretion from β cells, other stimuli, such as amino acids, hormones, and FFAs, also regulate insulin secretion. Thus, under normal settings, insulin secretion from β cells in response to food intake is evoked by the collective stimuli of nutrients, such as glucose, amino acids, and FFAs, and hormones like the incretin glucagon-like peptide 1 (GLP-1). Fatty acids are also known to stimulate the secretion of several gut satiety hormones, including cholocystokinine (CCK), GLP-1, and peptide YY (PYY).

G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells. GPR40 (e.g., human GPR40, RefSeq mRNA ID NM_005303; e.g., mouse GPR40 RefSeq mRNA ID NM_194057) is a GPCR located at chromosome 19q13.12. GPR40 is activated by medium to long chain fatty acids and thereby triggering a signaling cascade that results in increased levels of $[Ca^{2+}]_i$ in β cells and subsequent stimulation of insulin secretion (Itoh et al., *Nature,* 422:173-176 (2003)). Selective small molecule agonists of GPR40 have been shown to promote GSIS and reduce blood glucose in mice (Tan et al., *Diabetes,* 57:2211-2219 (2008)). Briefly, when activators of GPR40 are administered to either normal mice or mice that are prone to diabetes due to genetic mutation, prior to a glucose tolerance test, improvements in glucose tolerance are observed. A short-lived increase in plasma insulin levels are also observed in these treated mice. It has also been shown that GPR40 agonists restore GSIS in pancreatic β-cells from the neonatal STZ rats suggesting that GPR40 agonists will be efficacious in diabetics with compromised β-cell function and mass. Fatty acids are known to stimulate the secretion of several gut satiety hormones, including cholocystokinine (CCK), GLP-1, and peptide YY (PYY), and GPR40 has been shown to colocalize with cells that secrete such hormones (Edfalk et al., *Diabetes,* 57:2280-2287 (2008)). Fatty acids are also known to play a role in neuronal development and function, and GPR40 has been reported as a potential modulator of the fatty acid effects on neurons (Yamashima, T., *Progress in Neurobiology,* 84:105-115 (2008)).

Given the increase in the worldwide patient population afflicted by type 2 diabetes, there is a need for novel therapies which are effective with minimal adverse events. To decrease medical burden of type 2 diabetes through enhanced glycemic control, GPR40 modulator compounds of the present invention are being investigated here for their incretin effect to promote GSIS as well as the potential combination with a broad range of anti-diabetic drugs.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a GPR40 modulator.

Exemplary subjects include human beings of any age with risk factors for metabolic disease. Common risk factors include, but are not limited to, age, sex, weight, family history, or signs of insulin resistance such as acanthosis nigricans, hypertension, dislipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate GPR40 and/or to prevent or treat the disorders listed herein. When applied to a combination, the term refers to combined amounts of the active ingredients that result in the preventive or therapeutic effect, whether administered in combination, serially, or simultaneously.

A. In Vitro GPR40 Assays

FDSS-Based Intracellular Calcium Assay

Cell lines expressing GPR40 are generated using the pDEST 3xflag gene expression system and are cultured in culture medium comprising the following components: F12 (Gibco #11765), 10% lipid deprived fetal bovine serum, 250 ug/ml zeocin and 500 ug/ml G418. To conduct the fluorescent imaging plate reader (FLIPR)-based calcium flux assay to measure intracellular $Ca^{2+}$ response, cells expressing GPR40 are plated on 384 well plates (BD Biocoat #356697) at a density of 20,000 cells/20 ul medium per well in phenol red and serum-free DMEM (Gibco #21063-029) and incubated overnight. Using BD kit #s 80500-310 or -301, the cells are incubated with 20 ul per well of Hank's buffered salt solution with 1.7 mM probenecid and Fluo-3 at 37° C. for 30 minutes. Compounds are dissolved in DMSO and diluted to desired concentrations with assay buffer and added to the cells as 3× solution (20 ul per well). Run fluorescence/luminescence reader FDSS (Hamamatsu) to read intracellular $Ca^{2+}$ response.

Examples 1 to 109 disclosed below were tested in the Human GRP40 In Vitro assay described immediately above and found having hGRP40 modulating activity. Table 1 below lists hGPR40 $EC_{50}$ values measured for the following examples.

TABLE 1

| Example No. | hGPR40 EC$_{50}$ (nM) |
|---|---|
| 1 | 1632 |
| 4 | 3804 |
| 5 | 65 |
| 40 | 61 |
| 44 | 352 |
| 41 | 56 |
| 50 | 55 |
| 52 | 305 |
| 56 | 2324 |
| 58 | 331 |
| 68 | 314 |
| 76 | 4394 |
| 103 | 63 |
| 106 | 299 |
| 109 | 4342 |

In Vivo GPR40 Assays

Acute oral glucose tolerance test

C57Bl6 mice were housed individually and fed standard low fat rodent chow diet. At approximately 10 weeks age, after 5 h fast, these mice were orally treated with vehicle or compounds 60 minutes before the glucose challenge (2 g/kg). Blood glucose levels were determined from tail bleeds taken at −60, 0, 15, 30, 60 and 120 minutes after glucose challenge. The blood glucose excursion profile from t=0-120 minutes was used to calculate an area under the curve (AUC) for compound treatment.

The compounds of the present invention possess activity as modulators of GPR40, and, therefore, may be used in the treatment of diseases associated with GPR40 activity. Via modulation of GPR40, the compounds of the present invention may preferably be employed to increase the production/secretion of insulin and/or gut hormones, such as GLP-1, GIP, CCK and amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, vascular restenosis, peripheral arterial disease, lipid disorders, bone disease (including osteoporosis), PCOS, HIV protease associated lipodystrophy, glaucoma and inflammatory diseases, such as, psoriasis, rheumatoid arthritis and osteoarthritis, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR40 modulators or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, or cognition promoting agents, appetite suppressants, treatments for heart failure, treatments for peripheral arterial disease and anti-inflammatory agents.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the GPR40 receptor. Such compounds may be provided in a commercial kit, for example, for use in pharmaceutical research involving GPR40 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving GPR40.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of multiple diseases or disorders associated with GPR40 (as defined previously). In another embodiment, the package insert states that the pharmaceutical composition can be used in combination (as defined previously) with a second therapeutic agent for the treatment and/or prophylaxis of multiple diseases or disorders associated with GPR40. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS and Preparatory/Analytical HPLC Methods Employed in Characterization or Purification of Examples Analytical HPLC/MS (unless otherwise noted) was performed on Shimadzu SCL-10A liquid chromatographs and Waters MICROMASS® ZQ Mass Spectrometers (Desalvation Gas: Nitrogen; Desalvation Temp. 250° C.; Ion Source Temp: 120° C.; Positive Electrospray conditions) using the following method:

Linear Gradient of 0% to 100% solvent B over 2 minutes, with 1 minute hold at 100% B;
UV visualization at 220 nm;
Column: PHENOMENEX® Luna C18 (2) 30 mm×4.60 mm; 5 m particle (Heated to Temp. 40° C.);
Flow rate: 5 ml/min;
Solvent A: 10% ACN, 90% Water, 0.1% TFA; or, 10% MeOH, 90% water, 0.1% TFA; and
Solvent B: 90% ACN, 10% Water, 0.1% TFA; or, 90% MeOH, 10% water, 0.1% TFA.

Preparatory HPLC (unless otherwise noted) was performed on a Shimadzu SCL-10A liquid chromatograph with a linear gradient of 20-100% Solvent B over 10 or 30 minutes, with either a 2 or 5 minutes (respectively) hold at 100% Solvent B;
UV visualization at 220 nm;
Column: PHENOMENEX® Luna Axia 5u C18 30×100 mm;
Flow rate: 20 mL/min;
Solvent A: 10% ACN, 90% water, 0.1% trifluoroacetic Acid; and
Solvent B: 90% ACN, 10% water, 0.1% trifluoroacetic Acid.

Analytical HPLC (unless otherwise noted) was performed to determine compound purity on a Shimadzu SIL-10A using the following method (Unless otherwise stated, retention times listed in Examples refer the retention times of Column 1):
Linear Gradient of 10% to 100% solvent B over 15 minutes;
UV visualization at 220 nm and 254 nm;
Column 1: SunFire C18 3.5 um, 4.6×150 mm;
Column 2: Xbridge Phenyl 3.5 um, 4.6×150 mm;
Flow rate: 1 ml/min (for both columns);
Solvent A: 5% MeCN-95% H2O-0.05% TFA; and
Solvent B: 95% MeCN-5% H2O-0.05% TFA.

NMR Employed in Characterization of Examples $^1$H NMR spectra (unless otherwise noted) were obtained with JEOL or Bruker FOURIER® transform spectrometers operating at 400 MHz or 500 MHz. $^1$H-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2$ H, 3.30 ppm for $CD_2$ HOD, 1.94 for $CHD_2CN$, 7.24 ppm for $CHCl_3$).

Example 1

(S)-2-(1-(3-fluoro-4-(o-tolyloxy)phenyl)pyrrolidin-2-yl)acetic acid, TFA

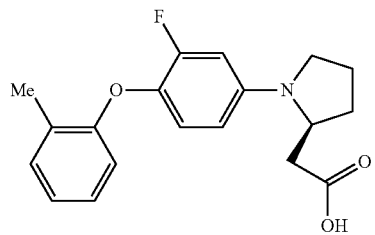

1A. 2-fluoro-4-nitro-1-(o-tolyloxy)benzene: To a solution of o-cresol (1.359 g, 12.57 mmol) and 1,2-difluoro-4-nitrobenzene (2 g, 12.57 mmol) in DMF (10 mL) was added K₂CO₃ (3.47 g, 25.1 mmol). The reaction mixture was heated at 70° C. for 2.5 h and, after cooling to rt, the mixture was diluted with Et₂O, washed with water, brine, dried over Na₂SO₄, and concentrated. Purification via silica gel chromatography gave 1A (colorless oil, 2.96 g, 11.97 mmol, 95% yield). LC-MS Anal. Calc'd for $C_{13}H_{10}FNO_3$: 247.06. found [M+H] 248.0.

1B. 3-fluoro-4-(o-tolyloxy)aniline: To a solution of 1A (2.96 g, 11.97 mmol) in methanol (50 mL) and CH₂Cl₂ (50.0 mL) was added NH₄Cl (6.40 g, 120 mmol), then zinc (4.70 g, 71.8 mmol), and the mixture was stirred at for 3 h. The reaction mixture was filtered and evaporated. The residue was diluted with EtOAc, washed with NaHCO₃ (sat), brine, dried and concentrated to give 1B (light yellow oil, 2.4 g, 11.05 mmol, 92% yield). LC-MS Anal. Calc'd for $C_{13}H_{12}FNO$: 217.09. found [M+H] 218.3.

1C. 2-fluoro-4-iodo-1-(o-tolyloxy)benzene: To a solution of 1B (2.4 g, 11.05 mmol) and p-toluenesulfonic acid monohydrate (6.30 g, 33.1 mmol) in acetonitrile (48.3 mL) at 0° C. was added a solution of KI (4.58 g, 27.6 mmol) and sodium nitrite (1.524 g, 22.10 mmol) in water (7 mL). After stirring 1.5 h, the reaction mixture was diluted with CH₂Cl₂, washed with sat. NaHCO₃ (aq), sat. Na₂S₂O₃ (aq), and brine. The organic layer was dried over Na₂SO₄, and concentrated. Purification via silica gel chromatography gave 1C (colorless oil, 1.45 g, 4.42 mmol, 40.0% yield). ¹H NMR (400 MHz, chloroform-d) δ ppm 7.49 (1 H, dd, J=9.9, 2.2 Hz), 7.34 (1 H, d, J=8.8 Hz), 7.22-7.28 (1 H, m), 7.16 (1 H, t, J=7.7 Hz), 7.03-7.10 (1 H, m), 6.82 (1 H, d, J=8.2 Hz), 6.57 (1 H, t, J=8.5 Hz), 2.26 (3 H, s).

1D. (S)-(1-(3-fluoro-4-(o-tolyloxy)phenyl)pyrrolidin-2-yl)methanol: To a mixture of 1C (1.45 g, 4.42 mmol), (S)-pyrrolidin-2-ylmethanol (0.447 g, 4.42 mmol) and NaOH (0.530 g, 13.26 mmol) in 2-propanol (7.37 mL) was added copper (I) iodide (0.021 g, 0.110 mmol). The reaction vessel was purged with argon and the mixture was stirred at 110° C. for 10 min. The reaction mixture was stirred at 90° C. for 10 h. The resulting mixture was diluted with EtOAc, washed with water, brine, dried over Na₂SO₄, and concentrated. Purification via silica gel chromatography gave 1D (yellow oil, 0.69 g, 2.290 mmol, 51.8% yield). LC-MS Anal. Calc'd for $C_{18}H_{20}FNO_2$: 301.15. found [M+H] 302.1.

1E. (S)-2-(1-(3-fluoro-4-(o-tolyloxy)phenyl)pyrrolidin-2-yl)acetonitrile: To a solution of 1D (0.69 g, 2.290 mmol) in CH₂Cl₂ (10 mL) at 0° C. was added TEA (0.638 mL, 4.58 mmol), followed by slow addition of methanesulfonyl chloride (0.268 mL, 3.43 mmol). The reaction mixture was stirred for 1 h. The resulting mixture was diluted with CH₂Cl₂, and the organic layer was washed with NH₄Cl (sat.), NaHCO₃ (sat.) and brine, dried over Na₂SO₄, MgSO₄, and concentrated to give (S)-(1-(3-fluoro-4-(o-tolyloxy)phenyl)pyrrolidin-2-yl)methyl methanesulfonate (0.89 g, 2.346 mmol, 102% yield) as a brown oil that was used as is. To a solution of (S)-(1-(3-fluoro-4-(o-tolyloxy)phenyl)pyrrolidin-2-yl) methyl methanesulfonate (0.89 g) in DMSO (5 mL) was added NaCN (0.281 g, 5.72 mmol). The mixture was heated at 50° C. for 10 h. The reaction mixture was diluted with EtOAc, washed with water, brine, dried over Na₂SO₄, and concentrated. Purification via silica gel chromatography gave 1E (colorless oil, 350 mg, 1.128 mmol, 49.3% yield). LC-MS Anal. Calc'd for $C_{19}H_{19}FN_2O$: 310.15. found [M+H] 311.1. ¹H NMR (400 MHz, chloroform-d) δ ppm 7.14-7.27 (1 H, m), 7.06 (1 H, t, J=7.7 Hz), 6.86-6.98 (2 H, m), 6.64 (1 H, d, J=8.2 Hz), 6.38 (1 H, dd, J=13.2, 2.7 Hz), 6.17-6.31 (1 H, m), 3.87-4.05 (1 H, m), 3.39-3.56 (1 H, m), 3.05-3.28 (1 H, m), 2.66 (1 H, dd, J=17.0, 3.3 Hz), 2.47 (1 H, dd, J=17.0, 8.2 Hz), 2.35 (3 H, s), 2.15-2.27 (2 H, m), 2.06-2.14 (2 H, m).

1F (Example 1. (S)-2-(1-(3-fluoro-4-(o-tolyloxy)phenyl) pyrrolidin-2-yl)acetic acid, TFA): To a solution of 1E (50 mg, 0.161 mmol) in ethanol (0.5 mL) was added KOH (600 μL, 3.60 mmol). The reaction mixture was stirred at 120° C. for 40 min. The resulting mixture was evaporated and TFA and water were added. The mixture was extracted with EtOAc, washed with brine, dried and concentrated. Purification via preparative RP-HPLC gave Example 1 (colorless foam, 27 mg, 0.060 mmol, 37.4% yield). LC-MS Anal. Calc'd for $C_{19}H_{20}FNO_3$: 329.14. found [M+H] 330.1. ¹H NMR (400 MHz, acetonitrile-d₃) δ ppm 7.23 (1 H, d, J=8.2 Hz), 7.10 (1 H, t, J=7.7 Hz), 6.87-7.03 (2 H, m), 6.60-6.70 (2 H, m), 6.54 (1 H, d, J=9.3 Hz), 4.05 (1 H, d, J=2.2 Hz), 3.48 (1 H, br. s.), 3.20 (1 H, d, J=8.2 Hz), 2.68 (1 H, dd, J=15.9, 2.7 Hz), 2.34 (1 H, dd, J=15.9, 9.9 Hz), 2.28 (3 H, s), 2.01-2.17 (2 H, m), 1.84-1.96 (2 H, m). Analytical HPLC: RT=11.34 min, HI: 99.2%.

Example 2

(S)-2-(1-(4-(2-fluorophenoxy)phenyl)pyrrolidin-2-yl)acetic acid, TFA

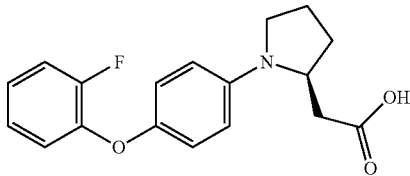

2A. ethyl 6-(tosyloxy)hex-2-enoate: To a cooled (−78° C.) of LiHMDS (1M in THF, 50.6 mL, 50.6 mmol) was added ethyl 2-(tetrahydrofuran-2-yl)acetate (8 g, 50.6 mmol). After 1 h, the mixture was warmed to −40° C. for 10 min, and was cooled to −78° C. To this solution was added 4-methylbenzene-1-sulfonyl chloride (9.64 g, 50.6 mmol), and the mixture was allowed to warm to rt over 1 h. The mixture was diluted with diethyl ether and 1N HCl. The layers were extracted and the organic layer was washed with sat. NaHCO₃ (aq) and brine. The organic layer was dried over Na₂SO₄, was filtered, and was evaporated to give 20 g of a clear oil (crude). The material was purified via silica gel chromatography to give 7.4 g of 2A (colorless oil, 23.62 mmol, 46.7% yield). Anal. Calc'd for $C_{15}H_{20}O_5S$=312.1. found $[M+Na]^+$=334.9. ¹H NMR (400 MHz, chloroform-d) δ ppm 7.79 (2 H, d, J=8.24 Hz), 7.36 (2 H, d, J=8.24 Hz), 6.84-6.80 (1 H, m), 5.74 (1 H, d, J=15.94 Hz), 4.17-4.04 (4 H, m), 2.46 (3 H, s), 2.13-2.37 (2 H, m), 1.63-1.84 (2 H, m), 1.16-1.40 (3 H, m).

2B. 1-fluoro-2-(4-nitrophenoxy)benzene: To a solution of 1-fluoro-4-nitrobenzene (0.5 g, 3.54 mmol) and 2-fluorophenol (0.397 g, 3.54 mmol) in DMF (5 mL) was added Cs₂CO₃ (2.309 g, 7.09 mmol). The mixture was stirred at 80° C. for 2 h, and the mixture was cooled to rt. The resulting mixture was diluted with EtOAc and water, and the layers were extracted. The organic layer was washed with brine, was dried over MgSO₄, was filtered and evaporated to give a light yellow oil. Purification via silica gel chromatography gave 0.64 g of 2B (white solid, 2.74 mmol, 77% yield). Anal Calc'd for $C_{12}H_8FNO_3$, 233.05. found [M+H] 234.0. ¹H NMR (400 MHz, chloroform-d) δ ppm 8.22 (2 H, d, J=9.23 Hz), 7.14-7.33 (4 H, m), 7.01 (2 H, d, J=9.23 Hz).

2C. 4-(2-fluorophenoxy)aniline: A solution of 2B (490 mg, 2.1 mmol) in acetic acid (5 mL) was degassed with argon. Zinc dust (824 mg, 12.6 mmol) was added, and the mixture was stirred for 20 h. Solids were filtered off, and the filtrate was neutralized with 5N NaOH. The resulting mixture was extracted with methylene chloride and water. The organic layer was dried over MgSO$_4$, filtered and evaporated to give a dark oil that was purified via silica gel chromatography to give 0.27 g of 2C (brown oil, 1.3 mmol, 63% yield). Anal Calc'd for C$_{12}$H$_{10}$FNO, 203.07. found [M+H] 204.4.

2D. (S)-ethyl 2-(1-(4-(2-fluorophenoxy)phenyl)pyrrolidin-2-yl)acetate: 2A (0.269 g, 0.861 mmol) and 2C (0.175 g, 0.861 mmol) were mixed and heated at 130° C. for 2 h. The reaction mixture was allowed to cool to rt, and it was diluted with EtOAc. The resulting mixture was extracted successively with water and sat'd NaCl solution (aq), dried with Na$_2$SO$_4$ and filtered, and concentrated in vacuo. Purification via silica gel chromatography gave (R,S)-ethyl 2-(1-(4-(2-fluorophenoxy)phenyl)pyrrolidin-2-yl)acetate (181 mg, 61.2%) as a colorless oil. The racemic material was separated by SFC to give (R)-ethyl 2-(1-(4-(2-fluorophenoxy)phenyl) pyrrolidin-2-yl)acetate (96 mg, 0.280 mmol, 32.5% yield) and 2D (85 mg, 0.248 mmol, 28.7% yield). LC-MS Anal. Calc'd for C$_{20}$H$_{22}$FNO$_3$ 343.16. found [M+H] 343.9.

2E (Example 2. (S)-2-(1-(4-(2-fluorophenoxy)phenyl)pyrrolidin-2-yl)acetic acid, TFA): To a solution of 2D (85 mg, 0.248 mmol) in THF (1 mL) and methanol (0.6 mL) was added 2N NaOH (0.6 mL, 1.200 mmol). The reaction was stirred at rt for 2 h. Volatile solvents were evaporated, and the residue was diluted with 1N HCl to pH~2-3 and EtOAc. The layers were extracted, and the organic layer was washed with brine, dried and concentrated. The residue was purified via RP-prep. HPLC to yield Example 2 (white powder, 59 mg, 0.137 mmol, 55.5% yield). LC-MS Anal. Calc'd for C$_{18}$H$_{18}$FNO$_3$ 315.13. found [M+H] 316.4. $^1$H NMR (400 MHz, methanol-d$_3$) δ ppm 7.13-7.35 (5 H, m), 6.96-7.11 (3 H, m), 4.20 (1 H, br. s.), 3.74 (1 H, br. s.), 3.50 (1 H, d, J=8.79 Hz), 2.73 (1 H, dd, J=16.04, 4.17 Hz), 2.51 (1 H, dd, J=16.26, 8.79 Hz), 2.41 (1 H, dd, J=12.74, 7.91 Hz), 2.10-2.28 (2 H, m), 1.87-2.06 (1 H, m). Analytical HPLC: RT=7.03 min, HI: 98.4%.

Examples 3 to 10 were synthesized following the procedures described in Example 2.

Example 3

(S)-2-(1-(4-(2,6-dimethylphenoxy)phenyl)pyrrolidin-2-yl)acetic acid, HCl

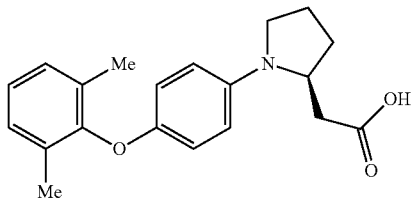

Example 3 (white powder, 28 mg, 0.077 mmol, 29.8% yield). LC-MS Anal. Calc'd for C$_{20}$H$_{23}$NO$_3$ 325.17. found [M+H] 326.6. $^1$H NMR (400 MHz, acetonitrile-d$_3$) δ ppm 7.39 (2 H, br. s.), 7.00-7.21 (3 H, m), 6.79 (2 H, d, J=9.23 Hz), 4.02 (1 H, dq, J=7.25, 7.10 Hz), 3.71 (1 H, d, J=10.11 Hz), 3.24-3.45 (1 H, m), 2.75 (2 H, d, J=6.15 Hz), 2.28-2.46 (1 H, m), 2.11-2.25 (2 H, m), 2.09 (6 H, s), 1.96-2.04 (1 H, m). Analytical HPLC: RT=6.64 min, HI: 99.2%.

Example 4

(R)-2-(1-(4-(2,6-dimethylphenoxy)phenyl)pyrrolidin-2-yl)acetic acid, HCl

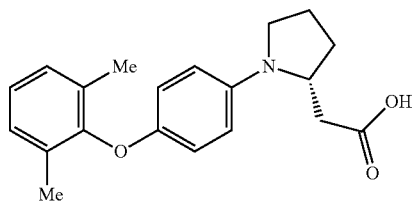

Example 4 (white powder, 64 mg, 0.175 mmol, 68.8% yield). LC-MS Anal. Calc'd for C$_{20}$H$_{23}$NO$_3$ 325.17. found [M+H] 326.6. $^1$H NMR (400 MHz, acetonitrile-d$_3$) δ ppm 7.58 (2 H, d, J=8.35 Hz), 6.96-7.19 (3 H, m), 6.76 (2 H, d, J=8.79 Hz), 3.86-4.05 (1 H, m), 3.65-3.80 (1 H, m), 3.22-3.44 (1 H, m), 2.79-2.95 (1 H, m), 2.63-2.74 (1 H, m), 2.27-2.45 (1 H, m), 2.13 (2 H, dt, J=14.94, 7.47 Hz), 1.97-2.04 (6 H, m), 1.90-1.96 (1 H, m). Analytical HPLC: RT=6.64 min, HI: 99.0%.

Example 5

(S)-2-(1-(4-(o-tolyloxy)phenyl)pyrrolidin-2-yl)acetic acid, HCl

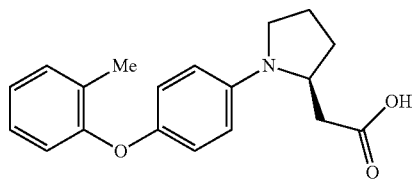

Example 5 (white powder, 70 mg, 0.199 mmol, 88% yield). LC-MS Anal. Calc'd for C$_{19}$H$_{21}$NO$_3$ 311.15 found [M+H] 312.0. $^1$H NMR (400 MHz, acetonitrile-d$_3$) δ ppm 7.77 (2 H, d, J=9.23 Hz), 7.33 (1 H, d, J=7.03 Hz), 7.25 (1 H, t, J=6.81 Hz), 7.09-7.19 (1 H, m), 6.86-7.05 (3 H, m), 4.05 (1 H, br. s.), 3.79-3.91 (1 H, m), 3.34-3.52 (1 H, m), 2.99 (1 H, br. s.), 2.79

(1 H, d, J=4.39 Hz), 2.43-2.55 (1 H, m), 2.17-2.28 (2 H, m), 2.13-2.21 (3 H, m), 1.98-2.13 (1 H, m). Analytical HPLC: RT=6.57 min, HI: 99.1%.

Example 6

(S)-2-(1-(4-phenoxyphenyl)pyrrolidin-2-yl)acetic acid, HCl

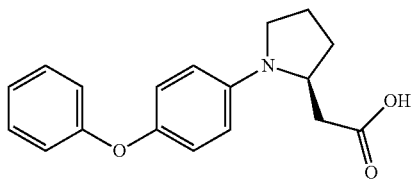

Example 6 (colorless foam, 24 mg, 0.071 mmol, 39.3% yield). LC-MS Anal. Calc'd for $C_{18}H_{19}NO_3$: 297.14. found [M+H] 298.0. $^1$H NMR (400 MHz, acetonitrile-$d_3$) δ ppm 7.81 (2 H, d, J=8.79 Hz), 7.41 (2 H, t, J=8.13 Hz), 7.20 (1 H, t, J=7.47 Hz), 6.96-7.12 (4 H, m), 4.02-4.18 (1 H, m), 3.80-3.98 (1 H, m), 3.40-3.59 (1 H, m), 2.92-3.07 (1 H, m), 2.74-2.87 (1 H, m), 2.45-2.59 (1 H, m), 2.17-2.36 (2 H, m), 1.99-2.14 (1 H, m). Analytical HPLC: RT=6.59 min, HI: 99.1%.

Example 7

(S)-2-(1-(4-(2-ethoxyphenoxy)phenyl)pyrrolidin-2-yl)acetic acid, HCl

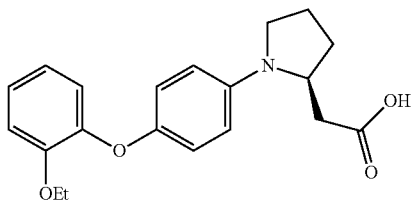

Example 7 (colorless foam, 42 mg, 0.110 mmol, 47.9% yield). LC-MS Anal. Calc'd for $C_{20}H_{23}NO_4$: 341.16. found [M+H] 341.0. $^1$H NMR (400 MHz, acetonitrile-$d_3$) δ ppm 7.72 (2 H, d, J=9.23 Hz), 7.16-7.30 (1 H, m), 7.04-7.14 (2 H, m), 6.83-7.01 (3 H, m), 3.94-4.17 (3 H, m), 3.78-3.93 (1 H, m), 3.35-3.53 (1 H, m), 2.98 (1 H, dd, J=16.48, 9.01 Hz), 2.76 (1 H, dd, J=16.70, 4.39 Hz), 2.40-2.58 (1 H, m), 2.14-2.28 (2 H, m), 1.99-2.13 (1 H, m), 1.15 (3 H, t). Analytical HPLC: RT=6.42 min, HI: 99.1%.

Example 8

(S)-2-(1-(4-(2-benzylphenoxy)phenyl)pyrrolidin-2-yl)acetic acid, HCl

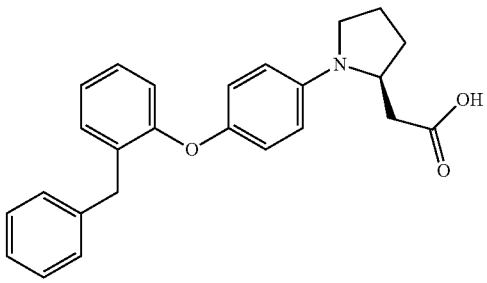

Example 8 (colorless oil, 28 mg, 0.065 mmol, 31.6% yield). LC-MS Anal. Calc'd for $C_{25}H_{25}NO_3$: 387.18. found [M+H] 388.5. $^1$H NMR (400 MHz, acetonitrile-$d_3$) δ ppm 7.35-7.46 (1 H, m), 7.32 (1 H, d, J=7.47 Hz), 7.03-7.27 (8 H, m), 6.88 (3 H, d, J=9.23 Hz), 3.98-4.11 (1 H, m), 3.95 (2 H, s), 3.71 (1 H, br. s.), 3.25-3.42 (1 H, m), 2.76 (2 H, d, J=4.39 Hz), 2.31-2.47 (1 H, m), 2.17 (2 H, qd, J=7.18, 7.03 Hz), 1.98-2.07 (1 H, m). Analytical HPLC: RT=8.70 min, HI: 99.1%.

Example 9

(R)-2-(1-(4-(2-benzylphenoxy)phenyl)pyrrolidin-2-yl)acetic acid, HCl

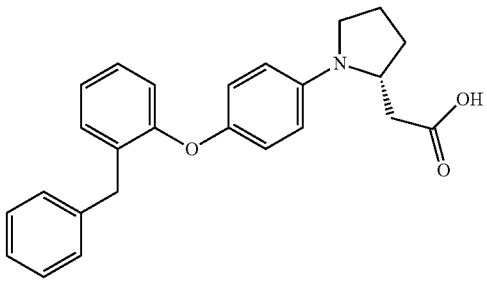

Example 9 (colorless foam, 38 mg, 0.089 mmol, 42.8% yield). LC-MS Anal. Calc'd for $C_{25}H_{25}NO_3$: 387.18. found [M+H] 388.5. $^1$H NMR (400 MHz, acetonitrile-$d_3$) δ ppm 7.66 (2 H, d, J=7.47 Hz), 7.08-7.43 (8H, m), 6.83-7.04 (3 H, m), 4.03 (1 H, dd, J=7.03, 4.83 Hz), 3.94 (2 H, s), 3.77-3.89 (1 H, m), 3.32-3.50 (1 H, m), 2.96 (1 H, br. s.), 2.70-2.83 (1 H, m), 2.41-2.59 (1 H, m), 2.16-2.30 (2 H, m), 2.01-2.12 (1 H, m). Analytical HPLC: RT=8.69 min, HI: 98.8%.

Example 10

(S)-2-(1-(4-(biphenyl-2-yloxy)phenyl)pyrrolidin-2-yl)acetic acid, HCl

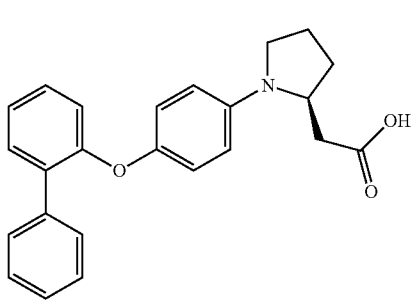

Example 10 (colorless foam, 47 mg, 0.114 mmol, 48.0% yield) as a colorless foam. LC-MS Anal. Calc'd for $C_{24}H_{23}NO_3$: 373.17 found [M+H] 374.5. $^1$H NMR (400 MHz, acetonitrile-$d_3$) δ ppm 7.44-7.64 (5 H, m), 7.24-7.44 (5 H, m), 7.05 (1 H, d, J=8.35 Hz), 6.85-6.98 (2 H, m), 3.88-4.09 (1 H, m), 3.67-3.81 (1 H, m), 3.24-3.45 (1 H, m), 2.82 (1 H, d, J=9.23 Hz), 2.59-2.73 (1 H, m), 2.29-2.50 (1 H, m), 2.10-2.26 (2 H, m), 1.98-2.07 (1 H, m). Analytical HPLC: RT=8.38 min, HI: 99.1%.

Example 11

(S)-2-(1-(4-((2-methyl-6-(trifluoromethyl)pyridin-3-yl)methoxy)phenyl)pyrrolidin-2-yl)acetic acid, HCl

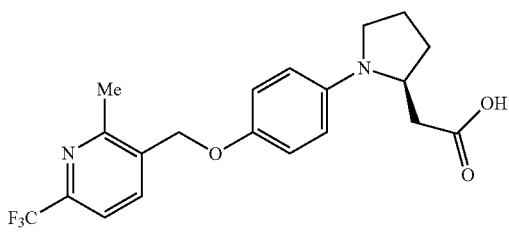

11A. 2-methyl-3-((4-nitrophenoxy)methyl)-6-(trifluoromethyl)pyridine: A solution of 4-nitrophenol (0.5 g, 3.59 mmol) and 3-(chloromethyl)-2-methyl-6-(trifluoromethyl)pyridine (0.753 g, 3.59 mmol) in DMF (10 mL) were stirred with $K_2CO_3$ (0.994 g, 7.19 mmol) at 80° C. for 2 h. The mixture was diluted with EtOAc and water. The layers were extracted, and the organic layer was washed with brine, was dried over $MgSO_4$, was filtered and evaporated to give a solid that was purified via silica gel chromatography to give 1.02 g of 11A (3.27 mmol, 91% yield). Anal Calc'd for $C_{14}H_{11}F_3N_2O_3$, 312.07. found [M+H] 313.0.

11B (Example 11. (S)-2-(1-(4-((2-methyl-6-(trifluoromethyl)pyridin-3-yl)methoxy)phenyl)pyrrolidin-2-yl)acetic acid, HCl): Example 11 (white powder, 60 mg, 0.135 mmol, 82% yield) was prepared by following the steps described in Example 2 and replacing 2B with 11A. LC-MS Anal. Calc'd for $C_{20}H_{21}F_3N_2O_3$: 394.15. found [M+H] 395.0. Analytical HPLC: RT=6.30 min, HI: 97.1%.

Example 12

(S)-2-(1-(4-(benzyloxy)phenyl)pyrrolidin-2-yl)acetic acid, HCl

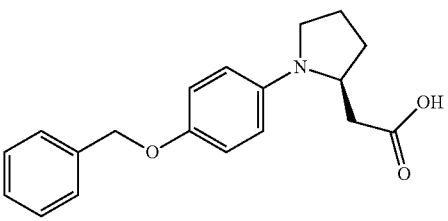

12A. (S)-ethyl 2-(1-(4-(benzyloxy)phenyl)pyrrolidin-2-yl)acetate: 12A (0.58 g) was synthesized from 4-benzyloxyaniline according to the steps described in Example 2. Anal. Calc'd for $C_{21}H_{25}NO_3$, 339.18 found [M+H] 340.1. $^1$H NMR (400 MHz, chloroform-d) δ ppm 7.23-7.47 (5 H, m), 6.83-7.02 (2 H, m), 6.49-6.68 (2 H, m), 5.00 (2 H, s), 4.03-4.28 (3 H, m), 3.27-3.48 (1 H, m), 3.12 (1 H, m), 2.75 (1 H, dd, J=14.94, 2.64 Hz), 2.19 (1 H, dd, J=14.94, 10.55 Hz), 1.93-2.12 (3 H, m), 1.28 (3 H, t, J=7.25 Hz).

12B (Example 12. (S)-2-(1-(4-(benzyloxy)phenyl)pyrrolidin-2-yl)acetic acid, HCl): A solution of 12A (14 mg, 0.041 mmol) in dioxane (0.2 mL) and MeOH (0.200 mL) was stirred with 2N NaOH (0.5 mL, 1.000 mmol) at rt for 1 h. The pH of the reaction mixture was adjusted to pH~2-3 with 1N HCl, and the mixture was extracted with EtOAc. The organic layer was washed with brine, dried over $MgSO_4$, filtered and evaporated. The residue was purified via RP prep HPLC. The product containing fraction was evaporated and redissolved in 3N HCl—$CH_3CN$, and evaporated to dryness to give Example 12 (white powder, 7.43 mg, 0.021 mmol, 51.2% yield). LC-MS Anal. Calc'd for $C_{19}H_{21}NO_3$: 311.15. found [M+H] 312.3. $^1$H NMR (400 MHz, acetonitrile-$d_3$) δ ppm 7.76 (2 H, d, J=9.34 Hz), 7.22-7.53 (5 H, m), 6.97-7.20 (2 H, m), 5.12 (2 H, s), 3.93-4.17 (1 H, m), 3.75-3.93 (1 H, m), 3.36-3.57 (1 H, m), 2.99 (1 H, br. s.), 2.79 (1 H, dd, J=16.49, 4.40 Hz), 2.40-2.61 (1 H, m, J=12.92, 6.60, 6.46, 6.46 Hz), 2.16-2.30 (2 H, m), 2.01-2.15 (1 H, m). Analytical HPLC: RT=5.99 min, HI: 98.9%.

Example 13

(S)-2-(1-(4-(2-methylbenzyloxy)phenyl)pyrrolidin-2-yl)acetic acid, HCl

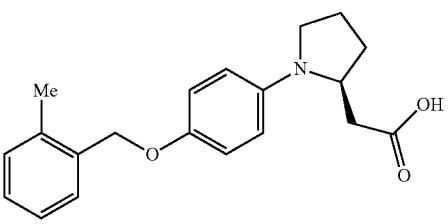

13A. (S)-ethyl 2-(1-(4-hydroxyphenyl)pyrrolidin-2-yl)acetate: To a solution of 12A (1 g, 2.95 mmol) in ethanol (30 mL) and MeOH (20 mL) was added 10% Pd/C (0.063 g, 0.059 mmol). The reaction vessel was evacuated and flushed with N$_2$ gas, and then evacuated and flushed with H$_2$ gas 3 times. The resulting mixture was stirred vigorously overnight. The reaction mixture was filtered through CELITE® and concentrated to give 13A (dark brown oil, 0.49 g, 1.965 mmol, 66.7% yield). LC-MS Anal. Calc'd for C$_{14}$H$_{19}$NO$_3$: 249.14 found [M+H] 250.0.

13B. (S)-2-(1-(4-(2-methylbenzyl)phenyl)pyrrolidin-2-yl)acetonitrile: A solution of 13A (20 mg, 0.080 mmol), and 1-(chloromethyl)-2-methylbenzene (13.54 mg, 0.096 mmol) in DMF (0.5 mL) was stirred with K$_2$CO$_3$ (33.3 mg, 0.241 mmol) at 80° C. for 1 h. The reaction mixture was allowed to cool to rt and was diluted with EtOAc. The organic layer was washed with water and sat'd NaCl solution (aq), dried with Na$_2$SO$_4$ and filtered, and concentrated in vacuo. Purification via silica gel chromatography gave 13B (light brown oil, 102 mg, 0.351 mmol, 103% yield). LC-MS Anal. Calc'd for C$_{22}$H$_{27}$NO$_3$: 353.2. found [M+H] 354.1.

13C (Example 13. (S)-2-(1-(4-(2-methylbenzyloxy)phenyl)pyrrolidin-2-yl)acetic acid, HCl): A solution of 13B (22 mg, 0.062 mmol) in MeOH (0.2 mL) and dioxane (0.2 mL) was stirred with 2N NaOH (0.25 mL) at rt for 1 h. Solvents were removed in vacuo and 1N HCl was added to pH~2-3. The resulting mixture was extracted with EtOAc, washed with brine, dried and concentrated. The residue was purified via RP prep HPLC. The product containing fraction was evaporated and redissolved in 3N HCl—CH$_3$CN, and evaporated to dryness to give Example 13 (white powder, 14 mg, 0.036 mmol, 45.3% yield). LC-MS Anal. Calc'd for C$_{20}$H$_{23}$NO$_3$: 325.17. found [M+H] 326.0. $^1$H NMR (400 MHz, acetonitrile-d$_3$) δ ppm 7.78 (2 H, d, J=8.79 Hz), 7.40 (1 H, d, J=7.47 Hz), 7.19-7.33 (3 H, m), 7.14 (2 H, d, J=8.79 Hz), 5.11 (2 H, s), 4.05 (1 H, br. s.), 3.86 (1 H, br. s.), 3.45 (1 H, br. s.), 3.00 (1 H, br. s.), 2.82 (2 H, br. s.), 2.51 (1 H, ddd, J=13.07, 6.48, 6.37 Hz), 2.35 (3 H, s), 2.19-2.30 (2 H, m), 2.00-2.13 (1 H, m). Analytical HPLC: RT=6.50 min, HI: 94%.

Example 14

(S)-2-(1-(4-(2,4-dichlorobenzyloxy)phenyl)pyrrolidin-2-yl)acetic acid

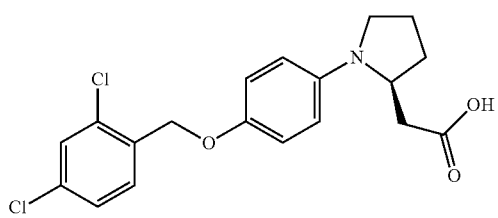

Example 14 (white powder, 12 mg, 0.029 mmol, 42.0% yield) was synthesized following the procedures described in Example 13. LC-MS Anal. Calc'd for C$_{19}$H$_{19}$Cl$_2$NO$_3$: 379.07. found [M+H] 379.9. $^1$H NMR (400 MHz, acetonitrile-d$_3$) δ ppm 7.76 (2 H, d, J=8.79 Hz), 7.49-7.61 (2 H, m), 7.38 (1 H, dd, J=8.35, 2.20 Hz), 6.91-7.20 (2 H, m), 5.16 (2 H, s), 4.04 (1 H, br. s.), 3.75-3.93 (1 H, m), 3.36-3.55 (1 H, m), 2.97 (1 H, br. s.), 2.78 (1 H, dd, J=16.48, 4.17 Hz), 2.50 (1 H, ddd, J=13.07, 6.48, 6.37 Hz), 2.17-2.31 (2 H, m), 1.99-2.11 (1 H, m). Analytical HPLC: RT=7.30 min, HI: 96.7%.

Example 15

(S)-2-(1-(4-(3,4-dichlorobenzyloxy)phenyl)pyrrolidin-2-yl)acetic acid, HCl

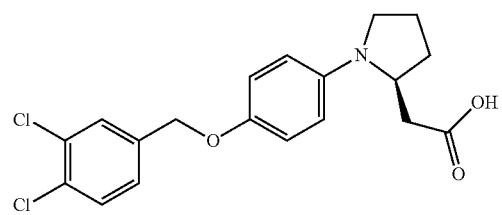

Example 15 (white powder, 14 mg, 0.033 mmol, 41.5% yield) was synthesized following the procedures described in Example 13. LC-MS Anal. Calc'd for C$_{19}$H$_{19}$Cl$_2$NO$_3$: 379.07. found [M+H] 379.9. $^1$H NMR (400 MHz, acetonitrile-d$_3$) δ ppm 7.60 (1 H, d, J=1.76 Hz), 7.52 (1 H, d, J=7.91 Hz), 7.35 (1 H, dd, J=8.35, 1.76 Hz), 6.80-6.95 (2 H, m), 6.43-6.64 (2 H, m), 4.98 (2 H, s), 3.86-4.04 (1 H, m), 3.27-3.45 (1 H, m), 3.00-3.12 (1 H, m), 2.63 (1 H, dd, J=15.38, 3.08 Hz), 2.08-2.31 (4 H, m), 1.75-1.88 (1 H, m). Analytical HPLC: RT=7.31 min, HI: 99%.

Example 16

(S)-2-(1-(4-((2-(isopropylthio)pyridin-3-yl)methoxy)phenyl)pyrrolidin-2-yl)acetic acid

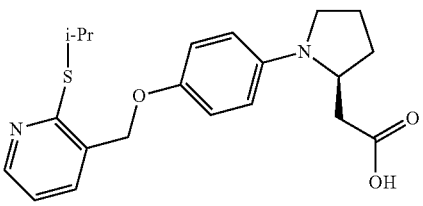

16A. 2-(isopropylthio)nicotinaldehyde: To a suspension of NaH (0.800 g, 19.99 mmol) in THF (66.6 mL) at 0° C. was added 2-propanethiol (1.671 mL, 17.99 mmol). The mixture was stirred for 30 min, and a solution of 2-chloronicotinaldehyde (2.83 g, 19.99 mmol) in 10 mL of THF was added. After 1 h, the reaction was quenched via addition of 5 mL of sat'd aq NH$_4$Cl. After 2 min, the reaction mixture was diluted with 200 mL each of ethyl acetate and water. The layers were extracted and the organic layer was washed with brine, dried over MgSO$_4$, filtered and evaporated to give 3.1 g of an orange oil. The residue purified via silica gel chromatography to give 2.0 g of 16A (light yellow oil, 2 g, 10.48 mmol, 52.4% yield). $^1$H NMR (400 MHz, chloroform-d) δ ppm 10.23 (1 H, s), 8.56 (1 H, dd, J=4.67, 1.90 Hz), 7.97 (1 H, dd, J=7.71, 1.89 Hz), 7.11 (1 H, dd, J=7.58, 4.80 Hz), 4.06-4.31 (1 H, m), 1.41 (6H, d, J=6.82 Hz). $^{13}$C NMR (400 MHz, chloroform-d) δ ppm 190.0, 162.7, 153.2, 139.0, 128.5, 118.9, 34.6, 23.0.

16B. (2-(isopropylthio)pyridin-3-yl)methanol: To a solution of 16A (2 g, 11.03 mmol) in THF (55.2 mL) was added NaBH$_4$ (0.417 g, 11.03 mmol). After 1.5 h, 2 mL of methanol was added. After 1 h at rt, excess borohydride was quenched with acetone, then acetic acid. The mixture was evaporated to dryness, and the mixture was diluted with 100 mL each of ethyl acetate and water. The layers were extracted and the organic layer was washed with brine, dried over MgSO$_4$, filtered and evaporated to give a clear oil. The residue was purified via silica gel chromatography to give 1.1 g of 16B (clear oil, 1.1 g, 5.70 mmol, 51.7% yield). $^1$H NMR (400 MHz, chloroform-d) δ ppm 8.38 (1 H, dd, J=4.93, 1.64 Hz), 7.62 (1 H, dd, J=7.58, 1.77 Hz), 7.02 (1 H, dd, J=7.58, 4.80 Hz), 4.66 (2 H, d, J=5.81 Hz), 4.10-4.31 (1 H, m), 1.42 (6 H, d, J=6.82 Hz). $^{13}$C NMR (400 MHz, chloroform-d) δ ppm 157.0, 148.1, 134.2, 134.0, 119.3, 61.7, 35.1, 23.3.

16C. (S)-ethyl 2-(1-(4-((2-(isopropylthio)pyridin-3-yl)methoxy)phenyl)pyrrolidin-2-yl)acetate: To a solution of 16B (5.88 mg, 0.032 mmol) and (S)-ethyl 2-(1-(4-hydroxyphenyl)pyrrolidin-2-yl)acetate (13A, 0.008 g, 0.032 mmol) in THF (0.3 mL) was added triphenylphosphine (8.42 mg, 0.032 mmol) and DEAD (5.08 μL, 0.032 mmol). After 20 h, triphenylphosphine (8.42 mg, 0.032 mmol) and DEAD (5.08 μL, 0.032 mmol) were added to the reaction mixture. The reaction mixture was stirred overnight, and the crude reaction mixture was purified directly via silica gel chromatography to give 3 mg of 16C as a light yellow oil. $^1$H NMR (400 MHz, acetonitrile-d$_3$) δ ppm 8.41 (1 H, dd, J=4.80, 1.77 Hz), 7.72 (1 H, dd, J=7.58, 1.77 Hz), 7.11 (1 H, dd, J=7.58, 4.80 Hz), 6.79-7.01 (2 H, m), 6.48-6.71 (2 H, m), 4.95 (2 H, s), 4.01-4.25 (5 H, m), 3.28-3.51 (1 H, m), 3.12 (1 H, t, J=8.08 Hz), 2.66 (1 H, dd, J=14.91, 3.03 Hz), 2.25 (1 H, dd, J=14.91, 9.85 Hz), 1.91-2.12 (4 H, m), 1.86 (1 H, dd, J=5.31, 1.52 Hz), 1.41 (6 H, d, J=6.82 Hz), 1.25 (3 H, t, J=7.07 Hz).

16D (Example 16. (S)-2-(1-(4-((2-(isopropylthio)pyridin-3-yl)methoxy)phenyl)pyrrolidin-2-yl)acetic acid): To a solution of 16C (0.003 g, 7.24 μmol) in THF (0.145 mL) was added NaOH (0.145 mL, 0.145 mmol). After 16 h, the crude reaction mixture was diluted with 1 mL of acetonitrile and the mixture was purified via prep RP-HPLC to give 2.3 mg of Example 16 as a clear oil. Anal. Calc'd for C$_{21}$H$_{26}$N$_2$O$_3$S: 386.17. found [M+H]=387.0. $^1$H NMR (400 MHz, acetonitrile-d$_3$) δ ppm 8.39 (1 H, d, J=4.83 Hz), 7.70 (1 H, d, J=7.47 Hz), 7.05-7.29 (4 H, m), 6.84-7.02 (1 H, m), 4.98 (2 H, s), 4.10 (2 H, dt, J=13.62, 6.81 Hz), 3.90-4.06 (2 H, m), 3.71 (2 H, d, J=4.39 Hz), 2.70 (1 H, d, J=3.95 Hz), 2.65 (1 H, d, J=3.95 Hz), 2.51-2.60 (1 H, m), 2.50 (1 H, d, J=5.71 Hz), 2.21-2.43 (3 H, m), 2.00-2.21 (2 H, m), 1.35 (6 H, d, J=7.03 Hz).

Example 17

(S)-2-(1-(4-(3-(trifluoromethyl)benzyloxy)phenyl)pyrrolidin-2-yl)acetic acid, HCl

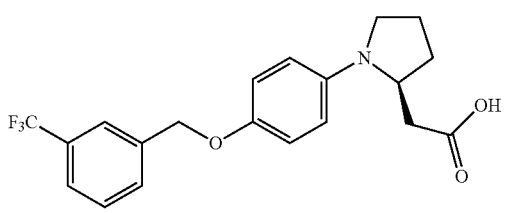

Example 17 (white powder, 12 mg, 0.028 mmol, 34.9% yield) was synthesized following the steps described in Example 13. LC-MS Anal. Calc'd for C$_{20}$H$_{20}$F$_3$NO$_3$: 379.14. found [M+H] 380.0. $^1$H NMR (500 MHz, acetonitrile-d$_3$) δ ppm 7.75-7.84 (3 H, m), 7.72 (1 H, d, J=7.70 Hz), 7.64-7.69 (1 H, m), 7.60 (1 H, t, J=7.70 Hz), 7.14 (2 H, d, J=8.80 Hz), 5.19 (2 H, s), 4.04 (1 H, br. s.), 3.86 (1 H, br. s.), 3.39-3.52 (1 H, m), 3.00 (1 H, br. s.), 2.81 (1 H, br. s.), 2.44-2.59 (1 H, m), 2.17-2.32 (2 H, m), 2.01-2.13 (1 H, m). Analytical HPLC: RT=6.95 min, HI: 94%.

Example 18

(S)-2-(1-(4-(3-chloro-5-(trifluoromethyl)pyridin-2-yloxy)phenyl)pyrrolidin-2-yl)acetic acid, TFA

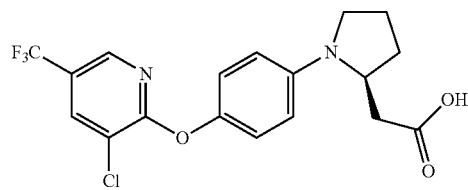

18A. (S)-ethyl 2-(1-(4-(3-chloro-5-(trifluoromethyl)pyridin-2-yloxy)phenyl)pyrrolidin-2-yl)acetate: A solution of (S)-ethyl 2-(1-(4-hydroxyphenyl)pyrrolidin-2-yl)acetate (13A, 25 mg, 0.100 mmol) and 2,3-dichloro-5-(trifluoromethyl)pyridine (28.2 mg, 0.130 mmol) in DMF (0.5 mL) was stirred with Cs$_2$CO$_3$ (65.3 mg, 0.201 mmol) at 80° C. for 2 h. The reaction mixture was allowed to cool to room temperature and was diluted with EtOAc. The organic layer was washed with water and sat'd NaCl solution (aq), dried with Na$_2$SO$_4$ and filtered, and concentrated in vacuo. Purification via silica gel chromatography gave 18A (light brown oil, 17 mg, 0.040 mmol, 39.5% yield). LC-MS Anal. Calc'd for C$_{20}$H$_{20}$ClF$_3$N$_2$O$_3$: 428.11. found [M+H] 428.8.

18B (Example 18. (S)-2-(1-(4-(3-chloro-5-(trifluoromethyl)pyridin-2-yloxy)phenyl)pyrrolidin-2-yl)acetic acid, TFA): A solution of 18A (17 mg, 0.040 mmol) in MeOH (0.2 mL) and dioxane (0.2 mL) was stirred with 2N NaOH (0.25 mL) at rt for 1 h. Solvents were removed in vacuo and 1N HCl was added to pH~2-3. The resulting mixture was extracted with EtOAc, washed with brine, dried and concentrated. The residue was purified via RP prep HPLC to give Example 18 (white solid, 10 mg, 0.019 mmol, 48.8% yield). LC-MS Anal. Calc'd for C$_{18}$H$_{16}$ClF$_3$N$_2$O$_3$: 400.08. found [M+H] 401.2. $^1$H NMR (400 MHz, acetonitrile-d$_3$) δ ppm 8.30 (1 H, s), 8.16 (1 H, s), 6.94-7.19 (2 H, m), 6.73 (2 H, d, J=9.34 Hz), 4.01-4.24 (1 H, m), 3.40-3.61 (1 H, m), 3.05-3.33 (1 H, m), 2.71 (1 H, dd, J=15.67, 3.02 Hz), 2.31 (1 H, dd, J=15.67, 10.17 Hz), 2.02-2.18 (3 H, m), 1.89 (1 H, d). Analytical HPLC: RT=9.6 min, HI: 92.8%.

Example 19

(S)-2-(1-(4-(2,4-dichlorophenoxy)phenyl)pyrrolidin-2-yl)acetic acid, TFA

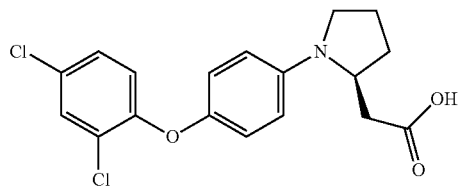

Example 19 (white powder, 13 mg, 0.027 mmol, 66.7% yield) was synthesized following the steps described in Example 18. LC-MS Anal. Calc'd for $C_{18}H_{17}Cl_2NO_3$: 365.06. found [M+H] 365.9. $^1$H NMR (400 MHz, acetonitrile-$d_3$) δ ppm 7.47-7.62 (1 H, m), 7.20-7.35 (1 H, m), 6.97 (2 H, d, J=8.79 Hz), 6.77-6.92 (3 H, m), 3.95-4.16 (1 H, m), 3.56 (1 H, d, J=4.39 Hz), 3.26 (1 H, d, J=7.91 Hz), 2.70 (1 H, d, J=15.38 Hz), 2.37 (1 H, d, J=15.38 Hz), 2.15-2.29 (1 H, m), 2.03-2.14 (2 H, m), 1.89 (1 H, m). Analytical HPLC: RT=8.64 min, HI: 99.4%.

Example 20

(S)-2-(1-(4-benzylphenyl)pyrrolidin-2-yl)acetic acid, HCl

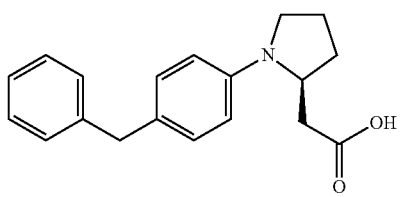

20A. (S)-(1-(4-bromophenyl)pyrrolidin-2-yl)methanol: A solution of 1-bromo-4-iodobenzene (3.64 g, 12.85 mmol), (S)-pyrrolidin-2-ylmethanol (1 g, 9.89 mmol), copper (I) iodide (0.047 g, 0.247 mmol) and NaOH (0.791 g, 19.77 mmol) in isopropanol (9.89 mL) was stirred under argon at 90° C. for 15 h. The reaction mixture was diluted with EtOAc and water. The layers were extracted, and the organic layer was dried and concentrated to give a residue that was purified via silica gel chromatography to give 2 g of 20A (brown oil, 7.81 mmol, 79% yield). Anal Calc'd for $C_{11}H_{14}BrNO$ 255.03. found [M+H]=255.9, 257.9.

20B. (S)-2-(1-(4-bromophenyl)pyrrolidin-2-yl)acetonitrile: To a solution of 20A (2 g, 7.81 mmol) in methylene chloride (16 mL) at 0° C. was added TEA (2.177 mL, 15.62 mmol), and methanesulfonyl chloride (0.913 mL, 11.71 mmol). After 1 h, the reaction mixture was diluted with water and methylene chloride. The layers were extracted, and the organic layer was dried and concentrated to give 2.6 g of 1-(4-bromophenyl)-2-(methylsulfonylmethyl)pyrrolidine (8.17 mmol, 105% yield) as a brown oil that was used directly in the next step. To a solution of 1-(4-bromophenyl)-2-(methylsulfonylmethyl)pyrrolidine (2.6 g, 8.17 mmol) in DMSO (16 mL) was added NaCN (1.531 g, 31.2 mmol) and the resultant mixture was stirred at 50° C. overnight. The reaction mixture was diluted with EtOAc and water. The layers were extracted, and the organic layer was washed successively with water and brine. The organic layer was dried and concentrated, and the resulting material was purified via silica gel chromatography to give 20B (brown oil, 2.1 g, 7.92 mmol, 101% yield). Anal Calc'd for $C_{12}H_{13}BrN_2$ 264.03. found [M+H]=264.9, 266.9.

20C. (S)-2-(1-(4-benzylphenyl)pyrrolidin-2-yl)acetonitrile: To a solution of 20B (60 mg, 0.226 mmol) in DMF (0.2 mL) was added Pd(Ph$_3$P)$_4$ (13.07 mg, 0.011 mmol) and benzylzinc(II) bromide (0.905 mL, 0.453 mmol). The reaction vessel was purged with argon and stirred at 100° C. for 1.5 h. The reaction mixture was allowed to cool to room temperature, and was diluted with EtOAc. The resulting mixture was washed with water and sat'd NaCl solution (aq), dried with Na$_2$SO$_4$ and filtered, and concentrated in vacuo. The residue was purified via silica gel chromatography to give 20C (colorless oil, 47 mg, 0.170 mmol, 75% yield). LC-MS Anal. Calc'd for $C_{19}H_{20}N_2$: 276.16, [M+H] 277.5.

20D (Example 20. (S)-2-(1-(4-benzylphenyl)pyrrolidin-2-yl)acetic acid, HCl): A solution of 20C (102 mg, 0.369 mmol) in 6N HCl and AcOH (0.15 mL, 2.62 mmol) was heated at 100° C. at for 1 h. The pH of the reaction mixture was adjusted to pH ~2-3 with 1N NaHCO$_3$, and the mixture was extracted with EtOAc. The organic layer was washed with brine, dried over MgSO$_4$, filtered and evaporated. The residue was purified via RP prep HPLC. The product containing fraction was evaporated and redissolved in 3N HCl—CH$_3$CN, and evaporated to dryness to give Example 20 (white solid, 35 mg, 0.102 mmol, 27.7% yield). LC-MS Anal. Calc'd for $C_{19}H_{21}NO_2$: 295.16. found [M+H] 295.9. $^1$H NMR (400 MHz, acetonitrile-$d_3$) δ ppm 7.04-7.40 (9 H, m), 3.98-4.17 (1 H, m, J=7.03, 6.81, 6.70, 6.70 Hz), 3.93 (2 H, s), 3.66 (1 H, d, J=3.95 Hz), 3.17-3.37 (1 H, m), 2.61-2.81 (2 H, m), 2.33 (1 H, dd, J=12.52, 6.81 Hz), 2.06-2.21 (2 H, m), 1.96-2.03 (1 H, m). Analytical HPLC: RT=7.37 min, HI: 97%.

Examples 21 to 27 were synthesized following the procedures described in Example 20.

Example 21

(S)-2-(1-(4-(2-methylbenzyl)phenyl)pyrrolidin-2-yl)acetic acid, TFA

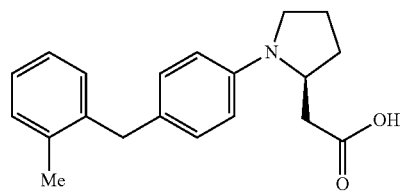

Example 21 (white powder, 40 mg, 0.091 mmol, 25.9% yield). LC-MS Anal. Calc'd for $C_{20}H_{23}NO_2$: 309.17. found [M+H] 309.5. $^1$H NMR (400 MHz, acetonitrile-$d_3$) δ ppm 6.93-7.22 (6 H, m), 6.80 (2 H, d, J=8.79 Hz), 4.05 (1 H, td, J=8.46, 3.74 Hz), 3.91 (2 H, s), 3.46-3.62 (1 H, m), 3.15-3.30 (1 H, m), 2.67 (1 H, dd, J=16.04, 3.30 Hz), 2.35 (1 H, dd, J=16.26, 9.23 Hz), 2.23 (3 H, s), 2.14-2.19 (1 H, m), 2.02-2.12 (2 H, m), 1.82-1.90 (1 H, m). Analytical HPLC: RT=7.37 min, HI: 97%.

Example 22

(S)-2-(1-(4-(2-fluorobenzyl)phenyl)pyrrolidin-2-yl)acetic acid, HCl

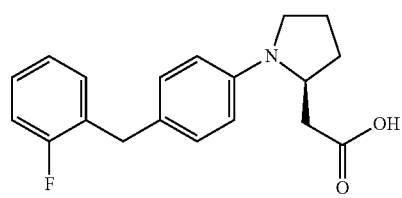

Example 22 (white powder, 16 mg, 0.044 mmol, 22.12% yield). LC-MS Anal. Calc'd for $C_{19}H_{20}FNO_2$: 313.15. found [M+H] 313.9. $^1$H NMR (400 MHz, acetonitrile-$d_3$) δ ppm 7.58 (2 H, br. s.), 7.35 (2 H, d, J=8.35 Hz), 7.22-7.30 (2 H, m), 7.05-7.19 (2 H, m), 3.93-4.16 (3 H, m), 3.74-3.88 (1 H, m), 3.26-3.50 (1 H, m), 2.86-3.00 (1 H, m), 2.67-2.82 (1 H, m), 2.37-2.54 (1 H, m), 2.21 (2 H, quin, J=7.47 Hz), 1.98-2.13 (1 H, m). Analytical HPLC: RT=7.72 min, HI: 93.2%.

Example 23

(S)-2-(1-(4-(2-chlorobenzyl)phenyl)pyrrolidin-2-yl)acetic acid, TFA

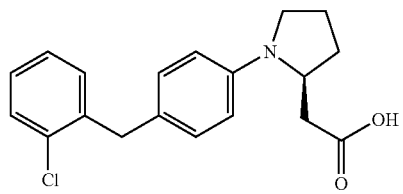

Example 23 (white powder, 25 mg, 0.053 mmol, 23.20% yield). LC-MS Anal. Calc'd for $C_{19}H_{20}ClNO_2$: 329.12. found [M+H] 329.9. $^1$H NMR (400 MHz, acetonitrile-$d_3$) δ ppm 8.76 (1 H, br. s.), 7.40 (1 H, d, J=8.25 Hz), 7.25-7.31 (2 H, m), 7.19-7.25 (3 H, m), 6.96-7.08 (2 H, m), 4.02-4.13 (3 H, m), 3.68 (1 H, ddd, J=10.72, 6.87, 4.40 Hz), 3.29-3.42 (1 H, m), 2.69 (1 H, dd, J=16.49, 3.85 Hz), 2.46 (1 H, dd, J=16.49, 8.79 Hz), 2.23-2.36 (1 H, m), 2.04-2.18 (2 H, m), 1.91-1.96 (1 H, m). Analytical HPLC: RT=8.42 min, HI: 94.1%.

Example 24

(S)-2-(1-(4-(naphthalen-2-ylmethyl)phenyl)pyrrolidin-2-yl)acetic acid, TFA

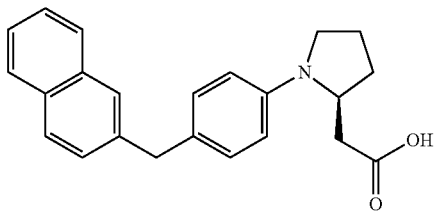

Example 24 (white powder, 10 mg, 0.022 mmol, 23.68% yield). LC-MS Anal. Calc'd for $C_{23}H_{23}NO_2$: 345.17 found [M+H] 345.9. $^1$H NMR (400 MHz, acetonitrile-$d_3$) δ ppm 7.76-7.90 (3 H, m), 7.70 (1 H, s), 7.41-7.51 (2 H, m), 7.35 (1 H, dd, J=8.79, 1.76 Hz), 7.26 (2 H, d, J=8.35 Hz), 6.95 (2 H, d, J=8.79 Hz), 3.97-4.21 (4 H, m), 3.52-3.70 (1 H, m), 3.20-3.40 (1 H, m), 2.68 (1 H, dd, J=16.26, 3.52 Hz), 2.41 (1 H, dd, J=16.26, 8.79 Hz), 2.19-2.30 (1 H, m), 2.02-2.15 (2 H, m), 1.80-1.93 (1 H, m). Analytical HPLC: RT=9.62 min, HI: 94.2%.

Example 25

(S)-2-(1-(4-(3,5-difluorobenzyl)phenyl)pyrrolidin-2-yl)acetic acid, TFA

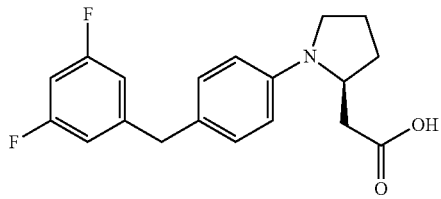

Example 25 (white powder, 35 mg, 0.075 mmol, 58.9% yield). LC-MS Anal. Calc'd for $C_{19}H_{19}F_2NO_2$: 331.14. found [M+H] 331.9. $^1$H NMR (400 MHz, acetonitrile-$d_3$) δ ppm 7.18 (2 H, d, J=8.35 Hz), 6.64-6.92 (5 H, m), 4.07 (1 H, tt, J=8.35, 3.95 Hz), 3.90 (2 H, s), 3.57 (1 H, ddd, J=10.33, 5.49, 5.27 Hz), 3.19-3.32 (1 H, m), 2.68 (1 H, dd, J=16.04, 3.30 Hz), 2.38 (1 H, dd, J=16.26, 9.23 Hz), 2.14-2.30 (1 H, m), 2.02-2.12 (2 H, m), 1.80-1.93 (1 H, m). Analytical HPLC: RT=8.28 min, HI: 94.4%.

Example 26

(S)-2-(1-(4-(2-methoxybenzyl)phenyl)pyrrolidin-2-yl)acetic acid, TFA

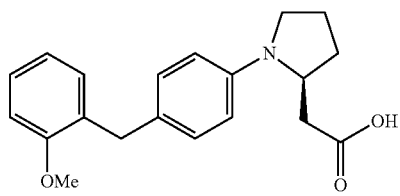

Example 26 (white powder, 16 mg, 0.036 mmol, 55.2% yield). LC-MS Anal. Calc'd for $C_{20}H_{23}NO_3$: 325.17. found [M+H] 326.0. $^1$H NMR (400 MHz, acetonitrile-$d_3$) δ ppm 7.01-7.27 (4 H, m), 6.70-6.98 (4 H, m), 4.05 (1 H, dd, J=8.57, 4.17 Hz), 3.86 (2 H, s), 3.79 (3 H, s), 3.49-3.62 (1 H, m), 3.14-3.33 (1 H, m), 2.67 (1 H, dd, J=16.26, 3.52 Hz), 2.37 (1

H, dd, J=16.26, 9.23 Hz), 2.15-2.27 (1 H, m), 2.02-2.11 (2 H, m), 1.89 (1 H, dd). Analytical HPLC: RT=7.04 min, HI: 96.7%.

Example 27

(S)-2-(1-(4-(2,6-difluorobenzyl)phenyl)pyrrolidin-2-yl)acetic acid, TFA

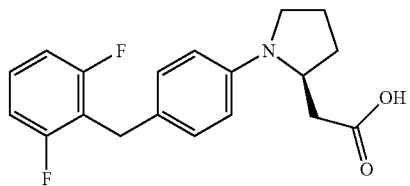

27A. (S)-2-(1-(4-(2,6-difluorobenzyl)phenyl)pyrrolidin-2-yl)acetonitrile: 27A (colorless oil, 28 mg, 0.090 mmol, 39.6% yield) was synthesized according to the steps described in Example 20. LC-MS Anal. Calc'd for $C_{19}H_{18}F_2N_2$: 312.14. found [M+H] 312.9.

27B (Example 27. (S)-2-(1-(4-(2,6-difluorobenzyl)phenyl)pyrrolidin-2-yl)acetic acid, TFA): To a solution of 27A (28 mg, 0.090 mmol) in EtOH (1 mL) was added KOH (0.060 mL, 0.090 mmol), and the resulting mixture was heated at 100° C. overnight. Solvents were removed in vacuo and 1N HCl was added to adjust the pH to ~2-3. The residue was diluted with EtOAc, and the organic layer was washed with brine, dried over $MgSO_4$, filtered and evaporated. The residue was purified via RP prep HPLC. The product containing fraction was evaporated to dryness to give Example 27 (white powder, 25 mg, 0.053 mmol, 59.5% yield). LC-MS Anal. Calc'd for $C_{19}H_{19}F_2NO_2$: 331.14. found [M+H] 332.0. $^1$H NMR (400 MHz, acetonitrile-$d_3$) δ ppm 7.22-7.33 (1 H, m), 7.16 (2 H, d, J=8.25 Hz), 6.97 (2 H, t, J=7.97 Hz), 6.78 (2 H, d, J=8.79 Hz), 4.01-4.13 (1 H, m), 3.94 (2 H, s), 3.53 (1 H, ddd, J=10.17, 5.50, 5.22 Hz), 3.17-3.30 (1 H, m), 2.66 (1 H, dd, J=16.49, 3.30 Hz), 2.33 (1 H, dd, J=15.94, 9.34 Hz), 2.12-2.22 (1 H, m), 2.00-2.10 (2 H, m), 1.98 (1 H, td). Analytical HPLC: RT=8.01 min, HI: 93.6%.

Example 28

(S)-2-(1-(4-(4-chlorobenzyl)phenyl)pyrrolidin-2-yl)acetic acid, TFA

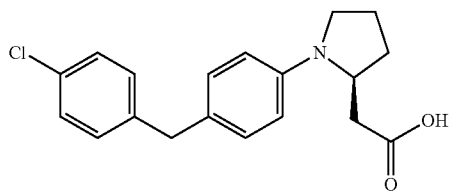

Example 28 (white powder, 20 mg, 0.045 mmol, 56.0% yield) was synthesized according to the steps described in Example 27. LC-MS Anal. Calc'd for $C_{19}H_{20}ClNO_2$: 329.12. found [M+H] 329.9. $^1$H NMR (400 MHz, acetonitrile-$d_3$) δ ppm 7.26-7.39 (2 H, m), 7.19 (2 H, d, J=8.79 Hz), 7.14 (2 H, d, J=8.79 Hz), 6.80 (2 H, d, J=8.79 Hz), 3.98-4.22 (1 H, m), 3.87 (2 H, s), 3.44-3.66 (1 H, m), 3.16-3.34 (1 H, m), 2.67 (1 H, dd, J=15.94, 3.30 Hz), 2.34 (1 H, dd, J=15.94, 9.34 Hz), 2.17 (1 H, ddd, J=12.37, 7.97, 7.70 Hz), 2.04-2.11 (2 H, m), 1.97-2.01 (1 H, m). Analytical HPLC: RT=8.40 min, HI: 97.9%.

Example 29

(S)-2-(1-(4-(2-(trifluoromethyl)benzyl)phenyl)pyrrolidin-2-yl)acetic acid, TFA

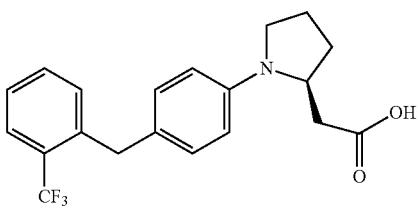

Example 29 (white powder, 12 mg, 0.025 mmol, 18.85% yield) was synthesized according to the steps described in Example 27. LC-MS Anal. Calc'd for $C_{20}H_{20}F_3NO_2$: 363.14. found [M+H] 363.9. $^1$H NMR (400 MHz, acetonitrile-$d_3$) δ ppm 7.69 (1 H, d, J=7.91 Hz), 7.52 (1 H, t, J=7.69 Hz), 7.37 (1 H, t, J=7.69 Hz), 7.23-7.31 (1 H, m), 7.02 (2 H, d, J=8.79 Hz), 6.63 (2 H, d, J=8.79 Hz), 3.91-4.21 (3 H, m), 3.33-3.51 (1 H, m), 3.02-3.22 (1 H, m), 2.66 (1 H, dd, J=15.60, 2.86 Hz), 2.26 (1 H, dd, J=15.82, 10.11 Hz), 1.98-2.14 (3 H, m), 1.88 (1 H, dddd, J=7.85, 5.22, 4.94, 2.64 Hz). Analytical HPLC: RT=9.90 min, HI: 96%.

Example 30

2-((2S)-1-(4-(1-phenylethyl)phenyl)pyrrolidin-2-yl)acetic acid, TFA

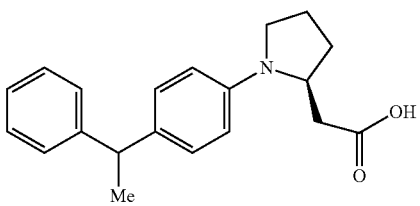

30A. (S)-2-(1-(4-(1-phenylvinyl)phenyl)pyrrolidin-2-yl)acetonitrile: To a solution of 1-phenylvinylboronic acid (120 mg, 0.811 mmol) and 20B (165 mg, 0.624 mmol) in toluene (0.9 mL) was added $Na_2CO_3$ (0.936 mL, 1.872 mmol), and $Pd(Ph_3P)_4$ (36.0 mg, 0.031 mmol). The reaction vessel was purged with argon, and the mixture was heated to 90° C. for 16 h. The reaction mixture was cooled to rt and was diluted with EtOAc. The organic layer was washed with water, then brine. The combined organic layers were dried and evaporated. Purification via silica gel chromatography gave 30A (clear oil, 115 mg, 0.399 mmol, 63.9% yield). LC-MS Anal. Calc'd for $C_{20}H_{20}N_2$: 288.16. found [M+H] 289.0.

30B. 2-((2S)-1-(4-(1-phenylethyl)phenyl)pyrrolidin-2-yl)acetonitrile: To a solution of 30A (115 mg, 0.399 mmol) in ethanol (4 mL) was added Pd/C (12.73 mg, 0.012 mmol). The reaction vessel was evacuated and flushed with $H_2$ gas 3×, and the mixture was stirred under $H_2$ for 3 h. The reaction mixture was filtered through CELITE® and the filtrate was concentrated. The residue was purified via silica gel chromatography to give 30B (light brown oil, 28 mg, 0.096 mmol, 24.18% yield). LC-MS Anal. Calc'd for $C_{20}H_{22}N_2$: 290.18. found [M+H] 291.0.

30C (Example 30. 2-((2S)-1-(4-(1-phenylethyl)phenyl) pyrrolidin-2-yl)acetic acid, TFA): To a solution of 30B (28 mg, 0.096 mmol) in ethanol (0.3 mL) was added 1.5N KOH (0.321 mL, 0.482 mmol). The reaction mixture was stirred at 80° C. for 16 h, then the mixture was heated to 100° C. for 1 h. Volatile solvents were evaporated, and the residue was diluted with TFA (to pH~2-3) and EtOAc. The layers were extracted, and the organic layer was washed with brine, dried and concentrated. The residue was purified via RP-prep. HPLC to give Example 30 (brown powder, 8 mg, 0.017 mmol, 17.58% yield). LC-MS Anal. Calc'd for $C_{20}H_{23}NO_2$: 309.17. found [M+H] 310.0. $^1$H NMR (500 MHz, acetonitrile-$d_3$) δ ppm 7.12-7.29 (4 H, m), 6.99-7.12 (3 H, m), 6.64 (2 H, d, J=8.8 Hz), 3.79-4.08 (2 H, m), 3.27-3.50 (1 H, m), 3.10 (1 H, d, J=8.2 Hz), 2.57 (1 H, dd, J=15.9, 3.3 Hz), 2.13-2.30 (1 H, m), 2.00-2.11 (1 H, m), 1.88-1.99 (2 H, m), 1.79 (1 H, ddd, J=9.1, 6.3, 3.3 Hz), 1.48 (3 H, d). Analytical HPLC: RT=8.20 min, HI: 91.2%.

Example 31

(S)-2-(1-(4-(2,4-dimethylphenoxy)phenyl)pyrrolidin-2-yl)acetic acid, TFA

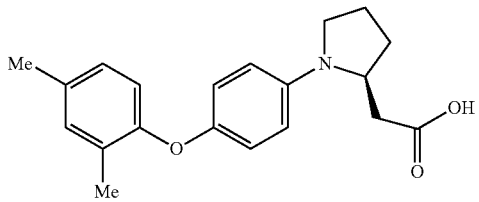

31A. (S)-2-(1-(4-(2,4-dimethylphenoxy)phenyl)pyrrolidin-2-yl)acetonitrile: A flask was charged with 20B (0.05 g, 0.247 mmol), copper (II) acetate (0.045 g, 0.247 mmol), 2,4-dimethylphenylboronic acid (0.111 g, 0.742 mmol), and powdered 4 Å molecular sieves to make a thick slurry in dichloromethane (1.236 mL). To this mixture was added triethylamine (0.172 mL, 1.236 mmol) and the mixture became a thick pale blue slurry that was stirred vigorously at ambient temperature in air overnight. The reaction mixture was filtered, and the solids were washed several times with ethyl acetate. The filtrate was concentrated to 0.177 g brown oil. The residue was purified via silica gel chromatography to give 31A (0.0385 g, 0.107 mmol, 43.2% yield). LC-MS Anal. Calc'd for $C_{20}H_{22}N_2O$: 306.17. found [M+H] 307.0.

31B (Example 31. (S)-2-(1-(4-(2,4-dimethylphenoxy)phenyl)pyrrolidin-2-yl)acetic acid, TFA): To a solution of 31A (0.0375 g, 0.122 mmol) in ethanol (3.06 mL) was added 4N KOH (0.459 mL, 1.836 mmol). The mixture was heated to 150° C. in the microwave. Volatile solvents were evaporated, and the residue was diluted with TFA (to pH~2-3) and EtOAc. The layers were extracted, and the organic layer was washed with brine, dried and concentrated. The residue was purified via RP-prep. HPLC to give Example 31 (beige solid, 18 mg, 0.040 mmol, 32.8% yield). LC-MS Anal. Calc'd for $C_{20}H_{23}NO_3$: 325.17. found [M+H] 326.0. $^1$H NMR (400 MHz, acetonitrile-$d_3$) δ ppm 7.07 (1 H, s), 6.95 (1 H, d, J=7.7 Hz), 6.85 (4 H, s), 6.68 (1 H, d, J=8.2 Hz), 4.03 (1 H, br. s.), 3.46-3.69 (1 H, m), 3.23 (1 H, d, J=8.2 Hz), 2.67 (1 H, dd, J=15.9, 3.3 Hz), 2.37 (1 H, dd, J=16.2, 9.1 Hz), 2.26 (3 H, s), 2.16-2.23 (1 H, m), 2.15 (3 H, s), 2.01-2.12 (2 H, m), 1.79-1.90 (1 H, m). Analytical HPLC: RT=7.78 min, HI: 98.3%.

Example 32

2-((2S,4R)-4-hydroxy-1-(4-(2-methylbenzyl)phenyl) pyrrolidin-2-yl)acetic acid, TFA

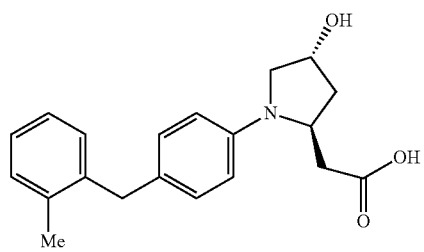

32A. (2S,4R)-tert-butyl 4-(benzyloxy)-2-(hydroxymethyl)pyrrolidine-1-carboxylate: To a solution of (2S,4R)-4-(benzyloxy)-1-(tert-butoxycarbonyl)pyrrolidine-2-carboxylic acid (1.00 g, 3.11 mmol) in tetrahydrofuran (10 mL) at −10° C. (ice water-brine) was added N-methyl morpholine (0.359 mL, 3.27 mmol). To this solution was added slowly isobutyl chloroformate (0.429 mL, 3.27 mmol). After 30 min, the mixture was filtered and added to a solution of $NaBH_4$ (0.247 g, 6.53 mmol) in water (1.5 mL) at 0° C. After 30 min, the reaction was quenched via addition of $NH_4Cl$ (sat.). The resulting mixture was extracted with EtOAc, and the combined organic layer was washed with brine, dried and concentrated to give 1.12 g colorless oil. Purification via silica gel chromatography gave 32A (colorless oil, 1.04 g, 3.38 mmol, 109% yield). LC-MS Anal. Calc'd for $C_{17}H_{25}NO_4$: 307.18. found [M-Boc+H] 208.0. $^1$H NMR (400 MHz, chloroform-d) δ ppm 7.27-7.39 (5 H, m), 4.91 (1 H, d, J=7.1 Hz), 4.47-4.55 (2 H, m), 4.05 (1 H, br. s.), 3.60-3.76 (2 H, m), 3.51-3.59 (1 H, m), 3.41 (1 H, dd, J=12.1, 4.4 Hz), 2.19 (1 H, dd, J=13.7, 7.1 Hz), 1.57-1.69 (1 H, m), 1.52 (1 H, d, J=7.7 Hz), 1.47 (9 H, s).

32B. ((2S,4R)-4-(benzyloxy)pyrrolidin-2-yl)methanol: A solution of 32A (1 g, 3.25 mmol) in HCl/dioxane (8.13 mL, 32.5 mmol) was stirred at rt for 30 min. The resulting mixture was evaporated to give 32B (0.7 g, 2.87 mmol, 88% yield). LC-MS Anal. Calc'd for $C_{12}H_{17}NO_2$: 207.13. found [M+H] 208.0.

32C. ((2S,4R)-4-(benzyloxy)-1-(4-bromophenyl)pyrrolidin-2-yl)methanol: A solution of 1-bromo-4-iodobenzene (579 mg, 2.048 mmol), 32B (384 mg, 1.576 mmol), copper(I) iodide (12 mg, 0.063 mmol) and NaOH (189 mg, 4.73 mmol) in isopropanol (3 mL) was stirred at 90° C. for 12 h under argon. The resulting mixture was diluted with EtOAc, washed with water, brine, dried and concentrated. Purification via silica gel chromatography gave 32C (colorless oil, 0.38 g, 66.6%). LC-MS Anal. Calc'd for $C_{18}H_{20}BrNO_2$: 361.07. found [M+H] 361.8. $^1$H NMR (400 MHz, chloroform-d) δ ppm 7.11-7.44 (7H, m), 6.52 (2 H, d, J=9.3 Hz), 4.47-4.63 (2 H, m), 4.34-4.44 (1 H, m), 4.00 (1 H, d, J=3.8 Hz), 3.75-3.86 (1 H, m), 3.70 (1 H, dd, J=9.6, 5.8 Hz), 3.57 (1 H, s), 3.25 (1 H, dd, J=9.6, 5.2 Hz), 2.32 (1 H, d, J=3.8 Hz), 2.20 (1 H, s), 1.44 (1 H, dd).

32D. 2-((2R,4R)-4-(benzyloxy)-1-(4-bromophenyl)pyrrolidin-2-yl)acetonitrile: To a solution of 32C (0.38 g, 1.049 mmol) in dichloromethane (5.24 mL) at 0° C. was added TEA (0.292 mL, 2.098 mmol), then methanesulfonyl chloride (0.123 mL, 1.573 mmol). The reaction mixture was stirred for 1 h, and the mixture was diluted with water and dichloromethane. The layers were extracted and the organic layer was dried (MgSO$_4$) and concentrated to give ((2S,4R)-4-(benzyloxy)-1-(4-bromophenyl)pyrrolidin-2-yl)methyl methanesulfonate (white solid, 0.53 g, 1.204 mmol, 115% yield). This white solid was then dissolved in DMSO (5 mL), and NaCN (0.206 g, 4.20 mmol) was added. The mixture was heated to 50° C. for 4 h. The reaction mixture was diluted with EtOAc, and the organic layer was washed with water, brine, dried and concentrated. Purification via silica gel chromatography gave 32D (colorless oil, 235 mg, 0.633 mmol, 60.3% yield). LC-MS Anal. Calc'd for $C_{19}H_{19}BrN_2O$: 370.07. found [M+H] 372.9.

32E. 2-((2R,4R)-4-(benzyloxy)-1-(4-(2-methylbenzyl)phenyl)pyrrolidin-2-yl)acetonitrile: To a solution of 32D (235 mg, 0.633 mmol) in DMF (2.5 mL) was added Pd(Ph$_3$P)$_4$ (36.6 mg, 0.032 mmol) and a 0.5M solution of (2-methylbenzyl)zinc(II) chloride (2.53 mL, 1.266 mmol) in THF. The reaction vessel was purged with argon and was heated at 100° C. for 1 h. The mixture was cooled to rt and was diluted with EtOAc. The organic layer was washed with NH$_4$Cl (sat.) water, brine, dried and concentrated. Purification via silica gel chromatography gave 32E (light brown oil, 230 mg, 0.580 mmol, 92% yield). LC-MS Anal. Calc'd for $C_{27}H_{28}N_2O$: 396.22. found [M+H] 397.0.

32F. 2-((2S,4R)-4-(benzyloxy)-1-(4-(2-methylbenzyl)phenyl)pyrrolidin-2-yl)acetic acid, TFA: To a solution of 32E (100 mg, 0.25 mmol) in ethanol (1.5 mL) was added 1.5N KOH (0.8 mL, 1.2 mmol). The reaction mixture was heated to 100° C. overnight. Volatile solvents were evaporated, and the residue was diluted with TFA (to pH~2-3) and EtOAc. The layers were extracted, and the organic layer was washed with brine, dried and concentrated. The residue was purified via RP-prep. HPLC to give 32F (brown foam, 88 mg, 0.166 mmol, 66% yield). LC-MS Anal. Calc'd for $C_{27}H_{29}NO_3$: 415.52. found [M+H] 416.4.

32G (Example 32. 2-((2S,4R)-4-hydroxy-1-(4-(2-methylbenzyl)phenyl)pyrrolidin-2-yl)acetic acid, TFA): To a solution of 32F (85 mg, 0.161 mmol) in methanol (4 mL) was added Pd/C (24 mg, 0.023 mmol). The reaction vessel was evacuated and flushed with H$_2$ gas 2 times, and the mixture was stirred under H$_2$ overnight. The reaction mixture was filtered and evaporated, and the residue was purified via RP-prep. HPLC to give Example 32 (colorless foam, 30 mg, 0.066 mmol, 40.8% yield). LC-MS Anal. Calc'd for $C_{20}H_{23}NO_3$: 325.17. found [M+H] 326.0. $^1$H NMR (400 MHz, acetonitrile-d$_3$) δ ppm 6.99-7.20 (6 H, m), 6.88 (2 H, d, J=8.8 Hz), 4.37-4.59 (1 H, m), 4.04-4.23 (1 H, m), 3.89 (2 H, s), 3.75-3.84 (1 H, m), 3.16 (1 H, dd, J=11.0, 2.2 Hz), 2.72 (1 H, dd, J=16.5, 3.3 Hz), 2.38 (1 H, dd, J=16.2, 9.1 Hz), 2.10-2.19 (1 H, m), 1.97-2.08 (1 H, m). Analytical HPLC: RT=7.30 min, HI: 96.6%.

Example 33

(R)-2-(4,4-difluoro-1-(4-(2-methylbenzyl)phenyl)pyrrolidin-2-yl)acetic acid, TFA

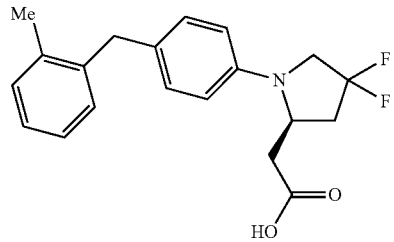

33A. (S)-tert-butyl 4,4-difluoro-2-(hydroxymethyl)pyrrolidine-1-carboxylate: A solution of (S)-1-(tert-butoxycarbonyl)-4,4-difluoropyrrolidine-2-carboxylic acid (0.400 g, 1.59 mmol) in dry THF (6.5 mL) was cooled to −10° C. 4-Methylmorpholine (0.18 mL, 1.7 mmol) and isobutyl chloroformate (0.22 mL, 1.7 mmol) were added sequentially and the mixture was stirred at −10° C. for 45 min. The resulting mixture was filtered and the filtrate was added dropwise to a solution of NaBH$_4$ (0.120 g, 3.18 mmol) in water (0.85 mL) that had been cooled to 0° C. The mixture was stirred for 2 h and slowly warmed to rt. The reaction was quenched with sat. NH$_4$Cl (aq) and the product was extracted with EtOAc. The combined organic layers were washed with brine, dried (MgSO$_4$), and concentrated. The crude product was purified by silica gel chromatography to provide 33A (colorless oil, 0.381 g, 1.61 mmol, 100% yield). LC-MS Anal. Calc'd for $C_{10}H_{17}F_2NO_3$ 237.24. found [M+H] 238.0. $^1$H NMR (400 MHz, chloroform-d) δ ppm 4.17 (1 H, br. s.), 3.75-3.90 (1 H, m), 3.72 (2 H, t, J=5.31 Hz), 3.64 (1 H, q, J=12.97 Hz), 2.41-2.56 (1 H, m), 2.16 (1 H, br. s.), 1.48 (9 H, s).

33B. (S)-(4,4-difluoropyrrolidin-2-yl)methanol, HCl: A solution of 33A (0.378 g, 1.59 mmol) in 4 N HCl/dioxane (5.97 mL, 23.9 mmol) was stirred for 1 h at rt. The reaction mixture was concentrated to give 33B (white solid, 0.247 g, 1.42 mmol, 89% yield). LC-MS Anal. Calc'd for $C_5H_9F_2NO$ 137.13. found [M+H] 137.9. $^1$H NMR (400 MHz, methanol-d$_4$) δ ppm 4.05 (1 H, dddd, J=9.92, 7.64, 6.19, 3.54 Hz), 3.89 (1 H, dd, J=12.13, 3.54 Hz), 3.68-3.82 (3 H, m), 2.67 (1 H, dddd, J=15.06, 7.64, 7.45 Hz), 2.37-2.54 (1 H, m).

33C. (S)-(1-(4-bromophenyl)-4,4-difluoropyrrolidin-2-yl)methanol: A mixture of 1-bromo-4-iodobenzene (0.502 g, 1.78 mmol), 33B (0.237 g, 1.37 mmol), CuI (6.5 mg, 0.034 mmol), and NaOH (0.164 g, 4.10 mmol) in a vial that was sealed and purged with argon. Isopropanol (4.0 mL) was added and the reaction mixture was heated to 90° C. for 15 h. The reaction mixture was cooled to rt and diluted with water, and the product was extracted with CH$_2$Cl$_2$. The combined organic layers were washed with brine, dried (MgSO$_4$), and concentrated. The crude product was purified by silica gel chromatography to give 33C (yellow oil, 0.259 g, 0.885 mmol, 64.8% yield). LC-MS Anal. Calc'd for $C_{11}H_{12}BrF_2NO$ 292.12. found [M+H] 293.9. $^1$H NMR (400 MHz, chloroform-d) δ ppm 7.34 (2 H, d, J=9.09 Hz), 6.52 (2 H, d, J=8.84 Hz), 4.06-4.18 (1 H, m), 3.72-3.84 (3 H, m), 3.62 (1 H, td, J=13.52, 11.12 Hz), 2.51-2.64 (2 H, m), 1.58 (1 H, t, J=4.55 Hz).

33D. (R)-2-(1-(4-bromophenyl)-4,4-difluoropyrrolidin-2-yl)acetonitrile: To a cooled (0° C.) solution of 33C (0.259 g, 0.885 mmol) in CH$_2$Cl$_2$ (4 mL) was added methanesulfonyl chloride (0.10 mL, 1.3 mmol) and triethylamine (0.25 mL, 1.8 mmol). The reaction mixture was stirred at 0° C. for 1 h. The resulting solution was diluted with EtOAc and washed with 1 N HCl, sat. NaHCO$_3$ (aq), and brine. The organic layer was dried (MgSO$_4$) and concentrated. The crude product was dissolved in DMSO (4 mL) and NaCN (0.174 g, 3.54 mmol) was added. The reaction mixture was stirred at 50° C. for 15 h. The resulting mixture was cooled to rt and quenched with water. The product was extracted with EtOAc and the combined organic layers were washed with brine, dried (MgSO$_4$), and concentrated. The crude product was purified by silica gel chromatography to provide 33D (white solid, 0.267 g, 0.885 mmol, 99% yield over 2 steps). LC-MS Anal. Calc'd for C$_{12}$H$_{11}$BrF$_2$N$_2$ 301.13. found [M+H] 302.8. $^1$H NMR (400 MHz, chloroform-d) δ ppm 7.39 (2 H, d, J=8.84 Hz), 6.44 (2 H, d, J=8.84 Hz), 4.29-4.38 (1 H, m), 3.80 (1 H, ddd, J=14.72, 10.80, 7.83 Hz), 3.66 (1 H, dt, J=15.98, 11.59 Hz), 2.69-2.86 (2 H, m), 2.53-2.65 (2 H, m).

33E. (R)-2-(4,4-difluoro-1-(4-(2-methylbenzyl)phenyl)pyrrolidin-2-yl)acetonitrile: 33D (0.100 g, 0.332 mmol) and Pd(Ph$_3$P)$_4$ (0.019 g, 0.017 mmol) were combined in a 10 mL round bottom flask, which was purged with argon. Anhydrous DMF (1 mL) was added followed by a 0.5 M solution of (2-methylbenzyl)zinc(II) chloride in THF (1.3 mL, 0.66 mmol) and the mixture was heated to 100° C. for 1 h. The reaction mixture was cooled to rt and quenched with sat. NaHCO$_3$ (aq). The mixture was diluted with EtOAc and water and the layers were separated. The organic layer was washed with brine, dried (MgSO$_4$), and concentrated. The crude product was purified by silica gel chromatography to provide 33E (colorless oil, 0.0800 g, 0.245 mmol, 73.8% yield). LC-MS Anal. Calc'd for C$_{20}$H$_{20}$F$_2$N$_2$ 326.38. found [M+H] 326.9. $^1$H NMR (400 MHz, chloroform-d) δ ppm 7.12-7.20 (3 H, m), 7.06-7.11 (1 H, m), 7.06 (2 H, d, J=8.84 Hz), 6.49 (2 H, d, J=8.59 Hz), 4.27-4.41 (1 H, m), 3.91 (2 H, s), 3.80 (1 H, ddd, J=14.72, 10.93, 8.46 Hz), 3.67 (1 H, ddd, J=16.04, 11.75, 11.62 Hz), 2.66-2.87 (2 H, m), 2.48-2.64 (2 H, m), 2.25 (3 H, s).

33F (Example 33. (R)-2-(4,4-difluoro-1-(4-(2-methylbenzyl)phenyl)pyrrolidin-2-yl)acetic acid, TFA): 33E (0.033 g, 0.10 mmol) was dissolved in ethanol (0.4 mL) in a microwave tube and a 1.5 N aq. solution of KOH (0.34 mL, 0.51 mmol) was added. The reaction was heated to 150° C. in the microwave for 15 min. The reaction mixture was concentrated, redissolved in EtOAc and acidified to pH 2 with 1 N HCl. The layers were separated and the product was extracted from the aqueous layer with EtOAc. The combined organic layers were dried (MgSO$_4$) and concentrated. The crude product was purified by RP-prep. HPLC to afford Example 33 (brown solid, 0.004 g, 8.8 μmol, 9% yield). LC-MS Anal. Calc'd for C$_{20}$H$_{21}$F$_2$NO$_2$ 345.38. found [M+H] 345.9. $^1$H NMR (400 MHz, acetonitrile-d$_3$) δ ppm 7.08-7.17 (4 H, m), 7.03 (2 H, d, J=8.84 Hz), 6.56 (2 H, d, J=8.59 Hz), 4.30-4.42 (1 H, m), 3.88 (2 H, s), 3.56-3.79 (2 H, m), 2.62-2.85 (2 H, m), 2.38 (2 H, dd, J=15.54, 11.24 Hz), 2.24 (3 H, s). Analytical HPLC: RT=9.8 min, HI: 98.2%.

Example 34

(S)-2-(1-(4-(4-(2-fluorobenzyloxy)benzyl)phenyl)pyrrolidin-2-yl)acetic acid, TFA

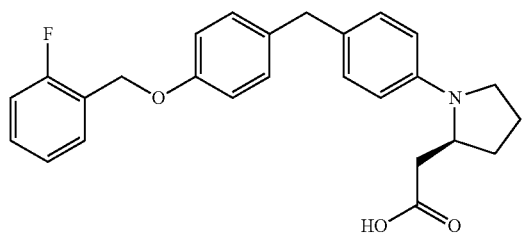

34A. (S)-2-(1-(4-(4-(2-fluorobenzyloxy)benzyl)phenyl)pyrrolidin-2-yl)acetonitrile: 34A (0.019 g, 0.048 mmol, 52% yield) was prepared from (S)-2-(1-(4-(4-hydroxybenzyl)phenyl)pyrrolidin-2-yl)acetonitrile and 1-(bromomethyl)-2-fluorobenzene according to the procedure of 13B. LC-MS Anal. Calc'd for C$_{26}$H$_{25}$FN$_2$O 400.49. found [M+H] 401.1. $^1$H NMR (400 MHz, chloroform-d) δ ppm 7.51 (1 H, td, J=7.43, 1.65 Hz), 7.27-7.34 (1 H, m), 7.16 (1 H, t, J=7.57 Hz), 7.03-7.13 (5 H, m), 6.91 (2 H, d, J=8.53 Hz), 6.52 (2 H, d, J=8.80 Hz), 5.11 (2 H, s), 4.00-4.10 (1 H, m), 3.84 (2 H, s), 3.45-3.57 (1 H, m), 3.13-3.26 (1 H, m), 2.70 (1 H, dd, J=16.92, 3.16 Hz), 2.42 (1 H, dd, J=16.78, 8.53 Hz), 2.12-2.25 (2 H, m), 2.00-2.12 (2 H, m).

34B (Example 34. (S)-2-(1-(4-(4-(2-fluorobenzyloxy)benzyl)phenyl)pyrrolidin-2-yl)acetic acid, TFA): Example 34 (colorless oil, 0.015 g, 0.027 mmol, 56% yield) was prepared from 34A according to the procedure of 36C. LC-MS Anal. Calc'd for C$_{26}$H$_{26}$FNO$_3$ 419.49. found [M+H] 420.1. $^1$H NMR (400 MHz, acetonitrile-d$_3$) δ ppm 7.50 (1 H, t, J=7.45 Hz), 7.33-7.42 (1 H, m), 7.09-7.26 (6 H, m), 6.98 (2 H, d, J=8.08 Hz), 6.92 (2 H, d, J=8.59 Hz), 5.11 (2 H, s), 4.01-4.13 (1 H, m), 3.86 (2 H, s), 3.58-3.73 (1 H, m), 3.32 (1 H, q, J=8.51 Hz), 2.69 (1 H, dd, J=16.42, 3.54 Hz), 2.44 (1 H, dd, J=16.17, 8.84 Hz), 2.20-2.35 (1 H, m), 2.04-2.18 (2 H, m), 1.86-1.93 (1 H, m). Analytical HPLC: RT=10.6 min, HI: 95.1%.

Example 35

2-((2S,4S)-4-methyl-1-(4-(2-methylbenzyl)phenyl)pyrrolidin-2-yl)acetic acid, TFA

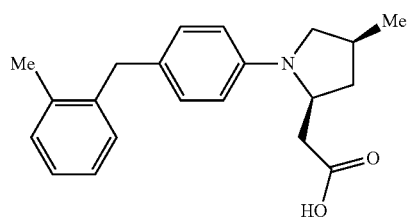

35A. (2S,4S)-tert-butyl 2-(hydroxymethyl)-4-methylpyrrolidine-1-carboxylate: 35A (colorless oil, 0.168 g, 0.780 mmol, 73.5% yield) was prepared from (2S,4S)-1-(tert-butoxycarbonyl)-4-methylpyrrolidine-2-carboxylic acid following the procedure of 33A. LC-MS Anal. Calc'd for $C_{11}H_{21}NO_3$ 215.29. found [M+H] 216.0. $^1$H NMR (400 MHz, chloroform-d) δ ppm 5.16-5.34 (1 H, m), 3.81-4.03 (1 H, m), 3.52-3.80 (3 H, m), 2.63-2.88 (1 H, m), 1.99-2.23 (2 H, m), 1.47 (9H, s), 0.96-1.17 (4 H, m).

35B. ((2S,4S)-1-(4-bromophenyl)-4-methylpyrrolidin-2-yl)methanol: ((2S,4S)-4-methylpyrrolidin-2-yl)methanol, HCl was prepared from 35A following the procedure of 33B. The crude amine salt was used directly in the next step following the procedure described in 33C to afford 35B (yellow oil, 0.160 g, 0.591 mmol, 76% yield). LC-MS Anal. Calc'd for $C_{12}H_{16}BrNO$ 270.17. found [M+H] 271.8. $^1$H NMR (400 MHz, chloroform-d) δ ppm 7.21 (2 H, d, J=8.84 Hz), 6.46 (3 H, d, J=7.33 Hz), 3.77-3.85 (1 H, m), 3.71-3.77 (1 H, m), 3.51-3.61 (1 H, m), 3.38 (1 H, t, J=8.59 Hz), 2.98 (1 H, t, J=8.84 Hz), 2.09-2.30 (2 H, m), 1.59-1.75 (1 H, m), 1.06 (3 H, d, J=6.32 Hz).

35C. 2-((2S,4S)-1-(4-bromophenyl)-4-methylpyrrolidin-2-yl)acetonitrile: 35C (colorless oil, 0.113 g, 0.406 mmol, 68.7% yield) was prepared from 35B following the procedure of 33D. LC-MS Anal. Calc'd for $C_{13}H_{15}BrN_2$ 279.18. found [M+H] 280.9. $^1$H NMR (400 MHz, chloroform-d) δ ppm 7.32 (2 H, d, J=9.09 Hz), 6.44 (2 H, d, J=8.84 Hz), 4.06 (1 H, qd, J=7.41, 3.03 Hz), 3.46 (1 H, t, J=8.59 Hz), 3.14 (1 H, t, J=9.22 Hz), 2.74 (1 H, dd, J=16.67, 2.78 Hz), 2.52-2.62 (2 H, m), 2.25-2.39 (1 H, m), 1.69 (1 H, ddd, J=12.69, 10.29, 7.58 Hz), 1.17 (3 H, d).

35D. 2-((2S,4S)-4-methyl-1-(4-(2-methylbenzyl)phenyl)pyrrolidin-2-yl)acetonitrile: 35D (colorless oil, 0.060 g, 0.20 mmol, 49% yield) was prepared from 35C following the procedure of 33E. LC-MS Anal. Calc'd for $C_{21}H_{24}N_2$ 304.43. found [M+H] 305.4. $^1$H NMR (400 MHz, chloroform-d) δ ppm 7.11-7.18 (3 H, m), 7.06-7.12 (1 H, m), 7.01 (2 H, d, J=8.59 Hz), 6.53 (2 H, d, J=8.59 Hz), 4.06 (1 H, qd, J=7.49, 3.03 Hz), 3.89 (2 H, s), 3.44-3.53 (1 H, m), 3.17 (1 H, t, J=9.22 Hz), 2.79 (1 H, dd, J=16.93, 3.03 Hz), 2.48-2.61 (2 H, m), 2.26-2.38 (1 H, m), 2.26 (3 H, s), 1.68 (1 H, ddd, J=12.69, 10.04, 7.58 Hz), 1.17 (3 H, d, J=6.57 Hz).

35E (Example 35. 2-((2S,4S)-4-methyl-1-(4-(2-methylbenzyl)phenyl)pyrrolidin-2-yl)acetic acid, TFA): Example 35 (white solid, 0.016 g, 0.036 mmol, 69% yield) was prepared from 35D following the procedure of 33F. LC-MS Anal. Calc'd for $C_{21}H_{25}NO_2$ 323.43. found [M+H] 324.0. $^1$H NMR (400 MHz, acetonitrile-$d_3$) δ ppm 7.09-7.21 (6H, m), 6.98 (2 H, d, J=8.34 Hz), 4.03-4.16 (1 H, m), 3.94 (2 H, s), 3.53 (1 H, t, J=9.22 Hz), 3.26-3.36 (1 H, m), 2.80 (1 H, dd, J=16.17, 3.79 Hz), 2.48-2.58 (2 H, m), 2.43 (1 H, dd, J=16.17, 8.84 Hz), 2.23 (3 H, s), 1.48-1.64 (1 H, m), 1.13 (3 H, d, J=6.32 Hz). Analytical HPLC: RT=10.1 min, HI: 99.0%.

Example 36

2-((2R,4S)-4-fluoro-1-(4-(o-tolyloxy)phenyl)pyrrolidin-2-yl)acetic acid, TFA

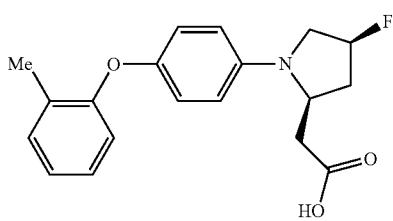

36A. ((2S,4S)-4-fluoro-1-(4-(o-tolyloxy)phenyl)pyrrolidin-2-yl)methanol: 36A (yellow oil, 0.110 g, 0.365 mmol, 56.8% yield) was prepared from ((2S,4S)-4-fluoropyrrolidin-2-yl)methanol, HCl and 1-(4-iodophenoxy)-2-methylbenzene following the procedure of 33C. LC-MS Anal. Calc'd for $C_{18}H_{20}FNO_2$ 301.36. found [M+H] 302.0. $^1$H NMR (400 MHz, chloroform-d) δ ppm 7.22 (1 H, d, J=7.33 Hz), 7.09 (1 H, t, J=7.71 Hz), 6.97 (1 H, t, J=7.33 Hz), 6.90 (2 H, d, J=9.09 Hz), 6.76 (1 H, d, J=8.08 Hz), 6.68 (2 H, d, J=8.84 Hz), 5.37 (1 H, dt, J=53.75, 4.20 Hz), 3.94-4.03 (1 H, m), 3.87 (1 H, dd, J=10.61, 4.80 Hz), 3.68-3.83 (2 H, m), 3.43 (1 H, ddd, J=35.94, 11.68, 3.92 Hz), 2.31-2.46 (1 H, m), 2.30 (3 H, s), 2.13-2.28 (1 H, m).

36B. 2-((2R,4S)-4-fluoro-1-(4-(o-tolyloxy)phenyl)pyrrolidin-2-yl)acetonitrile: 36B (colorless oil, 0.0744 g, 0.240 mmol, 65.7% yield) was prepared from 36A following the procedure of 33D. LC-MS Anal. Calc'd for $C_{19}H_{19}FN_2O$ 310.37. found [M+H] 311.0. $^1$H NMR (400 MHz, chloroform-d) δ ppm 7.23 (1 H, d, J=7.33 Hz), 7.11 (1 H, t, J=7.71 Hz), 6.99 (1 H, t, J=7.33 Hz), 6.93 (2 H, d, J=8.84 Hz), 6.76 (1 H, d, J=8.08 Hz), 6.55 (2 H, d, J=8.84 Hz), 5.43 (1 H, dt, J=53.05, 4.04 Hz), 4.17-4.27 (1 H, m), 3.66-3.82 (1 H, m, J=24.76, 11.87 Hz), 3.52 (1 H, ddd, J=36.38, 11.87, 4.04 Hz), 2.89 (1 H, dd, J=16.67, 3.28 Hz), 2.60 (1 H, dd, J=16.80, 10.48 Hz), 2.47-2.56 (1 H, m), 2.31-2.47 (1 H, m), 2.29 (3 H, s).

36C (Example 36. 2-((2R,4S)-4-fluoro-1-(4-(o-tolyloxy)phenyl)pyrrolidin-2-yl)acetic acid, TFA): To a solution of 36B (0.0586 g, 0.189 mmol) in ethanol (2 mL) was added a 6 N solution of KOH (0.60 mL, 3.6 mmol). The reaction vessel was sealed and heated to 150° C. in the microwave for 30 min. The reaction mixture was concentrated and the residue was redissolved in EtOAc. The solution was acidified to pH 2 with 1 N HCl and the product was extracted with EtOAc. The combined organic layers were dried ($MgSO_4$), and concentrated. The crude product was purified by RP-prep. HPLC to provide Example 36 (purple solid, 0.021 g, 0.045 mmol, 24% yield). LC-MS Anal. Calc'd for $C_{19}H_{20}FNO_3$ 329.37. found [M+H] 329.9. $^1$H NMR (400 MHz, acetonitrile-$d_3$) δ ppm 7.25 (1 H, d, J=6.82 Hz), 7.12 (1 H, t, J=8.08 Hz), 6.99 (1 H, t, J=7.45 Hz), 6.87 (2 H, d, J=9.09 Hz), 6.72 (1 H, d, J=8.08 Hz), 6.64 (2 H, d, J=8.59 Hz), 5.40 (1 H, dt, J=53.75, 4.07 Hz), 4.13-4.25 (1 H, m), 3.58-3.74 (1 H, m), 3.38-3.54 (1 H, m), 2.83 (1 H, dd, J=15.79, 2.91 Hz), 2.46 (1 H, dd, J=15.92, 10.61 Hz), 2.28-2.45 (1 H, m), 2.26 (3 H, s), 2.18-2.28 (1 H, m). Analytical HPLC: RT=9.0 min, HI: 99.3%.

Example 37

2-((2R,4R)-4-fluoro-1-(4-(2-methylbenzyl)phenyl)pyrrolidin-2-yl)acetic acid, TFA

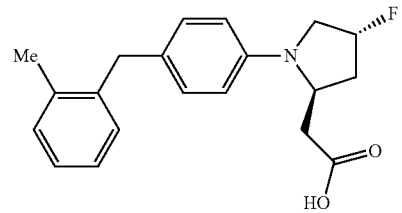

37A. (2S,4R)-tert-butyl 4-fluoro-2-(hydroxymethyl)pyrrolidine-1-carboxylate: 37A (colorless oil, 0.4785 g, 2.182 mmol, 96% yield) was prepared from (2S,4R)-1-(tert-butoxycarbonyl)-4-fluoropyrrolidine-2-carboxylic acid following the procedure of 33A. LC-MS Anal. Calc'd for $C_{10}H_{18}FNO_3$ 219.25. found [M+H] 220.0. $^1$H NMR (400 MHz, chloroform-d) δ ppm 5.10 (1 H, d, J=53.05 Hz), 4.68-4.86 (1 H, m), 4.05-4.24 (1 H, m), 3.69-3.96 (2 H, m), 3.54-3.61 (1 H, m), 3.31-3.53 (1 H, m), 2.26-2.43 (1 H, m), 1.55-1.84 (1 H, m), 1.48 (9 H, s).

37B. (2R,4R)-tert-butyl 2-(cyanomethyl)-4-fluoropyrrolidine-1-carboxylate: 37B (colorless oil, 0.250 g, 1.10 mmol, 99% yield) was prepared from 37A following the procedure of 33D. LC-MS Anal. Calc'd for $C_{11}H_{17}FN_2O_2$ 228.26. found [M+H] 229.0. $^1$H NMR (400 MHz, chloroform-d) δ ppm 5.19 (1 H, dt, J=52.30, 3.28 Hz), 4.10-4.26 (1 H, m), 3.78-3.93 (1 H, m, J=22.23, 13.64 Hz), 3.39-3.66 (1 H, m, J=37.64, 12.13 Hz), 3.26 (1 H, dd, J=16.80, 5.43 Hz), 2.68 (1 H, dd, J=16.93, 2.27 Hz), 2.44-2.61 (1 H, m), 2.07 (1 H, dddd, J=40.17, 13.64, 9.35, 3.79 Hz), 1.48 (9 H, s).

37C. 2-((2R,4R)-4-fluoro-1-(4-(2-methylbenzyl)phenyl)pyrrolidin-2-yl)acetonitrile: 37C was prepared from 37B according to the procedure of 33B. The crude amine salt was used directly in the next step. 1-(4-iodobenzyl)-2-methylbenzene (0.120 g, 0.389 mmol), 2-((2R,4R)-4-fluoropyrrolidin-2-yl)acetonitrile (0.077 g, 0.467 mmol), Xantphos (4.51 mg, 7.79 μmol), $Pd_2(dba)_3$ (3.57 mg, 3.89 μmol), and $Cs_2CO_3$ (0.317 g, 0.974 mmol) were combined and the vessel was purged with argon. Dioxane (0.79 mL) and t-BuOH (0.39 mL) was added and the reaction mixture was heated to 100° C. for 15 h. The reaction was cooled to rt, filtered, and concentrated. The product was purified via silica gel chromatography to provide 37C (yellow oil, 0.0051 g, 0.017 mmol, 4.3% yield). LC-MS Anal. Calc'd for $C_{20}H_{21}FN_2$ 308.39. found [M+H] 309.0. $^1$H NMR (400 MHz, chloroform-d) δ ppm 7.12-7.18 (3 H, m), 7.07-7.12 (1 H, m), 7.03 (2 H, d, J=8.59 Hz), 6.54 (2 H, d, J=8.59 Hz), 5.37 (1 H, dt, J=53.37, 4.01 Hz), 4.29 (1 H, tt, J=7.23, 4.77 Hz), 3.91 (2 H, s), 3.79-3.93 (1 H, m, J=34.36, 11.87, 3.79, 3.79 Hz), 3.61 (1 H, dd, J=24.00, 11.87 Hz), 2.71 (1 H, d, J=4.80 Hz), 2.61-2.78 (1 H, m), 2.25-2.27 (3 H, m), 2.19-2.37 (1 H, m).

37D. methyl 2-((2R,4R)-4-fluoro-1-(4-(2-methylbenzyl)phenyl)pyrrolidin-2-yl)acetate: A ~3 M solution of HCl/MeOH/$CH_2Cl_2$/MeOAc was prepared by addition of acetyl chloride (0.64 mL) to a 1:1 solution of MeOH/$CH_2Cl_2$ (2.4 mL) at 0° C. The resulting solution of HCl was added to 37C (0.0051 g, 0.017 mmol). After stirring at rt for 2 h, the reaction was basified with sat. $Na_2CO_3$ (aq) and the desired product was extracted with $CH_2Cl_2$. The combined organic layers were washed with brine, dried ($MgSO_4$), and concentrated. The crude product was purified by silica gel chromatography to provide 37D (yellow oil, 0.0021 g, 6.2 mmol, 37% yield). LC-MS Anal. Calc'd for $C_{21}H_{24}FNO_2$ 341.42. found [M+H] 342.0. $^1$H NMR (400 MHz, chloroform-d) δ ppm 7.14 (3 H, q, J=4.77 Hz), 7.07-7.11 (1 H, m), 7.01 (2 H, d, J=8.25 Hz), 6.56 (2 H, d, J=8.25 Hz), 5.30 (1 H, d, J=53.34 Hz), 4.29-4.38 (1 H, m), 3.89 (2 H, s), 3.67-3.69 (1 H, m), 3.63-3.75 (3 H, m), 3.50-3.61 (1 H, m), 2.99 (1 H, dd, J=15.40, 2.75 Hz), 2.54-2.68 (1 H, m), 2.25 (3 H, s), 2.17 (2 H, dd, J=15.40, 9.90 Hz).

37E (Example 37. 2-((2R,4R)-4-fluoro-1-(4-(2-methylbenzyl)phenyl)pyrrolidin-2-yl)acetic acid, TFA): To a cooled (0° C.) solution of 37D (0.0021 g, 6.15 mmol) in THF (0.14 mL) was added (dropwise) 0.4 M aqueous solution of LiOH (0.043 mL, 0.017 mmol). The resultant mixture was warmed to rt and stirred for 1 h. The reaction was quenched with 1 N HCl (0.022 mL) and the mixture was concentrated. The crude product was purified by RP-prep. HPLC to give Example 37 (white solid, 0.001 g, 2.8 mmol, 46% yield). LC-MS Anal. Calc'd for $C_{20}H_{22}FNO_2$ 327.39. found [M+H] 328.3. $^1$H NMR (400 MHz, acetonitrile-$d_3$) δ ppm 7.06-7.23 (4 H, m), 7.01 (2 H, d, J=8.59 Hz), 6.59 (2 H, d, J=8.84 Hz), 5.32 (1 H, d, J=53.81 Hz), 4.24 (1 H, dddd, J=9.57, 7.03, 2.91 Hz), 3.88 (2 H, s), 3.66 (1 H, ddd, J=34.36, 12.13, 4.04 Hz), 3.48 (1 H, dd, J=24.25, 12.13 Hz), 2.83 (1 H, dd, J=15.66, 3.03 Hz), 2.46-2.61 (1 H, m), 2.24 (3 H, s), 2.08-2.26 (2 H, m). Analytical HPLC: RT=9.2 min, HI: 91.2%.

Example 38

2-((2R,3S)-3-methyl-1-(4-(2-methylbenzyl)phenyl)pyrrolidin-2-yl)acetic acid, TFA

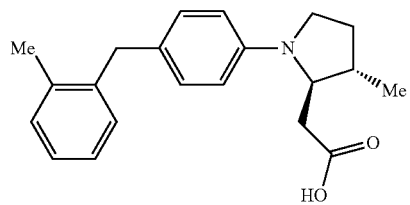

38A. (2S,3S)-tert-butyl 2-(hydroxymethyl)-3-methylpyrrolidine-1-carboxylate: 38A (colorless oil, 0.204 g, 0.946 mmol, 98% yield) was prepared from (2S,3S)-1-(tert-butoxycarbonyl)-3-methylpyrrolidine-2-carboxylic acid following the procedure of 33A. LC-MS Anal. Calc'd for $C_{11}H_{21}NO_3$ 215.29. found [M+H] 216.0. $^1$H NMR (400 MHz, chloroform-d) δ ppm 4.98-5.17 (1 H, m), 3.66-3.75 (1 H, m), 3.50-3.62 (2 H, m), 3.36-3.48 (1 H, m), 3.16-3.28 (1 H, m), 1.85-1.99 (1 H, m), 1.69-1.85 (1 H, m), 1.46 (9H, s), 1.37-1.49 (1 H, m), 1.08 (3 H, d, J=6.57 Hz).

38B. ((2S,3S)-3-methyl-1-(4-(2-methylbenzyl)phenyl)pyrrolidin-2-yl)methanol: ((2S,3S)-3-methylpyrrolidin-2-yl)methanol, HCl was prepared from 38A following the procedure of 33B. The crude amine salt was used directly in the next coupling to 1-(4-iodobenzyl)-2-methylbenzene following the procedure of 33C to provide 38B (yellow oil, 0.219 g, 0.741 mmol, 78% yield). LC-MS Anal. Calc'd for $C_{20}H_{25}NO$ 295.42. found [M+H] 296.0. $^1$H NMR (400 MHz, chloroform-d) δ ppm 7.07-7.17 (4 H, m), 6.99 (2 H, d, J=8.24 Hz), 6.61 (2 H, d, J=8.79 Hz), 3.88 (2 H, s), 3.72 (1 H, dt, J=10.99, 5.50 Hz), 3.63 (1 H, ddd, J=10.99, 7.15, 3.85 Hz), 3.42-3.49 (1 H, m), 3.40 (1 H, ddd, J=5.77, 3.30, 3.02 Hz), 3.28 (1 H, dd, J=15.94, 8.25 Hz), 2.32-2.42 (1 H, m, J=10.31, 7.01, 6.87, 6.87, 3.57 Hz), 2.27 (3 H, s), 2.10-2.24 (1 H, m), 1.56-1.64 (1 H, m, J=3.85, 3.85 Hz), 1.53 (1 H, dd, J=7.42, 5.22 Hz), 1.03 (3 H, d, J=7.15 Hz).

38C. 2-((2R,3S)-3-methyl-1-(4-(2-methylbenzyl)phenyl)pyrrolidin-2-yl)acetonitrile: To a solution of 38B (0.030 g, 0.102 mmol) in $CH_2Cl_2$ (0.34 mL) was added triphenylphosphine (0.040 g, 0.15 mmol) and DEAD (0.024 mL, 0.15 mmol). The resulting mixture was stirred for 15 min, and acetone cyanohydrin (0.019 mL, 0.20 mmol) was added. After 3 h at rt, the reaction mixture was directly purified by silica gel chromatography to afford 38C (colorless oil, 0.011 g, 0.034 mmol, 34% yield). LC-MS Anal. Calc'd for $C_{21}H_{24}N_2$ 304.43. found [M+H] 305.3. $^1$H NMR (400 MHz, chloroform-d) δ ppm 7.12-7.19 (3 H, m), 7.07-7.12 (1 H, m), 7.02 (2 H, d, J=8.59 Hz), 6.49 (2 H, d, J=8.34 Hz), 3.89 (2 H, s), 3.62 (1 H, dt, J=8.15, 2.62 Hz), 3.48 (1 H, td, J=8.65, 3.92 Hz), 3.33 (1 H, q, J=8.25 Hz), 2.71 (1 H, dd, J=16.80, 2.91 Hz), 2.39-2.51 (2 H, m), 2.27 (3 H, s), 2.20-2.34 (1 H, m), 1.70 (1 H, dq, J=16.30, 3.75 Hz), 1.12 (3 H, d, J=7.07 Hz).

38D (Example 38. 2-((2R,3S)-3-methyl-1-(4-(2-methylbenzyl)phenyl)pyrrolidin-2-yl)acetic acid, TFA): Example 38 (colorless oil, 0.005 g, 11 μmol, 31% yield) was prepared from 38C following the procedure of 36C. LC-MS Anal. Calc'd for $C_{21}H_{25}NO_2$ 323.43. found [M+H] 324.1. $^1$H NMR (400 MHz, acetonitrile-$d_3$) δ ppm 7.04-7.24 (6H, m), 6.93 (2 H, d, J=8.08 Hz), 3.94 (2 H, s), 3.66-3.74 (1 H, m), 3.52-3.66 (1 H, m), 3.30-3.48 (1 H, m), 2.70 (1 H, dd, J=16.42, 3.79 Hz), 2.41 (1 H, dd, J=16.55, 7.96 Hz), 2.24-2.34 (2 H, m), 2.23 (3 H, s), 1.70-1.82 (1 H, m), 1.08 (3 H, d, J=6.57 Hz). Analytical HPLC: RT=10.0 min, HI: 94.2%.

Example 39

2-((2R,4S)-4-fluoro-1-(4-(2-methylbenzyloxy)phenyl)pyrrolidin-2-yl)acetic acid, TFA

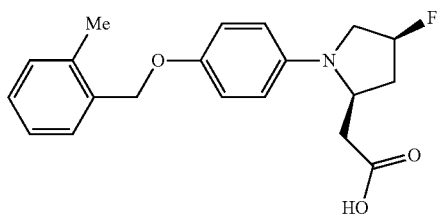

39A. 1-((4-iodophenoxy)methyl)-2-methylbenzene: To a solution of 4-iodophenol (1.00 g, 4.55 mmol) in DMF (11 mL) was added $K_2CO_3$ (1.26 g, 9.09 mmol) and 1-(chloromethyl)-2-methylbenzene (0.601 mL, 4.55 mmol). The mixture was heated to 60° C. for 2 h. The reaction mixture was cooled to rt and diluted with water. The product was extracted with EtOAc. The combined organic layers were washed with brine, dried ($MgSO_4$) and concentrated to afford 39A (off white solid, 1.31 g, 4.04 mmol, 89% yield). $^1$H NMR (400 MHz, chloroform-d) δ ppm 7.58 (2 H, d, J=9.09 Hz), 7.38 (1 H, d, J=7.07 Hz), 7.17-7.31 (3 H, m), 6.77 (2 H, d, J=8.84 Hz), 5.01 (2 H, s), 2.37 (3 H, s).

39B. ((2S,4S)-4-fluoro-1-(4-(2-methylbenzyloxy)phenyl)pyrrolidin-2-yl)methanol: 39A and ((2S,4S)-4-fluoropyrrolidin-2-yl)methanol, HCl were coupled following the procedure of 33C to provide 39B (yellow oil, 0.0708 g, 0.224 mmol, 46.6% yield). LC-MS Anal. Calc'd for $C_{19}H_{22}FNO_2$ 315.38. found [M+H] 316.0. $^1$H NMR (400 MHz, chloroform-d) δ ppm 7.37-7.43 (1 H, m), 7.16-7.26 (3 H, m), 6.94 (2 H, d, J=9.10 Hz), 6.69 (2 H, d, J=9.09 Hz), 5.35 (1 H, dt, J=53.87, 3.88 Hz), 4.98 (2 H, s), 3.90-4.00 (1 H, m), 3.67-3.89 (3 H, m), 3.40 (1 H, ddd, J=35.87, 11.62, 4.04 Hz), 2.38 (3 H, s), 2.31-2.44 (1 H, m), 2.13-2.32 (1 H, m), 1.66-1.72 (1 H, m).

39C. 2-((2R,4S)-4-fluoro-1-(4-(2-methylbenzyloxy)phenyl)pyrrolidin-2-yl)acetonitrile: 39C (colorless oil, 0.0598 g, 0.184 mmol, 82% yield) was prepared from 39B following the procedure of 33D. LC-MS Anal. Calc'd for $C_{20}H_{21}FN_2O$ 324.39. found [M+H] 325.0. $^1$H NMR (400 MHz, chloroform-d) δ ppm 7.39 (1 H, d, J=7.07 Hz), 7.16-7.28 (3 H, m), 6.96 (2 H, d, J=9.09 Hz), 6.54 (2 H, d, J=9.09 Hz), 5.41 (1 H, dt, J=53.05, 4.04 Hz), 4.98 (2 H, s), 4.13-4.22 (1 H, m), 3.71 (1 H, ddd, J=24.76, 11.87, 1.26 Hz), 3.49 (1 H, ddd, J=36.13, 11.62, 4.04 Hz), 2.86 (1 H, dd, J=16.93, 3.03 Hz), 2.57 (1 H, dd, J=16.93, 10.36 Hz), 2.44-2.55 (1 H, m), 2.37 (3 H, s), 2.23-2.44 (1 H, m).

39D (Example 39. 2-((2R,4S)-4-fluoro-1-(4-(2-methylbenzyloxy)phenyl)pyrrolidin-2-yl)acetic acid, TFA): Example 39 (brown solid, 0.019 g, 0.039 mmol, 35% yield) was prepared from 39C following the procedure of 36C. LC-MS Anal. Calc'd for $C_{20}H_{22}FNO_3$ 324.39. found [M+H] 325.0. $^1$H NMR (400 MHz, acetonitrile-$d_3$) δ ppm 7.39 (1 H, d, J=7.07 Hz), 7.16-7.29 (3 H, m), 6.99 (2 H, d, J=9.09 Hz), 6.81 (2 H, br. s.), 5.41 (1 H, dt, J=53.69, 4.55, 4.42 Hz), 5.03 (2 H, s), 3.99-4.29 (1 H, m), 3.64-3.91 (1 H, m), 3.34-3.65 (1 H, m), 2.81 (1 H, dd, J=16.17, 3.28 Hz), 2.51 (2 H, dd, J=16.30, 9.73 Hz), 2.36 (3 H, s), 2.15-2.29 (1 H, m). Analytical HPLC: RT=8.6 min, HI: 96.1%.

Example 40

2-((2S,4S)-1-(4-(2-methylbenzyl)phenyl)-4-(trifluoromethyl)pyrrolidin-2-yl)acetic acid, TFA

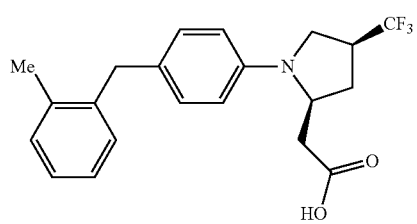

40A. (2S,4S)-tert-butyl 2-(hydroxymethyl)-4-(trifluoromethyl)pyrrolidine-1-carboxylate: 40A (colorless oil, 0.215 g, 0.797 mmol, 90% yield) was prepared from (2S,4S)-1-(tert-butoxycarbonyl)-4-(trifluoromethyl)pyrrolidine-2-carboxylic acid following the procedure of 33A. LC-MS Anal. Calc'd for $C_{11}H_{18}F_3NO_3$ 269.26. found [M+H] 270.0. $^1$H NMR (400 MHz, chloroform-d) δ ppm 4.67-4.89 (1 H, m), 3.94-4.09 (1 H, m), 3.77-3.90 (1 H, m), 3.59-3.77 (3 H, m), 3.33 (1 H, t, J=10.61 Hz), 2.77-2.91 (1 H, m), 2.22-2.36 (1 H, m), 1.48 (9 H, s).

40B. ((2S,4S)-4-(trifluoromethyl)pyrrolidin-2-yl)methanol, HCl: 40B (viscous colorless oil, 0.179 g, 0.869 mmol, 99% yield) was prepared from 40A following the procedure of 33B. LC-MS Anal. Calc'd for $C_6H_{10}F_3NO$ 169.14. found [M+H] 170.0. $^1$H NMR (400 MHz, methanol-$d_4$) δ ppm 3.86-3.92 (1 H, m, J=11.87, 3.54 Hz), 3.77-3.86 (1 H, m), 3.70 (1 H, dd, J=11.75, 5.94 Hz), 3.61 (1 H, d, J=2.78 Hz), 3.37-3.51 (2 H, m), 2.42 (1 H, dt, J=13.83, 6.85 Hz), 1.98 (1 H, ddd, J=13.20, 10.61, 10.29 Hz).

40C. ((2S,4S)-1-(4-(2-methylbenzyl)phenyl)-4-(trifluoromethyl)pyrrolidin-2-yl)methanol: 40C (yellow oil, 0.0550 g, 0.157 mmol, 61.6% yield) was prepared from 40B and 1-(4-iodobenzyl)-2-methylbenzene following the procedure of 33C. LC-MS Anal. Calc'd for $C_{20}H_{22}F_3NO$ 349.39. found [M+H] 350.0. $^1$H NMR (400 MHz, chloroform-d) δ ppm 7.12-7.19 (3 H, m), 7.07-7.12 (1 H, m), 7.02 (2 H, d, J=8.84 Hz), 6.64 (2 H, d, J=8.59 Hz), 3.96-4.04 (1 H, m, J=7.48, 7.48, 4.99, 2.78 Hz), 3.90 (2 H, s), 3.78-3.87 (1 H, m), 3.63-3.72 (1 H, m), 3.59 (2 H, d, J=8.59 Hz), 2.95 (1 H, qd, J=17.18, 8.59 Hz), 2.27-2.45 (2 H, m), 2.27 (3 H, s).

40D. 2-((2S,4S)-1-(4-(2-methylbenzyl)phenyl)-4-(trifluoromethyl)pyrrolidin-2-yl)acetonitrile: 40D (colorless oil, 0.024 g, 0.068 mmol, 43% yield) was prepared from 40C following the procedure of 33D. $^1$H NMR (400 MHz, chloroform-d) δ ppm 7.11-7.19 (3 H, m), 7.07-7.11 (1 H, m), 7.05 (2 H, d, J=8.59 Hz), 6.56 (2 H, d, J=8.59 Hz), 4.17-4.28 (1 H, m, J=8.21, 8.21, 5.56, 3.28 Hz), 3.91 (2 H, s), 3.53-3.65 (2 H, m), 2.97-3.15 (1 H, m), 2.81 (1 H, dd, J=16.93, 3.03 Hz), 2.68 (1 H, ddd, J=13.83, 9.16, 7.83 Hz), 2.44 (1 H, dd, J=16.93, 8.84 Hz), 2.25 (3 H, s), 2.21 (1 H, d, J=13.64, 8.08, 5.56 Hz).

40E (Example 40. 2-((2S,4S)-1-(4-(2-methylbenzyl)phenyl)-4-(trifluoromethyl)pyrrolidin-2-yl)acetic acid, TFA):

Example 40 (peach oil, 0.010 g, 0.020 mmol, 53% yield) was prepared from 40D following the procedure of 36C. LC-MS Anal. Calc'd for $C_{21}H_{22}F_3NO_2$ 377.40. found [M+H] 378.0. $^1$H NMR (400 MHz, acetonitrile-$d_3$) δ ppm 7.07-7.22 (4 H, m), 7.03 (2 H, d, J=8.59 Hz), 6.66 (2 H, d, J=8.34 Hz), 4.14-4.28 (1 H, m), 3.89 (2 H, s), 3.43-3.64 (2 H, m), 3.06-3.27 (1 H, m), 2.81 (1 H, dd, J=15.92, 3.03 Hz), 2.62 (1 H, ddd, J=13.58, 9.16, 7.58 Hz), 2.24 (3 H, s), 2.26 (1 H, dd, J=15.79, 9.73 Hz), 1.96-2.03 (1 H, m). Analytical HPLC: RT=10.1 min, HI: 97.7%.

Example 41

2-((2S,4S)-1-(4-(o-tolyloxy)phenyl)-4-(trifluoromethyl)pyrrolidin-2-yl)acetic acid, TFA

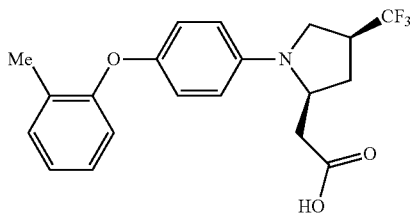

41A. ((2S,4S)-1-(4-(o-tolyloxy)phenyl)-4-(trifluoromethyl)pyrrolidin-2-yl)methanol: 41A (colorless oil, 0.0728 g, 0.207 mmol, 70.6% yield) was prepared from ((2S,4S)-4-(trifluoromethyl)pyrrolidin-2-yl)methanol, HCl (40B) and 1-(4-iodophenoxy)-2-methylbenzene following the procedure of 33C. LC-MS Anal. Calc'd for $C_{19}H_{20}F_3NO_2$ 351.36. found [M+H] 352.0. $^1$H NMR (400 MHz, chloroform-d) δ ppm 7.22 (1 H, d, J=7.33 Hz), 7.11 (1 H, t, J=7.83 Hz), 7.00 (1 H, t, J=7.45 Hz), 6.89 (2 H, d, J=9.09 Hz), 6.79 (1 H, d, J=8.08 Hz), 6.69 (2 H, d, J=9.09 Hz), 3.93-4.03 (1 H, m), 3.77-3.86 (1 H, m), 3.65-3.72 (1 H, m), 3.52-3.65 (2 H, m), 2.87-3.08 (1 H, m), 2.36-2.46 (1 H, m), 2.29 (3 H, s), 2.25-2.36 (1 H, m), 1.51-1.61 (1 H, m).

41B. 2-((2S,4S)-1-(4-(o-tolyloxy)phenyl)-4-(trifluoromethyl)pyrrolidin-2-yl)acetonitrile: 41B (colorless oil, 0.0750 g, 0.208 mmol, 100% yield) was prepared from 41A following the procedure of 33D. LC-MS Anal. Calc'd for $C_{20}H_{19}F_3N_2O$ 360.37. found [M+H] 360.9. $^1$H NMR (400 MHz, chloroform-d) δ ppm 7.24 (1 H, d, J=6.82 Hz), 7.09-7.16 (1 H, m), 6.97-7.06 (1 H, m), 6.91 (2 H, d, J=9.09 Hz), 6.80 (1 H, d, J=8.08 Hz), 6.62 (2 H, d, J=9.09 Hz), 4.20 (1 H, dddd, J=10.71, 5.68, 5.46, 3.16 Hz), 3.59 (2 H, d, J=8.34 Hz), 3.00-3.18 (1 H, m), 2.79 (1 H, dd, J=16.80, 3.16 Hz), 2.69 (1 H, ddd, J=13.71, 9.28, 7.58 Hz), 2.47 (1 H, dd, J=16.93, 8.84 Hz), 2.28 (3 H, s), 2.22 (1 H, ddd, J=13.71, 8.02, 5.81 Hz).

41C (Example 41. 2-((2S,4S)-1-(4-(o-tolyloxy)phenyl)-4-(trifluoromethyl)pyrrolidin-2-yl)acetic acid, TFA): Example 41 (brown solid, 0.021 g, 0.042 mmol, 43% yield) was prepared from 41B following the procedure of 36C. LC-MS Anal. Calc'd for $C_{20}H_{20}F_3NO_3$ 379.37. found [M+H] 379.9. $^1$H NMR (400 MHz, acetonitrile-$d_3$) δ ppm 7.25 (1 H, d, J=7.58 Hz), 7.13 (1 H, t, J=7.71 Hz), 7.01 (1 H, t, J=7.33 Hz), 6.86 (2 H, d, J=9.09 Hz), 6.75 (1 H, d, J=8.08 Hz), 6.70 (2 H, d, J=9.09 Hz), 4.14-4.26 (1 H, m), 3.45-3.60 (2 H, m), 3.08-3.27 (1 H, m), 2.81 (1 H, dd, J=15.92, 3.03 Hz), 2.62 (1 H, ddd, J=13.45, 9.28, 7.83 Hz), 2.24 (3 H, s), 2.19-2.31 (1 H, m), 1.96-2.04 (1 H, m). Analytical HPLC: RT=9.8 min, HI: 98.6%.

Example 42

2-((2S,4S)-1-(4-(2-methylbenzyloxy)phenyl)-4-(trifluoromethyl)pyrrolidin-2-yl)acetic acid, TFA

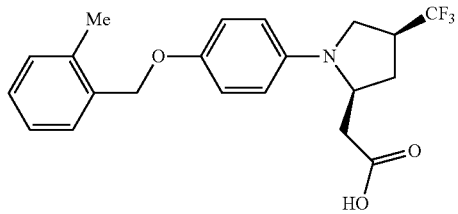

42A. ((2S,4S)-1-(4-(2-methylbenzyloxy)phenyl)-4-(trifluoromethyl)pyrrolidin-2-yl)methanol: 42A (colorless oil, 0.0831 g, 0.227 mmol, 79% yield) was prepared from ((2S,4S)-4-(trifluoromethyl)pyrrolidin-2-yl)methanol, HCl (40B) and 1-((4-iodophenoxy)methyl)-2-methylbenzene following the procedure of 33C. LC-MS Anal. Calc'd for $C_{20}H_{22}F_3NO_2$ 365.39. found [M+H] 366.0. $^1$H NMR (400 MHz, chloroform-d) δ ppm 7.40 (1 H, d, J=7.07 Hz), 7.18-7.29 (3 H, m), 6.94 (2 H, d, J=9.09 Hz), 6.71 (2 H, d, J=9.09 Hz), 4.99 (2 H, s), 3.87-3.99 (1 H, m, J=7.45, 7.45, 4.80, 2.78 Hz), 3.80 (1 H, ddd, J=11.18, 4.36, 4.17 Hz), 3.58-3.69 (2 H, m), 3.51 (1 H, t, J=9.22 Hz), 2.38 (3 H, s), 2.21-2.45 (2 H, m), 1.62 (1 H, dd, J=7.71, 3.92 Hz).

42B. 2-((2S,4S)-1-(4-(2-methylbenzyloxy)phenyl)-4-(trifluoromethyl)pyrrolidin-2-yl)acetonitrile: 42B (white solid, 0.0656 g, 0.175 mmol, 77% yield) was prepared from 42A following the procedure of 33D. LC-MS Anal. Calc'd for $C_{21}H_{21}F_3N_2O$ 374.40. found [M+H] 375.0. $^1$H NMR (400 MHz, chloroform-d) δ ppm 7.40 (1 H, d, J=7.07 Hz), 7.18-7.30 (3 H, m), 6.96 (2 H, d, J=9.09 Hz), 6.64 (2 H, d, J=9.09 Hz), 5.00 (2 H, s), 4.09-4.21 (1 H, m), 3.49-3.63 (2 H, m), 2.98-3.17 (1 H, m), 2.76 (1 H, dd, J=16.80, 3.16 Hz), 2.67 (1 H, ddd, J=13.64, 9.35, 7.58 Hz), 2.39-2.47 (1 H, m), 2.39 (3 H, s), 2.20 (1 H, ddd, J=13.64, 8.08, 5.56 Hz).

42C (Example 42. 2-((2S,4S)-1-(4-(2-methylbenzyloxy)phenyl)-4-(trifluoromethyl)pyrrolidin-2-yl)acetic acid, TFA): Example 42 (brown solid, 0.024 g, 0.045 mmol, 41% yield) was prepared from 42B following the procedure of 36C. LC-MS Anal. Calc'd for $C_{21}H_{22}F_3NO_3$ 393.40. found [M+H] 393.9. $^1$H NMR (400 MHz, acetonitrile-$d_3$) δ ppm 7.39 (1 H, d, J=7.07 Hz), 7.15-7.29 (3 H, m), 6.94 (2 H, d, J=9.09 Hz), 6.73 (2 H, d, J=8.08 Hz), 5.01 (2 H, s), 4.06-4.25 (1 H, m), 3.50 (2 H, d, J=7.07 Hz), 3.07-3.27 (1 H, m), 2.76 (1 H, dd, J=15.92, 3.03 Hz), 2.60 (1 H, ddd, J=13.39, 9.22, 7.45

Hz), 2.35 (3 H, s), 2.25 (1 H, dd, J=15.79, 9.73 Hz), 1.95-2.02 (1 H, m). Analytical HPLC: RT=9.7 min, HI: 98.1%.

Example 43

2-((2R,4S)-4-fluoro-1-(4-(2-methylbenzyl)phenyl)pyrrolidin-2-yl)acetic acid, TFA

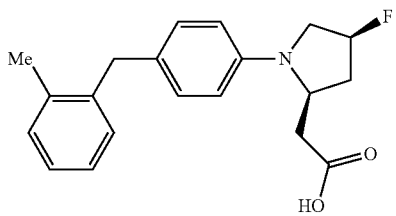

43A. (2S,4S)-tert-butyl 4-fluoro-2-(hydroxymethyl)pyrrolidine-1-carboxylate: 43A (colorless oil, 1.24 g, 5.67 mmol, 90% yield) was prepared from (2S,4S)-1-(tert-butoxycarbonyl)-4-fluoropyrrolidine-2-carboxylic acid following the procedure of 33A. LC-MS Anal. Calc'd for $C_{10}H_{18}FNO_3$ 219.25. found [M+H] 220.0. $^1$H NMR (400 MHz, chloroform-d) δ ppm 5.16 (1 H, d, J=52.80 Hz), 4.06-4.25 (2 H, m), 3.79-3.91 (1 H, m), 3.66-3.76 (1 H, m), 3.45-3.66 (2 H, m), 2.11-2.40 (1 H, m), 2.04 (1 H, s), 1.48 (9 H, s).

43B. ((2S,4S)-1-(4-bromophenyl)-4-fluoropyrrolidin-2-yl)methanol: ((2S,4S)-4-fluoropyrrolidin-2-yl)methanol, HCl was prepared from 43A following the procedure of 33B. The crude amine salt was used directly in the next coupling to 1-bromo-4-iodobenzene following the procedure of 33C to provide 43B (colorless oil, 0.344 g, 1.26 mmol, 78% yield). LC-MS Anal. Calc'd for $C_{11}H_{13}FNO$ 274.13. found [M+H] 275.9. $^1$H NMR (400 MHz, chloroform-d) δ ppm 7.31 (2 H, d, J=8.79 Hz), 6.57 (2 H, d, J=8.79 Hz), 5.37 (1 H, dt, J=53.59, 4.12, 3.85 Hz), 3.93-4.02 (1 H, m), 3.86 (1 H, ddd, J=10.31, 5.08, 4.95 Hz), 3.62-3.79 (2 H, m), 3.42 (1 H, ddd, J=36.14, 11.96, 4.12 Hz), 2.40 (1 H, dd, J=20.89, 15.39 Hz), 2.23 (1 H, dddd, J=43.42, 14.84, 8.79, 4.40 Hz), 1.75 (1 H, t, J=5.22 Hz).

43C. 2-((2R,4S)-1-(4-bromophenyl)-4-fluoropyrrolidin-2-yl)acetonitrile: 43C (white solid, 0.264 g, 0.931 mmol, 74% yield) was prepared from 43B following the procedure of 33D. LC-MS Anal. Calc'd for $C_{12}H_{12}BrFN_2$ 283.14. found [M+H] 285.0. $^1$H NMR (400 MHz, chloroform-d) δ ppm 7.36 (2 H, d, J=9.09 Hz), 6.46 (2 H, d, J=9.09 Hz), 5.43 (1 H, dt, J=53.05, 4.04 Hz), 4.16-4.25 (1 H, m), 3.72 (1 H, ddd, J=25.01, 12.00, 1.39 Hz), 3.51 (1 H, ddd, J=36.57, 11.94, 4.04 Hz), 2.86 (1 H, dd, J=16.93, 3.54 Hz), 2.60 (1 H, dd, J=16.80, 10.48 Hz), 2.54 (1 H, dd, J=18.44, 15.16 Hz), 2.36 (1 H, dddd, J=42.95, 14.65, 8.08, 4.04 Hz).

43D. (S)-2-(4-fluoro-1-(4-(2-methylbenzyl)phenyl)pyrrolidin-2-yl)acetonitrile: 43D (light brown oil, 0.045 g, 0.15 mmol, 39% yield) was prepared from 43C following the procedure of 33E. LC-MS Anal. Calc'd for $C_{20}H_{21}FN_2$ 308.39. found [M+H] 308.9. $^1$H NMR (400 MHz, chloroform-d) δ ppm 7.12-7.19 (3 H, m), 7.07-7.11 (1 H, m), 7.06 (2 H, d, J=8.79 Hz), 6.51 (2 H, d, J=8.25 Hz), 5.42 (1 H, dt, J=53.18, 3.99, 3.85 Hz), 4.22 (1 H, ddd, J=10.72, 7.97, 3.30 Hz), 3.91 (2 H, s), 3.73 (1 H, ddd, J=24.87, 11.96, 1.10 Hz), 3.51 (1 H, ddd, J=36.97, 11.96, 3.85 Hz), 2.89 (1 H, dd, J=16.76, 3.57 Hz), 2.58 (1 H, dd, J=17.04, 10.44 Hz), 2.52 (1 H, dd, J=18.41, 15.12 Hz), 2.27-2.43 (1 H, m), 2.26 (3 H, s).

43E (Example 43. 2-((2R,4S)-4-fluoro-1-(4-(2-methylbenzyl)phenyl)pyrrolidin-2-yl)acetic acid, TFA): 43D (0.035 g, 0.113 mmol) was dissolved in conc. HCl (0.50 mL, 16 mmol) and AcOH (0.050 mL, 0.87 mmol) in a microwave tube. The reaction vessel was sealed and heated to 100° C. in the microwave for 20 min. The reaction mixture was concentrated and the residue was purified by RP-prep. HPLC to give 2-((2S,4S)-4-fluoro-1-(4-(2-methylbenzyl)phenyl)pyrrolidin-2-yl)acetic acid, TFA (brown solid, 0.015 g, 0.031 mmol, 27% yield) and Example 43 (brown solid, 0.016 g, 0.034 mmol, 30% yield). LC-MS Anal. Calc'd for $C_{20}H_{22}FNO_2$ 327.39. found [M+H] 327.9. $^1$H NMR (400 MHz, methanol-$d_4$) δ ppm 7.04-7.13 (4 H, m), 6.98 (2 H, d, J=8.79 Hz), 6.58 (2 H, d, J=8.79 Hz), 5.28-5.46 (1 H, m), 4.15-4.28 (1 H, m), 3.87 (2 H, s), 3.59-3.71 (1 H, m), 3.39-3.55 (1 H, m), 2.82 (1 H, dd, J=15.39, 3.30 Hz), 2.48 (1 H, dd, J=15.67, 10.72 Hz), 2.22-2.44 (2 H, m), 2.20 (3 H, s). Analytical HPLC: RT=10.1 min, HI: 96.3%.

Example 44

(S)-2-(1-(4-(o-tolylthio)phenyl)pyrrolidin-2-yl)acetic acid, TFA

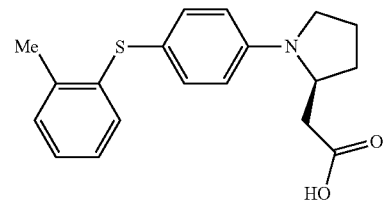

44A. 1-(4-fluorophenylsulfonyl)-2-methylbenzene: 2-methylbenzene-1-sulfonyl chloride (1.00 g, 5.25 mmol) and fluorobenzene (3.0 mL, 32 mmol) were combined and heated to 60° C. $FeCl_3$ (1.02 g, 6.29 mmol) was added in one portion and the reaction mixture was stirred at 60° C. for 1 h. The reaction mixture was cooled to rt, diluted with $CH_2Cl_2$, and quenched with 1 N HCl. The aqueous layer was extracted with $CH_2Cl_2$ and the combined organic layers were washed with brine, dried ($MgSO_4$), and concentrated. The product was purified by silica gel chromatography to afford 44A (pale brown oil, 0.828 g, 3.31 mmol, 63% yield). LC-MS Anal. Calc'd for $C_{13}H_{11}FO_2S$ 250.29. found [M+H] 250.9. $^1$H NMR (400 MHz, chloroform-d) δ ppm 8.15-8.23 (1 H, m), 7.83-7.93 (2 H, m), 7.45-7.53 (1 H, m), 7.40 (1 H, t, J=7.70 Hz), 7.21-7.28 (1 H, m), 7.12-7.21 (2 H, m), 2.45 (3 H, s).

44B. (S)-(1-(4-(o-tolylsulfonyl)phenyl)pyrrolidin-2-yl)methanol: 44A (0.100 g, 0.400 mmol) and (S)-pyrrolidin-2-ylmethanol (0.078 mL, 0.80 mmol) were combined in DMSO (0.80 mL) and heated to 130° C. for 6 h. The reaction mixture was cooled to rt and diluted with water (5 mL). The mixture was extracted with EtOAc and the combined organic layers were then washed with water and then brine, dried ($MgSO_4$), and concentrated. The crude product was purified by silica gel chromatography to afford 44B (colorless viscous oil, 0.133 g, 0.400 mmol, 99% yield). LC-MS Anal. Calc'd for $C_{18}H_{21}NO_3S$ 331.43. found [M+H] 332.0. $^1$H NMR (400 MHz, chloroform-d) δ ppm 8.10 (1 H, dd, J=7.83, 1.26 Hz), 7.67 (2 H, d, J=9.09 Hz), 7.37-7.43 (1 H, m), 7.32 (1 H, t, J=7.33 Hz), 7.19 (1 H, d, J=7.58 Hz), 6.65 (2 H, d, J=8.84 Hz), 3.89-3.98 (1 H, m), 3.64-3.74 (1 H, m), 3.54-3.63 (1 H, m), 3.48 (1 H, t, J=8.21 Hz), 3.15-3.27 (1 H, m), 2.50 (3 H, s), 1.95-2.16 (5 H, m).

44C. (S)-(1-(4-(o-tolylthio)phenyl)pyrrolidin-2-yl)methanol: 44B (0.3758 g, 1.134 mmol) was dissolved in anhydrous toluene (11 mL) and a 1.5 M solution of DIBAL-H (6.80 mL, 10.2 mmol) in toluene was added dropwise. The reaction mixture was refluxed for 16 h. The reaction mixture was cooled to rt and quenched with slow addition of water. The mixture was diluted with EtOAc and the layers were separated. The aqueous layer was extracted with EtOAc and the combined organic layers were washed with brine, dried ($MgSO_4$), and concentrated. The crude product was purified by silica gel chromatography to provide 44C (colorless oil, 0.232 g, 0.774 mmol, 68% yield). LC-MS Anal. Calc'd for $C_{18}H_{21}NOS$ 299.43. found [M+H] 299.9. $^1$H NMR (400 MHz, chloroform-d) δ ppm 7.30-7.36 (2 H, m), 7.13 (1 H, dd, J=5.18, 3.92 Hz), 6.99-7.05 (2 H, m), 6.83-6.89 (1 H, m), 6.69 (2 H, d, J=8.84 Hz), 3.85-3.94 (1 H, m), 3.62-3.74 (2 H, m), 3.51 (1 H, td, J=8.46, 1.77 Hz), 3.14-3.25 (1 H, m), 2.39 (3 H, s), 1.96-2.18 (5 H, m).

44D. (S)-2-(1-(4-(o-tolylthio)phenyl)pyrrolidin-2-yl)acetonitrile: 44D (colorless oil, 0.044 g, 0.14 mmol, 75% yield) was prepared from 44C following the procedure of 33D. LC-MS Anal. Calc'd for $C_{19}H_{20}N_2S$ 308.44. found [M+H] 309.0. $^1$H NMR (400 MHz, chloroform-d) δ ppm 7.36 (2 H, d, J=8.84 Hz), 7.13-7.17 (1 H, m), 7.00-7.08 (2 H, m), 6.85-6.93 (1 H, m), 6.58 (2 H, d, J=8.84 Hz), 4.06-4.16 (1 H, m), 3.50-3.61 (1 H, m), 3.21-3.32 (1 H, m), 2.71 (1 H, dd, J=16.80, 3.16 Hz), 2.48 (1 H, dd, J=16.80, 8.46 Hz), 2.40 (3 H, s), 2.17-2.31 (2 H, m), 2.06-2.17 (2 H, m).

44E (Example 44. (S)-2-(1-(4-(o-tolylthio)phenyl)pyrrolidin-2-yl)acetic acid, TFA): 44D (0.022 g, 0.073 mmol) was dissolved in conc. HCl (0.50 mL, 16 mmol) and AcOH (0.050 mL, 0.87 mmol) in a microwave tube. The reaction vessel was sealed and microwaved at 100° C. for 20 min. The reaction mixture was concentrated and the residue was purified by RP-prep. HPLC to give Example 44 (white solid, 0.017 g, 0.037 mmol, 50% yield). LC-MS Anal. Calc'd for $C_{19}H_{21}NO_2S$ 327.44. found [M+H] 327.9. $^1$H NMR (400 MHz, methanol-$d_4$) δ ppm 7.27 (2 H, d, J=8.79 Hz), 7.09-7.15 (1 H, m), 6.94-7.04 (2 H, m), 6.76-6.84 (1 H, m), 6.68 (2 H, d, J=8.79 Hz), 4.11-4.23 (1 H, m), 3.47 (1 H, br. s.), 3.22 (1 H, d, J=7.70 Hz), 2.73 (1 H, dd, J=15.39, 2.75 Hz), 2.33 (3 H, s), 2.27 (1 H, dd, J=15.39, 10.44 Hz), 2.02-2.19 (3 H, m), 1.92-2.01 (1 H, m). Analytical HPLC: RT=10.1 min, HI: 94.8%.

Example 45

2-((2S,4S)-1-(4-(2,3-dimethylphenoxy)phenyl)-4-(trifluoromethyl)pyrrolidin-2-yl)acetic acid, TFA

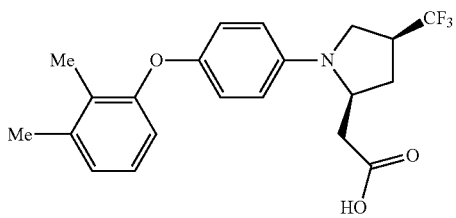

45A. 1-(4-iodophenoxy)-2,3-dimethylbenzene: To a mixture of 2,3-dimethylphenol (0.493 g, 4.04 mmol), 4-iodophenylboronic acid (1 g, 4.04 mmol), copper(II) acetate (0.733 g, 4.04 mmol), and 4 Å mol. sieves (3 g, 4.04 mmol) was added $CH_2Cl_2$ (40 mL). Triethylamine (2.8 mL, 20 mmol) was added and the reaction was stirred under a drying tube packed with Drierite overnight. The reaction mixture was filtered through CELITE®, rinsed with $CH_2Cl_2$, and concentrated. The crude product mixture as a brown semisolid was rediluted with $CH_2Cl_2$ and filtered through a plug of silica gel, rinsing with additional $CH_2Cl_2$. The solution was concentrated and the product was purified via silica gel chromatography to give 45A (colorless oil, 0.623 g, 1.92 mmol, 48% yield). LC-MS Anal. Calc'd for $C_{14}H_{13}IO$ 324.16. found [M+H] 324.9. $^1$H NMR (400 MHz, chloroform-d) δ ppm 7.55 (2 H, d, J=9.09 Hz), 7.08 (1 H, t, J=7.83 Hz), 7.00 (1 H, d, J=7.58 Hz), 6.78 (1 H, d, J=7.83 Hz), 6.64 (2 H, d, J=8.84 Hz), 2.32 (3 H, s), 2.11 (3 H, s).

45B. ((2S,4S)-1-(4-(2,3-dimethylphenoxy)phenyl)-4-(trifluoromethyl)pyrrolidin-2-yl)methanol: 45B (colorless oil, 0.112 g, 0.308 mmol, 76% yield) was prepared from 45A and ((2S,4S)-4-(trifluoromethyl)pyrrolidin-2-yl)methanol, HCl (40B) following the procedure of 33C. LC-MS Anal. Calc'd for $C_{20}H_{22}F_3NO_2$ 365.39. found [M+H] 366.0. $^1$H NMR (400 MHz, chloroform-d) δ ppm 7.01 (1 H, t, J=7.83 Hz), 6.91 (1 H, d, J=7.33 Hz), 6.86 (2 H, d, J=9.09 Hz), 6.68 (2 H, d, J=8.84 Hz), 6.67 (1 H, d, J=6.82 Hz), 3.92-4.01 (1 H, m), 3.82 (1 H, dt, J=11.12, 4.55 Hz), 3.67 (1 H, ddd, J=10.86, 7.83, 2.78 Hz), 3.58 (2 H, td, J=18.51, 9.73 Hz), 2.89-3.04 (1 H, m), 2.35-2.45 (1 H, m), 2.31-2.33 (3 H, m), 2.25-2.35 (1 H, m), 2.20 (3 H, s).

45C. 2-((2S,4S)-1-(4-(2,3-dimethylphenoxy)phenyl)-4-(trifluoromethyl)pyrrolidin-2-yl)acetonitrile: 45C (white solid, 0.101 g, 0.27 mmol, 87% yield) was prepared from 45B following the procedure of 33D. LC-MS Anal. Calc'd for $C_{21}H_{21}F_3N_2O$ 374.40. found [M+H] 375.0. $^1$H NMR (400 MHz, chloroform-d) δ ppm 7.02 (1 H, t, J=7.71 Hz), 6.93 (1 H, d, J=7.33 Hz), 6.88 (2 H, d, J=9.09 Hz), 6.67 (1 H, d, J=7.83 Hz), 6.60 (2 H, d, J=8.84 Hz), 4.12-4.26 (1 H, m), 3.58 (2 H, d, J=8.34 Hz), 2.99-3.17 (1 H, m), 2.79 (1 H, dd, J=16.80, 3.16 Hz), 2.68 (1 H, ddd, J=13.64, 9.09, 7.83 Hz), 2.46 (1 H, dd, J=16.80, 8.72 Hz), 2.32 (3 H, s), 2.19-2.26 (1 H, m), 2.19 (3 H, s).

45D (Example 45. 2-((2S,4S)-1-(4-(2,3-dimethylphenoxy)phenyl)-4-(trifluoromethyl)pyrrolidin-2-yl)acetic acid, TFA): Example 45 (peach solid, 0.033 g, 0.074 mmol, 58% yield) was prepared from 45C following the procedure of 36C. LC-MS Anal. Calc'd for $C_{21}H_{22}F_3NO_3$ 393.40. found [M+H] 394.0. $^1$H NMR (400 MHz, acetonitrile-$d_3$) δ ppm 7.03 (1 H, t, J=7.83 Hz), 6.94 (1 H, d, J=7.33 Hz), 6.83 (2 H, d, J=9.09 Hz), 6.72 (2 H, d, J=8.84 Hz), 6.63 (1 H, d, J=8.08 Hz), 4.14-4.25 (1 H, m), 3.46-3.60 (2 H, m), 3.10-3.29 (1 H, m), 2.80 (1 H, dd, J=15.92, 2.78 Hz), 2.62 (1 H, ddd, J=13.45, 9.28, 7.83 Hz), 2.30 (3 H, s), 2.20-2.29 (1 H, m), 2.16 (3 H, s), 1.96-2.04 (1 H, m). Analytical HPLC: RT=10.9 min, HI: 97.0%.

Example 46

2-((2S,4S)-1-(4-(3-chloro-2-methylphenoxy)phenyl)-4-(trifluoromethyl)pyrrolidin-2-yl)acetic acid, TFA

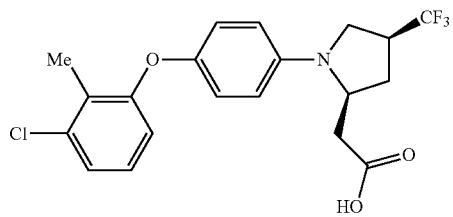

46A. 1-chloro-3-(4-iodophenoxy)-2-methylbenzene: 46A (colorless oil, 0.773 g, 2.24 mmol, 56% yield) was prepared from 3-chloro-2-methylphenol and 4-iodophenylboronic acid following the procedure of 45A. $^1$H NMR (400 MHz, chloroform-d) δ ppm 7.59 (2 H, d, J=8.84 Hz), 7.20 (1 H, d, J=8.08 Hz), 7.10 (1 H, t, J=7.96 Hz), 6.81 (1 H, d, J=8.08 Hz), 6.66 (2 H, d, J=9.09 Hz), 2.27 (3 H, s).

46B. ((2S,4S)-1-(4-(3-chloro-2-methylphenoxy)phenyl)-4-(trifluoromethyl)pyrrolidin-2-yl)methanol: 46B (colorless oil, 0.104 g, 0.269 mmol, 72% yield) was prepared from 46A and ((2S,4S)-4-(trifluoromethyl)pyrrolidin-2-yl)methanol, HCl (40B) following the procedure of 33C. LC-MS Anal. Calc'd for $C_{19}H_{19}ClF_3NO_2$ 385.81. found [M+H] 386.0. $^1$H NMR (400 MHz, chloroform-d) δ ppm 7.09 (1 H, dd, J=8.08, 1.26 Hz), 7.02 (1 H, t, J=7.83 Hz), 6.88 (2 H, d, J=9.10 Hz), 6.69 (2 H, d, J=9.09 Hz), 6.66-6.70 (1 H, m), 3.99 (1 H, dddd, J=7.48, 4.99, 2.78 Hz), 3.82 (1 H, dt, J=11.31, 4.58 Hz), 3.69 (1 H, ddd, J=11.12, 7.83, 2.78 Hz), 3.53-3.65 (2 H, m), 2.89-3.07 (1 H, m), 2.37-2.48 (1 H, m), 2.33-2.37 (3 H, m), 2.26-2.33 (1 H, m).

46C. 2-((2S,4S)-1-(4-(3-chloro-2-methylphenoxy)phenyl)-4-(trifluoromethyl)pyrrolidin-2-yl)acetonitrile: 46C (white solid, 0.093 g, 0.236 mmol, 87% yield) was prepared from 46B following the procedure of 33D. LC-MS Anal. Calc'd for $C_{20}H_{18}ClF_3N_2O$ 394.82. found [M+H] 395.0. $^1$H NMR (400 MHz, chloroform-d) δ ppm 7.11 (1 H, d, J=8.08 Hz), 7.03 (1 H, t, J=8.08 Hz), 6.91 (2 H, d, J=9.09 Hz), 6.69 (1 H, d, J=8.08 Hz), 6.62 (2 H, d, J=9.09 Hz), 4.20 (1 H, br. s.), 3.60 (2 H, d, J=8.34 Hz), 3.00-3.18 (1 H, m), 2.79 (1 H, dd, J=16.80, 3.16 Hz), 2.70 (1 H, ddd, J=13.64, 9.09, 7.83 Hz), 2.48 (1 H, dd, J=16.93, 8.59 Hz), 2.34 (3 H, s), 2.23 (1 H, ddd, J=13.77, 8.08, 5.68 Hz).

46D (Example 46. 2-((2S,4S)-1-(4-(3-chloro-2-methylphenoxy)phenyl)-4-(trifluoromethyl)pyrrolidin-2-yl)acetic acid, TFA): Example 46 (peach solid, 0.030 g, 0.065 mmol, 60.2% yield) was prepared from 46C following the procedure of 36C. LC-MS Anal. Calc'd for $C_{20}H_{19}ClF_3NO_3$ 413.82. found [M+H] 414.0. $^1$H NMR (400 MHz, acetonitrile-$d_3$) δ ppm 7.06-7.17 (2 H, m), 6.89 (2 H, d, J=9.09 Hz), 6.73 (2 H, d, J=8.84 Hz), 6.70 (1 H, d, J=7.83 Hz), 4.14-4.29 (1 H, m), 3.46-3.63 (2 H, m), 3.11-3.27 (1 H, m), 2.82 (1 H, dd, J=15.92, 2.78 Hz), 2.64 (1 H, dt, J=13.39, 8.46 Hz), 2.32 (3 H, s), 2.22-2.30 (1 H, m), 1.96-2.05 (1 H, m). Analytical HPLC: RT=12.5 min, HI: 97.5%.

Example 47

2-((2S,4S)-4-methyl-1-(4-(o-tolyloxy)phenyl)pyrrolidin-2-yl)acetic acid, TFA

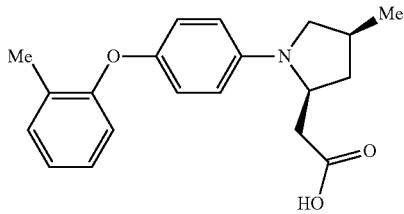

47A. ((2S,4S)-4-methyl-1-(4-(o-tolyloxy)phenyl)pyrrolidin-2-yl)methanol: 47A (colorless oil, 0.082 g, 0.28 mmol, 60% yield) was prepared from 1-(4-iodophenoxy)-2-methylbenzene and ((2S,4S)-4-methylpyrrolidin-2-yl)methanol, HCl following the procedure of 36C. LC-MS Anal. Calc'd for $C_{19}H_{23}NO_2$ 297.39. found [M+H] 298.1. $^1$H NMR (400 MHz, chloroform-d) δ ppm 7.21 (1 H, d, J=7.58 Hz), 7.09 (1 H, t, J=7.71 Hz), 6.96 (1 H, td, J=7.45, 1.26 Hz), 6.87 (2 H, d, J=9.09 Hz), 6.77 (1 H, d, J=8.08 Hz), 6.64 (2 H, d, J=8.84 Hz), 3.79-3.98 (2 H, m), 3.56-3.72 (1 H, m), 3.47 (1 H, t, J=8.72 Hz), 3.12 (1 H, t, J=8.84 Hz), 2.30 (3 H, s), 2.21-2.29 (2 H, m), 1.66-1.81 (1 H, m), 1.13 (3 H, d, J=6.06 Hz).

47B. 2-((2S,4S)-4-methyl-1-(4-(o-tolyloxy)phenyl)pyrrolidin-2-yl)acetonitrile: 47A (0.110 g, 0.369 mmol) was dissolved in THF (1.2 mL) and cooled to 0° C. Triphenylphosphine (0.145 g, 0.554 mmol) and DEAD (0.088 mL, 0.55 mmol) were added to the reaction mixture, which was stirred for 15 min. Next, acetone cyanohydrin (0.068 mL, 0.74 mmol) was added and the reaction mixture was warmed to rt and stirred overnight. The reaction mixture was concentrated and the crude material was purified via silica gel chromatography to provide 47B (colorless oil, 0.023 g, 0.074 mmol, 20% yield). LC-MS Anal. Calc'd for $C_{20}H_{22}N_2O$ 306.40. found [M+H] 307.1. $^1$H NMR (400 MHz, chloroform-d) δ ppm 7.14 (1 H, d, J=7.43 Hz), 7.02 (1 H, td, J=7.77, 1.24 Hz), 6.90 (1 H, td, J=7.43, 1.10 Hz), 6.81 (2 H, d, J=9.08 Hz), 6.69 (1 H, d, J=7.98 Hz), 6.46 (2 H, d, J=9.08 Hz), 3.98 (1 H, qd, J=7.43, 3.03 Hz), 3.39 (1 H, t, J=8.25 Hz), 3.09 (1 H, t, J=9.08 Hz), 2.69 (1 H, dd, J=16.78, 3.03 Hz), 2.44-2.52 (2 H, m), 2.23-2.30 (1 H, m), 2.22 (3 H, s), 1.61 (1 H, ddd, J=12.65, 10.18, 7.43 Hz), 1.10 (3 H, d, J=6.60 Hz).

47C (Example 47. 2-((2S,4S)-4-methyl-1-(4-(o-tolyloxy)phenyl)pyrrolidin-2-yl)acetic acid, TFA): Example 47 (white solid, 0.021 g, 0.044 mmol, 60% yield) was prepared from 47B following the procedure of 36C. LC-MS Anal. Calc'd for $C_{20}H_{23}NO_3$ 325.40. found [M+H] 326.1. $^1$H NMR (400 MHz, acetonitrile-$d_3$) δ 7.08-7.36 (4 H, m), 6.94 (2 H, d, J=8.59 Hz), 6.90 (2 H, d, J=8.08 Hz), 3.99-4.22 (1 H, m), 3.55-3.70 (1 H, m), 3.41-3.55 (1 H, m), 2.73-2.85 (1 H, m), 2.50-2.72 (3 H, m), 2.20 (3 H, s), 1.62 (1 H, ddd, J=12.38, 10.11, 9.85 Hz), 1.15 (3 H, d, J=6.57 Hz). Analytical HPLC: RT=10.6 min, HI: 90.7%.

Example 48

2-((2S,4S)-1-(4-(benzyloxy)phenyl)-4-(trifluoromethyl)pyrrolidin-2-yl)acetic acid, TFA

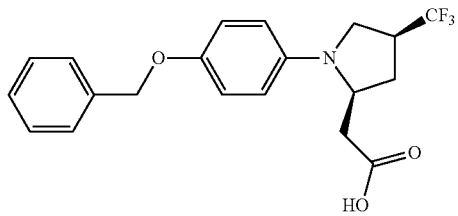

48A. ((2S,4S)-1-(4-(benzyloxy)phenyl)-4-(trifluoromethyl)pyrrolidin-2-yl)methanol: 48A (brown oil, 1.52 g, 4.32 mmol, 80% yield) was prepared from 1-(benzyloxy)-4-iodobenzene and ((2S,4S)-4-(trifluoromethyl)pyrrolidin-2-yl)methanol, HCl (40B) following the procedure of 33C. LC-MS Anal. Calc'd for $C_{19}H_{20}F_3NO_2$ 351.36. found [M+H] 352.0. $^1$H NMR (400 MHz, chloroform-d) δ ppm 7.28-7.46 (5 H, m), 6.92 (2 H, d, J=9.09 Hz), 6.70 (2 H, d, J=9.09 Hz), 5.01 (2 H, s), 3.93 (1 H, dddd, J=7.36, 4.99, 2.78 Hz), 3.79 (1 H, ddd, J=11.24, 4.42, 4.29 Hz), 3.57-3.68 (2 H, m), 3.50 (1 H, t, J=9.22 Hz), 2.86-3.05 (1 H, m), 2.23-2.43 (2 H, m), 1.58 (1 H, dd, J=7.83, 3.79 Hz).

48B. 2-((2S,4S)-1-(4-(benzyloxy)phenyl)-4-(trifluoromethyl)pyrrolidin-2-yl)acetonitrile: 48B (white solid, 1.22 g, 3.36 mmol, 78% yield) was prepared from 48A following the procedure of 33D. LC-MS Anal. Calc'd for $C_{20}H_{19}F_3N_2O$ 360.37. found [M+H] 361.0. $^1$H NMR (400 MHz, chloroform-d) δ ppm 7.28-7.47 (5 H, m), 6.94 (2 H, d, J=8.79 Hz), 6.61 (2 H, d, J=9.34 Hz), 5.02 (2 H, s), 4.10-4.22 (1 H, m, J=8.25, 8.25, 5.50, 2.75 Hz), 3.47-3.62 (2 H, m), 2.99-3.14 (1 H, m), 2.76 (1 H, dd, J=16.76, 3.02 Hz), 2.67 (1 H, ddd, J=13.74, 9.34, 7.70 Hz), 2.41 (1 H, dd, J=16.76, 9.07 Hz), 2.19 (1 H, ddd, J=13.60, 8.11, 5.77 Hz).

48C (Example 48. 2-((2S,4S)-1-(4-(benzyloxy)phenyl)-4-(trifluoromethyl)pyrrolidin-2-yl)acetic acid, TFA): Example 48 (off white solid, 0.015 g, 0.036 mmol, 58% yield) was prepared from 48B following the procedure of 36C. LC-MS Anal. Calc'd for $C_{20}H_{20}F_3NO_3$ 379.37. found [M+H] 380.0. $^1$H NMR (400 MHz, acetonitrile-$d_3$) δ ppm 7.28-7.48 (5 H, m), 6.92 (2 H, d, J=9.09 Hz), 6.70 (2 H, d, J=9.09 Hz), 5.02 (2 H, s), 4.07-4.22 (1 H, m), 3.48 (2 H, d, J=8.08 Hz), 3.06-3.27 (1 H, m), 2.75 (1 H, dd, J=15.92, 3.03 Hz), 2.59 (1 H, ddd, J=13.39, 9.35, 7.58 Hz), 2.23 (1 H, dd, J=15.79, 9.73 Hz), 1.96-2.02 (1 H, m). Analytical HPLC: RT=10.0 min, HI: 97.1%.

Example 49

2-((2S,4S)-1-(4-(4-(benzyloxy)-2-methylphenoxy)phenyl)-4-(trifluoromethyl)pyrrolidin-2-yl)acetic acid, TFA

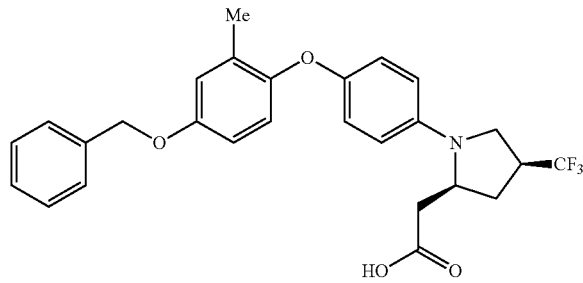

49A. 2-((2S,4S)-1-(4-hydroxyphenyl)-4-(trifluoromethyl)pyrrolidin-2-yl)acetonitrile: 2-((2S,4S)-1-(4-(benzyloxy)phenyl)-4-(trifluoromethyl)pyrrolidin-2-yl)acetonitrile (1.21 g, 3.36 mmol) was dissolved in EtOAc (56 mL). AcOH (0.39 mL, 6.7 mmol) and Pd/C (0.143 g, 0.135 mmol) were added. The reaction vessel was evacuated and purged with argon (3×) and then the vessel was evacuated and purged with $H_2$ (3×) and stirred at rt. After 3 days, additional Pd/C (0.143 g, 0.135 mmol) and a fresh balloon of $H_2$ was added to the reaction after additional purging. After stirring for an additional day, AcOH (0.39 mL, 6.7 mmol) and additional Pd/C (0.143 g, 0.135 mmol) was added with a fresh balloon of H2 after purging the reaction. After another day, additional Pd/C (0.143 g, 0.135 mmol) was added with a fresh balloon of H2 after purging the reaction. The reaction mixture was stirred at rt for 24 more hours and then the reaction mixture was filtered and concentrated. The crude product was purified by silica gel chromatography to afford 49A (white solid, 0.826 g, 3.06 mmol, 91% yield). LC-MS Anal. Calc'd for $C_{13}H_{13}F_3N_2O$ 270.25. found [M+H] 271.1. $^1$H NMR (400 MHz, chloroform-d) δ ppm 6.80 (2 H, d, J=8.59 Hz), 6.58 (2 H, d, J=8.59 Hz), 4.46 (1 H, br. s.), 4.04-4.24 (1 H, m), 3.42-3.64 (2 H, m), 2.98-3.13 (1 H, m), 2.74 (1 H, dd, J=16.80, 2.65 Hz), 2.61-2.71 (1 H, m), 2.41 (1 H, dd, J=16.80, 8.72 Hz), 2.11-2.24 (1 H, m).

49B. 2-((2S,4S)-1-(4-(4-(benzyloxy)-2-methylphenoxy)phenyl)-4-(trifluoromethyl)pyrrolidin-2-yl)acetonitrile: 49A (0.030 g, 0.11 mmol), 4-(benzyloxy)-2-methylphenylboronic acid (0.054 g, 0.22 mmol), copper (II) acetate (0.020 g, 0.11 mmol), and 4 Å molecular sieves were combined and suspended in $CH_2Cl_2$ (1.1 mL). Triethylamine (0.077 mL, 0.56 mmol) was added and the reaction was stirred under a drying tube filled with Drierite. After 3 h of stirring at rt, the reaction mixture was filtered, rinsed with $CH_2Cl_2$, and concentrated. The crude product was purified by silica gel chromatography to give 49B (pale brown oil, 0.016 g, 0.035 mmol, 32% yield). LC-MS Anal. Calc'd for $C_{27}H_{25}F_3N_2O_2$ 466.49. found [M+H] 467.1. $^1$H NMR (400 MHz, chloroform-d) δ ppm 7.29-7.48 (5 H, m), 6.71-6.94 (5 H, m), 6.59 (2 H, d, J=8.84 Hz), 5.04 (2 H, s), 4.12-4.24 (1 H, m), 3.57 (2 H, dd, J=8.34, 2.53 Hz), 3.00-3.16 (1 H, m), 2.77 (1 H, dd, J=16.93, 3.03 Hz), 2.68 (1 H, ddd, J=13.64, 8.97, 7.71 Hz), 2.44 (1 H, dd, J=16.93, 8.84 Hz), 2.21 (3 H, s), 2.15-2.27 (1 H, m).

49C (Example 49. 2-((2S,4S)-1-(4-(4-(benzyloxy)-2-methylphenoxy)phenyl)-4-(trifluoromethyl)pyrrolidin-2-yl)acetic acid, TFA): Example 49 (off white solid, 0.010 g, 0.019 mmol, 53% yield) was prepared from 49B following the procedure of 36C. LC-MS Anal. Calc'd for $C_{27}H_{26}F_3NO_4$ 485.49. found [M+H] 486.1. $^1$H NMR (400 MHz, acetonitrile-$d_3$) δ ppm 7.43-7.47 (2 H, m), 7.40 (2 H, t, J=7.43 Hz), 7.34 (1 H, d, J=7.15 Hz), 6.89-6.93 (1 H, m), 6.74-6.83 (4 H, m), 6.68 (2 H, d, J=9.08 Hz), 5.05 (2 H, s), 4.11-4.22 (1 H, m), 3.46-3.56 (2 H, m), 3.10-3.24 (1 H, m), 2.79 (1 H, dd, J=15.96, 3.03 Hz), 2.61 (1 H, ddd, J=13.48, 9.35, 7.70 Hz), 2.24 (1 H, dd, J=15.82, 9.77 Hz), 2.17 (3 H, s), 1.95-2.01 (1 H, m, J=7.98, 5.78 Hz). Analytical HPLC: RT=10.8 min, HI: 96.1%.

Example 50

2-((2S,4S)-1-(4-(4-methoxy-2-methylphenoxy)phenyl)-4-(trifluoromethyl)pyrrolidin-2-yl)acetic acid, TFA

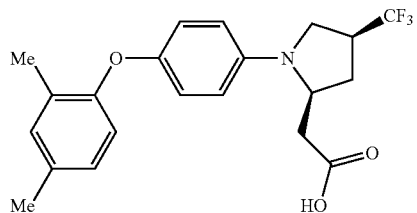

50A. 2-((2S,4S)-1-(4-(4-methoxy-2-methylphenoxy)phenyl)-4-(trifluoromethyl)pyrrolidin-2-yl)acetonitrile: 50A (colorless oil, 0.011 g, 0.028 mmol, 25% yield) was prepared from 2-((2S,4S)-1-(4-hydroxyphenyl)-4-(trifluoromethyl)pyrrolidin-2-yl)acetonitrile (49A) and 4-methoxy-2-methylphenylboronic acid following the procedure of 49B. LC-MS Anal. Calc'd for $C_{21}H_{21}F_3N_2O_2$ 390.40. found [M+H] 391.0. $^1$H NMR (400 MHz, chloroform-d) δ ppm 6.83 (2 H, d, J=8.84 Hz), 6.77-6.81 (2 H, m), 6.66-6.72 (1 H, m), 6.59 (2 H, d, J=9.09 Hz), 4.12-4.24 (1 H, m), 3.79 (3 H, s), 3.56 (2 H, dd, J=8.34, 2.27 Hz), 2.99-3.16 (1 H, m), 2.77 (1 H, dd, J=16.80, 3.16 Hz), 2.62-2.73 (1 H, m), 2.44 (1 H, dd, J=16.93, 8.84 Hz), 2.21 (3 H, s), 2.15-2.26 (1 H, m).

50B (Example 50. 2-((2S,4S)-1-(4-(4-methoxy-2-methylphenoxy)phenyl)-4-(trifluoromethyl)pyrrolidin-2-yl)acetic acid, TFA): Example 50 (brown solid, 0.006 g, 0.01 mmol, 50% yield) was prepared from 50A following the procedure of 36C. LC-MS Anal. Calc'd for $C_{21}H_{22}F_3NO_4$ 409.40. found [M+H] 410.0. $^1$H NMR (400 MHz, acetonitrile-$d_3$) δ ppm 6.84 (1 H, d, J=3.03 Hz), 6.76-6.81 (3 H, m), 6.71-6.73 (1 H, m), 6.69 (2 H, d, J=9.35 Hz), 4.12-4.23 (1 H, m), 3.75 (3 H, s), 3.46-3.57 (2 H, m), 3.11-3.24 (1 H, m), 2.79 (1 H, dd, J=15.96, 3.03 Hz), 2.61 (1 H, ddd, J=13.48, 9.35, 7.70 Hz), 2.25 (1 H, dd, J=15.96, 9.90 Hz), 2.17 (3 H, s), 1.95-2.01 (1 H, m). Analytical HPLC: RT=10.3 min, HI: 98.1%.

Example 51

2-((2S,4S)-1-(4-(2,6-dimethylphenoxy)phenyl)-4-(trifluoromethyl)pyrrolidin-2-yl)acetic acid, TFA

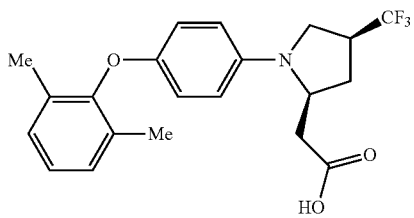

51A. 2-((2S,4S)-1-(4-(2,6-dimethylphenoxy)phenyl)-4-(trifluoromethyl)pyrrolidin-2-yl)acetonitrile: 51A (colorless oil, 0.001 g, 3 mmol, 3% yield) was prepared from 2,6-dimethylphenylboronic acid and 2-((2S,4S)-1-(4-hydroxyphenyl)-4-(trifluoromethyl)pyrrolidin-2-yl)acetonitrile (49A) following the procedure of 49B. LC-MS Anal. Calc'd for $C_{21}H_{21}F_3N_2O$ 374.40. found [M+H] 375.1. $^1$H NMR (400 MHz, chloroform-d) δ ppm 7.00-7.13 (3 H, m), 6.71 (2 H, d, J=8.84 Hz), 6.56 (2 H, d, J=8.84 Hz), 4.07-4.21 (1 H, m), 3.47-3.61 (2 H, m), 2.96-3.14 (1 H, m), 2.76 (1 H, dd, J=16.80, 3.16 Hz), 2.66 (1 H, ddd, J=13.71, 9.03, 7.83 Hz), 2.42 (1 H, dd, J=16.93, 8.84 Hz), 2.19 (1 H, ddd, J=13.77, 7.96, 5.81 Hz), 2.13 (6 H, s).

51B (Example 51. 2-((2S,4S)-1-(4-(2,6-dimethylphenoxy)phenyl)-4-(trifluoromethyl)pyrrolidin-2-yl)acetic acid, TFA): Example 51 (colorless oil, 0.001 g, 2 mmol, 92% yield) was prepared from 51A following the procedure of 36C. LC-MS Anal. Calc'd for $C_{21}H_{22}F_3NO_3$ 393.40. found [M+H] 394.0. $^1$H NMR (400 MHz, acetonitrile-$d_3$) δ ppm 7.10-7.16 (2 H, m), 7.02-7.09 (1 H, m), 6.66 (4 H, s), 4.08-4.21 (1 H, m), 3.44-3.54 (2 H, m), 3.08-3.24 (1 H, m), 2.77 (1 H, dd, J=15.79, 2.91 Hz), 2.54-2.66 (1 H, m), 2.23 (1 H, dd, J=15.79, 9.73 Hz), 2.13 (6 H, s), 1.96-1.99 (1 H, m). Analytical HPLC: RT=10.8 min, HI: 98.3%.

Example 52

2-((2S,4S)-4-(trifluoromethyl)-1-(4-(2-(trifluoromethyl)phenoxy)phenyl)pyrrolidin-2-yl)acetic acid, TFA

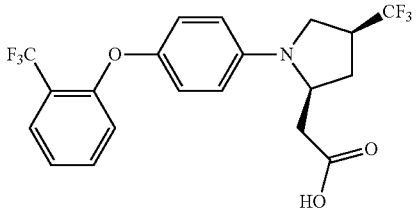

52A. 2-((2S,4S)-4-(trifluoromethyl)-1-(4-(2-(trifluoromethyl)phenoxy)phenyl)pyrrolidin-2-yl)acetonitrile: 52A (colorless oil, 0.002 g, 6 mmol, 5% yield) was prepared from 2-((2S,4S)-1-(4-hydroxyphenyl)-4-(trifluoromethyl)pyrrolidin-2-yl)acetonitrile (49A) and 2-(trifluoromethyl)phenylboronic acid following the procedure of 49B. LC-MS Anal. Calc'd for $C_{20}H_{16}F_6N_2O$ 414.34. found [M+H] 415.0. $^1$H NMR (400 MHz, chloroform-d) δ ppm 7.65 (1 H, d, J=7.83 Hz), 7.41 (1 H, t, J=8.08 Hz), 7.11 (1 H, t, J=7.58 Hz), 7.02 (2 H, d, J=8.84 Hz), 6.85 (1 H, d, J=8.34 Hz), 6.64 (2 H, d, J=8.84 Hz), 4.16-4.31 (1 H, m), 3.62 (2 H, d, J=8.34 Hz), 3.00-3.20 (1 H, m), 2.80 (1 H, dd, J=16.93, 3.03 Hz), 2.71 (1 H, ddd, J=13.77, 8.97, 7.58 Hz), 2.51 (1 H, dd, J=16.93, 8.59 Hz), 2.24 (1 H, ddd, J=13.83, 8.15, 5.56 Hz).

52B (Example 52. 2-((2S,4S)-4-(trifluoromethyl)-1-(4-(2-(trifluoromethyl)phenoxy)phenyl)pyrrolidin-2-yl)acetic acid, TFA): Example 52 (pale blue solid, 0.001 g, 2 μmol, 38% yield) was prepared from 52A following the procedure of 36C. LC-MS Anal. Calc'd for $C_{20}H_{17}F_6NO_3$ 433.34. found [M+H] 434.0. $^1$H NMR (400 MHz, acetonitrile-$d_3$) δ ppm 7.70 (1 H, d, J=7.33 Hz), 7.51 (1 H, t, J=7.58 Hz), 7.18 (1 H, t, J=7.58 Hz), 6.98 (2 H, d, J=8.84 Hz), 6.87 (1 H, d, J=8.34 Hz), 6.73 (2 H, d, J=9.10 Hz), 4.17-4.34 (1 H, m), 3.60 (1 H, t, J=9.35 Hz), 3.46-3.55 (1 H, m), 3.10-3.26 (1 H, m), 2.84 (1 H, dd, J=15.92, 2.78 Hz), 2.64 (1 H, ddd, J=13.64, 9.09, 7.83 Hz), 2.27 (1 H, dd, J=15.79, 9.98 Hz), 2.02 (1 H, ddd, J=13.64, 8.08, 6.06 Hz). Analytical HPLC: RT=10.4 min, HI: 97.3%.

Example 53

2-((2S,4S)-1-(4-(2-(trifluoromethoxy)benzyloxy)phenyl)-4-(trifluoromethyl)pyrrolidin-2-yl)acetic acid, TFA

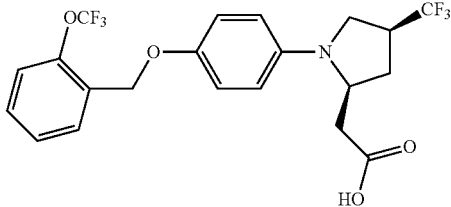

53A. 2-((2S,4S)-1-(4-(2-(trifluoromethoxy)benzyloxy)phenyl)-4-(trifluoromethyl)pyrrolidin-2-yl)acetonitrile: 53A (0.027 g, 0.060 mmol, 65% yield) was prepared from 1-(bromomethyl)-2-(trifluoromethoxy)benzene and 2-((2S,4S)-1-(4-hydroxyphenyl)-4-(trifluoromethyl)pyrrolidin-2-yl)acetonitrile (49A) according to the procedure of 13B. LC-MS Anal. Calc'd for $C_{21}H_{18}F_6N_2O_2$ 444.37. found [M+H] 445.0. $^1$H NMR (400 MHz, chloroform-d) δ ppm 7.60 (1 H, d, J=7.07 Hz), 7.27-7.41 (3 H, m), 6.94 (2 H, d, J=8.84 Hz), 6.62 (2 H, d, J=8.84 Hz), 5.10 (2 H, s), 4.11-4.22 (1 H, m), 3.47-3.63 (2 H, m), 2.98-3.16 (1 H, m), 2.76 (1 H, dd, J=16.80, 3.16 Hz), 2.67 (1 H, dt, J=13.71, 8.43 Hz), 2.42 (1 H, dd, J=16.93, 8.84 Hz), 2.19 (1 H, ddd, J=13.58, 7.89, 5.81 Hz).

53B (Example 53. 2-((2S,4S)-1-(4-(2-(trifluoromethoxy)benzyloxy)phenyl)-4-(trifluoromethyl)pyrrolidin-2-yl)acetic acid, TFA): Example 53 (0.015 g, 0.029 mmol, 49% yield) was prepared from 53A following the procedure of 36C. LC-MS Anal. Calc'd for $C_{21}H_{19}F_6NO_4$ 463.37. found [M+H] 464.0. $^1$H NMR (400 MHz, acetonitrile-$d_3$) δ ppm 7.62 (1 H, d, J=7.58 Hz), 7.31-7.51 (3 H, m), 6.93 (2 H, d, J=9.09 Hz), 6.74 (2 H, br. s.), 5.10 (2 H, s), 4.07-4.24 (1 H, m), 3.41-3.65 (2 H, m), 3.07-3.28 (1 H, m), 2.76 (1 H, dd, J=15.92, 2.78 Hz), 2.61 (1 H, ddd, J=13.33, 9.03, 7.71 Hz), 2.26 (1 H, dd, J=15.92, 9.85 Hz), 1.96-2.03 (1 H, m). Analytical HPLC: RT=10.6 min, HI: 98.2%.

Example 54

2-((2S,4S)-1-(4-(2-(difluoromethoxy)benzyloxy)phenyl)-4-(trifluoromethyl)pyrrolidin-2-yl)acetic acid, TFA

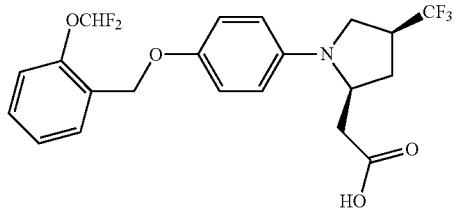

54A. methyl 2-((2S,4S)-1-(4-hydroxyphenyl)-4-(trifluoromethyl)pyrrolidin-2-yl)acetate: To a mixture of $CH_2Cl_2$ (1.2 mL) and MeOH (0.77 mL) at 0° C. was added 0.5 mL acetyl chloride. After stirring for 5 min, 1 2-((2S,4S)-1-(4-hydroxyphenyl)-4-(trifluoromethyl)pyrrolidin-2-yl)acetonitrile (49A, 0.030 g, 0.111 mmol) was added to the reaction mixture and slowly warmed to rt. After stirring for 3 h at rt, the reaction mixture was diluted with $CH_2Cl_2$ and neutralized with sat. $NaHCO_3$ (aq). The layers were separated and the product was extracted with $CH_2Cl_2$. The combined organic layers were washed with brine, dried ($MgSO_4$), and concentrated. The crude product was purified by silica gel chromatography to provide 54A (yellow oil, 0.018 g, 0.059 mmol, 53% yield). LC-MS Anal. Calc'd for $C_{14}H_{16}F_3NO_3$ 303.28. found [M+H] 304.0. $^1$H NMR (400 MHz, chloroform-d) δ ppm 6.78 (2 H, d, J=8.59 Hz), 6.59 (2 H, d, J=8.59 Hz), 4.40 (1 H, s), 4.14-4.28 (1 H, m), 3.69 (3 H, s), 3.47 (2 H, dd, J=8.34, 2.78 Hz), 2.93-3.10 (1 H, m), 2.86 (1 H, dd, J=15.54, 2.91 Hz), 2.60 (1 H, ddd, J=13.58, 9.28, 7.71 Hz), 2.22 (1 H, dd, J=15.54, 9.98 Hz), 1.96 (1 H, ddd, J=13.52, 7.83, 5.68 Hz).

54B. methyl 2-((2S,4S)-1-(4-(2-(difluoromethoxy)benzyloxy)phenyl)-4-(trifluoromethyl)pyrrolidin-2-yl)acetate: 54B (colorless oil, 0.022 g, 0.048 mmol, 81% yield) was prepared from 54A and 1-(bromomethyl)-2-(difluoromethoxy)benzene according to the procedure of 13B. LC-MS Anal. Calc'd for $C_{22}H_{22}F_5NO_4$ 459.41. found [M+H] 460.0. $^1$H NMR (400 MHz, chloroform-d) δ ppm 7.56 (1 H, d, J=7.33 Hz), 7.34 (1 H, t, J=7.20 Hz), 7.21-7.28 (1 H, m), 7.16 (1 H, d, J=8.08 Hz), 6.93 (2 H, d, J=8.84 Hz), 6.63 (2 H, d, J=8.84 Hz), 6.55 (1 H, t, J=74.28 Hz), 5.07 (2 H, s), 4.17-4.30 (1 H, m), 3.63-3.75 (3 H, m), 3.41-3.58 (2 H, m), 2.93-3.10 (1 H, m), 2.88 (1 H, dd, J=15.66, 3.03 Hz), 2.61 (1 H, ddd, J=13.39, 9.22, 7.71 Hz), 2.23 (1 H, dd, J=15.66, 10.11 Hz), 1.97 (1 H, ddd, J=13.39, 7.83, 5.56 Hz).

54C (Example 54. 2-((2S,4S)-1-(4-(2-(difluoromethoxy)benzyloxy)phenyl)-4-(trifluoromethyl)pyrrolidin-2-yl)acetic acid, TFA): 54B (0.022 g, 0.048 mmol) was dissolved THF (1 mL). A 0.4 M aqueous solution of LiOH (0.33 mL, 0.13 mmol) was added dropwise and the reaction mixture was stirred for 1 h at rt. The reaction was quenched with 1 N HCl (0.022 mL) and concentrated. The crude product was purified by RP-prep. HPLC to provide Example 54 (colorless oil, 0.0152 g, 0.032 mmol, 68% yield). LC-MS Anal. Calc'd for $C_{21}H_{20}F_5NO_4$ 445.38. found [M+H] 446.0. $^1$H NMR (400 MHz, acetonitrile-d$_3$) δ ppm 7.55 (1 H, d, J=7.58 Hz), 7.40 (1 H, t, J=7.83 Hz), 7.28 (1H, t, J=7.45 Hz), 7.21 (1 H, d, J=8.08 Hz), 6.93 (2 H, d, J=8.84 Hz), 6.73 (2 H, d, J=8.59 Hz), 6.55-7.00 (1 H, m, J=74.53, 74.53 Hz), 5.07 (2 H, s), 4.10-4.23 (1 H, m), 3.51 (2 H, d, J=8.08 Hz), 3.07-3.26 (1 H, m), 2.76 (1 H, dd, J=15.92, 2.78 Hz), 2.60 (1 H, dt, J=13.39, 8.34 Hz), 2.25 (1 H, dd, J=15.92, 9.60 Hz), 1.96-2.03 (1 H, m). Analytical HPLC: RT=10.0 min, HI: 98.4%.

Example 55

2-((2R,4S)-4-fluoro-1-(4-(2-methylphenethyl)phenyl)pyrrolidin-2-yl)acetic acid, TFA

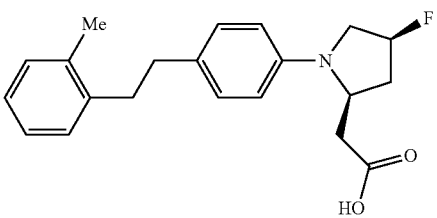

55A. 2-((2R,4S)-4-fluoro-1-(4-(2-methylphenethyl)phenyl)pyrrolidin-2-yl)acetonitrile: 2-((2R,4S)-1-(4-bromophenyl)-4-fluoropyrrolidin-2-yl)acetonitrile (43C, 0.075 g, 0.265 mmol), RuPhos (4.94 mg, 10.60 mmol), potassium (2-methylphenethyl) trifluoroborate (0.060 g, 0.265 mmol), Pd(OAc)$_2$ (1.2 mg, 5.3 mmol), and $K_2CO_3$ (0.110 g, 0.795 mmol) were combined in a microwave tube, which was sealed and purged with nitrogen (3×). Toluene (1.3 mL) and degassed water (0.13 mL) were added to the mixture. The reaction was heated (thermally) to 80° C. for 48 h. The reaction was cooled to rt, diluted with water, and the layers were separated. The aqueous layer was extracted with EtOAc (3×). The combined organic layers were dried ($MgSO_4$) and concentrated. The crude product was purified by silica gel chromatography to afford 55A (colorless oil, 0.035 g, 0.11 mmol, 41% yield). LC-MS Anal. Calc'd for $C_{21}H_{23}FN_2$ 322.42. found [M+H] 323.0. $^1$H NMR (400 MHz, chloroform-d) δ ppm 7.07-7.22 (6 H, m), 6.54 (2 H, d, J=8.59 Hz), 5.43 (1 H, dt, J=53.05, 4.04 Hz), 4.18-4.30 (1 H, m), 3.75 (1 H, ddd, J=25.01, 11.87, 1.26 Hz), 3.53 (1 H, ddd, J=36.63, 11.87, 4.04 Hz), 2.75-2.95 (4 H, m), 2.60 (1 H, dd, J=16.93, 10.61 Hz), 2.53 (1 H, dd, J=18.57, 15.03 Hz), 2.41 (1 H, ddd, J=14.72, 8.27, 4.04 Hz), 2.32 (3 H, s), 2.25-2.31 (1 H, m).

55B (Example 55. 2-((2R,4S)-4-fluoro-1-(4-(2-methylphenethyl)phenyl)pyrrolidin-2-yl)acetic acid, TFA): Example 55 (brown oil, 0.011 g, 0.024 mmol, 45% yield) was prepared from 2-((2R,4S)-4-fluoro-1-(4-(2-methylphenethyl)phenyl)pyrrolidin-2-yl)acetonitrile following the procedure of 36C. LC-MS Anal. Calc'd for $C_{21}H_{24}FNO_2$ 341.42. found [M+H] 342.0. $^1$H NMR (400 MHz, acetonitrile-d$_3$) δ ppm 7.01-7.19 (6 H, m), 6.56 (2 H, d, J=8.34 Hz), 5.39 (1 H, dt, J=54.06, 4.04 Hz), 4.12-4.27 (1 H, m), 3.56-3.71 (1 H, m, J=25.01, 11.87 Hz), 3.46 (1 H, ddd, J=36.63, 11.87, 4.04 Hz), 2.78-2.87 (2 H, m), 2.67-2.78 (2 H, m), 2.44 (1 H, dd, J=15.92, 10.61 Hz), 2.33-2.41 (1 H, m), 2.30 (3 H, s), 2.16-2.29 (2 H, m). Analytical HPLC: RT=10.7 min, HI: 95.7%.

Example 56

2-((2S,4S)-4-methoxy-1-(4-(o-tolyloxy)phenyl)pyrrolidin-2-yl)acetic acid, TFA

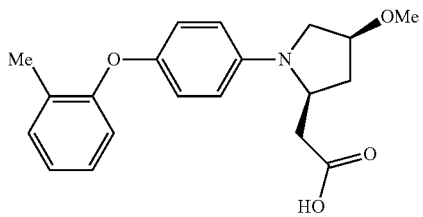

56A. (2S,4S)-tert-butyl 2-(hydroxymethyl)-4-methoxypyrrolidine-1-carboxylate: 56A (0.17 g, 0.73 mmol, 60% yield) was prepared from (2S,4S)-1-(tert-butoxycarbonyl)-4-methoxypyrrolidine-2-carboxylic acid following the procedure of 33A. LC-MS Anal. Calc'd for $C_{11}H_{21}NO_4$ 231.29. found [M+H] 332.0. $^1$H NMR (400 MHz, chloroform-d) δ ppm 4.37-4.51 (1 H, m), 3.98-4.13 (1 H, m), 3.80-3.92 (1 H, m), 3.64-3.75 (1 H, m), 3.51 (1 H, dd, J=12.09, 4.95 Hz), 3.37-3.45 (1 H, m), 3.31 (3 H, s), 2.12-2.28 (1 H, m), 1.93-2.08 (1 H, m), 1.73-1.82 (1 H, m), 1.46 (9 H, s).

56B. ((2S,4S)-4-methoxypyrrolidin-2-yl)methanol, HCl: 56B (colorless oil, 0.126 g, 0.752 mmol, 100% yield) was prepared from 56A following the procedure of 33B. LC-MS Anal. Calc'd for $C_6H_{13}NO_2$ 131.17. found [M+H] 132.0. $^1$H NMR (400 MHz, methanol-$d_4$) δ ppm 4.06-4.17 (1 H, m), 3.69-3.88 (2 H, m), 3.57-3.69 (1 H, m), 3.43 (1 H, d, J=12.38 Hz), 3.29 (3 H, s), 3.24 (1 H, dd, J=12.38, 4.29 Hz), 2.32 (1 H, ddd, J=14.34, 8.91, 5.81 Hz), 1.74-1.88 (1 H, m).

56C. ((2S,4S)-4-methoxy-1-(4-(o-tolyloxy)phenyl)pyrrolidin-2-yl)methanol: 56C (0.011 g, 0.034 mmol, 10% yield) was prepared from 1-(4-iodophenoxy)-2-methylbenzene and 56B following the procedure of 33C. LC-MS Anal. Calc'd for $C_{19}H_{23}NO_3$ 313.39. found [M+H] 314.1. $^1$H NMR (400 MHz, chloroform-d) δ ppm 7.20 (1 H, d, J=7.33 Hz), 7.08 (1 H, t, J=7.33 Hz), 6.96 (1 H, t, J=7.45 Hz), 6.88 (2 H, d, J=8.84 Hz), 6.75 (1 H, d, J=8.08 Hz), 6.63 (2 H, d, J=9.09 Hz), 4.08 (1 H, t, J=4.55 Hz), 3.88-4.02 (2 H, m), 3.61-3.73 (2 H, m), 3.41 (3 H, s), 3.32 (1 H, dd, J=10.74, 4.67 Hz), 2.75-2.92 (1 H, m), 2.30 (3 H, s), 2.16-2.29 (2 H, m).

56D. 2-((2R,4S)-4-methoxy-1-(4-(o-tolyloxy)phenyl)pyrrolidin-2-yl)acetonitrile: 56D (colorless oil, 0.007 g, 0.02 mmol, 65% yield) was prepared from 56C following the procedure of 33D. LC-MS Anal. Calc'd for $C_{20}H_{22}N_2O_2$ 322.40. found [M+H] 323.1. $^1$H NMR (400 MHz, chloroform-d) δ ppm 7.22 (1 H, d, J=7.07 Hz), 7.09 (1 H, t, J=7.33 Hz), 6.98 (1 H, t, J=7.33 Hz), 6.91 (2 H, d, J=9.09 Hz), 6.75 (1 H, d, J=8.08 Hz), 6.53 (2 H, d, J=9.10 Hz), 4.07-4.18 (2 H, m), 3.53 (1 H, d, J=10.61 Hz), 3.42 (1 H, d, J=6.32 Hz), 3.39 (3 H, s), 2.70-2.85 (2 H, m), 2.33-2.40 (1 H, m), 2.30 (3 H, s), 2.16-2.27 (1 H, m).

56E (Example 56. 2-((2S,4S)-4-methoxy-1-(4-(o-tolyloxy)phenyl)pyrrolidin-2-yl)acetic acid, TFA): Example 56 (brown oil, 0.005 g, 0.01 mmol, 51% yield) was prepared from 56D following the procedure of 36C. LC-MS Anal. Calc'd for $C_{20}H_{23}NO_4$ 341.40. found [M+H] 342.1. $^1$H NMR (400 MHz, acetonitrile-$d_3$) δ ppm 7.25 (1 H, d, J=7.33 Hz), 7.13 (1 H, t, J=7.33 Hz), 7.00 (1 H, t, J=7.20 Hz), 6.87 (2 H, d, J=8.84 Hz), 6.73 (2 H, d, J=8.08 Hz), 6.65-6.72 (1 H, m), 4.06-4.16 (2 H, m), 3.46-3.59 (1 H, m), 3.35-3.46 (1 H, m), 3.32 (3 H, s), 2.76 (1 H, d, J=15.41 Hz), 2.47-2.63 (1 H, m, J=15.92, 10.11 Hz), 2.26-2.32 (1 H, m), 2.25 (3 H, s), 2.09 (1 H, d, J=13.90 Hz). Analytical HPLC: RT=9.8 min, HI: 98.8%.

Example 57

2-((2S,4S)-4-ethyl-1-(4-(o-tolyloxy)phenyl)pyrrolidin-2-yl)acetic acid, TFA

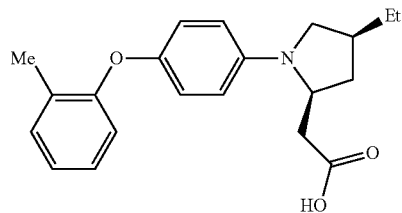

57A. (2S,4S)-1-(tert-butoxycarbonyl)-4-ethylpyrrolidine-2-carboxylic acid: To a mixture of KOtBu (0.176 g, 1.57 mmol) and (ethyl)triphenylphosphonium bromide (0.581 g, 1.57 mmol) was added THF (3.1 mL) at rt. The mixture was stirred for 1 h. Next, a solution of (S)-2-benzyl 1-tert-butyl 4-oxopyrrolidine-1,2-dicarboxylate (0.200 g, 0.581 mmol) dissolved in THF (1 mL) was added via cannula and the flask was rinsed with THF (0.5 mL). The reaction was stirred overnight at rt. The reaction was quenched with water and diluted with EtOAc. The layers were separated and the organic layer was washed with brine, dried (MgSO$_4$), and concentrated. The crude product was purified by silica gel chromatography to provide (S)-2-benzyl 1-tert-butyl 4-ethylidenepyrrolidine-1,2-dicarboxylate as a colorless oil as a mixture of E/Z isomers. The E/Z mixture was used directly in the next reaction. (S)-2-benzyl 1-tert-butyl 4-ethylidenepyrrolidine-1,2-dicarboxylate (0.0866 g, 0.261 mmol) was dissolved in EtOH (5.2 mL) and 10% Pd/C (0.092 g, 0.086 mmol) was added. The reaction was purged with argon and then H$_2$ and stirred overnight under a H$_2$ balloon. The reaction was filtered and concentrated. The crude product was purified by silica gel chromatography to provide 57A (colorless oil, 0.0358 g, 0.147 mmol, 23.5% yield). LC-MS Anal. Calc'd for $C_{12}H_{21}NO_4$ 243.30. found [M+H] 244.0. $^1$H NMR (400 MHz, chloroform-d) δ ppm 4.13-4.34 (1 H, m), 3.63-3.83 (1 H, m), 2.91-3.04 (1 H, m), 2.31-2.51 (1 H, m), 1.99-2.12 (1 H, m, J=14.31, 10.18, 7.15, 7.15 Hz), 1.54-1.82 (1 H, m), 1.33-1.51 (11 H, m), 0.91 (3 H, t, J=7.02 Hz).

57B. (2S,4S)-tert-butyl 4-ethyl-2-(hydroxymethyl)pyrrolidine-1-carboxylate: 57B (colorless oil, 0.0641 g, 0.280 mmol, 67% yield) was prepared from 57A following the procedure of 33A. LC-MS Anal. Calc'd for $C_{12}H_{23}NO_3$ 229.32. found [M+H] 230.0. $^1$H NMR (400 MHz, chloroform-d) δ ppm 5.19-5.42 (1 H, m), 3.83-4.02 (1 H, m), 3.47-3.77 (3 H, m), 2.79 (1 H, t, J=10.48 Hz), 2.10-2.25 (1 H, m), 1.85-2.04 (1 H, m), 1.47 (9 H, s), 1.28-1.43 (2 H, m), 0.92 (3 H, t, J=7.45 Hz).

57C. ((2S,4S)-4-ethylpyrrolidin-2-yl)methanol, HCl: 57C (colorless oil, 0.048 g, 0.29 mmol, 100% yield) was isolated from 57B following the procedure of 33B. LC-MS Anal. Calc'd for $C_7H_{15}NO$ 129.20. found [M+H] 130.1. $^1$H NMR (400 MHz, methanol-$d_4$) δ ppm 3.83 (1 H, dd, J=11.62, 3.28 Hz), 3.56-3.80 (3 H, m), 3.43 (1 H, dd, J=11.24, 8.21 Hz), 2.85 (1 H, t, J=10.36 Hz), 2.20-2.37 (1 H, m), 2.25 (1 H, dd, J=12.88, 6.32 Hz), 1.34-1.61 (3 H, m), 0.98 (3 H, t, J=7.45 Hz).

57D. ((2S,4S)-4-ethyl-1-(4-(o-tolyloxy)phenyl)pyrrolidin-2-yl)methanol: 57D (colorless oil, 0.068 g, 0.22 mmol, 76% yield) was prepared from 1-(4-iodophenoxy)-2-methylbenzene and 57C following the procedure of 33C. LC-MS Anal. Calc'd for $C_{20}H_{25}NO_2$ 311.42. found [M+H] 312.1. $^1$H NMR (400 MHz, chloroform-d) δ ppm 7.21 (1 H, d, J=7.07 Hz), 7.09 (1 H, t, J=7.71 Hz), 6.96 (1 H, t, J=7.33 Hz), 6.87 (2 H, d, J=8.84 Hz), 6.77 (1 H, d, J=8.34 Hz), 6.65 (2 H, d, J=8.84 Hz), 3.78-3.97 (2 H, m), 3.57-3.73 (2 H, m), 3.49 (1 H, t, J=8.59 Hz), 3.15 (1 H, t, J=9.09 Hz), 2.30 (3 H, s), 2.22-2.30 (1 H, m), 2.00-2.17 (1 H, m), 1.70-1.84 (1 H, m), 1.44-1.59 (2 H, m), 0.97 (3 H, t, J=7.45 Hz).

57E. 2-((2S,4S)-4-ethyl-1-(4-(o-tolyloxy)phenyl)pyrrolidin-2-yl)acetonitrile: 57E (colorless oil, 0.008 g, 0.02 mmol, 24% yield) was prepared from 57D following the procedure of 33D. LC-MS Anal. Calc'd for $C_{21}H_{24}N_2O$ 320.43. found [M+H] 321.1. $^1$H NMR (400 MHz, chloroform-d) δ ppm 7.22 (1 H, d, J=7.33 Hz), 7.10 (1 H, t, J=7.20 Hz), 6.98 (1 H, t, J=7.20 Hz), 6.89 (2 H, d, J=9.09 Hz), 6.77 (1 H, d, J=8.08 Hz), 6.55 (2 H, d, J=8.84 Hz), 4.00-4.14 (1 H, m), 3.49 (1 H, t, J=8.34 Hz), 3.20 (1 H, t, J=9.09 Hz), 2.77 (1 H, dd, J=16.80, 2.91 Hz), 2.47-2.66 (2 H, m), 2.30 (3 H, s), 2.07-2.22 (1 H, m), 1.69 (1 H, ddd, J=12.57, 10.29, 7.45 Hz), 1.49-1.59 (2 H, m), 0.99 (3 H, t, J=7.33 Hz).

57F (Example 57. 2-((2S,4S)-4-ethyl-1-(4-(o-tolyloxy)phenyl)pyrrolidin-2-yl)acetic acid, TFA): Example 57 (colorless oil, 0.004 g, 9 μmol, 38% yield) was prepared from 57E following the procedure of 36C. LC-MS Anal. Calc'd for $C_{21}H_{25}NO_3$ 339.43. found [M+H] 340.1. $^1$H NMR (400 MHz, acetonitrile-$d_3$) δ ppm 7.29 (1 H, d, J=7.07 Hz), 7.18 (1 H, t, J=7.20 Hz), 7.01-7.12 (3 H, m), 6.91 (2 H, d, J=8.84 Hz), 6.84 (1 H, d, J=8.08 Hz), 4.02-4.14 (1 H, m), 3.47-3.63 (1 H, m), 3.30-3.45 (1 H, m), 2.81 (1 H, dd, J=16.30, 3.16 Hz), 2.54 (1 H, ddd, J=13.07, 6.82, 6.63 Hz), 2.44 (1 H, dd, J=16.30, 8.72 Hz), 2.35 (1 H, ddd, J=16.04, 8.21, 8.08 Hz), 2.22 (3 H, s), 1.44-1.67 (3 H, m), 0.95 (3 H, t, J=7.45 Hz). Analytical HPLC: RT=10.9 min, HI: 92.5%.

Example 58

(S)-2-(1-(4-(4-(benzyloxy)benzyl)phenyl)pyrrolidin-2-yl)acetic acid, TFA

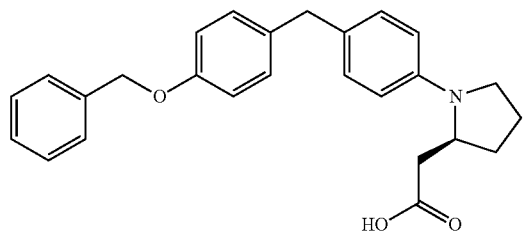

58A. (S)-2-(1-(4-(4-(benzyloxy)benzyl)phenyl)pyrrolidin-2-yl)acetonitrile: A 10 mL Schlenk flask was charged with lithium chloride (0.719 g, 17.0 mmol), which was flame dried under high vacuum. After cooling, the flask was purged with argon (3×). Zinc (1.110 g, 16.97 mmol) was added followed by THF (3 mL). 1,2-dibromoethane (0.049 mL, 0.57 mmol) was added and the reaction mixture was heated with a heat gun until ebullition occurred. After cooling to rt, TMS-Cl (0.014 mL, 0.11 mmol) was added and the reaction mixture was heated again until ebullition occurred. The reaction mixture was cooled to 0° C. and a 4 M solution of 1-(benzyloxy)-4-(chloromethyl)benzene (2.63 g, 11.3 mmol) in THF was added and the reaction mixture was warmed to rt and stirred for 3 h. It was then allowed to stand for 2 h to allow the precipitates to settle. In a separate flask, (S)-2-(1-(4-bromophenyl)pyrrolidin-2-yl)acetonitrile (20B, 1.50 g, 5.66 mmol) was dissolved in DMF (3.00 mL) and $Pd(Ph_3P)_4$ (0.327 g, 0.283 mmol) was added. The benzylzinc chloride was added to the mixture via syringe and the reaction mixture was heated to 100° C. for 1 h. The reaction mixture was cooled to rt and quenched with sat. $NaHCO_3$. The reaction mixture was diluted with EtOAc and the layers were separated. The organic layer was washed with brine, dried ($MgSO_4$), and concentrated. The crude product was redissolved in $CH_2Cl_2$ and filtered to remove some of the toluene byproduct. The material was then purified by silica gel chromatography to give an orange semisolid contaminated with an impurity as well as pure product. The impure material was redissolved in $CH_2Cl_2$, diluted with hexanes and placed in a −20° C. fridge for 48 h. The impurity crystallized into orange needles, leaving a colorless solution, which was filtered and combined with the pure fractions to provide 58A (white solid, 1.65 g, 4.30 mmol, 76% yield). LC-MS Anal. Calc'd for $C_{26}H_{26}N_2O$ 382.50. found [M+H] 383.1. $^1$H NMR (400 MHz, chloroform-d) δ ppm 7.28-7.49 (5 H, m), 7.08 (4 H, t, J=8.34 Hz), 6.89 (2 H, d, J=8.59 Hz), 6.51 (2 H, d, J=8.59 Hz), 5.03 (2 H, s), 4.00-4.12 (1 H, m), 3.83 (2 H, s), 3.43-3.58 (1 H, m), 3.19 (1 H, dd, J=16.17, 8.34 Hz), 2.69 (1 H, dd, J=16.80, 2.91 Hz), 2.41 (1 H, dd, J=16.93, 8.59 Hz), 1.99-2.29 (4 H, m).

58B (Example 58. (S)-2-(1-(4-(4-(benzyloxy)benzyl)phenyl)pyrrolidin-2-yl)acetic acid, TFA): Example 58 (colorless oil, 0.013 g, 0.023 mmol, 47% yield) was prepared from 58A following the procedure of 36C. LC-MS Anal. Calc'd for $C_{26}H_{27}NO_3$ 401.50. found [M+H] 402.1. $^1$H NMR (400 MHz, acetonitrile-$d_3$) δ ppm 7.28-7.49 (5 H, m), 7.12 (4 H, t, J=8.59 Hz), 6.90 (2 H, d, J=8.59 Hz), 6.81 (2 H, d, J=8.59 Hz), 5.05 (2 H, s), 4.06 (1 H, dq, J=12.85, 3.80 Hz), 3.82 (2 H, s), 3.47-3.62 (1 H, m), 3.23 (1 H, q, J=8.59 Hz), 2.67 (1 H, dd, J=15.92, 3.28 Hz), 2.36 (1 H, dd, J=16.04, 9.22 Hz), 2.18 (1 H, ddd, J=12.25, 8.08, 7.96 Hz), 2.01-2.13 (2 H, m), 1.84-1.93 (1 H, m). Analytical HPLC: RT=11.1 min, HI: 93.1%.

Example 59

2-((2S,4S)-1-(4-(2-chloro-4-(trifluoromethyl)phenoxy)phenyl)-4-(trifluoromethyl)pyrrolidin-2-yl)acetic acid

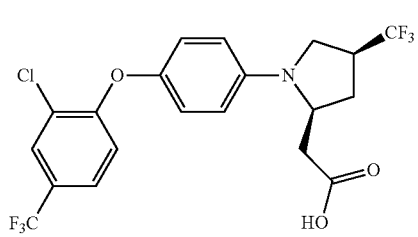

2-((2S,4S)-1-(4-hydroxyphenyl)-4-(trifluoromethyl)pyrrolidin-2-yl)acetonitrile (49A, 0.020 g, 0.074 mmol) and 2-chloro-1-fluoro-4-(trifluoromethyl)benzene (0.029 g, 0.15 mmol) were dissolved in DMF (0.8 mL) and cesium carbonate (0.060 g, 0.19 mmol) was added. The mixture was heated to 110° C. for 2 h. The reaction was cooled to rt and diluted with water and EtOAc. The layers were separated and the aqueous layer was extracted with EtOAc (2×). The combined organic layers were washed with water (2×), brine, dried (MgSO$_4$) and concentrated. The crude product was purified by silica gel chromatography to provide (S)-2-(1-(4-(2-chloro-4-(trifluoromethyl)phenoxy)phenyl)-4-(trifluoromethyl)pyrrolidin-2-yl)acetonitrile (0.029 g, 0.065 mmol, 87% yield) as an inseparable mixture of diastereomers which was taken on to the next step. Example 59 (off white solid, 0.002 g, 5 μmol, 15% yield) was prepared from (S)-2-(1-(4-(2-chloro-4-(trifluoromethyl)phenoxy)phenyl)-4-(trifluoromethyl)pyrrolidin-2-yl)acetonitrile following the procedure of 36C. LC-MS Anal. Calc'd for C$_{20}$H$_{16}$ClF$_6$NO$_3$ 467.79. found [M+H] 468.0. $^1$H NMR (400 MHz, acetonitrile-d$_3$) δ ppm 7.78-7.86 (1 H, m), 7.51 (1 H, d, J=8.59 Hz), 7.01 (2 H, d, J=8.84 Hz), 6.89 (1 H, d, J=8.59 Hz), 6.75 (2 H, d, J=9.09 Hz), 4.21-4.33 (1 H, m), 3.62 (1 H, t, J=9.35 Hz), 3.48-3.56 (1 H, m), 3.12-3.28 (1 H, m), 2.85 (1 H, dd, J=15.92, 2.78 Hz), 2.65 (1 H, dt, J=13.64, 8.59 Hz), 2.28 (1 H, dd, J=15.92, 9.85 Hz), 2.02 (1 H, ddd, J=13.58, 7.89, 5.81 Hz). Analytical HPLC: RT=11.2 min, HI: 99.0%.

Example 60

2-((2S,4S)-1-(4-(2-(trifluoromethoxy)phenoxy)phenyl)-4-(trifluoromethyl)pyrrolidin-2-yl)acetic acid, TFA

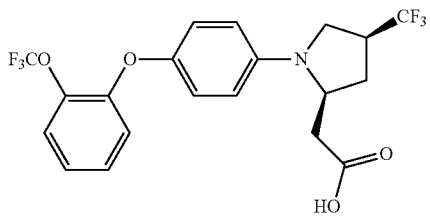

60A. 1-(4-iodophenoxy)-2-(trifluoromethoxy)benzene: 60A (colorless oil, 0.836 g, 2.20 mmol, 70% yield) was prepared from 2-(trifluoromethoxy)phenol and 4-iodophenylboronic acid following the procedure of 45A. $^1$H NMR (400 MHz, chloroform-d) δ ppm 7.62 (2 H, d, J=8.84 Hz), 7.35 (1 H, d, J=7.83 Hz), 7.21-7.29 (1 H, m), 7.16 (1 H, td, J=8.08, 1.26 Hz), 7.02 (1 H, d, J=8.08 Hz), 6.75 (2 H, d, J=8.84 Hz).

60B. ((2S,4S)-1-(4-(2-(trifluoromethoxy)phenoxy)phenyl)-4-(trifluoromethyl)pyrrolidin-2-yl)methanol: 60B (yellow oil, 0.034 g, 0.082 mmol, 29% yield) was prepared from 60A following the procedure of 33C. LC-MS Anal. Calc'd for C$_{19}$H$_{17}$F$_6$NO$_3$ 421.33. found [M+H] 422.0. $^1$H NMR (400 MHz, chloroform-d) δ ppm 7.31 (1 H, d, J=7.83 Hz), 7.13-7.22 (1 H, m), 7.00-7.08 (1 H, m), 6.96 (2 H, d, J=8.84 Hz), 6.88 (1 H, dd, J=8.08, 1.26 Hz), 6.70 (2 H, d, J=8.84 Hz), 3.96-4.07 (1 H, m), 3.79-3.88 (1 H, m), 3.70 (1 H, ddd, J=10.99, 7.71, 2.78 Hz), 3.54-3.66 (2 H, m), 2.89-3.10 (1 H, m), 2.43 (1 H, dt, J=13.20, 8.18 Hz), 2.32 (1 H, ddd, J=13.14, 9.60, 7.07 Hz).

60C. 2-((2S,4S)-1-(4-(2-(trifluoromethoxy)phenoxy)phenyl)-4-(trifluoromethyl)pyrrolidin-2-yl)acetonitrile: 60C (colorless oil, 0.034 g, 0.079 mmol, 96% yield) was prepared from 60B following the procedure of 33D. LC-MS Anal. Calc'd for C$_{20}$H$_{16}$F$_6$N$_2$O$_2$ 430.34. found [M+H] 431.0. $^1$H NMR (400 MHz, chloroform-d) δ ppm 7.32 (1 H, d, J=8.08 Hz), 7.14-7.22 (1 H, m), 7.06 (1 H, td, J=8.08, 1.52 Hz), 6.99 (2 H, d, J=9.09 Hz), 6.89 (1 H, d, J=8.34 Hz), 6.63 (2 H, d, J=9.09 Hz), 4.17-4.30 (1 H, m), 3.61 (2 H, d, J=8.34 Hz), 3.00-3.19 (1 H, m), 2.80 (1 H, dd, J=16.93, 3.03 Hz), 2.70 (1 H, dt, J=13.64, 8.46 Hz), 2.50 (1 H, dd, J=16.93, 8.59 Hz), 2.24 (1 H, ddd, J=13.77, 8.08, 5.68 Hz).

60D (Example 60. 2-((2S,4S)-1-(4-(2-(trifluoromethoxy)phenoxy)phenyl)-4-(trifluoromethyl)pyrrolidin-2-yl)acetic acid, TFA): Example 60 (brown oil, 0.012 g, 0.025 mmol, 32% yield) was prepared from 60C following the procedure of 36C. LC-MS Anal. Calc'd for C$_{20}$H$_{17}$F$_6$NO$_4$ 449.34. found [M+H] 450.1. $^1$H NMR (400 MHz, acetonitrile-d$_3$) δ ppm 7.39 (1 H, dd, J=8.21, 1.39 Hz), 7.24-7.32 (1 H, m), 7.08-7.17 (1 H, m), 6.95 (2 H, d, J=9.09 Hz), 6.88-6.96 (1 H, m), 6.69-6.76 (2 H, m), 4.19-4.29 (1 H, m), 3.55-3.62 (1 H, m), 3.47-3.55 (1 H, m), 3.11-3.28 (1 H, m), 2.83 (1 H, dd, J=15.92, 2.78 Hz), 2.56-2.69 (1 H, m), 2.27 (1 H, dd, J=15.92, 9.85 Hz), 1.97-2.05 (1 H, m). Analytical HPLC: RT=10.49 min, HI: 87.8%.

Example 61

(S)-2-(1-(4-(2-(trifluoromethylthio)benzyloxy)phenyl)pyrrolidin-2-yl)acetic acid

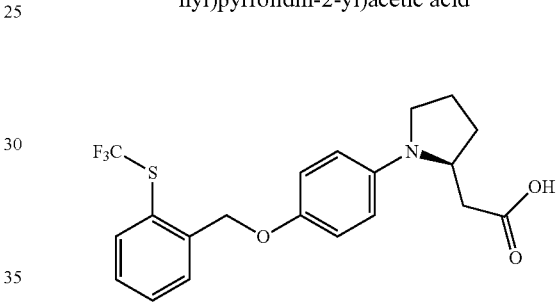

61A. (S)-ethyl 2-(1-(4-(2-(trifluoromethylthio)benzyloxy)phenyl)pyrrolidin-2-yl)acetate: A solution of (S)-ethyl 2-(1-(4-hydroxyphenyl)pyrrolidin-2-yl)acetate (13A, 25.0 mg, 0.10 mmol) and (2-(bromomethyl)phenyl)(trifluoromethyl)sulfane (27.0 mg, 0.10 mmol) in DMF (1.0 mL) was stirred with K$_2$CO$_3$ (42.0 mg, 0.301 mmol) at ambient temperature for 2 h and then at 80° C. for 4 h. The reaction mixture was allowed to cool to room temperature and was diluted with EtOAc. The organic layer was washed with water and sat'd NaCl solution (aq), dried with MgSO$_4$ and filtered, and concentrated in vacuo. Purification via silica gel chromatography (pretreated with 2% triethylamine/hexanes) gave 61A (clear colorless oil, 12 mg, 0.024 mmol, 23.8% yield). LC-MS Anal. Calc'd for C$_{22}$H$_{24}$F$_3$NO$_3$S: 439.49. found [M+H] 440.0.

61B (Example 61. (S)-2-(1-(4-(2-(trifluoromethylthio)benzyloxy)phenyl)pyrrolidin-2-yl)acetic acid): To a solution of 61B (11.9 mg, 0.027 mmol) in dioxane (0.06 mL) and methanol (0.06 mL) was added 2N NaOH (0.16 mL, 0.325 mmol). The reaction mixture was stirred at room temperature for 1 h. 1N HCl was added to pH~2-3 and the mixture was stored in the freezer in EtOAc overnight. The mixture was extracted with EtOAc, washed with brine, dried and concentrated. The residue was purified via RP prep HPLC. The product containing fraction was evaporated to dryness to give Example 61 (clear colorless oil, 3.8 mg, 0.009 mmol, 32.4% yield). LC-MS Anal. Calc'd for C$_{20}$H$_{20}$F$_3$NO$_3$S: 411.44. found [M+H] 411.9. $^1$H NMR (400 MHz, chloroform-d) δ ppm 7.77 (1 H, d, J=7.7 Hz), 7.60-7.67 (1 H, m), 7.57 (1 H, t, J=7.70 Hz), 7.57 (1 H, t, J=7.7 Hz), 7.40-7.50 (3 H, m), 7.08 (2 H, d, J=8.80 Hz), 5.32 (2 H, s), 3.90-4.22 (2 H, m), 3.36-

3.53 (1 H, m), 2.88-3.05 (1 H, m), 2.78-2.88 (1 H, m), 2.48-2.65 (1 H, m), 2.20-2.43 (2 H, m), 2.06-2.22 (1 H, m). Analytical HPLC: RT=7.08 min, HI: 95%.

Example 62

(S)-2-(1-(4-(2,3-dichlorobenzyloxy)phenyl)pyrrolidin-2-yl)acetic acid

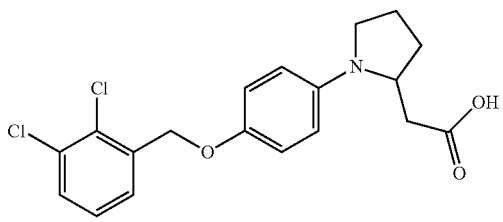

62A. (S)-ethyl 2-(1-(4-(2,3-dichlorobenzyloxy)phenyl)pyrrolidin-2-yl)acetate: 62A (clear colorless oil, 18 mg, 0.04 mmol, 39.6% yield) was prepared according to the procedure of 61A. LC-MS Anal. Calc'd for $C_{21}H_{23}Cl_2NO_3S$: 408.32. found [M+H] 409.8.

62B (Example 62. (S)-2-(1-(4-(2,3-dichlorobenzyloxy)phenyl)pyrrolidin-2-yl)acetic acid): Example 62 (clear colorless oil, 17.8 mg, 0.046 mmol, 105% yield) was prepared according to the procedure of 61B. LC-MS Anal. Calc'd for $C_{19}H_{19}Cl_2NO_3$: 380.27. found [M+H] 380.0. $^1$H NMR (400 MHz, chloroform-d) δ ppm 9.79 (1 H, br. s.), 7.37-7.53 (4 H, m), 7.27 (2 H, d, J=7.70 Hz), 7.06 (2 H, d, J=8.80 Hz), 5.18 (2 H, s), 3.94-4.17 (1 H, m), 3.33-3.55 (1 H, m), 2.85-2.98 (1 H, m), 2.73-2.85 (1 H, m), 2.48-2.72 (1 H, m), 2.19-2.40 (2 H, m), 1.99-2.19 (1 H, m). Analytical HPLC: RT=7.00 min, HI: 98%.

Example 63

(S)-2-(1-(4-(3-(2-fluorophenoxy)benzyloxy)phenyl)pyrrolidin-2-yl)acetic acid

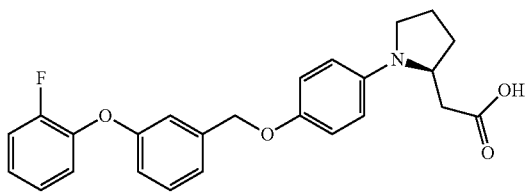

63A. (S)-ethyl 2-(1-(4-(3-(2-trifluorophenoxybenzyloxy)phenyl)pyrrolidin-2-yl)acetate: 63A (clear colorless oil, 10.7 mg, 0.020 mmol, 19.5% yield) was prepared according to the procedure of 61A. LC-MS Anal. Calc'd for $C_{27}H_{28}FNO_4$: 449.51. found [M+H] 450.0.

63B (Example 63. (S)-2-(1-(4-(3-(2-fluorophenoxy)benzyloxy)phenyl)pyrrolidin-2-yl)acetic acid): Example 63 (clear colorless oil, 10.2 mg, 0.024 mmol, 100% yield) was prepared according to the procedure of 61B. LC-MS Anal. Calc'd for $C_{25}H_{24}FNO_4$: 421.46. found [M+H] 421.9. $^1$H NMR (400 MHz, chloroform-d) δ ppm 7.46 (2 H, d, J=8.80 Hz), 7.30-7.38 (2 H, m), 7.06-7.24 (4 H, m), 7.03 (3 H, d, J=8.2 Hz), 6.93 (1 H, dd, J=8.0, 2.5 Hz), 5.05 (2 H, s), 4.13 (1 H, t, J=7.1 Hz), 3.95-4.08 (1 H, m), 3.44 (1 H, q, J=9.2 Hz), 2.90-3.03 (1 H, m), 2.82 (1 H, dd, J=17.0, 3.80 Hz), 2.52-2.65 (1 H, m), 2.22-2.40 (2 H, m), 2.08-2.21 (1 H, m). Analytical HPLC: RT=6.98 min, HI: 98%.

Example 64

(S)-2-(1-(4-(4-(methylthio)benzyloxy)phenyl)pyrrolidin-2-yl)acetic acid

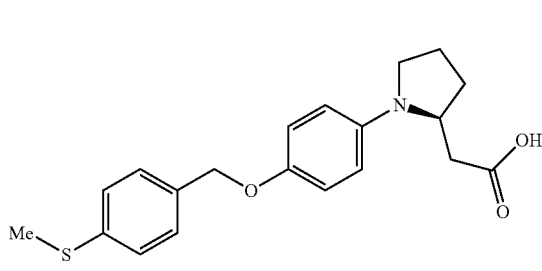

64A. (S)-ethyl 2-(1-(4-(4-(methylthio)benzyloxy)phenyl)pyrrolidin-2-yl)acetate: 64A (white solid, 4.0 mg, 0.009 mmol, 9.0% yield) was prepared according to the procedure of 61A. LC-MS Anal. Calc'd for $C_{22}H_{27}NO_3S$: 385.5. found [M+H] 386.0.

64B (Example 64. (S)-2-(1-(4-(4-(methylthio)benzyloxy)phenyl)pyrrolidin-2-yl)acetic acid): Example 64 (clear colorless oil, 5.0 mg, 0.013 mmol, 128% yield) was prepared according to the procedure of 61B. LC-MS Anal. Calc'd for $C_{20}H_{23}NO_3S$: 357.47. found [M+H] 357.9. $^1$H NMR (400 MHz, chloroform-d) δ ppm 7.42 (2 H, d, J=8.80 Hz), 7.31-7.36 (2 H, m), 7.27-7.30 (2 H, m), 7.04 (2 H, d, J=9.30 Hz), 5.03 (2 H, s), 3.90-4.16 (2 H, m), 3.32-3.48 (1 H, m), 2.87-3.00 (1 H, m), 2.75-2.87 (1 H, m), 2.52-2.63 (1 H, m), 2.50 (3 H, s), 2.17-2.40 (2 H, m), 1.99-2.19 (1 H, m). Analytical HPLC: RT=6.135 min, HI: 95%.

Example 65

(S)-2-(1-(4-(2-fluoro-3-methylbenzyloxy)phenyl)pyrrolidin-2-yl)acetic acid

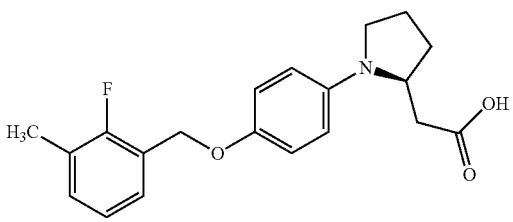

65A. (S)-ethyl 2-(1-(4-(2-fluoro-3-methylbenzyloxy)phenyl)pyrrolidin-2-yl)acetate: 65A (clear colorless oil, 10.5 mg, 0.023 mmol, 22.6% yield) was prepared according to the procedure of 61A. LC-MS Anal. Calc'd for $C_{22}H_{26}FNO_3$: 371.45. found [M+H] 371.9.

65B (Example 65. (S)-2-(1-(4-(2-fluoro-3-methybenzyloxy)phenyl)pyrrolidin-2-yl)acetic acid): Example 65 (beige solid, 9.4 mg, 0.027 mmol, 91% yield) was prepared according to the procedure of 61B. LC-MS Anal. Calc'd for $C_{20}H_{22}FNO_3$: 343.39. found [M+H] 344.1. $^1$H NMR (400 MHz, chloroform-d) δ ppm 8.93 (1 H, br. s.), 7.43 (2 H, d, J=8.80 Hz), 7.23-7.31 (2 H, m), 7.19 (1 H, t, J=7.40 Hz), 7.00-7.11 (2 H, m), 5.12 (2 H, s), 3.89-4.15 (2 H, m), 3.34-

3.53 (1 H, m), 2.87-2.99 (1 H, m), 2.72-2.86 (1 H, m), 2.49-2.65 (1 H, m), 2.19-2.39 (5 H, m), 2.02-2.20 (1 H, m). Analytical HPLC: RT=6.21 min, HI: 98%.

Example 66

(S)-2-(1-(4-(4-(1H-pyrazol-1-yl)benzyloxy)phenyl)pyrrolidin-2-yl)acetic acid

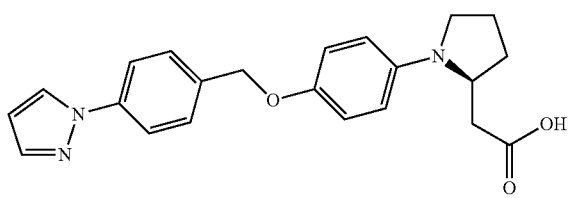

66A. (S)-ethyl 2-(1-(4-(4-(1H-pyrazol-1-yl)benzyloxy)phenyl)pyrrolidin-2-yl)acetate: 66A (white solid, 2.8 mg, 0.007 mmol, 6.9% yield) was prepared according to the procedure of 61A. LC-MS Anal. Calc'd for $C_{24}H_{27}N_3O_3$: 405.49. found [M+H] 405.9.

66B (Example 66. (S)-2-(1-(4-(4-(1H-pyrazol-1-yl)benzyloxy)phenyl)pyrrolidin-2-yl)acetic acid): Example 66 (clear colorless oil, 1.8 mg, 0.005 mmol, 67.7% yield) was prepared according to the procedure of 61B. LC-MS Anal. Calc'd for $C_{22}H_{23}N_3O_3$: 377.44. found [M+H] 377.9. $^1$H NMR (400 MHz, chloroform-d) δ ppm 7.93 (1 H, d, J=2.20 Hz), 7.80 (1 H, s), 7.65-7.73 (2 H, m), 7.46-7.55 (2 H, m), 7.13 (1 H, br. s.), 7.06 (2 H, d, J=7.7 Hz), 6.52 (2 H, s), 5.15 (2 H, s), 3.38-4.00 (4 H, m), 2.72-3.08 (2 H, m), 2.09-2.68 (3 H, m). Analytical HPLC: RT=6.98 min, HI: 98%.

Example 67

(S)-2-(1-(3-(2-chlorobenzyloxy)phenyl)pyrrolidin-2-yl)acetic acid

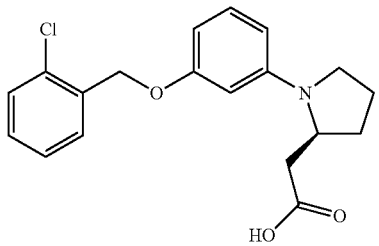

67A. (S)-2-(1-(3-hydroxyphenyl)pyrrolidin-2-yl)acetonitrile: 67A (colorless oil, 23 mg, 0.114 mmol, 33% yield) was synthesized according to the procedure of 13A. LC-MS Anal. Calc'd for $C_{12}H_{14}N_2O$: 202.11. found [M+H] 203.0. $^1$H NMR (400 MHz, chloroform-d) δ ppm 7.10 (1 H, t, J=8.2 Hz), 6.22 (1 H, d, J=8.2 Hz), 6.13-6.19 (1 H, m), 6.08 (1 H, t, J=2.5 Hz), 5.11-5.22 (1 H, m), 3.98-4.10 (1 H, m), 3.40-3.52 (1 H, m), 3.07-3.26 (1 H, m), 2.70 (1 H, dd, J=16.8, 3.0 Hz), 2.43 (1 H, dd, J=16.8, 8.5 Hz), 2.01-2.25 (4 H, m).

67B. (S)-2-(1-(3-(2-chlorobenzyloxy)phenyl)pyrrolidin-2-yl)acetonitrile: 67A (23 mg, 0.114 mmol) and $K_2CO_3$ (47.1 mg, 0.341 mmol) in DMF (0.3 mL) was added 1-(bromomethyl)-2-chlorobenzene (0.030 mL, 0.227 mmol) and the resulting mixture was stirred at 60° C. for 2 days. The reaction mixture was diluted with EtOAc, washed with water, brine, dried and concentrated. The residue was purified via silica gel chromatography to give 67B (colorless oil, 15 mg, 0.046 mmol, 40.4% yield). LC-MS Anal. Calc'd for $C_{19}H_{19}ClN_2O$: 326.12. found [M+H] 327.0.

67C (Example 67. (S)-2-(1-(3-(2-chlorobenzyloxy)phenyl)pyrrolidin-2-yl)acetic acid, TFA): To a solution of 67B (15 mg, 0.046 mmol) in EtOH (0.3 mL) was added KOH (300 mL, 1.800 mmol). The reaction mixture was stirred at 120° C. for 1 h. The reaction mixture was evaporated and redissolved in water with 0.4 ml of TFA to PH~3. The mixture was extracted with EtOAc, dried and concentrated. Purification via RP-prep. HPLC gave Example 67 (colorless foam, 13 mg, 0.027 mmol, 58.8% yield). LC-MS Anal. Calc'd for $C_{19}H_{20}ClNO_3$: 345.11. found [M+H] 346.0. $^1$H NMR (400 MHz, acetonitrile-$d_3$) δ ppm 7.47-7.64 (1 H, m), 7.36-7.48 (1 H, m), 7.25-7.36 (2 H, m), 7.10 (1 H, t, J=8.2 Hz), 6.15-6.42 (3 H, m), 5.13 (2 H, s), 3.97-4.16 (1 H, m), 3.33-3.48 (1 H, m), 2.98-3.21 (2 H, m), 2.62 (2 H, dd, J=15.7, 3.0 Hz), 2.23 (1 H, dd, J=15.4, 9.9 Hz), 1.94-2.10 (2 H, m). Analytical HPLC: RT=10.58 min, HI: 95.4%.

Example 68

2-((2S)-1-(4-(2'-fluoro-5'-methoxy-2-methylbiphenyl-3-yloxy)phenyl)pyrrolidin-2-yl)acetic acid, TFA

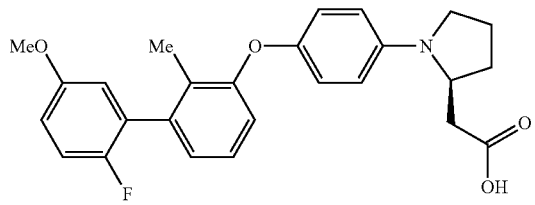

68A. 3-bromo-2-methylphenol: To a solution of 3-bromo-2-methylaniline (6 g, 32.2 mmol) in sulfuric acid (38.7 mL, 38.7 mmol) at 0° C. was added slowly of a solution of sodium nitrite (2.67 g, 38.7 mmol). After stirring at 0° C. for 15 min, sulfuric acid (13.75 mL, 258 mmol) was added and the solution was heated at 100° C. for 1 h. The mixture was diluted with water, extracted with $Et_2O$, dried and concentrated. Purification via silica gel chromatography gave 68A (light brown solid, 4.92 g, 82% yield).

68B. 1-bromo-2-methyl-3-(4-nitrophenoxy)benzene: To a solution of 68A (0.72 g, 3.85 mmol) and $Cs_2CO_3$ (2.509 g, 7.70 mmol) in DMF (5 mL) was added 1-fluoro-4-nitrobenzene (0.408 mL, 3.85 mmol). The mixture was stirred at 80° C. for 2 h. The reaction mixture was diluted with EtOAc, washed with water, brine, dried and concentrated. Purification via silica gel chromatography gave 68B (light brown solid, 0.58 g, 1.882 mmol, 48.9% yield). LC-MS Anal. Calc'd for $C_{13}H_{10}BrNO_3$: 306.98. found [M+H] 307.9. $^1$H NMR (400 MHz, chloroform-d) δ ppm 8.21 (2 H, d, J=8.8 Hz), 7.50 (1 H, d, J=7.7 Hz), 7.13 (1 H, t, J=8.0 Hz), 6.82-7.03 (3 H, m), 2.26 (3 H, s).

68C. 4-(3-bromo-2-methylphenoxy)aniline: To a solution of 68B (0.58 g, 1.882 mmol) in methanol (9 mL) and $CH_2Cl_2$ (9.00 mL) was added ammonium chloride (1.007 g, 18.82 mmol), then zinc (0.985 g, 15.06 mmol), and the mixture was stirred for 4 h. The resulting mixture was filtered through CELITE®, and was diluted with EtOAc, washed with $NaHCO_3$ (sat), dried and concentrated to give 68C (light yellow oil, 0.52 g, 1.870 mmol, 99% yield). LC-MS Anal. Calc'd for $C_{13}H_{12}BrNO$: 277.01. found [M+H] 277.9.

68D. 1-bromo-3-(4-iodophenoxy)-2-methylbenzene: To a solution of 68C (0.52 g, 1.870 mmol) in acetonitrile (8.18 mL) at ice bath was added p-toluenesulfonic acid monohydrate (0.889 g, 4.67 mmol), sodium nitrite (0.258 g, 3.74 mmol) and KI (0.931 g, 5.61 mmol) in water (2 mL). The resulting mixture was stirred overnight, and was diluted with water, $NaHCO_3$, $Na_2S_2O_3$, and was extracted with $CH_2Cl_2$. The organic layer was washed with water, dried and concentrated. Purification via silica gel chromatography gave 68D (colorless foam, 192 mg, 0.494 mmol, 26.4% yield). $^1H$ NMR (400 MHz, chloroform-d) δ ppm 7.47-7.67 (2 H, m), 7.36 (1 H, d, J=8.2 Hz), 7.01 (1 H, t, J=8.2 Hz), 6.84 (1 H, d, J=8.2 Hz), 6.64 (2 H, d, J=8.8 Hz), 2.20-2.41 (3 H, m).

68E. (S)-(1-(4-(3-bromo-2-methylphenoxy)phenyl)pyrrolidin-2-yl)methanol: To a solution of (S)-pyrrolidin-2-ylmethanol (49.9 mg, 0.494 mmol), 68D (192 mg, 0.494 mmol) and NaOH (59.2 mg, 1.481 mmol) in 2-propanol (823 µL) was added copper (I) iodide (2.350 mg, 0.012 mmol). The resulting mixture was purged with Ar, and the mixture was stirred at 120° C. for 5 min in a sealed tube, then the vessel was heated at 90° C. for 4 h. The reaction mixture was diluted with EtOAc, washed with water, brine, dried and concentrated. Purification via silica gel chromatography gave 68E (colorless oil, 65 mg, 0.179 mmol, 36.4% yield). LC-MS Anal. Calc'd for $C_{18}H_{20}BrNO_2$: 361.07. found [M+H] 361.9. $^1H$ NMR (500 MHz, chloroform-d) δ ppm 7.14-7.35 (1 H, m), 6.93 (1 H, t, J=8.2 Hz), 6.80-6.91 (2 H, m), 6.68 (3 H, t, J=9.9 Hz), 3.81 (1 H, t, J=4.9 Hz), 3.60-3.75 (2 H, m), 3.45-3.56 (1 H, m), 3.02-3.20 (1 H, m), 2.40 (3 H, s), 1.94-2.14 (4 H, m), 1.65 (1 H, t).

68F. (S)-2-(1-(4-(3-bromo-2-methylphenoxy)phenyl)pyrrolidin-2-yl)acetonitrile: To a solution of 68E (65 mg, 0.179 mmol) and TEA (0.075 mL, 0.538 mmol) in DCM (1 mL) at 0° C. was added methanesulfonyl chloride (0.021 mL, 0.269 mmol). After 5 min, the reaction mixture was warmed to rt for 30 min. The reaction mixture was diluted with $CH_2Cl_2$, washed with $NH_4Cl$ (sat), then water. The organic layer was dried and concentrated to give (S)-(1-(4-(3-bromo-2-methylphenoxy)phenyl)pyrrolidin-2-yl)methyl methanesulfonate (yellow solid, 65 mg, 0.148 mmol, 82% yield) that was used as is. To a solution of (S)-(1-(4-(3-bromo-2-methylphenoxy)phenyl)pyrrolidin-2-yl)methyl methanesulfonate (65 mg, 0.148 mmol) in DMSO (0.3 mL) was added NaCN (30 mg, 0.612 mmol). The reaction mixture was stirred at 55° C. for 4 h. The reaction mixture was diluted with EtOAc, washed with water, brine, dried and concentrated. Purification via silica gel chromatography gave 68F (colorless oil, 32 mg, 0.086 mmol, 48.0% yield). LC-MS Anal. Calc'd for $C_{19}H_{19}BrN_2O$: 370.07. found [M+H] 371.0. $^1H$ NMR (400 MHz, chloroform-d) δ ppm 7.22-7.29 (1 H, m), 6.82-7.00 (3 H, m), 6.69 (1 H, d, J=7.7 Hz), 6.55 (2 H, d, J=8.8 Hz), 4.05 (1 H, br. s.), 3.52 (1 H, d, J=8.8 Hz), 3.20 (1 H, d, J=7.1 Hz), 2.69 (1 H, dd, J=16.8, 3.0 Hz), 2.46 (1 H, dd, J=17.0, 8.2 Hz), 2.39 (3 H, s), 2.21 (2 H, ddd, J=11.1, 7.6, 3.3 Hz), 2.09 (2 H, td).

68G. 2-((2S)-1-(4-(2'-fluoro-5'-methoxy-2-methylbiphenyl-3-yloxy)phenyl)pyrrolidin-2-yl)acetonitrile: To a mixture of 68F (32 mg, 0.086 mmol), 2-fluoro-5-methoxyphenylboronic acid (29.3 mg, 0.172 mmol) and $K_3PO_4$ (45.7 mg, 0.215 mmol) in DMF (1 mL) was added $Pd(Ph_3P)_4$ (25 mg, 0.022 mmol). The reaction mixture was purged with Ar, and was heated at 100° C. for 50 min in a sealed vial. The resulting mixture was diluted with EtOAc, washed with water, brine, dried and concentrated. Purification via silica gel chromatography gave 68G (colorless oil, 8 mg, 0.019 mmol, 22.29% yield). This material was combined with the product of two other runs to give 18 mg of product. LC-MS Anal. Calc'd for $C_{26}H_{25}FN_2O_2$: 416.19. found [M+H] 417.1. $^1H$ NMR (400 MHz, chloroform-d) δ ppm 7.10-7.18 (1 H, m), 7.06 (1 H, t, J=8.8 Hz), 6.93-6.99 (3 H, m), 6.83-6.91 (1 H, m), 6.76-6.82 (2 H, m), 6.54-6.60 (2 H, m), 4.00-4.12 (1 H, m), 3.81 (3 H, s), 3.47-3.60 (1 H, m), 3.13-3.28 (1 H, m), 2.65-2.75 (1 H, m), 2.38-2.51 (1 H, m), 2.18-2.28 (2 H, m), 2.14-2.18 (3 H, m), 2.06-2.13 (2 H, m).

68H (Example 68. 2-((2S)-1-(4-(2'-fluoro-5'-methoxy-2-methylbiphenyl-3-yloxy)phenyl)pyrrolidin-2-yl)acetic acid, TFA): To a solution of 68G (18 mg, 0.043 mmol) in ethanol (0.3 mL) was added KOH (300 µL, 1.800 mmol). The mixture was stirred at 120° C. for 1.5 h. Solvents were removed in vacuo, the residue was diluted with water and 0.15 mL of TFA. The resulting mixture was extracted with EtOAc, washed with brine and concentrated to give Example 68 (14.29 mg, 0.026 mmol, 60.2% yield). LC-MS Anal. Calc'd for $C_{26}H_{26}FNO_4$: 435.18. found [M+H] 436.0. $^1H$ NMR (400 MHz, acetonitrile-$d_3$) δ ppm 7.17 (1 H, t, J=8.0 Hz), 7.08 (1 H, t, J=9.1 Hz), 6.97 (1 H, d, J=7.7 Hz), 6.83-6.94 (5 H, m), 6.75-6.82 (2 H, m), 3.96-4.09 (1 H, m), 3.74 (3 H, s), 3.49-3.59 (2 H, m), 3.19-3.28 (1 H, m), 2.66 (1 H, dd, J=15.9, 3.3 Hz), 2.35 (1 H, dd, J=15.9, 9.3 Hz), 2.18 (1 H, dd, J=12.1, 8.8 Hz), 2.06 (1 H, d, J=8.2 Hz), 2.02 (3 H, s), 1.86-1.97 (2 H, m). Analytical HPLC: RT=9.66 min, HI: 100%.

Example 69

(S)-2-(1-(4-(3-methylbenzyloxy)phenyl)pyrrolidin-2-yl)acetic acid

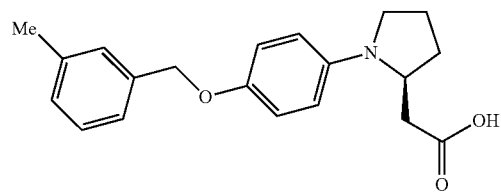

To a solution of (S)-ethyl 2-(1-(4-hydroxyphenyl)pyrrolidin-2-yl)acetate (13A, 24.93 mg, 0.10 mmol) in DMF (1 mL) was added 1-(bromomethyl)-3-methylbenzene (19.6 mg, 0.105 mmol) following with $K_2CO_3$ (28 mg, 0.200 mmol). The reaction was stirred at 80° C. for 18 h. Volatile solvents were evaporated and the residue was diluted with 1:1 methanol:dioxane (0.35 0 mL, 0.152 M). To this solution was added 1M NaOH (0.350 mL) and the reaction was stirred at rt for 18 h. Volatile solvents were evaporated and the residue was diluted in DMF (1.250 mL) and distilled water (0.250 mL) and purified using Waters Sunfire (19×100 mm, 5 nm C18, 5:95 $CH_3CN$:Water,

Example 70

2-((2S)-1-(4-((2-(5,5-dimethylcyclopent-1-enyl)-2'-fluoro-5'-methoxybiphenyl-4-yl)methoxy)phenyl)pyrrolidin-2-yl)acetic acid, TFA

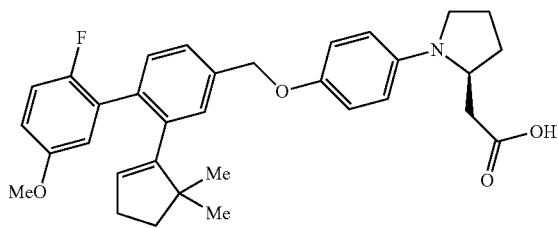

70A. 5,5-dimethylcyclopent-1-enyl trifluoromethanesulfonate: To 2,2-dimethylcyclopentanone (3.36 mL, 26.7 mmol) in THF (80 mL) at −78° C., 2M lithium diisopropylamide in THF/n-heptane (14.24 mL, 28.5 mmol) was added dropwise. The mixture was stirred at −78° C. for 1 h and N-phenyl-bis(trifluoromethanesulfonimide) (10.03 g, 28.1 mmol) in THF (16.00 mL) was added. The reaction was stirred at −78° C. for 1 h and the mixture was slowly warmed up to rt and stirred for 16 h. The reaction mixture was diluted with 200 mL hexane, washed with sat. NaHCO₃ and brine and dried and concentrated. Chromatography on silica gel (ISCO) using 0 to 25% hexane/EtOAc gradient provided 70A (colorless liquid, 1.41 g, 21.6% yield).

70B. 2-(5,5-dimethylcyclopent-1-enyl)-4,4,5,5-tetramethyl-1,3,2-dioxaborolane: A mixture of 70A (407 mg, 1.666 mmol), 4,4,4',4',5,5,5',5'-octamethyl-2,2'-bi(1,3,2-dioxaborolane) (423 mg, 1.666 mmol), bis(triphenylphosphine)palladium chloride (35.1 mg, 0.050 mmol), phosphorus triphenyl (39.3 mg, 0.150 mmol) and sodium phenate (290 mg, 2.500 mmol) in toluene (6.23 mL) was heated at 50° C. under argon for 3 h. The mixture was diluted with EtOAc, washed with H₂O, brine, dried and concentrated. Chromatography on silica gel (ISCO) using 0 to 15% hexane/EtOAc gradient provided 70B (colorless liquid, 282 mg, 76% yield).

70C. methyl 3-bromo-4-hydroxybenzoate: To 3-bromo-4-hydroxybenzoic acid (10.85 g, 50 mmol) in MeOH (60 mL), sulfuric acid (0.533 mL, 10.00 mmol) was added and the reaction was refluxed for 18 h. The reaction mixture was concentrated and diluted with EtOAc. The mixture was washed with sat. NaHCO₃, brine, dried and concentrated to give 70C (white solid, 10.4 g, 90% yield). HPLC RT=2.66 min.

70D. methyl 3-bromo-4-(tetrahydro-2H-pyran-2-yloxy)benzoate: To a solution of 70C (5.4 g, 23.37 mmol) and 3,4-dihydro-2H-pyran (6.40 mL, 70.1 mmol) in CH₂Cl₂ (50 mL) was added 4-toluenesulfonic acid monohydrate (0.089 g, 0.467 mmol). The reaction was stirred at room temperature for 1.5 h. The mixture was washed with NaHCO₃ (aq) and water and dried and concentrated. Chromatography on silica gel (ISCO) using 0 to 10% hexane/EtOAc gradient provided 70D (1.8 g, 24.4% yield). HPLC RT=3.78 min.

70E. methyl 3-(5,5-dimethylcyclopent-1-enyl)-4-(tetrahydro-2H-pyran-2-yloxy)benzoate: A stirred mixture of 70D (1022 mg, 3.24 mmol), 2-dicyclohexylphosphino-2',6'-dimethoxy-1,1'-biphenyl (333 mg, 0.810 mmol), palladium acetate (91 mg, 0.405 mmol), and potassium orthophosphate (1433 mg, 6.75 mmol) in DMF (7 mL) and water (0.350 mL) was purged with argon. 71B (600 mg, 2.70 mmol) was added and the mixture was again purged with argon. The reaction mixture was stirred at 75° C. for 22 h. The mixture was diluted with EtOAc, washed with H₂O, brine, dried and concentrated. Chromatography on silica gel (ISCO) using 0 to 10% hexane/EtOAc gradient provided 70E (colorless oil, 744 mg, 83.4% yield). HPLC RT=4.33 min. LC-MS [M+H] 331.

70F. methyl 3-(5,5-dimethylcyclopent-1-enyl)-4-hydroxybenzoate: To 70E (744 mg, 2.252 mmol) in MeOH (6 mL), pyridinium p-toluenesulfonate (56.6 mg, 0.225 mmol) was added and the reaction was stirred at 50° C. for 5 h and concentrated. Chromatography on silica gel (ISCO) using 0 to 15% hexane/EtOAc gradient provided 70F (white solid, 476 mg, 86% yield). HPLC RT=3.60 min. LC-MS [M+H] 247.

70G. methyl 3-(5,5-dimethylcyclopent-1-enyl)-4-(trifluoromethylsulfonyloxy)benzoate: To 70F (475 mg, 1.929 mmol) in CH₂Cl₂ (2.77 mL), triethylamine (0.538 mL, 3.86 mmol) and 4-dimethylaminopyridine (23.56 mg, 0.193 mmol) were added and the mixture was stirred at rt for 20 min. 1,1,1-trifluoro-N-phenyl-N-(trifluoromethylsulfonyl)methanesulfonamide (827 mg, 2.314 mmol) was added portions. The reaction was stirred at rt for 2 h. The mixture was diluted with brine, extracted with CH₂Cl₂. The combined organic extracts were dried and concentrated. Chromatography on silica gel (ISCO) using 0 to 10% hexane/EtOAc gradient provided 70G (oil, 730 mg, 100% yield). HPLC RT=4.32 min.

70H. methyl 2-(5,5-dimethylcyclopent-1-enyl)-2'-fluoro-5'-methoxybiphenyl-4-carboxylate: To a stirred solution of 70G (730 mg, 1.929 mmol) and 2-fluoro-5-methoxyphenylboronic acid (656 mg, 3.86 mmol) was added potassium carbonate (800 mg, 5.79 mmol) followed by tetrakis(triphenylphosphine)palladium(0) (223 mg, 0.193 mmol). The reaction mixture was purged with argon and heated at 90° C. for 23 h. The mixture was diluted with EtOAc, washed with H₂O, brine, dried and concentrated. Chromatography on silica gel (ISCO) using 0 to 10% hexane/EtOAc gradient provided 70G (oil, 670 mg, 97.9% yield). HPLC RT=4.26 min. LC-MS [M+H] 355.

70I. (2-(5,5-dimethylcyclopent-1-enyl)-2'-fluoro-5'-methoxybiphenyl-4-yl)methanol: To 70H (238 mg, 0.672 mmol) in THF (3 mL) at 0° C., lithium aluminum hydride (0.806 mL, 0.806 mmol) (1 M in THF) was added and the reaction was stirred at rt for 1.5 h. The mixture was cooled with ice-water, quenched with 1 N NaOH. The residue was diluted with EtOAc, washed with H₂O, brine, dried and concentrated. Chromatography on silica gel (ISCO) using 0 to 35% hexane/EtOAc gradient provided 70I (gum, 195 mg, 89% yield). HPLC RT=3.87 min. LC-MS [M−OH] 309.

70J. 4-(chloromethyl)-2-(5,5-dimethylcyclopent-1-enyl)-2'-fluoro-5'-methoxybiphenyl: To 70I (195 mg, 0.597 mmol) in CH₂Cl₂ (2.5 mL) at 0° C., thionyl chloride (0.087 mL, 1.195 mmol) was added. The reaction was stirred at rt for 1 h and concentrated. Chromatography on silica gel (ISCO) using 0 to 5% hexane/EtOAc gradient provided 70J (oil, 190 mg, 92% yield). HPLC RT=4.37 min. LC-MS [M+H] 345.

70K. 2-((2S)-1-(4-((2-(5,5-dimethylcyclopent-1-enyl)-2'-fluoro-5'-methoxybiphenyl-4-yl)methoxy)phenyl)pyrrolidin-2-yl)acetonitrile: 70K (oil, 32 mg, 0.063 mmol, 63% yield) was prepared from 70J and (S)-2-(1-(4-hydroxyphenyl)pyrrolidin-2-yl)acetonitrile (92C) following the procedure of 33D. LC-MS Anal. Calc'd for $C_{33}H_{35}FN_2O_2$ 510.64. found [M+H] 511.4. ¹H NMR (500 MHz, chloroform-d) δ ppm 7.24-7.40 (3H, m), 6.95 (3H, m), 6.79 (2H, m), 6.55 (2H, m), 5.51 (1H, s), 5.03 (2H, s), 4.02 (1H, m), 3.75 (3H, s), 3.50 (1H, m), 3.18 (1H, m), 2.67 (1H, m), 2.43 (1H, m), 2.0-2.24 (6H, m), 1.66 (2H, m), 1.26 (1H, m), 0.86 (6H, s).

70L (Example 70. 2-((2S)-1-(4-((2-(5,5-dimethylcyclopent-1-enyl)-2'-fluoro-5'-methoxybiphenyl-4-yl)methoxy)phenyl)pyrrolidin-2-yl)acetic acid, TFA): Example 70 (white solid, 16 mg, 0.025 mmol, 40% yield) was prepared from 70K following the procedure of 36C. LC-MS Anal. Calc'd for $C_{33}H_{36}FNO_4$ 529.64. found [M+H] 530.4. $^1$H NMR (500 MHz, chloroform-d) δ ppm 7.24-7.40 (5H, m), 7.08 (2H, m), 6.95 (1H, m), 6.78 (2H, m), 5.52 (1H, s), 5.10 (2H, s), 4.02 (1H, m), 3.75 (3H, s), 2.10-3.50 (10H, m), 1.66 (2H, m), 0.84 (6H, s).

Example 71

2-((2S)-1-(3-((2-(5,5-dimethylcyclopent-1-enyl)-2'-fluoro-5'-methoxybiphenyl-4-yl)methoxy)phenyl)pyrrolidin-2-yl)acetic acid, TFA

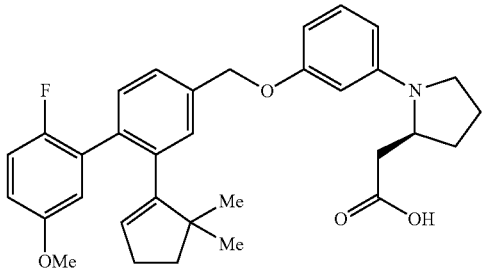

71A. 2-((2S)-1-(3-((2-(5,5-dimethylcyclopent-1-enyl)-2'-fluoro-5'-methoxybiphenyl-4-yl)methoxy)phenyl)pyrrolidin-2-yl)acetonitrile: 71A (oil, 17 mg, 0.033 mmol, 57.4% yield) was prepared from 4-(chloromethyl)-2-(5,5-dimethylcyclopent-1-enyl)-2'-fluoro-5'-methoxybiphenyl (70J) and (S)-2-(1-(3-hydroxyphenyl)pyrrolidin-2-yl)acetonitrile (75C) following the procedure of 70K. LC-MS Anal. Calc'd for $C_{33}H_{35}FN_2O_2$ 510.64. found [M+H] 511.5. $^1$H NMR (500 MHz, chloroform-d) δ ppm 7.25-7.40 (3H, m), 7.18 (1H, m), 6.95 (1H, m), 6.80 (2H, m), 6.42 (1H, m), 6.22 (2H), 5.51 (1H, s), 5.08 (2H, s), 4.06 (1H, m), 3.75 (3H, s), 3.51 (1H, m), 3.22 (1H, m), 2.67 (1H, m), 2.46 (1H, m), 2.0-2.25 (6H, m), 1.66 (2H, m), 1.26 (1H, m), 0.86 (6H, s).

71B (Example 71. 2-((2S)-1-(3-((2-(5,5-dimethylcyclopent-1-enyl)-2'-fluoro-5'-methoxybiphenyl-4-yl)methoxy)phenyl)pyrrolidin-2-yl)acetic acid, TFA): Example 71 (white solid, 16.5 mg, 0.026 mmol, 74.7% yield) was prepared following the procedure of 70L. LC-MS Anal. Calc'd for $C_{33}H_{36}FNO_4$ 529.64. found [M+H] 530.5. $^1$H NMR (500 MHz, chloroform-d) δ ppm 6.75-7.40 (10H, m), 5.51 (1H, s), 5.10 (2H, s), 4.09 (1H, m), 3.88 (1H, m), 3.75 (3H, s), 3.40 (1H, m), 2.63-2.86 (2H, m), 2.00-2.48 (6H, m), 1.66 (2H, m), 0.84 (6H, s).

Examples 72 and 73

2-((2S,4S)-1-(4-(2-fluorophenoxy)phenyl)-4-(trifluoromethyl)pyrrolidin-2-yl)acetic acid

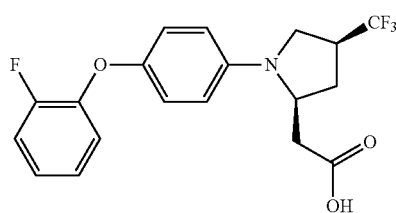

and 2-((2R,4S)-1-(4-(2-fluorophenoxy)phenyl)-4-(trifluoromethyl)pyrrolidin-2-yl)acetic acid

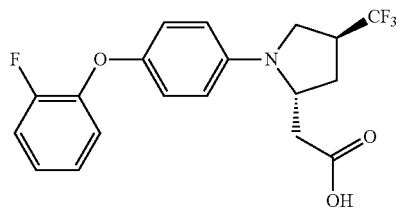

72A. 1-fluoro-2-(4-iodophenoxy)benzene: 72A (light yellow oil, 1.4 g, 4.46 mmol, 55.2% yield) was prepared from commercially available starting materials following the procedure of 45A. $^1$H NMR (400 MHz, chloroform-d) δ ppm 7.49-7.65 (2H, m), 7.01-7.21 (4H, m), 6.66-6.79 (2H, m). $^{19}$F NMR (400 MHz, chloroform-d) δ ppm 130.33.

72B. ((2S,4S)-1-(4-(2-fluorophenoxy)phenyl)-4-(trifluoromethyl)pyrrolidin-2-yl)methanol: 72B (yellow oil, 88 mg, 0.248 mmol, 63.7% yield) was prepared from 1-fluoro-2-(4-iodophenoxy)benzene and ((2S,4S)-4-(trifluoromethyl)pyrrolidin-2-yl)methanol, HCl (40B) following the procedure of 33C. LC-MS calc'd for $C_{18}H_{17}F_4NO_2$: 355.33. found [M+H]: 356.2. $^1$H NMR (400 MHz, chloroform-d) δ ppm 7.04-7.13 (1H, m), 6.92-7.01 (2H, m), 6.82-6.91 (3H, m), 6.56-6.65 (2H, m), 3.86-3.97 (1H, m), 3.71-3.79 (1H, m), 3.46-3.68 (3H, m), 2.82-2.98 (1H, m), 2.17-2.40 (2H, m).

72C. 2-((2S,4S)-1-(4-(2-fluorophenoxy)phenyl)-4-(trifluoromethyl)pyrrolidin-2-yl)acetonitrile: 72C (light yellow oil, 70 mg, 0.192 mmol, 78% yield) was prepared from 72B following the procedure of 33C. LC-MS calc'd for $C_{19}H_{16}F_4N_2O$: 364.3. found [M+H]: 364.9. $^1$H NMR (400 MHz, chloroform-d) δ ppm 7.10-7.18 (1H, m), 7.01-7.08 (2H, m), 6.88-6.98 (3H, m), 6.56-6.64 (2H, m), 4.14-4.25 (1H, m), 3.58 (2H, d, J=8.21 Hz), 2.98-3.15 (1H, m), 2.73 (1H, dd, J=16.96, 3.12 Hz), 2.63-2.72 (1H, m), 2.46 (1H, dd, J=16.84, 8.79 Hz), 2.16-2.25 (1H, m).

72D. (Example 72. 2-((2S,4S)-1-(4-(2-fluorophenoxy)phenyl)-4-(trifluoromethyl)pyrrolidin-2-yl)acetic acid and Example 73. 2-((2R,4S)-1-(4-(2-fluorophenoxy)phenyl)-4-(trifluoromethyl)pyrrolidin-2-yl)acetic acid): 72C (0.045 g, 0.124 mmol) was dissolved in isopropanol (1.5 mL) and ethanol (0.5 mL). Aqueous 6 N KOH solution (0.5 mL, 3.00 mmol) was added. The reaction was heated at 150° C. in a microwave oven for 30 min. To the reaction solution was added 6N KOH solution (0.5 mL, 3.00 mmol) and the mixture was heated at 150° C. in a microwave oven for 30 min. The reaction mixture was concentrated, and the residue was acidified to pH 2 with 1 N HCl and the product was extracted with EtOAc. The combined organic layers were dried over $MgSO_4$ and concentrated. The crude product was purified by RP-prep. HPLC to provide Example 72 (light yellow oil, 18.9 mg, 0.047 mmol, 38% yield). LC-MS calc'd for $C_{19}H_{17}F_4NO_3$: 383.3. found [M+H]: 384.0. $^1$H NMR (400 MHz, acetonitrile-$d_3$) δ ppm 7.07-7.18 (1H, m), 6.95-7.07 (2H, m), 6.78-6.92 (3H, m), 6.55-6.68 (2H, m), 4.05-4.18 (1H, m), 3.34-3.56 (2H, m), 2.98-3.17 (1H, m), 2.73 (1H, dd, J=15.91, 3.20 Hz), 2.47-2.58 (1H, m), 2.16 (1H, dd, J=15.84, 8.21 Hz), 1.87-1.95 (1H, m). Analytical HPLC: RT=10.8 min, HI: 98.2%. Also obtained was Example 73 (light yellow oil, 9.9 mg, 0.024 mmol, 19% yield). LC-MS calc'd for $C_{19}H_{17}F_4NO_3$: 383.3. found [M+H]: 384.0. $^1$H NMR (400 MHz, acetonitrile-$d_3$) δ ppm 7.09-7.17 (1H, m), 6.95-7.07 (2H, m), 6.78-6.89 (3H, m), 6.55-6.58 (2H, m), 4.12-4.23 (1H, m), 3.50 (1H, t, J=8.09 Hz), 3.18-3.35 (2H, m), 2.60 (1H, dd, J=15.98, 2.81 Hz), 2.14-2.26 (2H, m), 2.03-2.11 (1H, m). Analytical HPLC: RT=11.1 min, HI: 95.1%.

Example 74

2-((2R,4S)-4-fluoro-1-(4-(2-fluorophenoxy)phenyl) pyrrolidin-2-yl)acetic acid

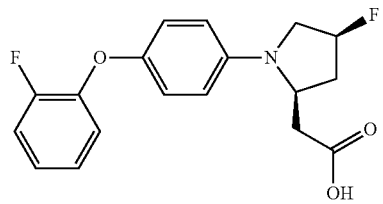

74A. ((2S,4S)-4-fluoro-1-(4-(2-fluorophenoxy)phenyl) pyrrolidin-2-yl)methanol: 74A (59 mg, 0.193 mmol, 30.1% yield) was prepared from 1-fluoro-2-(4-iodophenoxy)benzene and ((2S,4S)-4-fluoropyrrolidin-2-yl)methanol, HCl following the procedure of 33C. LC-MS calc'd for $C_{17}H_{17}F_2NO_2$: 305.32. found [M+H]: 306.1. $^1$H NMR (400 MHz, chloroform-d) δ ppm 7.15-7.45 (1H, m), 6.88-7.08 (5H, m), 6.68-6.75 (2H, m), 5.25-5.49 (1H, m), 3.66-4.09 (3H, m), 3.35-3.56 (2H, m), 2.31-2.48 (1H, m), 1.64-1.72 (1H, m).

74B. 2-((2R,4S)-4-fluoro-1-(4-(2-fluorophenoxy)phenyl) pyrrolidin-2-yl)acetonitrile: 74B (colorless oil, 30.2 mg, 0.096 mmol, 52.5% yield) was prepared from 74A following the procedure of 33D. LC-MS calc'd for $C_{18}H_{16}F_2N_2O$: 314.3. found [M+H]: 315.3. $^1$H NMR (400 MHz, chloroform-d) δ ppm 7.12-7.23 (1H, m), 6.97-7.09 (4H, m), 6.89-6.97 (1H, m), 6.54-6.63 (2H, m), 5.35-5.57 (1H, m), 4.17-4.29 (1H, m), 3.67-3.84 (1H, m), 3.46-3.64 (1H, m), 2.84-2.96 (1H, m), 2.50-2.69 (2H, m), 2.27-2.50 (1H, m).

74C (Example 74. 2-((2R,4S)-4-fluoro-1-(4-(2-fluorophenoxy)phenyl)pyrrolidin-2-yl)acetic acid): Example 74 (colorless oil, 2.48 mg, 0.0067 mmol, 21% yield) was prepared from 74B following the procedure of 36C. LC-MS calc'd for $C_{18}H_{17}F_2NO_3$: 333.3. found [M+H]: 334.0. $^1$H NMR (400 MHz, acetonitrile-$d_3$) δ ppm 7.18-7.27 (1H, m), 7.06-7.16 (2H, m), 6.92-7.01 (3H, m), 6.62-6.69 (2H, m), 5.31-5.52 (1H, m), 4.13-4.33 (1H, m), 3.55-3.74 (1H, m), 3.41-3.59 (1H, m), 2.74-2.88 (1H, m), 2.53-2.90 (2H, m), 2.20-2.52 (1H, m). Analytical HPLC: RT=9.8 min, HI: 90.1%.

Example 75

(S)-2-(1-(3-(o-tolyloxy)phenyl)pyrrolidin-2-yl)acetic acid, TFA

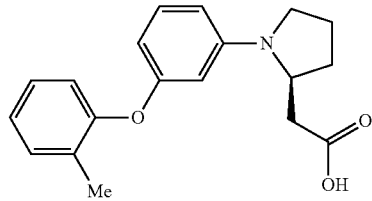

75A. (S)-(1-(3-(benzyloxy)phenyl)pyrrolidin-2-yl)methanol: 75A (colorless oil, 1.44 g, 5.08 mmol, quantitative yield) was prepared from commercial available starting materials following the procedure of 33C. LC-MS calc'd for $C_{18}H_{21}NO_2$: 283.36. found [M+H]: 284.0.

75B. (S)-2-(1-(3-(benzyloxy)phenyl)pyrrolidin-2-yl)acetonitrile: 75B (light yellow oil 1.32 g, 4.51 mmol, 44.1% yield) was prepared from 75A following the procedure of 33D. LC-MS calc'd for $C_{19}H_{20}N_2O$: 292.37. found [M+H]: 293.0. $^1$H NMR (400 MHz, chloroform-d) δ ppm 7.27-7.49 (5H, m), 7.09-7.18 (1H, t, J=8.21 Hz)), 6.35-6.46 (1H, m), 6.17-6.24 (2H, m), 3.98-4.11 (1H, m), 3.44-3.55 (1H, m), 3.16-3.27 (1H, m), 2.62-2.69 (1H, m), 2.35-2.44 (1H, m), 1.99-2.28 (4H, m).

75C. (S)-2-(1-(3-hydroxyphenyl)pyrrolidin-2-yl)acetonitrile: 75B (0.23 g, 0.787 mmol) was dissolved in MeOH (12 mL). Pd/C (10% dry basis) (0.084 g, 0.079 mmol) and acetic acid (0.090 mL, 1.573 mmol) were added. The reaction was purged with argon and it was stirred under $H_2$ balloon for 2 h. The mixture was concentrated and purified with silica gel chromatography to yield 75C (colorless viscous oil, 0.102 g, 0.503 mmol, 64% yield). LC-MS calc'd for $C_{12}H_{14}N_2O$: 202.25. found [M+H]: 203.1. $^1$H NMR (400 MHz, chloroform-d) δ ppm 7.08 (1H, t, J=8.02 Hz), 6.12-6.22 (1H, m), 6.04-6.08 (1H, m), 4.70 (1H, bs) 3.98-4.17 (1H, m), 3.44-3.55 (1H, m), 3.15-3.25 (1H, m), 2.62-2.68 (1H, m), 2.35-2.44 (1H, m), 1.99-2.29 (4H, m).

75D. (S)-2-(1-(3-(o-tolyloxy)phenyl)pyrrolidin-2-yl)acetonitrile: 75D (light yellow liquid, 33 mg, 0.113 mmol, 45% yield) was prepared from (S)-2-(1-(3-hydroxyphenyl)pyrrolidin-2-yl)acetonitrile following the procedure of 45A. LC-MS calc'd for $C_{19}H_{20}N_2O$: 292.37. found [M+H]: 293.1. $^1$H NMR (400 MHz, chloroform-d) δ ppm 7.20 (1H, d, J=8.01 Hz), 7.08-7.13 (1H, m), 6.97-7.07 (2H, m), 6.82 (1H, d, J=8.15 Hz), 6.29 (1H, dd, J=8.34, 1.81 Hz), 6.12-6.15 (1H, m), 6.02-6.06 (1H, m), 3.92-3.97 (1H, m), 3.31-3.37 (1H, m), 3.01-3.09 (1H, m), 2.43-2.60 (2H, m), 2.13 (3H, S), 2.02-2.12 (2H, m), 1.87-1.97 (2H, m).

75E (Example 75. (S)-2-(1-(3-(o-tolyloxy)phenyl)pyrrolidin-2-yl)acetic acid, TFA): Example 75 (colorless oil, 18.3 mg, 0.043 mmol, 41.5% yield) was prepared from 75D following the procedure of 36C. LC-MS calc'd for $C_{19}H_{21}NO_3$: 311.37. found [M+H]: 312.1. $^1$H NMR (500 MHz, acetonitrile-$d_3$) δ ppm 7.27 (1H, d, J=7.26 Hz), 7.17 (1H, t, J=7.76 Hz), 7.11 (1H, t, J=8.23 Hz), 7.07 (1H, t, J=7.53 Hz), 6.89 (1H, d, J=8.02 Hz), 6.30-6.36 (1H, m), 6.15-6.19 (1H, m), 6.06-6.14 (1H, m), 3.95-4.08 (1H, m), 3.29-3.38 (1H, m), 3.05-3.14 (1H, m), 2.59-2.68 (1H, m), 2.19 (3H, S), 2.20-2.37 (1H, m), 1.92-2.12 (3H, m), 1.81-1.89 (1H, m). Analytical HPLC: RT=10.7 min, HI: 100%.

Example 76

(S)-2-(1-(2-(2-methylbenzyloxy)pyridin-4-yl)pyrrolidin-2-yl)acetic acid, TFA

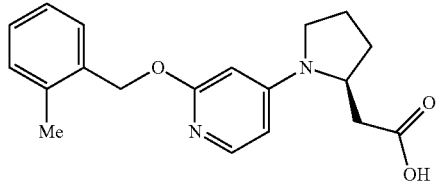

76A. (S)-(1-(2-chloropyridin-4-yl)pyrrolidin-2-yl)methanol: A mixture of (S)-pyrrolidin-2-ylmethanol (1.153 g, 11.40 mmol), 2-chloro-4-fluoropyridine (1 g, 7.60 mmol) and N-ethyl-N-isopropylpropan-2-amine (0.983 g, 7.60 mmol) was heated in the microwave oven for 10 min at 100° C. The thick mixture was dissolved in $CH_2Cl_2$, which was washed with aqueous 1N HCl, $NaHCO_3$ solution and brine. The combined aqueous solution was adjusted to pH ~8, then it was extracted 3× with $CH_2Cl_2$. The combined organic extracts were dried over $MgSO_4$ and concentrated. The residue was purified with silica gel chromatography to yield 76A (yellow oil, 1.58 g, 7.43 mmol, 98% yield). LC-MS calc'd for $C_{10}H_{13}ClN_2O$: 212.68. found [M+H]: 213.1. $^1$H NMR (400 MHz, chloroform-d) δ ppm 7.90 (1H, d, J=6.24 Hz), 6.46 (1H, d, J=2.24), 6.40 (1H, dd, J=6.24, 2.24 Hz), 3.83-3.96 (1H, m), 3.57-3.75 (2H, m), 3.41-3.52 (1H, m), 3.14-3.25 (1H, m), 1.96-2.24 (4H, m).

76B. (S)-2-(1-(2-chloropyridin-4-yl)pyrrolidin-2-yl)acetonitrile: 76B (colorless oil, 1.33 g, 6.00 mmol, 98% yield) was prepared from 76A following the procedure of 33D. LC-MS calc'd for $C_{11}H_{12}ClN_3$: 221.69. found [M+H]: 222.0. $^1$H NMR (400 MHz, chloroform-d) δ ppm 7.96 (1H, d, J=5.92 Hz), 6.35 (1H, d, J=2.12 Hz), 6.40 (1H, dd, J=6.01, 2.14 Hz), 4.01-4.11 (1H, m), 3.42-3.55 (1H, m), 3.14-3.31 (1H, m), 2.56-2.68 (1H, m), 2.41-2.56 (1H, m), 2.02-2.38 (4H, m).

76C (Example 76. (S)-2-(1-(2-(2-methylbenzyloxy)pyridin-4-yl)pyrrolidin-2-yl)acetic acid, TFA): The mixture of o-tolylmethanol (110 mg, 0.902 mmol) and sodium tert-butoxide (87 mg, 0.902 mmol) in dioxane (1 mL) was heated in a microwave oven at 150° C. for 20 min. To this solution was added 76B (100 mg, 0.451 mmol) in dioxane (1 mL) and the resulting mixture was heated in a microwave oven for 25 min at 180° C. To the resulting mixture was added aqueous 6N KOH (1 mL, 6.00 mmol) and the mixture was heated at 150° C. for 30 min in a microwave oven. The organic portion was evaporated and more KOH (1 mL, 6.00 mmol) was added, followed by ethanol (2 mL). The mixture was heated at 160° C. for 40 min in a microwave oven. The mixture was stripped and then neutralized to pH 7 first by addition of 12N HCl followed by $NaHCO_3$ solution. The aqueous solution was extracted 2× with ethyl acetate, followed by 2× of chloroform. The combined organic extracts were dried over $MgSO_4$, evaporated, and purified via silica gel chromatography. A portion of the material was re-purified by RP-prep. HPLC to yield Example 76 (colorless oil, 7.6 mg, 0.015 mmol, 3.3% yield). LC-MS calc'd for $C_{19}H_{22}N_2O_3$: 326.39. found [M+H]: 327.1. $^1$H NMR (500 MHz, acetonitrile-$d_3$) δ ppm 7.69 (1H, d, J=7.26 Hz), 7.35 (1H, d, J=7.21 Hz), 7.09-7.27 (1H, t, J=8.23 Hz), 7.07 (1H, t, J=7.53 Hz), 6.89 (1H, d, J=8.02 Hz), 6.30-6.36 (3H, m), 6.35-6.44 (1H, m), 6.02-6.11 (1H, m), 5.25 (2H, s), 4.23-4.35 (1H, m), 3.42-3.56 (1H, m), 3.22-3.37 (1H, m), 2.46-2.59 (1H, m), 2.31-2.41 (1H, m), 2.28 (3H, s), 1.89-2.13 (4H, m). Analytical HPLC: RT=5.0 min, HI: 98.8%.

Example 77

(S)-2-(1-(4-(2'-fluoro-5'-methoxybiphenyl-3-yloxy)phenyl)pyrrolidin-2-yl)acetic acid, TFA

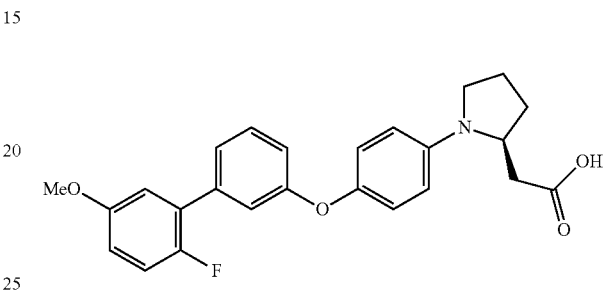

77A. (S)-2-(1-(4-(3-bromophenoxy)phenyl)pyrrolidin-2-yl)acetonitrile: To a stirred suspension of 3-bromophenylboronic acid (785 mg, 3.79 mmol), (S)-2-(1-(4-bromophenyl)pyrrolidin-2-yl)acetonitrile (20B, 382 mg, 1.889 mmol), anhydrous copper (II) acetate (343 mg, 1.851 mmol), and powdered molecular sieves (4A, <5 micron, activated, 2.06 g) in dichloromethane (9.0 mL) at rt was added triethylamine (0.53 mL, 3.78 mmol). The mixture was stirred at rt under an air atmosphere (balloon) for 48 h. At this time, the mixture was filtered through CELITE® and the filter cake was rinsed with EtOAc (120 mL). The combined filtrate and rinses were concentrated and the residue was chromatographed ($SiO_2$ 230-400 mesh, 9/1 to 4/1 Hex/EtOAc) to give contaminated diaryl ether (77.2 mg). Purification by chromatography ($SiO_2$ 230-400 mesh, 97/3 $CH_2Cl_2$/Ether) provided 77A (yellowish oil, 65.3 mg, 7.5% yield). LC-MS, [M+Na]$^+$=357, 359.

77B. (S)-2-(1-(4-(2'-fluoro-5'-methoxybiphenyl-3-yloxy)phenyl)pyrrolidin-2-yl)acetonitrile: To a stirred solution of 77A (35.2 mg, 0.075 mmol) in toluene (0.5 mL) under Ar were added a solution of 2-fluoro-5-methoxyphenylboronic acid (18 mg, 0.106 mmol) in MeOH (0.11 mL) and a solution of sodium carbonate (26 mg, 0.245 mmol) in water (0.4 mL). The mixture was degassed by ultrasound irradiation (5 min) under Ar and then dichlorobis(triphenylphosphine)-palladium(II) (4.0 mg, 5.69 µmol) was added. The resulting mixture was stirred at 95° C. for 4.0 h. After cooling to rt, the mixture was diluted with water (6 mL) and extracted with $CH_2Cl_2$ (3×20 mL). The combined organic extracts were dried ($Na_2SO_4$) and evaporated. Chromatography ($SiO_2$ 230-400 mesh, 4/1 Hex/EtOAc) of the crude afforded 77B (colorless oil, 24.9 mg, 81% yield). LC-MS, [M+H]$^+$=403.

77C. (S)-methyl 2-(1-(4-(2'-fluoro-5'-methoxybiphenyl-3-yloxy)phenyl)pyrrolidin-2-yl)acetate: 77B (19 mg, 0.047 mmol) was dissolved in 3M HCl/MeOH, MeOAc solution [6.3 mL, prepared by addition of AcCl (1.3 mL) to MeOH (5.0 mL) at 0° C. and then stirring at rt for 30 min). The resulting solution was stirred at rt for 23 h and then at 40° C. for 5.5 h. The final solution was cooled to rt and evaporated. The residue was taken up in EtOAc (50 mL) and washed with 5% $NaHCO_3$ (2×20 mL). The organic layer was dried ($Na_2SO_4$) and concentrated. Chromatography ($SiO_2$ 230-400 mesh, 9/1 to 4/1 Hex/EtOAc) of the crude provided 77C (colorless oil, 19.2 mg, 92%). LC-MS, [M+H]+=436.

77D (Example 77. (S)-2-(1-(4-(2'-fluoro-5'-methoxybiphenyl-3-yloxy)phenyl)pyrrolidin-2-yl)acetic acid, TFA): To a stirred solution of 77C (19 mg, 0.044 mmol) in THF (0.8 mL) at 0° C. was added 0.48M aqueous lithium hydroxide (0.19 mL, 0.091 mmol) dropwise. The resulting solution was stirred at 0° C. for 1.5 h and then at rt for 2.5 h. At this time, an additional amount of 0.48M aqueous lithium hydroxide (0.19 mL, 0.091 mmol) and 2-propanol (0.1 mL) were added and stirring at RT was continued for 5.0 h. The final solution was cooled to 0° C. and acidified with 1M HCl (0.23 mL). The organic solvents were mostly evaporated and the remaining aqueous mixture was injected in a Prep HPLC column (YMC-Pack ODS, 100×20 mm). Elution (CH$_3$CN—H$_2$O-TFA, solvent B % start 20, final 100; grad t 15 min; flow r 20 mL/min; wv 220 nm) of the column afforded Example 77 (yellowish oil, 20.3 mg, 87% yield). LC-MS, [M+H]E=422. $^1$H NMR (CD$_3$OD, 500 MHz): δ 7.40 (t, J=7.7 Hz, 1H), 7.24 (d, J=7.2 Hz, 1H) 7.12-6.99 (m, 6H), 6.97-6.87 (m, 3H), 4.18 (m, 1H), 3.79 (s, 3H), 3.65 (m, 1H), 3.40 (m, 1H), 2.73 (dd, J=15.4, 3.9 Hz, 1H), 2.42 (dd, J=15.9, 9.3 Hz, 1H), 2.31 (m, 1H), 2.16 (m, 2H), 1.97 (m, 1H). HPLC-(ZORBAX®, 50 Start % B): RT=6.53 min, purity=100%. Unless noted, HPLC conditions for ZORBAX® column are: ZORBAX®SB C18, 4.6×75 mm; Grad. T: 8 min; Flow R.: 2.5 mL/min.; Solvent Grad.: 0-100% B; Wave: 220 nm. (A=10% MeOH-90% H$_2$O-0.2% H$_3$PO$_4$; B=90% MeOH-10% H$_2$O –0.2% H$_3$PO$_4$).

Example 78

(S)-2-(1-(4-(3-(2-methylbenzyl)phenoxy)phenyl) pyrrolidin-2-yl)acetic acid, TFA

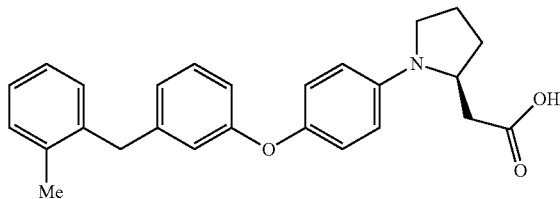

78A. (S)-2-(1-(4-(3-(2-methylbenzyl)phenoxy)phenyl) pyrrolidin-2-yl)acetonitrile: THF (1.9 mL) was added to an Ar-purged flask containing 77A (29.0 mg, 0.062 mmol) and tetrakis(triphenylphosphine)palladium (0) (7 mg, 6.05 μmol) and the mixture was stirred until a clear solution was formed. Then, 0.5M (2-methylbenzyl)zinc(II) chloride/THF (0.33 mL, 0.165 mmol) was added dropwise and the mixture was heated at 56° C. for 11 h. At this time, the reaction was quenched by addition of ice, 1M K$_2$CO$_3$ (6 mL) and EDTA (120 mg, 0.41 mmol). The aqueous mixture was extracted with CH$_2$Cl$_2$ (3×30 mL) and, the combined extract was dried (Na$_2$SO$_4$) and concentrated. Chromatography (SiO$_2$ 230-400 mesh, 9/1 Hex/EtOAc) of the crude gave 78A (yellowish oil, 26 mg, 83% yield). LC-MS, [M+H]+=429.

78B. (S)-methyl 2-(1-(4-(3-(2-methylbenzyl)phenoxy) phenyl)pyrrolidin-2-yl)acetate: Following the procedure of 77C, 78A (25 mg, 0.049 mmol) was converted to 78B (15.7 mg, 76% yield) as a colorless oil. LC-MS, [M+H]+=416.

78C (Example 78. (S)-2-(1-(4-(3-(2-methylbenzyl)phenoxy)phenyl)-pyrrolidin-2-yl)acetic acid, TFA): Following the procedure of 77D, 78B was converted to Example 78 (brownish oil, 17 mg, 95% yield). LC-MS, [M+H]+=402. $^1$H NMR (CD$_3$OD, 500 MHz): δ 7.23 (t, J=7.7 Hz, 1H), 7.20-7.06 (m, 6H), 6.99 (d, J=8.8 Hz, 2H), 6.88 (d, J=7.7 Hz, 1H), 6.77 (dd, J=8.2, 2.2 Hz, 1H), 6.70 (s, 1H), 4.18 (broad s, 1H), 3.95 (s, 2H), 3.73 (broad s, 1H), 3.49 (broad s, 1H), 2.70 (dd, J=15.9, 3.9 Hz, 1H), 2.50 (dd, J=15.9, 8.2 Hz, 1H), 2.41 (m, 1H), 2.27-2.12 (m, 2H), 2.18 (s, 3H), 1.97 (m, 1H). HPLC-(ZORBAX®, 60 Start % B): Rt 6.35 min, purity=99%.

Example 79

(S)-2-(1-(4-(3-bromophenoxy)phenyl)pyrrolidin-2-yl)acetic acid, TFA

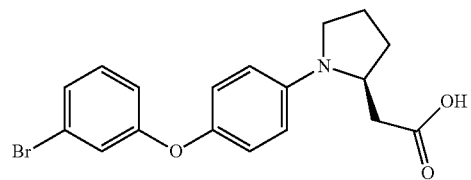

79A. (S)-methyl 2-(1-(4-hydroxyphenyl)pyrrolidin-2-yl) acetate: (S)-2-(1-(4-hydroxyphenyl)pyrrolidin-2-yl)acetonitrile (91C, 231 mg, 1.142 mmol) was dissolved in ~3M HCl/ MeOH, MeOAc, CH$_2$Cl$_2$ solution [25.2 mL, prepared by addition of AcCl (5.2 mL) to 3/2 CH$_2$Cl$_2$/MeOH (20 mL) at 0° C. and then stirring at rt for 30 min]. The resulting solution was stirred at rt for 13 h and then evaporated. The residue was taken up in EtOAc (60 mL) and, washed with 5% NaHCO$_3$ (3×20 mL) and sat'd NaCl (20 mL). The organic layer was dried (Na$_2$SO$_4$) and concentrated. Chromatography (SiO$_2$ 230-400 mesh, 7/3 Hex/EtOAc) of the crude afforded 79A (off-white solid, 194 mg, 71% yield). LC-MS, [M+H]+=236.

79B. (S)-methyl 2-(1-(4-(3-bromophenoxy)phenyl)pyrrolidin-2-yl)acetate: To a stirred suspension of 3-bromophenylboronic acid (338 mg, 1.633 mmol), 79A (192 mg, 0.816 mmol), anhydrous copper(II) acetate (148 mg, 0.799 mmol), and powdered molecular sieves (4 Å, <5 micron, activated, 866 mg) in CH$_2$Cl$_2$ (9.0 mL) at rt was added pyridine (0.33 mL, 4.08 mmol). The mixture was stirred at rt under an air atmosphere (balloon) for 24 h. The final mixture was filtered through CELITE® and the filter cake was rinsed with CH$_2$Cl$_2$ (100 mL). The combined filtrate and rinses were concentrated and the residue was chromatographed (SiO$_2$ 230-400 mesh, 95/5 Hex/EtOAc) to afford 79B (yellowish oil, 90 mg, 26% yield). LC-MS, [M+H]+=390, 392.

79C (Example 79. (S)-2-(1-(4-(3-bromophenoxy)phenyl) pyrrolidin-2-yl)-acetic acid, TFA): To a stirred solution of 79B (5.0 mg, 0.013 mmol) in THF (0.5 mL) and 2-propanol (0.05 mL) at rt was added 0.48M aqueous lithium hydroxide (0.3 mL, 0.144 mmol) dropwise. The resulting solution was stirred at rt for 19 h. At this time, the solution was cooled to 0° C. and acidified with 1M HCl (0.16 mL). The organic solvents were mostly evaporated and the remaining aqueous mixture was injected in a Prep HPLC column (YMC-Pack ODS, 100×20 mm). Elution (CH$_3$CN—H$_2$O-TFA, solvent B % start 30, final 100; grad t 15 min; flow r 20 mL/min; wv 220 nm) of the column afforded Example 79 (yellowish oil, 5.5 mg, 88% yield). LC-MS, [M+H]+=376, 378. $^1$H NMR (CD$_3$OD, 500 MHz): δ 7.19 (m, 2H), 6.98 (m, 6H), 4.16 (broad s, 1H), 3.57 (broad s, 1H), 3.33 (broad s, 1H), 2.73 (dd, J=15.4, 3.3 Hz, 1H), 2.36 (dd, J=15.4, 9.3 Hz, 1H), 2.24 (m, 1H), 2.13 (m, 2H), 1.96 (m, 1H). HPLC-(ZORBAX®, 50 Start % B): RT=6.16 min, purity=100%.

Example 80

(S)-2-(1-(4-(3-(2-fluorobenzyl)phenoxy)phenyl)pyrrolidin-2-yl)acetic acid, TFA

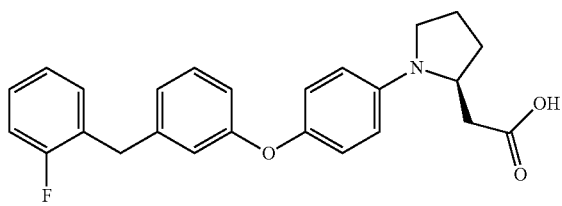

80A. (S)-methyl 2-(1-(4-(3-(2-fluorobenzyl)phenoxy)phenyl)pyrrolidin-2-yl)acetate: THF (1.0 mL) was added to an Ar-purged flask containing (S)-methyl 2-(1-(4-(3-bromophenoxy)phenyl)pyrrolidin-2-yl)acetate (79B, 12.1 mg, 0.031 mmol) and tetrakis(triphenylphosphine)palladium (0) (4.0 mg, 3.46 µmol) and the mixture was stirred until a clear solution was formed. Then, 0.5M (2-fluorobenzyl)zinc(II) chloride/THF (0.19 mL, 0.095 mmol) was added dropwise and the mixture was stirred at 55° C. for 5.3 h. At this time, an additional amount of 0.5M (2-fluorobenzyl)zinc(II) chloride/THF (0.19 mL, 0.095 mmol) was added and stirring at 55° C. was continued for an additional 6.0 h. After cooling to 0° C., 1M $K_2CO_3$ (6 mL) and EDTA (308 mg, 1.05 mmol) were added and the aqueous mixture was extracted with $CH_2Cl_2$ (3×30 mL). The combined extract was dried ($Na_2SO_4$) and concentrated. Chromatography ($SiO_2$ 230-400 mesh, 95/5 Hex/EtOAc) of the crude gave 80A (yellowish oil, 5.5 mg 37% yield). LC-MS, [M+H]$^+$=420.

80B (Example 80. (S)-2-(1-(4-(3-(2-fluorobenzyl)phenoxy)phenyl)-pyrrolidin-2-yl)acetic acid, TFA): 80A (4.5 mg, 9.44 µmol) was converted to Example 80 (yellow oil, 3.5 mg, 68% yield) following the procedure of 79C. LC-MS, [M+H]$^+$=406. $^1$H NMR (CD$_3$OD, 500 MHz): δ 7.19 (m, 3H), 7.05 (m, 2H), 6.98 (m, 6H), 6.93-6.80 (m, 5H), 6.75 (s, 1H), 6.70 (d, J=7.7 Hz, 1H), 4.14 (broad s, 1H), 3.92 (s, 2H), 3.54 (broad s, 1H), 3.25 (broad s, 1H), 2.73 (d, J=15.4 Hz, 1H), 2.38 (m, 1H), 2.21 (m, 1H), 2.11 (m, 2H), 2.18 (s, 3H), 1.94 (m, 1H). HPLC-(ZORBAX®, 50 Start % B): RT=6.51 min, purity=95%.

Example 81

(S)-2-(1-(4-(2'-fluorobiphenyl-3-yloxy)phenyl)pyrrolidin-2-yl)acetic acid, TFA

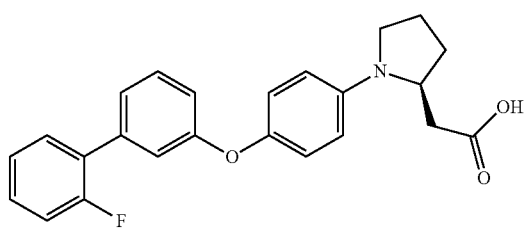

81A. (S)-methyl 2-(1-(4-(2'-fluorobiphenyl-3-yloxy)phenyl)pyrrolidin-2-yl)acetate: To a stirred solution of (S)-methyl 2-(1-(4-(3-bromophenoxy)phenyl)pyrrolidin-2-yl)acetate (79B, 15 mg, 0.038 mmol) in toluene (0.4 mL) under Ar were added a solution of 2-fluorophenylboronic acid (10 mg, 0.070 mmol) in MeOH (0.1 mL) and a solution of sodium carbonate (16 mg, 0.151 mmol) in water (0.3 mL). The mixture was degassed by ultrasound irradiation (5 min) under Ar and then dichlorobis(triphenylphosphine)-palladium(II) (4 mg, 5.69 µmol) was added. The resulting mixture was stirred at 95° C. for 3.7 h. After cooling to rt, the mixture was diluted with water (6 mL) and extracted with $CH_2Cl_2$ (3×20 mL). The combined organic extracts were dried ($Na_2SO_4$) and evaporated. Chromatography ($SiO_2$ 230-400 mesh, 9/1 Hex/EtOAc) of the crude afforded 81A (colorless oil, 7.0 mg, 43% yield). LC-MS, [M+H]$^+$=406.

81B (Example 81. (S)-2-(1-(4-(2'-fluorobiphenyl-3-yloxy)phenyl)-pyrrolidin-2-yl)acetic acid): 81A (7.0 mg, 0.017 mmol) was converted to Example 81 (brownish oil, 8.1 mg, 91% yield) following the procedure of 79C. LC-MS, [M+H]$^+$=392. $^1$H NMR (CD$_3$OD, 400 MHz): δ 7.47-7.33 (m, 3H), 7.29-7.04 (m, 8H), 6.97 (dd, J=8.2, 1.7 Hz, 1H), 4.19 (broad s, 1H), 3.68 (broad s, 1H), 3.44 (broad s, 1H), 2.74 (dd, J=15.9, 3.8 Hz, 1H), 2.45 (dd, J=15.9, 8.8 Hz, 1H), 2.33 (m, 1H), 2.18 (m, 2H), 1.97 (m, 1H). HPLC-(ZORBAX®, 50 Start % B): RT=6.46 min, purity=98%.

Example 82

(S)-2-(1-(4-(4-bromo-3-methylbenzyloxy)phenyl)pyrrolidin-2-yl)acetic acid, TFA

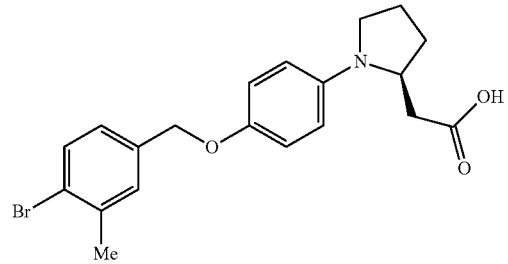

82A. (4-bromo-3-methylphenyl)methanol: To a stirred solution of methyl 4-bromo-3-methylbenzoate (1.18 g, 5.00 mmol) in THF (14 mL) at 0° C. was added 2M lithium borohydride/THF (3.00 mL, 6.00 mmol). The mixture was stirred for 45 min at 0° C. and then warmed to rt. After stirring for 22 h at rt, the mixture was cooled back to 0° C. and an additional amount of 2M lithium borohydride/THF (3.00 mL, 6.00 mmol) was added. The mixture was stirred for 30 min at 0° C. and then warmed at rt for an additional 17 h. The reaction mixture was cooled to 0° C. and quenched with 10% $KHSO_4$ (25 mL, gas evolved). The aqueous mixture was warmed up to rt and extracted with $CH_2Cl_2$ (3×50 mL). The combined extracts were dried ($Na_2SO_4$) and concentrated. The crude was chromatographed ($SiO_2$ 230-400 mesh, 9/1 to 1/1 Hex/EtOAc) to furnish 82A (colorless oil, 778.3 mg, 70% yield). LC-MS, [M+H–H$_2$O]$^+$=183, 185.

82B. 1-bromo-4-(bromomethyl)-2-methylbenzene: To a stirred solution of 82A (775 mg, 3.85 mmol) and carbon tetrabromide (1.69 g, 5.05 mmol) in dichloromethane (19 mL) at rt was added triphenylphosphine (1.35 g, 5.10 mmol). The resulting solution was stirred at rt for 22 h and then mostly evaporated. The residue was taken up in ether (50 mL) and sonicated. The resulting suspension was filtered and the solid was rinsed with ether (2×5 mL). The filtrate and the rinses were combined and evaporated. Chromatography (SiO$_2$ 230-400 mesh, Hex to 95/5 Hex/EtOAc) of the crude afforded 82B (colorless liquid, 872.3 mg, 81% yield). $^1$H NMR (CDCl$_3$, 400 MHz): δ 7.49 (d, J=8.2 Hz, 1H), 7.26 (s, 1H), 7.07 (dd, J=8.2, 2.2 Hz, 1H), 4.41 (s, 2H), 2.39 (s, 3H).

82C. (S)-methyl 2-(1-(4-(4-bromo-3-methylbenzyloxy)phenyl)pyrrolidin-2-yl)acetate: To a stirred suspension of (S)-methyl 2-(1-(4-hydroxyphenyl)pyrrolidin-2-yl)acetate (79A, 270 mg, 1.148 mmol) and cesium carbonate (1.56 g, 4.78 mmol) in MeCN (10 mL) at 50° C. was added a solution of 83B (320 mg, 1.212 mmol) in MeCN (2.0 mL). The mixture was stirred at 50° C. for 2.0 h and then, cooled to rt and partitioned between CH$_2$Cl$_2$ (70 mL) and water (12 mL). The aqueous layer was extracted with CH$_2$Cl$_2$ (2×20 mL) and, the combined organic layers were dried (Na$_2$SO$_4$) and concentrated. Chromatography (SiO$_2$ 230-400 mesh, 9/1 hex/EtOAc) of the crude gave 82C (off-white solid, 472 mg, 92% yield). LC-MS, [M+H]$^+$=418, 420.

82D (Example 82. (S)-2-(1-(4-(4-bromo-3-methylbenzyloxy)phenyl)pyrrolidin-2-yl)acetic acid, TFA): To a stirred solution of 82C (10.2 mg, 0.024 mmol) in THF (0.5 mL) and 2-propanol (0.05 mL) at rt was added 0.48M aqueous lithium hydroxide (0.32 mL, 0.154 mmol) dropwise. The resulting solution was stirred at rt for 17 h. At this time, an additional amount of 0.48M aqueous lithium hydroxide (0.32 mL, 0.154 mmol) was added and stirring was continued for an additional 20 h at rt. The final solution was cooled to 0° C. and acidified with 1M HCl (0.34 mL). The organic solvents were mostly evaporated and the remaining aqueous mixture was injected in a Prep HPLC column (PHENOMENEX® Luna Axia, 100×20 mm). Elution (CH$_3$CN—H$_2$O-TFA, solvent B % start 20, final 100; grad t 15 min; flow r 20 mL/min; wv 220 nm) of the column afforded Example 82 (yellowish oil, 6.0 mg, 48% yield). LC-MS, [M+H]$^+$=404, 406. $^1$H NMR (CD$_3$OD, 500 MHz): δ 7.53 (d, J=8.2 Hz, 1H), 7.36 (s, 1H), 7.25-7.13 (m, 3H), 7.07 (d, J=9.3 Hz, 2H), 5.03 (s, 2H), 4.16 (broad s, 1H), 3.74 (broad s, 1H), 3.52 (broad s, 1H), 2.68 (dd, J=15.9, 3.8 Hz, 1H), 2.52-2.37 (m, 2H), 2.39 (s, 3H), 2.28-2.11 (m, 2H), 1.96 (m, 1H). HPLC-(ZORBAX®): RT=6.73 min, purity=100%.

Example 83

2-((2S)-1-(442'-fluoro-5'-methoxy-2-methylbiphenyl-4-yl)methoxy)phenyl)pyrrolidin-2-yl)acetic acid, TFA

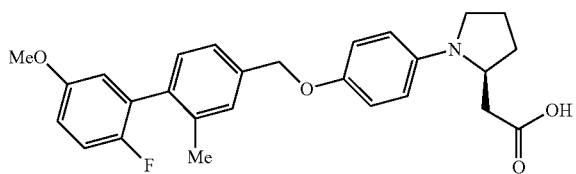

83A. methyl 2-((2S)-1-(442'-fluoro-5'-methoxy-2-methylbiphenyl-4-yl)methoxy)phenyl)pyrrolidin-2-yl)acetate: To a stirred solution of (S)-methyl 2-(1-(4-(4-bromo-3-methylbenzyloxy)phenyl)pyrrolidin-2-yl)acetate (82C, 53 mg, 0.127 mmol) in toluene (0.75 mL) under Ar were added a solution of 2-fluoro-5-methoxyphenylboronic acid (31 mg, 0.182 mmol) in MeOH (0.16 mL) and a solution of sodium carbonate (45 mg, 0.425 mmol) in water (0.6 mL). The mixture was degassed by ultrasound irradiation (5 min) under Ar and then dichlorobis(triphenylphosphine)-palladium(II) (7.0 mg, 9.96 µmol) was added. The resulting mixture was stirred at 95° C. for 5.0 h. After cooling to rt, the mixture was diluted with sat'd NH$_4$Cl (6 mL) and extracted with CH$_2$Cl$_2$ (3×30 mL). The combined organic extracts were dried (Na$_2$SO$_4$) and evaporated. Chromatography (SiO$_2$ 230-400 mesh, 9/1 Hex/EtOAc) of the crude afforded 83A (colorless oil, 27.7 mg, 45% yield). LC-MS, [M+H]$^+$=464.

83B (Example 83. 2-((2S)-1-(4-((2'-fluoro-5'-methoxy-2-methylbiphenyl-4-yl)methoxy)phenyl)pyrrolidin-2-yl)acetic acid, TFA): 84A (27 mg, 0.058 mmol) was converted to Example 83 (brownish oil, 12.2 mg, 36% yield) following the procedure of 79C. LC-MS, [M+H]$^+$=450. $^1$H NMR (CD$_3$OD, 400 MHz): δ 7.43-7.34 (m, 3H), 7.31 (d, J=8.2 Hz, 1H), 7.17 (m, 3H), 7.07 (t, J=9.0 Hz, 1H), 6.92 (m, 1H), 6.74 (dd, J=6.1, 3.3 Hz, 1H), 5.14 (s, 2H), 4.20 (broad s, 1H), 3.86 (broad s, 1H), 3.78 (s, 3H) 3.64 (m, 1H), 2.70 (dd, J=16.5, 4.4 Hz, 1H), 2.63-2.48 (m, 2H), 2.36-2.13 (m, 2H), 2.18 (s, 3H), 1.99 (m, 1H). HPLC-(ZORBAX®): RT=7.03 min, purity=98%.

Example 84

2-((2S)-1-(442'-fluoro-2-methylbiphenyl-4-yl)methoxy)phenyl)pyrrolidin-2-yl)acetic acid, TFA

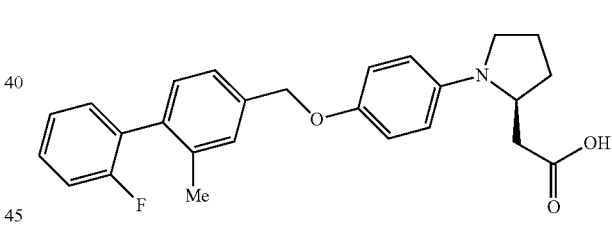

84A. methyl 242S)-1-(4-((2'-fluoro-2-methylbiphenyl-4-yl)methoxy)phenyl)pyrrolidin-2-yl)acetate: Following the procedure of 83A, (S)-methyl 2-(1-(4-(4-bromo-3-methylbenzyloxy)phenyl)pyrrolidin-2-yl)acetate (82C, 46.5 mg, 0.111 mmol) was converted to 84A (colorless oil, 8.4 mg, 17% yield). LC-MS, [M+H]$^+$=434.

84B (Example 84. 2-((2S)-1-(4-((2'-fluoro-2-methylbiphenyl-4-yl)methoxy)phenyl)pyrrolidin-2-yl)acetic acid, TFA): Following the procedure of 79C, 84A (8 mg, 0.018 mmol) was converted to Example 84 (colorless oil, 5.0 mg, 50% yield). LC-MS, [M+H]$^+$=420. $^1$H NMR (CD$_3$OD, 400 MHz): δ 7.45-7.29 (m, 5H), 7.24 (m, 2H), 7.21-7.11 (m, 4H), 5.14 (s, 2H), 4.20 (broad s, 1H), 3.83 (broad s, 1H), 3.61 (broad s, 1H), 2.70 (d, J=14.2 Hz, 1H), 2.60-2.44 (m, 2H), 2.34-2.12 (m, 2H), 2.17 (s, 3H), 1.99 (m, 1H). HPLC-(ZOR-BAX®): RT=7.02 min, purity=99%.

Example 85

(S)-2-(1-(4-((3'-methoxy-2-methylbiphenyl-4-yl)methoxy)phenyl)pyrrolidin-2-yl)acetic acid, TFA

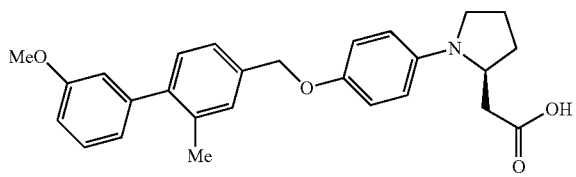

85A. (S)-methyl 2-(1-(4-((3'-methoxy-2-methylbiphenyl-4-yl)methoxy)phenyl)pyrrolidin-2-yl)acetate: Following the procedure of 83A, (S)-methyl 2-(1-(4-(4-bromo-3-methylbenzyloxy)phenyl)pyrrolidin-2-yl)acetate (82C, 39.7 mg, 0.095 mmol) was converted to 85A (colorless oil, 14.5 mg, 34% yield). LC-MS, [M+H]+=446.

85B (Example 85. (S)-2-(1-(4-((3'-methoxy-2-methylbiphenyl-4-yl)methoxy)phenyl)pyrrolidin-2-yl)acetic acid): Following the procedure of 79C, 85A (14.5 mg, 0.033 mmol) was converted to Example 85 (brownish oil, 16 mg, 90% yield). LC-MS, [M+H]+=432. $^1$H NMR (CD$_3$OD, 400 MHz): δ 7.44 (m, 2H), 7.35-7.26 (m, 3H), 7.18 (m, 3H), 6.90 (dd, J=8.2, 1.6 Hz, 1H), 6.85 (d, J=7.2 Hz, 1H), 6.81 (t, J=1.6 Hz, 1H), 5.14 (s, 2H), 4.21 (broad s, 1H), 3.89 (broad s, 1H), 3.81 (s, 3H), 3.67 (broad s, 1H), 2.74-2.50 (m, 3H), 2.38-2.15 (m, 2H), 2.25 (s, 3H), 2.00 (m, 1H). HPLC-(ZORBAX®): RT=7.14 min, purity=100%.

Example 86

2-(1-(4-(bis(2-methoxyphenyl)methyl)phenyl)pyrrolidin-2-yl)acetic acid

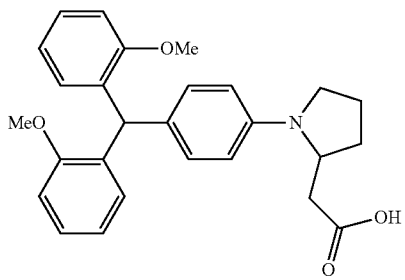

86A. (4-fluorophenyl)(2-methoxyphenyl)methanol: To a solution of 4-fluoro benzaldehyde (4 g, 32.2 mmol) in THF (40 mL) was added 2-methoxy phenylmagnesium bromide (7.49 g, 35.4 mmol, 1.1 equiv.) dropwise at 0° C. After addition the resultant solution was brought to ambient temperature and stirred for 1 h. Then the reaction mass was filtered through silica gel and concentrated to get the crude mixture which was then purified with silica gel (60-120 mesh) column chromatography with ethyl acetate and petroleum ether (3:7) as eluent to yield 86A (colorless oil, 6 g, 80% yield). LC-MS Anal. Calc'd for $C_{14}H_{13}FO_2$ 232. found [M+H–H$_2$O] 215.0.

86B. (4-fluorophenyl)(2-methoxyphenyl)methanone: To a solution of 86A (3 g, 12.9 mmol) in dichloromethane was added manganese dioxide (16.7 g, 194 mmol, 15 eq) under nitrogen atmosphere and the mass was stirred overnight at rt. The reaction mixture was filtered through CELITE® and concentrated to yield 86B (colorless oil, 2.7 g, 91% yield). LC-MS Anal. Calc'd for $C_{14}H_{11}FO_2$ 230. found [M+H] 231.

86C. (S)-(4-(2-(hydroxymethyl)pyrrolidin-1-yl)phenyl)(2-methoxyphenyl)methanone: A vial containing 86B (1.2 g, 5.21 mmol) and L-(+)-prolinol (1.017 mL, 10.43 mmol) was heated to 170° C. for 10 min in the microwave to result an orange gel. The residue was diluted with dichloromethane (100 mL) and given water (50 mL) and brine solution (30 mL) wash. The dried concentrate was purified by silica gel (60-120 mesh) column chromatography with ethyl acetate and petroleum ether (80:20) as eluent to yield 86C (yellow oil, 1.3 g, 80% yield). LC-MS Anal. Calc'd for $C_{19}H_{21}NO_3$ 311. found [M+H] 312.

86D. (S)-2-(1-(4-(2-methoxybenzoyl)phenyl)pyrrolidin-2-yl)acetonitrile: To a solution of 86C (1.3 g, 4.18 mmol) in toluene (15 mL) was added triphenylphosphine (1.64 g, 6.2 mmol), acetone cyanohydrin (0.6 mL, 7.106 mmol) and DEAD (1.2 mL, 7.106 mmol) under nitrogen atmosphere and stirred at rt. After 12 h, triphenylphosphine (0.82 g, 3.1 mmol), acetone cyanohydrin (0.3 mL, 3.553 mmol) and DEAD (0.6 mL, 3.553 mmol) was added and stirring continued for additional 24 h. Then the concentrate was directly loaded on to a silica gel column (60-120 mesh) and eluted with ethyl acetate: petroleum ether mixture (50:50) as eluent to yield 86D (yellow oil, 0.4 g. 30% yield). LC-MS Anal. Calc'd for $C_{20}H_{20}N_2O_2$ 320. found [M+H] 321.

86E. (S)-2-(1-(4-(hydroxybis(2-methoxyphenyl)methyl)phenyl)pyrrolidin-2-yl)acetonitrile: To a solution of 86D (0.2 g, 0.625 mmol) in THF (10 mL) was added 2-methoxy phenylmagnesium bromide (0.125 g, 0.593 mmol, 0.95 eq) dropwise at 0° C. and stirred for 1 h at rt. Then the mixture was quenched with water and extracted with ethyl acetate (30 mL). The extract was concentrated to yield 86E (yellow oil, 0.1 g, 40% yield). LC-MS Anal. Calc'd for $C_{27}H_{28}N_2O_3$ 428. found [M+H] 429.0. $^1$H NMR (400 MHz, DMSO-d$_6$) δ ppm 7.32 (2H, m), 7.04 (5H, m), 6.99 (2H, m), 6.54 (2H, m), 5.22 (1H, s), 4.04 (1H, m), 3.45 (1H, m), 3.11 (1H, m), 2.78 (2H, m), 2.17 (2H, m), 1.95 (2H, m).

86F. (S)-2-(1-(4-(bis(2-methoxyphenyl)methyl)phenyl)pyrrolidin-2-yl)acetonitrile: To a solution of 86D (0.1 g, 0.2 mmol) in dichloromethane (5 mL) was added trifluoroacetic acid (0.013 g, 0.1 mmol), triethyl silane (0.034 g, 0.3 mmol) and boron trifluoride (0.019 g, 0.14 mmol) at rt and stirred overnight. The reaction mass quenched with saturated sodium bicarbonate solution (20 mL) was extracted with ethyl acetate (40 mL) and given water (20 mL) and brine solution (15 mL) wash. The organic layer was concentrated to yield 86F (brown oil, 0.08 g, 83% yield). LC-MS Anal. Calc'd for $C_{27}H_{28}N_2O_2$ 412. found [M+H] 413.0.

86G. Ethyl 2-(1-(4-(bis(2-methoxyphenyl)methyl)phenyl)pyrrolidin-2-yl)acetate: To a solution of 86F (0.1 g, 0.24 mmol) in saturated ethanolic HCl (2 mL) was added acetyl chloride (0.5 mL) at 0° C. and stirred at the same temperature for 15 min. Then the reaction temperature was elevated to 80° C. and continued stirring for 3 h. The concentrate was neutralized with sodium bicarbonate and extracted with ethyl acetate. Finally the solvent was evaporated to yield 86G (yellow oil, 0.05 g, 56% yield). LC-MS Anal. Calc'd for $C_{29}H_{33}NO_4$ 459. found [M+H] 460.0. $^1$H NMR (400 MHz, DMSO-d$_6$) δ ppm 7.20 (2H, m), 6.96 (2H, d, J=8.0 Hz), 6.84 (2H, m), 6.81 (2H, m), 6.78 (2H, m), 6.72 (2H, d, J=8.0 Hz), 5.98 (1H, s), 4.09 (2H, q), 4.01 (1H, m), 3.66 (6H, s), 3.29 (1H, m), 3.06 (1H, m), 2.63 (1H, m), 2.28 (1H, m), 2.20 (3H, m), 1.99 (1H, m), 1.2 (3H, t).

86H (Example 86. 2-(1-(4-(bis(2-methoxyphenyl)methyl)phenyl)pyrrolidin-2-yl)acetic acid): To a solution of 86G (0.05 g, 0.11 mmol) in methanol was added aqueous sodium hydroxide (0.0065 mg in 1 mL water, 0.16 mmol) and stirred at rt for 12 h. The concentrate was neutralized to pH ~4 and extracted with ethyl acetate. The crude extract was purified with preparative TLC with methanol/dichloromethane (1:9) as eluent to yield Example 86 (brown solid, 0.018 g, 38% yield). LC-MS Anal. Calc'd for $C_{29}H_{33}NO_4$ 431. found [M+H] 432. $^1$H NMR (400 MHz, DMSO-$d_6$) δ ppm 12.3 (brs, 1H), 7.19 (2H, m), 6.95 (2H, d, J=8.0 Hz), 6.84 (2H, m), 6.80 (2H, m), 6.71 (2H, m), 6.45 (2H, d, J=8.0 Hz), 5.98 (1H, s), 3.97 (1H, m), 3.70 (6H, s), 3.28 (1H, m), 3.05 (1H, m), 2.17 (1H, m), 2.01 (4H, m), 1.89 (1H, m). Analytical HPLC: RT=17.6 min, HI: 94.6%.

Example 87

2-(1-(4-(2,4-dimethylbenzyl)phenyl)pyrrolidin-2-yl)acetic acid

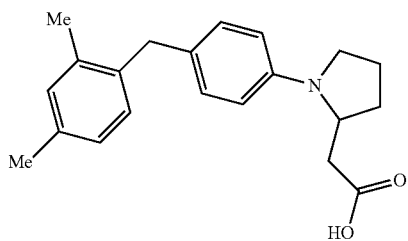

87A. (2,4-dimethylphenyl)(4-fluorophenyl)methanol: 87A (colorless oil, 1.7 g, 7.4 mmol, 46% yield) was prepared from 4-fluoro benzaldehyde following the procedure of 86A. LC-MS Anal. Calc'd for $C_{15}H_{15}FO$ 230. found [M−18+H] 213. $^1$H NMR (400 MHz, DMSO-$d_6$) δ ppm 7.31 (3H, m), 7.13 (2H, m), 7.01 (1H, m), 6.92 (1H, s), 5.802 (2H, m), 2.23 (3H, s), 2.14 (3H, s).

87B. (2,4-dimethylphenyl)(4-fluorophenyl)methanone: 87B (colorless oil, 1.5 g, 6.6 mmol, 89% yield) was prepared from 87A following the procedure of 86B. LC-MS Anal. Calc'd for $C_{15}H_{13}FO$ 228. found [M+H] 229. $^1$H NMR (400 MHz, DMSO-$d_6$) δ ppm 7.78 (2H, m), 7.38 (2H, m), 7.22 (2H, m), 7.19 (1H, m), 2.351 (3H, s), 2.22 (3H, s).

87C. (S)-(2,4-dimethylphenyl)(4-(2-(hydroxymethyl)pyrrolidin-1-yl)phenyl)methanone: 87C (yellow oil, 1.7 g, 5.5 mmol, 84% yield) was prepared from 87B following the procedure of 86C. LC-MS Anal. Calc'd for $C_{20}H_{23}NO_2$, 309. found [M+H] 310.

87D. (S)-2-(1-(4-(2,4-dimethylbenzoyl)phenyl)pyrrolidin-2-yl)acetonitrile: 87D (yellow oil, 0.4 g, 1.25 mmol, 39% yield) was prepared from 87C following the procedure of 86D. LC-MS Anal. Calc'd for $C_{21}H_{22}N_2O$, 318. found [M+H] 319.

87E. (S)-ethyl 2-(1-(4-(2,4-dimethylbenzoyl)phenyl)pyrrolidin-2-yl)acetate: 87E (colorless oil, 0.15 g, 0.41 mmol, 32% yield) was prepared from 87D following the procedure of 86G. LC-MS Anal. Calc'd for $C_{23}H_{27}NO_3$ 365. found [M+H] 366.

87F. (S)-ethyl 2-(1-(4-(2,4-dimethylbenzyl)phenyl)pyrrolidin-2-yl)acetate: 87F (brown oil, 0.08 g, 0.23 mmol, 55% yield) was prepared from 87E following the procedure of 86F.

LC-MS Anal. Calc'd for $C_{23}H_{29}NO_2$ 351. found [M+H] 352. $^1$H NMR (400 MHz, DMSO-$d_6$) δ ppm 6.95 (5H, m), 6.47 (2H, d, J=8.4 Hz), 4.10 (2H, q), 4.08 (1H, m), 3.99 (2H, s), 3.30 (1H, m), 3.02 (1H, m), 2.61 (1H, m), 2.27 (4H, m), 2.15 (3H, s), 2.01 (3H, m), 1.79 (1H, m), 1.20 (3H, t).

87G (Example 87. 2-(1-(4-(2,4-dimethylbenzyl)phenyl)pyrrolidin-2-yl)acetic acid): Example 87 (light brown oil, 0.048 g, 0.15 mmol, 65% yield) was prepared from 87F following the procedure of 86H. LC-MS Anal. Calc'd for $C_{21}H_{25}NO_2$ 323. found [M+H] 324. $^1$H NMR (400 MHz, DMSO-$d_6$) δ ppm 12.3 (1H, s), 6.97 (5H, m), 6.48 (2H, d, J=8.4 Hz), 3.96 (1H, m), 3.75 (2H, s), 3.30 (1H, m), 3.06 (1H, m), 2.56 (1H, m), 2.22 (3H, s), 2.20 (3H, s), 2.14 (1H, m), 1.98 (3H, m), 1.80 (1H, m). Analytical HPLC: RT=20.4 min, HI: 97.7%.

Example 88

2-(1-(4-(4-chloro-2-methylbenzyl)phenyl)pyrrolidin-2-yl)acetic acid

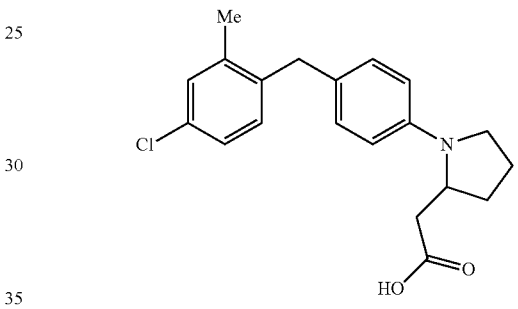

88A. (4-chloro-2-methylphenyl)(4-fluorophenyl)methanol: 88A (colorless oil, 4.0 g, 16 mmol, 99% yield) was prepared from 4-fluoro benzaldehyde following the procedure of 86A. LC-MS Anal. Calc'd for $C_{14}H_{12}ClFO$ 250. found [M−$H_2$O+H] 233.

88B. (4-chloro-2-methylphenyl)(4-fluorophenyl)methanone: 88B (colorless oil, 3.5 g, 14.1 mmol, 88% yield) was prepared from 88A following the procedure of 86B. LC-MS Anal. Calc'd for $C_{14}H_{10}ClFO$ 248. found [M+H] 249.

88C. (S)-(4-chloro-2-methylphenyl)(4-(2-(hydroxymethyl)pyrrolidin-1-yl)phenyl)methanone: 88C (yellow oil, 2.0 g, 6.07 mmol, 75% yield) was prepared from 88B following the procedure of 86C. LC-MS Anal. Calc'd for $C_{19}H_{20}ClNO_2$ 329. found [M+H] 330.

88D. (S)-2-(1-(4-(4-chloro-2-methylbenzoyl)phenyl)pyrrolidin-2-yl)acetonitrile: 88D (yellow oil, 0.9 g, 2.66 mmol, 44% yield) was prepared from 88C following the procedure of 86D. LC-MS Anal. Calc'd for $C_{20}H_{19}ClN_2O$ 338. found [M+H] 339.

88E. ethyl 2-(1-(4-(4-chloro-2-methylbenzoyl)phenyl)pyrrolidin-2-yl)acetate: 88E (colorless oil, 0.3 g, 0.78 mmol, 33% yield) was prepared from 88D following the procedure of 86G. LC-MS Anal. Calc'd for $C_{22}H_{24}ClNO_3$ 385. found [M+H] 386.

88F. Ethyl 2-(1-(4-(4-chloro-2-methylbenzyl)phenyl)pyrrolidin-2-yl)acetate: 88F (brown oil, 0.1 g, 0.27 mmol, 69% yield) was prepared from 88E following the procedure of 86F. LC-MS Anal. Calc'd for $C_{22}H_{26}ClNO_2$ 371. found [M+H] 372.

88G (Example 88. 2-(1-(4-(4-chloro-2-methylbenzyl)phenyl)pyrrolidin-2-yl)acetic acid): Example 88 (viscous brown oil, 0.017 g, 0.049 mmol, 66% yield) was prepared from 88F following the procedure of 86H. LC-MS Anal. Calc'd for $C_{20}H_{22}ClNO_2$ 343. found [M+H] 344. $^1$H NMR (400 MHz, DMSO-d$_6$) δ ppm 12.27 (1H, s), 7.22 (1H, s), 7.21 (1H, m), 7.18 (1H, m), 6.95 (2H, d, J=8.4 Hz), 6.49 (2H, d, J=8.4 Hz), 3.97 (1H, m), 3.79 (2H, s), 3.29 (1H, m), 3.05 (1H, m), 2.57 (1H, m), 2.21 (3H, s), 2.17 (1H, m), 1.98 (3H, m), 1.80 (1H, m). Analytical HPLC: RT=22.3 min, HI: 96.7%.

Example 89

2-(1-(4-(4-chloro-2-methylbenzoyl)phenyl)pyrrolidin-2-yl)acetic acid

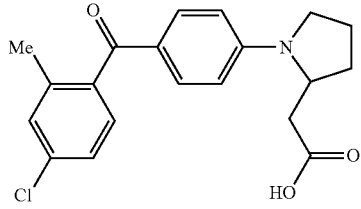

Example 89 (pale yellow oil, 0.017 g, 0.047 mmol, 36% yield) was prepared from ethyl 2-(1-(4-(4-chloro-2-methylbenzoyl)phenyl)pyrrolidin-2-yl)acetate (88E) following the procedure of 86H. LC-MS Anal. Calc'd for $C_{20}H_{20}ClNO_3$ 357. found [M+H] 358. $^1$H NMR (400 MHz, DMSO-d$_6$) δ ppm 12.4 (1H, brs), 7.55 (2H, d, J=8.8 Hz), 7.43 (1H, d, J=1.2 Hz), 7.36 (1H, dd, J=1.2, 8.0 Hz), 7.24 (1H, d, J=8.0 Hz), 6.62 (2H, d, J=8.8 Hz), 4.17 (1H, m), 3.47 (1H, m), 3.22 (1H, m), 2.58 (1H, m), 2.30 (1H, m), 2.17 (3H, s), 2.06 (3H, m), 1.99 (1H, m). Analytical HPLC: RT=18.7 min, HI: 92.9%.

Example 90

2-(1-(4-(1-o-tolylpropyl)phenyl)pyrrolidin-2-yl)acetic acid

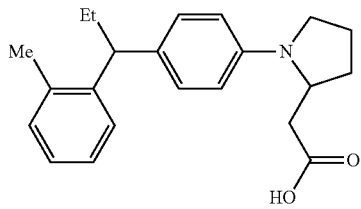

90A. (4-fluorophenyl)(o-tolyl)methanol: 90A (colorless oil, 3.0 g, 13.8 mmol, 86% yield) was prepared from 4-fluoro benzaldehyde following the procedure of 86A. LC-MS Anal. Calc'd for $C_{14}H_{13}FO$ 216. found [M−18+H] 199.

90B. (4-fluorophenyl)(o-tolyl)methanone: 90B (colorless oil, 2.6 g, 12.1 mmol, 87% yield) was prepared from 90A following the procedure of 86B. LC-MS Anal. Calc'd for $C_{14}H_{11}FO$ 214. found [M+H] 215.

90C. (S)-(4-(2-(hydroxymethyl)pyrrolidin-1-yl)phenyl)(o-tolyl)methanone: 90C (yellow oil, 1.0 g, 3.38 mmol, 72% yield) was prepared from 90B following the procedure of 86C. LC-MS Anal. Calc'd for $C_{19}H_{21}NO_2$ 295. found [M+H] 296.

90D. (S)-2-(1-(4-(2-methylbenzoyl)phenyl)pyrrolidin-2-yl)acetonitrile: 90D (yellow oil, 0.2 g, 0.66 mmol, 43% yield) was prepared from 90C following the procedure of 86D. LC-MS Anal. Calc'd for $C_{20}H_{20}N_2O$ 304. found [M+H] 305. $^1$H NMR (400 MHz, DMSO-d$_6$) δ ppm 7.58 (2H, d, J=8.8 Hz), 7.39 (1H, m), 7.35 (2H, m), 7.28 (1H, m), 6.74 (2H, d, J=8.8 Hz), 4.2 (1H, m), 3.51 (1H, m), 3.35 (1H, m), 2.85 (2H, m), 2.2 (3H, s), 2.02 (2H, m), 1.99 (1H, m).

90E. ethyl 2-(1-(4-(2-methylbenzoyl)phenyl)pyrrolidin-2-yl)acetate: 90E (0.4 g, 1.14 mmol, 53% yield) was prepared as a colorless oil from 90D following the procedure of 86G. LC-MS Anal. Calc'd for $C_{22}H_{25}NO_3$ 351. found [M+H] 352. $^1$H NMR (400 MHz, DMSO-d$_6$) δ ppm 7.56 (2H, d, J=8.80 Hz), 7.40 (1H, m), 7.37 (2H, m), 7.30 (1H, m), 6.62 (2H, d, J=8.80 Hz), 4.21 (1H, m), 4.11 (2H, q), 3.44 (1H, m), 3.22 (1H, m), 2.65 (2H, m), 2.40 (3H, s), 2.16 (2H, m), 1.90 (1H, m), 1.2 (3H, t).

90F. 2-(1-(4-(2-methylbenzoyl)phenyl)pyrrolidin-2-yl)acetic acid: 90F (pale yellow oil, 0.1 g, 0.31 mmol, 72% yield) was prepared from 90E following the procedure of 86H. LC-MS Anal. Calc'd for $C_{20}H_{21}NO_3$ 323. found [M+H] 324.

90G. 2-(1-(4-(1-hydroxy-1-o-tolylpropyl)phenyl)pyrrolidin-2-yl)acetic acid: 90G (brown oil, 0.04 g, 0.11 mmol, 36% yield) was prepared from 90F and ethyl magnesium bromide (3 M solution in THF) following the procedure of 86A. LC-MS Anal. Calc'd for $C_{22}H_{27}NO_3$ 353. found [M+H] 354.

90H (Example 91. 2-(1-(4-(1-o-tolylpropyl)phenyl)pyrrolidin-2-yl)acetic acid): Example 90 (brown oil, 0.007 g, 0.02 mmol, 18% yield) was prepared from 90G following the procedure of 86F. LC-MS Anal. Calc'd for $C_{22}H_{27}NO_2$ 337. found [M+H] 338. $^1$H NMR (400 MHz, DMSO-d$_6$) δ ppm 12.3 (1H, s), 7.32 (1H, m), 7.17 (1H, m), 7.09 (4H, m), 6.46 (2H, d, J=8.8 Hz), 3.95 (1H, m), 3.86 (1H, m), 3.31 (1H, m), 3.05 (1H, m), 2.55 (1H, s), 2.24 (3H, s), 2.18 (1H, m), 1.99 (5H, m), 1.8 (1H, m), 0.9 (3H, t). Analytical HPLC: RT=22.4 min, HI: 93.8%.

Example 91

2-(1-(4-(4-methoxy-2-methylphenoxy)phenyl)pyrrolidin-2-yl)acetic acid

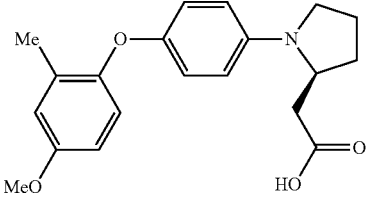

91A. (S)-(1-(4-(benzyloxy)phenyl)pyrrolidin-2-yl)methanol: A solution of (S)-pyrrolidin-2-ylmethanol (10.75 g, 106 mmol), 1-(benzyloxy)-4-iodobenzene (30 g, 96.7 mmol), and copper (I) iodide (14.71 g, 77 mmol) in isopropyl alcohol (300 mL) was degassed by evacuation and flushed with argon three times. To this tan heterogeneous solution at 0° C. was added sodium hydroxide (7.74 g, 193 mmol) and the mixture was then heated to 90° C. after keeping it cool for 5-10 min. The reaction mixture became rust orange in color remaining thick and heterogeneous and stirred at 90° C. overnight under argon. The reaction mixture was brought to rt and was diluted with ethyl acetate and washed with water. The aqueous phase was washed with ethyl acetate multiple times. The combined organics were washed with brine, dried over MgSO$_4$ and concentrated to 55 g of brown oil. The residue was dissolved in a minimum amount of CHCl$_3$ and this solution was loaded onto a silica gel column (60-120 mesh) for gradient purification (10-60% ethyl acetate/hexanes) yielding 91A (off-white solid, 20 g, 70 mmol, 66% yield). LC-MS Anal. Calc'd for $C_{18}H_{21}NO_2$ 283. found [M+H] 284.0. $^1$H NMR (400 MHz, DMSO-$d_6$) δ ppm 7.43 (5H, m), 6.88 (2H, d, J=8.80 Hz), 6.54 (2H, d, J=8.80 Hz), 4.98 (2H, s), 4.73 (1H, t), 3.56 (1H, m), 3.49 (1H, m), 3.35 (1H, m), 3.20 (1H, m), 2.95 (1H, m), 1.99 (4H, m).

91B. (S)-2-(1-(4-(benzyloxy)phenyl)pyrrolidin-2-yl)acetonitrile: To a clear, yellow homogeneous solution of 91A (14 g, 49.5 mmol) at 0° C. in methylene chloride (150 mL) was added triethylamine (13.3 mL, 98.9 mmol) and methanesulfonyl chloride (8.5 g, 74 mmol). The reaction mixture stirred at 0° C. becoming cloudy and orange in color. After 1 h, the reaction mixture was diluted with ethyl acetate and water. The combined organics were washed with 1N HCl, saturated sodium bicarbonate and brine, then were dried over $MgSO_4$ and concentrated to yield (S)-(1-(4-(benzyloxy)phenyl)pyrrolidin-2-yl)methyl methanesulfonate (thick brown oil, 15 g, 41.5 mmol). To the solution of (S)-(1-(4-(benzyloxy)phenyl)pyrrolidin-2-yl)methyl methanesulfonate (15 g, 41.5 mmol) in DMSO (50 mL) was added sodium cyanide (6.1 g, 49 mmol) and the mixture was heated to 50° C. After 4 h, the reaction mixture was diluted with 1000 mL of ethyl acetate and 350 mL of water. The layers were extracted and the organic layer was washed twice with 200 mL of water, then 200 mL of brine. The organic layer was dried over $MgSO_4$, filtered and evaporated to dryness to yield 15 g of an orange solid. The residue was purified silica gel column (60-120 mesh) with dichloromethane as eluent to yield 91B (off-white solid, 5 g, 34% yield). LC-MS Anal. Calc'd for $C_{19}H_{20}N_2O$ 292. found [M+H] 293.0. $^1$H NMR (400 MHz, DMSO-$d_6$) δ ppm 7.45 (5H, m), 6.91 (2H, d, J=8.80 Hz), 6.60 (2H, d, J=8.80 Hz), 5.03 (2H, s), 3.97 (1H, m), 3.42 (1H, m), 3.04 (1H, m), 2.71 (2H, m), 2.14 (2H, m), 1.9 (2H, m).

91C. (S)-2-(1-(4-hydroxyphenyl)pyrrolidin-2-yl)acetonitrile: A clear, colorless homogeneous solution of 92B (10 g, 34 mmol) in ethanol (400 mL) was repeatedly evacuated and flushed with nitrogen. 10% palladium on carbon (2 g) was added and the flask was flushed and evacuated again before being fit with a balloon of hydrogen. The reaction stirred vigorously under an atmosphere of hydrogen. After 2 h the suspension was filtered through CELITE®, rinsed with ethyl acetate, and concentrated to yield 91C (off-white solid, 6.5 g, 93% yield). LC-MS Anal. Calc'd for $C_{12}H_{14}N_2O$ 202. found [M+H] 203.

91D. (S)-2-(1-(4-(4-methoxy-2-methylphenoxy)phenyl)pyrrolidin-2-yl)acetonitrile: To a solution of 91C (0.2 g, 0.9 mmol) in dichloromethane (20 mL) was added 4-methoxy-2-methyl phenyl boronic acid (0.57 g, 3.46 mmol), copper acetate (0.18 g, 0.9 mmol), 4 Å molecular sieves (0.5 g) and triethyl amine (0.5 g, 4.9 mmol). Then the mass was stirred at room temperature for 24 hours. The reaction mass was then diluted with ethyl acetate, filtered and concentrated. The crude was purified with silica gel (60-120 mesh) column chromatography with ethyl acetate and petroleum ether (5:5) as eluent to yield 91D (yellow oil, 0.027 g, 8% yield). LC-MS Anal. Calc'd for $C_{20}H_{22}N_2O_2$ 322. found [M+H] 323.

91E (Example 91. 2-(1-(4-(4-methoxy-2-methylphenoxy)phenyl)pyrrolidin-2-yl)acetic acid): Example 91 (brown oil, 0.007 g, 0.02 mmol, 24% yield) was prepared from 91D following the procedure of 93E. LC-MS Anal. Calc'd for $C_{20}H_{23}NO_4$ 341. found [M+H] 342. $^1$H NMR (400 MHz, DMSO-$d_6$) δ ppm 6.84 (1H, s), 6.78 (2H, d, J=8.80 Hz), 6.70 (2H, m), 6.53 (2H, d, J=8.80 Hz), 3.96 (1H, m), 3.71 (3H, s), 3.31 (1H, m), 3.04 (1H, m), 2.16 (3H, s), 2.10 (1H, m), 2.08 (2H, m), 1.97 (2H, m), 1.88 (1H, m).

Analytical HPLC: RT=9.84 min, HI: 98.5%.

Example 92

2-(1-(4-(2,3-dimethylphenoxy)phenyl)pyrrolidin-2-yl)acetic acid

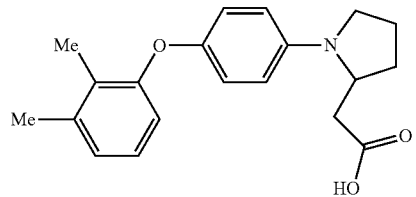

92A. (S)-ethyl 2-(1-(4-(2,3-dimethylphenoxy)phenyl)pyrrolidin-2-yl)acetate: 92A (yellow oil, 0.01 g, 0.028 mmol, 18% yield) was prepared from (S)-ethyl 2-(1-(4-hydroxyphenyl)pyrrolidin-2-yl)acetate (13A) following the procedure of 91D. LC-MS Anal. Calc'd for $C_{22}H_{27}NO_3$ 353. found [M+H] 354.

92B (Example 92. 2-(1-(4-(2,3-dimethylphenoxy)phenyl)pyrrolidin-2-yl)acetic acid): Example 92 (pale brown solid, 0.004 g, 0.012 mmol, 76% yield) was prepared from 92A following the procedure of 86H. LC-MS Anal. Calc'd for $C_{20}H_{23}NO_3$ 339. found [M+H] 340. $^1$H NMR (400 MHz, DMSO-$d_6$) δ ppm 12.3 (1H, s), 7.02 (1H, m), 6.98 (1H, m), 6.88 (3H, m), 6.56 (3H, m), 3.98 (1H, m), 3.07 (1H, m), 2.59 (1H, m), 2.51 (1H, m), 2.33 (3H, s), 2.29 (1H, m), 2.20 (3H, s), 2.09 (3H, m), 1.90 (1H, m). Analytical HPLC: RT=13.7 min, HI: 95.2%.

Example 93

2-(1-(4-phenethylphenyl)pyrrolidin-2-yl)acetic acid

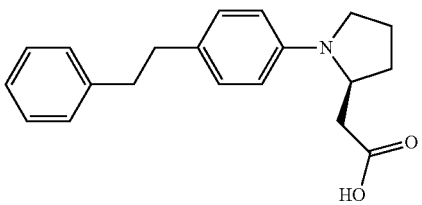

93A. (S)-(1-(4-bromophenyl)pyrrolidin-2-yl)methanol: 93A (brown gummy solid, 15 g, 58 mmol, 82% yield) was prepared from (S)-pyrrolidin-2-ylmethanol and 4-iodobromobenzene following the procedure of 91A. LC-MS Anal. Calc'd for $C_{11}H_{14}BrNO$ 256. found [M+H] 257. $^1$H NMR (400 MHz, DMSO-$d_6$) δ ppm 7.29 (2H, d, J=8.8 Hz), 6.56 (2H, d, J=8.8 Hz), 4.79 (1H, t), 3.63 (1H, m), 3.47 (1H, m), 3.34 (1H, m), 3.20 (1H, m), 3.00 (1H, m), 2.00 (4H, m).

93B. (S)-2-(1-(4-bromophenyl)pyrrolidin-2-yl)acetonitrile: 93B (white solid, 12 g, 45 mmol, 46% yield) was prepared from 93A following the procedure of 91B. LC-MS Anal. Calc'd for $C_{12}H_{13}BrN_2$ 264. found [M+H] 265.0. $^1$H NMR (400 MHz, DMSO-$d_6$) δ ppm 7.32 (2H, d, J=8.0 Hz), 6.63 (2H, d, J=8.00 Hz), 4.07 (1H, m), 3.44 (1H, m), 3.12 (1H, m), 2.77 (2H, m), 2.17 (2H, m), 1.98 (2H, m).

93C. (S)-2-(1-(4-(phenylethynyl)phenyl)pyrrolidin-2-yl)acetonitrile: A 25 mL pressure tube fitted with screw cap was charged with 93B (0.5 g, 18.8 mmol), phenyl acetylene (0.23 g, 22.6 mmol) and tetra butyl ammonium fluoride (1.47 g 5.6 mmol), nitrogen purged through the reaction mass for 15 min then added bis-triphenylphosphinepalladium(II) dichloride, this resulting mass was heated up to 80° C. for overnight, TLC showed new spot formation, crude LC-MS confirmed the formation of the product. The reaction mass was diluted with ethyl acetate and the organic layer was given water and brine washes, dried over sodium sulphate. Purification by silica column chromatography (230-400 mesh) using 0-10% ethyl acetate in hexane yielded 93C (dark brown oil, 0.23 g, 43% yield). LC-MS Anal. Calc'd for $C_{20}H_{20}N_2$ 288.16. found [M+H] 290.0.

93D. (S)-2-(1-(4-phenethylphenyl)pyrrolidin-2-yl)acetonitrile: To a solution of 93C (0.2 g, 0.69 mmol) in ethyl acetate was added 10% Pd\C (0.1 g) under $N_2$ and atmosphere was removed from the reaction mass then back filled with hydrogen, this process repeated for three times, then the reaction mass was fitted with hydrogen bladder and stirred at rt for 3 h, the reaction mass filtered through CELITE® and ethyl acetate solution was concentrated to pale brown oil. Purification by silica column (230-400 mesh) chromatography using 0-20% ethyl acetate in hexane yielded 93D (pale yellow solid, 0.1 g, 50% yield). LC-MS Anal. Calc'd for $C_{20}H_{22}N_2$ 290.18. found [M+H] 291.2 $^1$H NMR (400 MHz, DMSO-$d_6$) δ ppm 7.28 (5 H, m), 7.06 (2 H, dd, J=8.4 Hz), 6.56 (2 H, dd, J=8.4 Hz), 4.02 (1 H, m), 3.44 (1 H, m), 3.089 (1 H, m), 2.81 (6 H, m), 2.17 (2 H, m), 2.06 (2 H, m).

93E (Example 93. 2-(1-(4-phenethylphenyl)pyrrolidin-2-yl)acetic acid): A 25 mL pressure tube with screw cap was charged with 93D (0.1 g, 0.3 mmol), 6 N solution of potassium hydroxide (0.96 g, 17 mmol) and ethanol (10 mL), this reaction mixture was heated up to 120° C. for 48 h, LC-MS showed the product formation. The reaction mass was concentrated to remove ethanol and neutralized with 1.5 N HCl up to pH 5 then extracted with DCM, the organic layer was washed with water and brine, dried over sodium sulfate. The crude product was purified by Prep. HPLC using ammonium acetate to yield Example 93 (pale yellow solid, 0.025 g, 27% yield). LC-MS Anal. Calc'd for $C_{20}H_{23}NO_2$ 309.17. found [M+H] 310.2 $^1$H NMR (400 MHz, DMSO-$d_6$) δ ppm, 12.31 (1H, s), 7.29 (5H, m), 7.05 (2H, d, J=8.4 Hz), 6.48 (2H, d, J=8.4 Hz), 4.0 (1H, m), 3.3 (1H, m), 3.06 (1H, m), 2.83 (4H, m), 2.58 (1H, m), 2.3 (1H, m), 2.11 (3H, m), 1.9 (1H, m). Analytical HPLC: RT=9.57 min, HI: 99.8%.

Examples 94 to 107

Examples 94 to 107 were prepared by the following procedure:

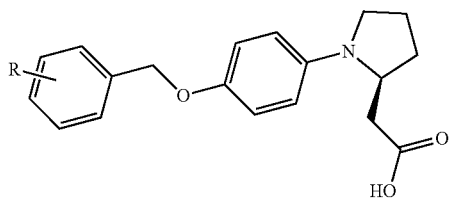

A stock solution of (S)-ethyl 2-(1-(4-hydroxyphenyl)pyrrolidin-2-yl)acetate (13A, 628 mg) in 13 mL of DMF was prepared. 0.5 mL of this stock solution was added to reaction vials containing benzyl bromides (1.105 mmols; 1.05 eq) and $Cs_2CO_3$ (0.200 mmols; 2 eq). The reactions were stirred overnight at 80° C. The LCMS analysis results showed complete disappearance of (S)-ethyl 2-(1-(4-hydroxyphenyl)pyrrolidin-2-yl)acetate (13A). DMF was removed by Genevac and to the residue was added a mixture of 1,4-dioxane and methanol (1:1) (0.5 mL) followed by the addition of 1N aq NaOH (0.5 mL) to each of the vials. The reaction mixture was stirred overnight at rt. The solvent was removed using Genevac and the reaction mixture was diluted with DCM, acidified to pH 2 using 1N HCl, DCM extracts were collected and the solvent removed. The crude product was purified by reverse phase AGILENT® HPLC system using ACN and 10 mm $NH_4OAc$ as mobile phase.

| Ex. No. | R | Formula | MW | % Purity | HPLC RT | Obs. MS Ion |
|---|---|---|---|---|---|---|
| 94 | 4-Me | $C_{20}H_{23}NO_3$ | 325.41 | 98.13 | 2.12 | 326.24 |
| 95 | 2-F | $C_{19}H_{20}FNO_3$ | 329.37 | 100.00 | 1.98 | 330.22 |
| 96 | 3-F | $C_{19}H_{20}FNO_3$ | 329.37 | 98.33 | 2.01 | 330.21 |
| 97 | 4-F | $C_{19}H_{20}FNO_3$ | 329.37 | 100.00 | 1.99 | 330.20 |
| 98 | 2-CN | $C_{20}H_{20}N_2O_3$ | 336.39 | 100.00 | 1.80 | 337.20 |
| 99 | 3,4-di-F | $C_{19}H_{19}F_2NO_3$ | 347.36 | 96.84 | 2.08 | 348.18 |
| 100 | 3,5-di-Me | $C_{21}H_{25}NO_3$ | 339.43 | 97.57 | 2.31 | 340.24 |
| 101 | 2-$CF_3$ | $C_{20}H_{20}F_3NO_3$ | 379.38 | 100.00 | 2.28 | 380.16 |
| 102 | 3-$OCF_3$ | $C_{20}H_{20}F_3NO_4$ | 395.38 | 90.31 | 2.36 | 396.16 |
| 103 | 2-$OCF_3$ | $C_{20}H_{20}F_3NO_4$ | 395.38 | 97.07 | 2.33 | 396.16 |
| 104 | 4-$CF_3$ | $C_{20}H_{20}F_3NO_3$ | 379.38 | 91.79 | 2.11 | 379.90 |
| 105 | 4-t-Bu | $C_{23}H_{29}NO_3$ | 367.49 | 98.78 | 2.61 | 368.26 |
| 106 | 2-Ph | $C_{25}H_{25}NO_3$ | 387.48 | 97.99 | 2.24 | 388.07 |
| 107 | 4-Ph | $C_{25}H_{25}NO_3$ | 387.48 | 100.00 | 2.26 | 388.01 |

Examples 108 to 117

Examples 108 to 117 Synthesized according to the procedures of Examples 94 to 107 using (R)-ethyl 2-(1-(4-hydroxyphenyl)pyrrolidin-2-yl)acetate.

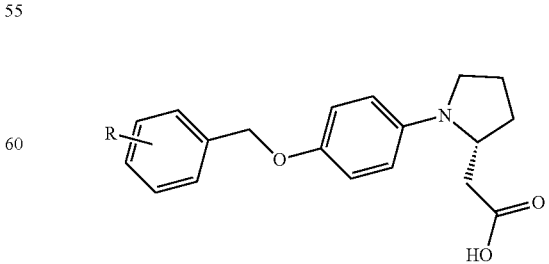

| Ex. No. | R | Formula | MW | % Purity | HPLC RT | Obs. MS Ion |
|---|---|---|---|---|---|---|
| 108 | 4-t-Bu | $C_{23}H_{29}NO_3$ | 367.48 | 86.7 | 4.78 | 366.6502075 |
| 109 | 4-Me | $C_{20}H_{23}NO_3$ | 325.4 | 94.6 | 3.81 | 324.5650024 |
| 110 | 3-$CF_3$ | $C_{20}H_{20}F_3NO_3$ | 379.37 | 79.7 | 4.13 | 378.5704956 |
| 111 | 4-$CF_3$ | $C_{20}H_{20}F_3NO_3$ | 379.37 | 89.6 | 4.19 | 378.5888062 |
| 112 | 3,5-di-Me | $C_{21}H_{25}NO_3$ | 339.43 | 85.2 | 4.1 | 338.6795044 |
| 113 | 4-Ph | $C_{25}H_{25}NO_3$ | 387.47 | 82.4 | 4.64 | 386.6416931 |
| 114 | 3-$OCF_3$ | $C_{20}H_{20}F_3NO_4$ | 395.37 | 79.9 | 4.3 | 394.5931091 |
| 115 | 2-Ph | $C_{25}H_{25}NO_3$ | 387.47 | 80.7 | 4.4 | 386.6878052 |
| 116 | 4-CN | $C_{19}H_{18}N_2O_3$ | 322.36 | 91.0 | 3.4 | 321.5309143 |
| 117 | 3-Ph | $C_{25}H_{25}NO_3$ | 387.47 | 79.9 | 4.47 | 386.6878052 |

Examples 118 to 124

Examples 118 to 124 were synthesized according to the procedure described for Examples 94 to 107 using R-Ph-L.G. instead of R-Bn-L.G.

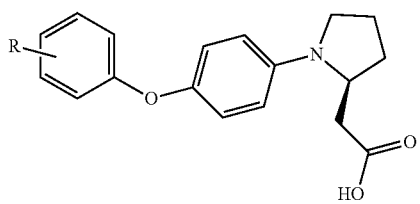

Compound Information

| Ex. No. | R | Formula | MW | % Purity | HPLC RT | Obs. MS Ion |
|---|---|---|---|---|---|---|
| 118 | 2-Cl-4-CN | $C_{19}H_{17}ClN_2O_3$ | 356.80 | 98.92 | 1.84 | 357.02 |
| 119 | 3-$CF_3$-4-CN | $C_{20}H_{17}F_3N_2O_3$ | 390.36 | 100.00 | 1.97 | 391.06 |
| 120 | 2-$CF_3$-4-CN | $C_{20}H_{17}F_3N_2O_3$ | 390.36 | 100.00 | 1.94 | 391.05 |
| 121 | 3-CN-4-$CF_3$ | $C_{20}H_{17}F_3N_2O_3$ | 390.36 | 94.67 | 2.01 | 391.05 |
| 122 | 4-CN | $C_{19}H_{18}N_2O_3$ | 322.36 | 99.25 | 1.66 | 323.09 |
| 123 | 2-F-4-CN | $C_{19}H_{17}FN_2O_3$ | 340.35 | 98.45 | 1.70 | 341.05 |
| 124 | 2-CN-4-$CF_3$ | $C_{20}H_{17}F_3N_2O_3$ | 390.36 | 97.10 | 1.96 | 390.99 |

Examples 125 to 140

Examples 125 to 140 were prepared by the following procedure:

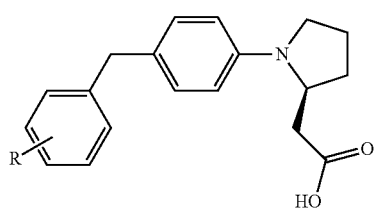

A stock solution of the template, (S)-2-(1-(4-(4,4,5,5-tetramethyl-1,3,2-dioxaborolan-2-yl)phenyl)pyrrolidin-2-yl)acetonitrile (900.0 mg) in 30.0 mL of anhydrous THF was made. To each Wheaton vial containing the various benzyl bromides (1.0 eq, 0.096 mmol) was added 1.0 mL of the template stock solution and 144.0 µL of 2 M sodium carbonate (144 µl, 0.288 mmol). The vials were degassed and purged with argon. To each of the vials was added 11 mg of Pd(PPh$_3$)$_4$ (11.1 mg, 9.61 mmol). The reactions were shaken overnight at 80° C. The LCMS analysis results showed complete disappearance of the starting material. The vials were concentrated down on the ZYMARK® to remove THF. To each dry residue was added 650 µL of ethanol and 500 µL of 5M NaOH. The contents of the vials were transferred to 0.5-2.0 mL microwave vials and the vials were irradiated in the BIOTAGE® Initiator (400 W) microwave at 150° C. for 20 min. The solvent was removed on the ZYMARK®. Dry residue was redissolved in 0.8 mL ethanol and 0.5 mL DMF, acidified to pH 2 using 1N HCl and then sonicated till everything dissolved. The crudes were purified by reverse phase Waters HPLC using ACN and 10 mm NH$_4$OAc as mobile phase.

| Ex. No. | R | Formula | MW | % Purity | HPLC RT | Obs. MS Ion |
|---|---|---|---|---|---|---|
| 125 | 3-Me | $C_{20}H_{23}NO_2$ | 309.4 | 100.00 | 6.07 | 310.3399963 |
| 126 | 4-Me | $C_{20}H_{23}NO_2$ | 309.4 | 95.16 | 6.04 | 310.3399963 |
| 127 | 3-F | $C_{19}H_{20}FNO_2$ | 313.37 | 96.33 | 5.69 | 314.2999878 |
| 128 | 3-$CF_3$ | $C_{20}H_{20}F_3NO_2$ | 363.37 | 96.54 | 6.24 | 364.269989 |
| 129 | 4-$CF_3$ | $C_{20}H_{20}F_3NO_2$ | 363.37 | 100.00 | 6.29 | 364.25 |
| 130 | 3-Cl | $C_{19}H_{20}ClNO_2$ | 329.82 | 100.00 | 6.06 | 330.2399902 |
| 131 | 3,4-di-F | $C_{19}H_{19}F_2NO_2$ | 331.36 | 100.00 | 5.79 | 332.2900085 |
| 132 | 2,4-di-F | $C_{19}H_{19}F_2NO_2$ | 331.36 | 100.00 | 5.74 | 332.2600098 |
| 133 | 3,4-$Cl_2$ | $C_{19}H_{19}Cl_2NO_2$ | 364.27 | 100.00 | 6.51 | 364.2200012 |
| 134 | 3-(4'-F)Ph | $C_{25}H_{24}FNO_3$ | 405.46 | 90.80 | 6.8 | 406.230011 |
| 135 | 2-F-4-Cl | $C_{19}H_{19}ClFNO_2$ | 347.81 | 100.00 | 6.17 | 348.2399902 |
| 136 | 3-F-4-Me | $C_{20}H_{22}FNO_2$ | 327.39 | 97.75 | 6.02 | 328.2999878 |
| 137 | 2-Cl-3-$CF_3$ | $C_{20}H_{19}ClF_3NO_2$ | 397.82 | 100.00 | 6.49 | 398.1900024 |
| 138 | 2,3-di-Cl | $C_{19}H_{19}Cl_2NO_2$ | 364.27 | 100.00 | 6.38 | 364.2000122 |
| 139 | 4-t-Bu | $C_{23}H_{29}NO_2$ | 351.48 | 96.95 | 5.1 | 352.3099976 |
| 140 | 2,4-$CF_3$ | $C_{21}H_{19}F_6NO_2$ | 431.37 | 97.49 | 6.91 | 432.1400146 |

Examples 141 to 151

Examples 141 to 151 were prepared by the following procedure:

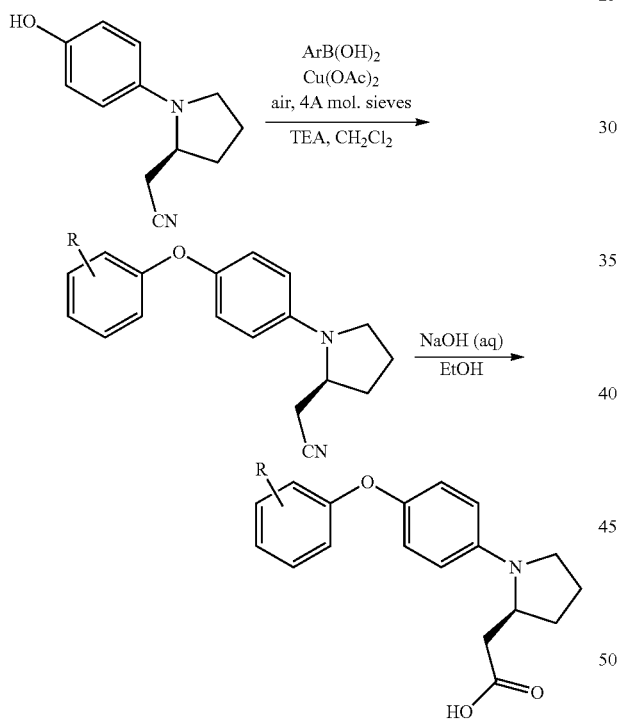

To a vial was added (S)-2-(1-(4-hydroxyphenyl)pyrrolidin-2-yl)acetonitrile (91C, 15 mg, 0.0742 mmol), boronic acid (0.1485 mmol, 2 eq), copper(II) acetate (0.0816 mmol, 1.1 eq), 30 mg of 4 Å molecular sieves (30 mg) and triethyl amine (0.371 mmol, 5 eq) in DCM (2 mL). The reaction mixture was stirred at rt overnight in air. The solvent was removed and to the vial containing this crude reaction mass 0.5 mL of 5M aq NaOH and 0.5 mL of ethanol were added. The vial was then placed in an oil bath preheated to 160° C. and stirred for 3 h. After 3 h the solvent was removed and redissolved in DCM, acidified to pH 2 using 1N HCl and extracted with DCM. The crude products were purified by reverse phase AGILENT® HPLC system using ACN and 10 mm $NH_4OAc$ as mobile phase.

| Ex. No. | R | Formula | MW | % Purity | Obs. MS Ion |
|---|---|---|---|---|---|
| 141 | 4-Cl | $C_{18}H_{18}ClNO_3$ | 331.79341 | 85.8 | 332.2 |
| 142 | 4-Me | $C_{19}H_{21}NO_3$ | 311.37493 | 97.5 | 312.2 |
| 143 | 4-OMe | $C_{19}H_{21}NO_4$ | 327.37434 | 94.1 | 328.2 |
| 144 | 3-Me | $C_{19}H_{21}NO_3$ | 311.37494 | 84.7 | 312.2 |
| 145 | 2,4-di-Cl | $C_{18}H_{17}Cl_2NO_3$ | 366.23848 | 95.6 | 366 |
| 146 | 4-PhO | $C_{24}H_{23}NO_4$ | 389.44372 | 90.9 | 390.2 |
| 147 | 3-Cl | $C_{18}H_{18}ClNO_3$ | 331.79342 | 94.2 | 332 |
| 148 | 4-BnO | $C_{25}H_{25}NO_4$ | 403.4703 | 94.4 | 404.2 |
| 149 | 3-$Me_2N$ | $C_{20}H_{24}N_2O_3$ | 340.41616 | 90.8 | 341.2 |
| 150 | 3-$CF_3O$ | $C_{19}H_{18}F_3NO_4$ | 381.34572 | 85.7 | 382 |
| 151 | 3-BnO | $C_{25}H_{25}NO_4$ | 403.4703 | 93.3 | 404.2 |

Example 152

(S)-2-(1-(5-(2,4-dichlorobenzyloxy)pyrimidin-2-yl)pyrrolidin-2-yl)acetic acid

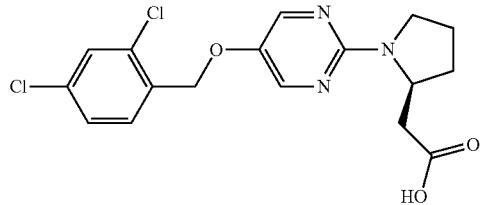

152A. (S)-methyl 2-(1-(5-(2,4-dichlorobenzyloxy)pyrimidin-2-yl)pyrrolidin-2-yl)acetate: To a round bottom flask was added 2-chloro-5-methoxypyrimidine (250 mg, 1.73 mmol) and $CH_2Cl_2$ (1 mL). The reaction mixture was cooled to −78° C. and 1N $BBr_3$ (4 eq) was added slowly over 15 min. The reaction mixture was slowly warmed to rt and was stirred ovn. The mixture was cooled to 0° C. and 1N $BBr_3$ (4 eq) was added. The reaction was slowly warmed to rt and then stirred for 24 h. The reaction was quenched via addition of methanol at 0° C., and the mixture was evaporated to dryness. The residue was dissolved in water (1 mL) and the pH of the solution was adjusted to 5 using 1N NaOH solution. The resulting mixture was extracted with EtOAc (2×25 mL), and the combined organics were washed successively with water (20 mL) and brine (20 mL), and the organic layer was dried ($MgSO_4$) and concentrated to give 2-chloropyrimidin-5-ol (170 mg, 75% yield). The crude product was dissolved in DMF (3 mL) and 2,4-dichloro-1-(chloromethyl)benzene (0.215 mL, 1.57 mmol), $K_2CO_3$ (270 mg, 1.96 mmol) were added. The reaction mixture was stirred at 60° C. for 4 h. The resulting solution was diluted with EtOAc (50 mL), and the organic layer was washed successively with water (4×30 mL) and brine (30 mL), and the organic layer was dried ($MgSO_4$) and concentrated. The residue was purified via silica gel chromatography to give 2-chloro-5-(2,4-dichlorobenzyloxy) pyrimidine (310 mg, 81% yield) as white solid containing ~50% of 2-bromo-5-(2,4-dichlorobenzyloxy)pyrimidine. The material was used as is in the subsequent step. To a microwave vial was added 2-chloro-5-(2,4-dichlorobenzyloxy)pyrimidine (54 mg, 0.19 mmol), (S)-methyl 2-(pyrrolidin-2-yl)acetate (80 mg, 0.56 mmol), Hunig's Base (0.16 mL, 0.93 mmol) and DMF (1.2 mL). The reaction was heated in a microwave at 180° C. for 30 min. The reaction mixture was diluted with MeOH, and the mixture was purified via preparative RP-HPLC to give 152A (clear oil, 40 mg, 0.101 mmol, 54.1% yield). LC-MS Anal. Calc'd for $C_{18}H_{19}Cl_2N_3O_3$: 396.27. found [M+H] 396.2.

152B (Example 152. (S)-2-(1-(5-(2,4-dichlorobenzyloxy) pyrimidin-2-yl)pyrrolidin-2-yl)acetic acid): To a round bottom flask was added 152A (33 mg, 0.083 mmol), THF (1 mL), water (0.200 mL) and LiOH (4.20 mg, 0.100 mmol). The reaction mixture was stirred at rt for 8 h. The mixture was evaporated and the residue was purified via prep RP-HPLC to give Example 152 (white solid, 22 mg, 0.056 mmol, 67.7% yield). Chiral HPLC showed the product to contain 2 isomers in a ratio of 7:3. LC-MS Anal. Calc'd for $C_{17}H_{17}Cl_2N_3O_3$: 382.24. found [M+H] 382.1; $^1H$ NMR (500 MHz, methanol-$d_3$) δ ppm 8.22 (s, 2 H), 7.45-7.64 (m, 2 H), 7.38 (dd, J=8.25, 2.20 Hz, 1 H), 5.14 (s, 2 H), 4.34-4.55 (m, 1 H), 3.59 (ddd, J=10.86, 7.56, 3.02 Hz, 1 H), 3.41-3.53 (m, 1 H), 2.97 (dd, J=15.40, 3.85 Hz, 1 H), 2.34 (dd, J=15.40, 9.90 Hz, 1 H), 1.87-2.21 (m, 4H); $^{13}C$ NMR (126 MHz, methanol-$d_3$) δ ppm 175.28, 147.54, 145.94, 135.59, 134.17, 131.85, 129.99, 128.23, 70.05, 56.16, 38.08, 31.57, 23.80. Analytical HPLC: RT=7.4 min, HI: 98.7%.

What is claimed is:
1. A compound of Formula (I):

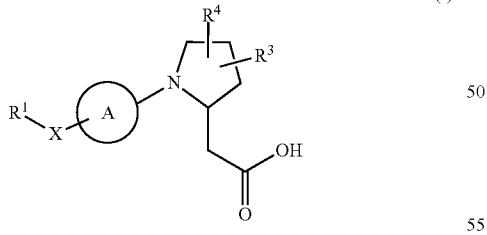

(I)

or a stereoisomer, a tautomer, or a pharmaceutically acceptable salt thereof, wherein:
X is selected from the group consisting of: O, S, $CH_2$, $CH(C_{1-4}$ alkyl), $C(C_{1-4}$ alkyl$)_2$, $CH(C_{1-4}$ alkoxy-phenyl), and C(O);
ring A is phenyl substituted with 0-2 $R^5$, pyridinyl substituted with 0-2 $R^5$, or pyrimidinyl substituted with 0-2 $R^5$;
$R^1$ is —$(CH_2)_n$-phenyl substituted with 0-3 $R^2$, —$(CH_2)_n$-naphthyl substituted with 0-3 $R^2$, or —$(CH_2)_n$-5- to 6-membered heteroaryl containing carbon atoms and 1-4 heteroatoms selected from the group consisting of N, O, and S(O)$_p$; wherein said heteroaryl is substituted with 0-3 $R^2$;
$R^2$, at each occurrence, is independently selected from the group consisting of: halo, $CF_3$, CN, $NO_2$, $OCF_3$, $SCF_3$, $C_{1-6}$ alkyl, $C_{1-6}$ alkoxy, $C_{1-6}$ alkylthio, $NH_2$, $NH(C_{1-4}$ alkyl), $N(C_{1-4}$ alkyl$)_2$, —$(CH_2)_n$—$C_{3-10}$ carbocycle, —$(CH_2)_n$—O—$C_{3-10}$ carbocycle, and —$(CH_2)_n$-3- to 10-membered heterocycle containing carbon atoms and 1-4 heteroatoms selected from the group consisting of N, O, and S(O)$_p$; wherein said carbocycle and heterocycle are substituted with 0-3 $R^6$;
$R^3$ and $R^4$, at each occurrence, are independently selected from the group consisting of: H, OH, halo, $CF_3$, $C_{1-4}$ alkyl, and $C_{1-4}$ alkoxy;
$R^5$, at each occurrence, is independently selected from the group consisting of: halo and $C_{1-4}$ alkyl;
$R^6$, at each occurrence, is independently selected from the group consisting of: halo, $CF_3$, $C_{1-4}$ alkyl, and $C_{1-4}$ alkoxy;
n, at each occurrence, is independently 0, 1, 2 or 3; and
p, at each occurrence, is independently 0, 1 or 2.
2. A compound according to claim 1, wherein:
X is selected from the group consisting of: O, S, $CH_2$, $CH(C_{1-4}$ alkyl), $CH(C_{1-4}$ alkoxy-phenyl), and C(O);
$R^1$ is —$(CH_2)_n$-phenyl substituted with 0-3 $R^2$, —$(CH_2)_n$-naphthyl substituted with 0-3 $R^2$, or —$(CH_2)_n$-pyridyl substituted with 0-3 $R^2$;
$R^2$, at each occurrence, is independently selected from the group consisting of: halo, $CF_3$, CN, $NO_2$, $OCF_3$, $SCF_3$, $C_{1-6}$ alkyl, $C_{1-6}$ alkoxy, $C_{1-6}$ alkylthio, $NH_2$, $NH(C_{1-4}$ alkyl), $N(C_{1-4}$ alkyl$)_2$, —$(CH_2)_n$—$C_{3-6}$ cycloalkyl, —$(CH_2)_n$—$C_{4-6}$ cycloalkenyl, —$(CH_2)_n$-phenyl, —$(CH_2)_n$—O-phenyl, and —$(CH_2)_n$-5- to 6-membered heteroaryl containing carbon atoms and 1-4 heteroatoms selected from the group consisting of N, O, and S(O)$_p$; wherein said cycloalkyl, cycloalkenyl, phenyl and heteroaryl are substituted with 0-2 $R^6$; and
n, at each occurrence, is independently 0, 1 or 2.
3. A compound according to claim 1, wherein the compound is of Formula (II):

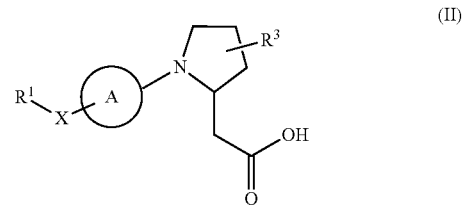

(II)

or a stereoisomer, a tautomer, or a pharmaceutically acceptable salt thereof, wherein:
X is selected from the group consisting of: O, S, $CH_2$, $CH(C_{1-4}$ alkyl), CH(2-(methoxy)-phenyl), and C(O);
ring A is selected from the group consisting of:

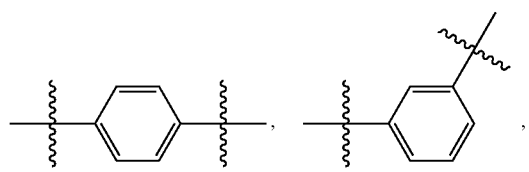

-continued

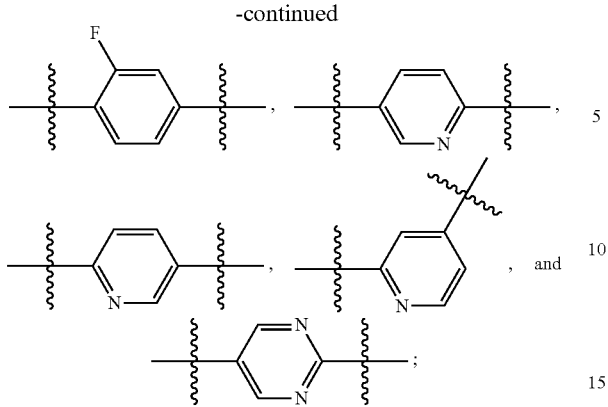

R², at each occurrence, is independently selected from the group consisting of: halo, CF₃, CN, NO₂, OCF₃, SCF₃, $C_{1-6}$ alkyl, $C_{1-6}$ alkoxy, $C_{1-6}$ alkylthio, NH, NH($C_{1-4}$ alkyl), N($C_{1-4}$ alkyl)₂, cyclopentenyl substituted with 0-2 R⁶, phenyl substituted with 0-2 R⁶, benzyl substituted with 0-2 R⁶, phenoxy substituted with 0-2 R⁶, benzoxy substituted with 0-2 R⁶, and pyrazol-1-yl; and R³ is selected from the group consisting of: H, OH, halo, CF₃, $C_{1-4}$ alkyl, and $C_{1-4}$ alkoxy.

4. A compound according to claim 3 wherein:
R¹ is selected from the group consisting of: phenyl, 2-halophenyl, 3-halophenyl, 4-halophenyl, 2-($C_{1-4}$ alkyl)phenyl, 3-($C_{1-4}$ alkyl)phenyl, 4-($C_{1-4}$ alkyl)phenyl, 2-($C_{1-4}$ alkoxy)phenyl, 4-($C_{1-4}$ alkoxy)phenyl, 2-trifluoromethylphenyl, 3-trifluoromethylphenyl, 4-trifluoromethylphenyl, 2-trifluoromethoxyphenyl, 3-trifluoromethoxyphenyl, 4-cyanophenyl, 3-(N,N-dimethylamino)-phenyl, 4-phenoxyphenyl, 3-(2-halophenyl)phenyl, 3-(4-halophenoxy)phenyl, 3-(2-halobenzyl)phenyl, 3-(2-($C_{1-4}$ alkyl)benzyl)phenyl, 4-(2-halobenzoxy)phenyl, 3-(2-halo-5-($C_{1-4}$ alkoxy)-phenyl)phenyl, 2-biphenyl, 2-benzylphenyl, 4-benzylphenyl, 3-benzoxyphenyl, 4-benzoxyphenyl, 2-($C_{1-4}$ alkyl)-3-($C_{1-4}$ alkyl)-phenyl, 2-($C_{1-4}$ alkyl)-4-($C_{1-4}$ alkyl)-phenyl, 2-($C_{1-4}$ alkyl)-6-($C_{1-4}$ alkyl)-phenyl, 2-halo-3-halophenyl, 2-halo-4-halo-phenyl, 3-halo-4-halophenyl, 3-halo-5-halophenyl, 2-halo-6-halophenyl, 2-($C_{1-4}$ alkyl)-4-($C_{1-4}$ alkoxy)-phenyl, 2-($C_{1-4}$ alkyl)-3-halo-phenyl, 2-($C_{1-4}$ alkyl)-4-halo-phenyl, 2-halo-3-($C_{1-4}$ alkyl)-phenyl, 3-halo-4-($C_{1-4}$ alkyl)-phenyl, 2,4-ditrifluoromethyl-phenyl, 2-halo-3-trifluoromethyl-phenyl, 2-halo-4-trifluoromethyl-phenyl, 2-($C_{1-4}$ alkyl)-4-benzoxy-phenyl, 2-trifluoromethyl-4-cyano-phenyl, 2-cyano-4-trifluoromethyl-phenyl, 3-cyano-4-trifluoromethyl-phenyl, 3-trifluoromethyl-4-cyano-phenyl, 2-halo-4-cyano-phenyl, 2-($C_{1-4}$ alkyl)-3-(2-halo-5-($C_{1-4}$ alkoxy)-phenyl)-phenyl, benzyl, 2-halobenzyl, 3-halobenzyl, 4-halobenzyl, 2-($C_{1-4}$ alkyl)benzyl, 4-($C_{1-4}$ alkyl)benzyl, 4-($C_{1-4}$ alkylthio)benzyl, 2-trifluoromethyl-benzyl, 3-trifluoromethyl-benzyl, 4-trifluoromethyl-benzyl, 2-trifluoromethoxy-benzyl, 3-trifluoromethoxy-benzyl, 4-trifluoromethoxy-benzyl, 2-trifluoromeththio-benzyl, 2-cyanobenzyl, 2-phenyl-benzyl, 3-phenylbenzyl, 4-phenylbenzyl, 2-halo-3-halo-benzyl, 2-halo-4-halo-benzyl, 2-halo-5-halo-benzyl, 3-halo-4-halo-benzyl, 2-halo-3-($C_{1-4}$ alkyl)-benzyl, 3-($C_{1-4}$ alkyl)-4-halo-benzyl, 3-(2-halophenoxy)-benzyl, 3-($C_{1-4}$ alkyl)-4-(2-halophenyl)-benzyl, 4-(pyrazol-1-yl)-benzyl, 3-($C_{1-4}$ alkyl)-5-($C_{1-4}$ alkyl)-benzyl, 3-($C_{1-4}$ alkyl)-4-(2-halo-5-($C_{1-4}$ alkoxy)-phenyl)-benzyl, 3-(2-halo-5-($C_{1-4}$ alkoxy)-phenyl)-4-($C_{1-4}$ alkyl)-benzyl, 3-(5,5-dimethylcyclopent-1-enyl)-4-(2-halo-5-($C_{1-4}$ alkoxy)-phenyl)benzyl, 3-halo-5-trifluoromethylpyrid-3-yl, (2-($C_{1-4}$ alkyl)-6-trifluoromethyl-pyrid-3-yl)methyl, and (2-($C_{1-4}$ alkylthio)-pyrid-3-yl)methyl, and 2-naphthyl.

5. A compound according to claim 1, wherein the compound is of Formula (III):

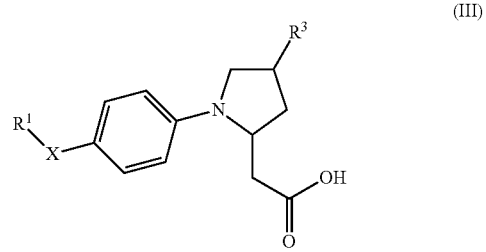

(III)

or a stereoisomer, a tautomer, or a pharmaceutically acceptable salt thereof, wherein:
X is selected from the group consisting of: O, S, CH₂, CH(CH₃), CH(CH₂CH₃), CH(2-methoxyphenyl), and C(O);
R¹ is selected from the group consisting of: phenyl, 2-methylphenyl, 3-methylphenyl, 4-methylphenyl, 4-(t-butyl)phenyl, 2-methoxyphenyl, 4-methoxyphenyl, 2-ethoxyphenyl, 2-fluorophenyl, 3-fluorophenyl, 2-chlorophenyl, 3-chlorophenyl, 4-chlorophenyl, 3-bromophenyl, 2-trifluoromethylphenyl, 3-trifluoromethylphenyl, 4-trifluoromethylphenyl, 2-trifluoromethoxyphenyl, 3-trifluoromethoxyphenyl, 4-cyanophenyl, 3-(N,N-dimethylamino)phenyl, 4-phenoxyphenyl, 3-(4-fluorophenoxy)-phenyl, 2-biphenyl, 2-benzylphenyl, 4-benzylphenyl, 3-benzoxyphenyl, 4-benzoxyphenyl, 3-(2-fluorophenyl)phenyl, 3-(2-fluorobenzyl)phenyl, 3-(2-methylbenzyl)phenyl, 4-(2-fluorobenzoxy)phenyl, 3-(2-fluoro-5-methoxy-phenyl)phenyl, 2,3-dimethylphenyl, 2,4-dimethylphenyl, 2,6-dimethylphenyl, 2,4-difluorophenyl, 2,6-difluorophenyl, 3,4-difluorophenyl, 3,5-difluorophenyl, 2,3-dichlorophenyl, 2,4-dichlorophenyl, 3,4-dichlorophenyl, 3,5-dichlorophenyl, 2,4-ditrifluoromethylphenyl, 3-fluoro-4-methyl-phenyl, 2-methyl-4-methoxy-phenyl, 2-methyl-3-chloro-phenyl, 2-methyl-4-chloro-phenyl, 2-fluoro-4-chloro-phenyl, 2-chloro-3-trifluoromethyl-phenyl, 2-chloro-4-trifluoromethyl-phenyl, 2-methyl-4-benzoxy-phenyl, 2-fluoro-4-cyano-phenyl, 2-chloro-4-cyano-phenyl, 2-cyano-4-trifluoromethyl-phenyl, 3-cyano-4-trifluoromethyl-phenyl, 2-trifluoromethyl-4-cyano-phenyl, 3-trifluoromethyl-4-cyano-phenyl, 2-methyl-3-(2-fluoro-5-methoxy-phenyl)-phenyl, benzyl, 2-methylbenzyl, 3-methylbenzyl, 4-methylbenzyl, 4-(n-butyl)benzyl, 4-(t-butyl)benzyl, 2-fluorobenzyl, 3-fluorobenzyl, 4-fluorobenzyl, 3-chlorobenzyl, 4-chlorobenzyl, 4-methylthiobenzyl, 2-trifluoromethylbenzyl, 3-trifluoromethylbenzyl, 4-trifluoromethylbenzyl, 2-trifluoromethoxybenzyl, 3-trifluoromethoxybenzyl, 2-trifluoromethylthiobenzyl, 2-cyanobenzyl, 2-phenylbenzyl, 3-phenylbenzyl, 4-phenylbenzyl, 3-(2-fluorophenoxy)benzyl, 4-(pyrazol-1-yl)benzyl, 3,5-dimethylbenzyl, 2,4-difluorobenzyl, 3,4-difluorobenzyl, 2,3-dichlorobenzyl, 2,4-dichlorobenzyl, 2,5-dichlorobenzyl, 3,4- dichlorobenzyl, 2-fluoro-3-methyl-benzyl, 3-methyl-4-bromo-benzyl, 3-methyl-4-(2-fluorophenyl)-benzyl, 3-methyl-4-(2-fluoro-5-methoxy-phenyl)-benzyl, 3-(2-fluoro-5-methoxy-phenyl)-4-(t-butyl)-benzyl, 3-(5,5-dimethylcyclopent-1-enyl)-4-(2-fluoro-5-methoxy-phenyl)benzyl, 3-chloro-5-trifluoromethylpyrid-2-yl, (2-(isopropylthio)-pyrid-3-yl)methyl, (2-methyl-6-trifluoromethylpyrid-3-yl)methyl, and 2-naphthyl; and $R^3$ is selected from the group consisting of: H, F, OH, $CH_3$, $CH_2CH_3$, $OCH_3$, and $CF_3$.

6. A compound according to claim 5, wherein:

X is selected from the group consisting of: O, S and $CH_2$;

$R^1$ is selected from the group consisting of: phenyl, 2-methylphenyl, 3-methylphenyl, 4-methylphenyl, 4-methoxyphenyl, 2-fluorophenyl, 2-chlorophenyl, 3-chlorophenyl, 4-chlorophenyl, 3-bromophenyl, 2-trifluoromethylphenyl, 3-trifluoromethylphenyl, 4-trifluoromethylphenyl, 2-trifluoromethoxyphenyl, 3-trifluoromethoxyphenyl, 4-phenoxyphenyl, 2-benzylphenyl, 3-benzoxyphenyl, 4-benzoxyphenyl, 3-(2-fluorophenyl)phenyl, 3-(2-fluorobenzyl)phenyl, 4-(2-fluorobenzoxy)phenyl, 3-(2-fluoro-5-methoxy-phenyl)phenyl, 2,3-dimethylphenyl, 2,4-dimethylphenyl, 2,6-dimethylphenyl, 2,4-difluorophenyl, 2,6-difluorophenyl, 3,5-difluorophenyl, 2,4-dichlorophenyl, 3,5-dichlorophenyl, 2,4-ditrifluoromethylphenyl, 3-fluoro-4-methyl-phenyl, 2-methyl-4-methoxy-phenyl, 2-methyl-3-chloro-phenyl, 2-methyl-4-chloro-phenyl, 2-fluoro-4-chloro-phenyl, 2-chloro-3-trifluoromethyl-phenyl, 2-chloro-4-trifluoromethyl-phenyl, 2-methyl-4-benzoxy-phenyl, 2-chloro-4-cyano-phenyl, 3-cyano-4-trifluoromethyl-phenyl, 2-trifluoromethyl-4-cyano-phenyl, 3-trifluoromethyl-4-cyano-phenyl, 2-methyl-3-(2-fluoro-5-methoxy-phenyl)-phenyl, benzyl, 2-methylbenzyl, 4-methylbenzyl, 2-fluorobenzyl, 3-fluorobenzyl, 3-chlorobenzyl, 4-chlorobenzyl, 4-methylthiobenzyl, 2-trifluoromethylbenzyl, 3-trifluoromethylbenzyl, 2-trifluoromethoxybenzyl, 3-trifluoromethoxybenzyl, 2-trifluoromethylthiobenzyl, 2-cyanobenzyl, 2-phenylbenzyl, 4-phenylbenzyl, 3-(2-fluorophenoxy)benzyl, 3,5-dimethylbenzyl, 2,3-dichlorobenzyl, 2,4-dichlorobenzyl, 3,4-dichlorobenzyl, 2-fluoro-3-methyl-benzyl, 3-methyl-4-bromo-benzyl, 3-(5,5-dimethylcyclopent-l-enyl)-4-(2-fluoro-5-methoxy-phenyl)benzyl, (2-(isopropylthio)-pyrid-3-yl)methyl, (2-methyl-6-trifluoromethylpyrid-3-yl)methyl, and 2-naphthyl; and $R^3$ is selected from the group consisting of: H, F, $CH_3$, $CH_2CH_3$, and $CF_3$.

7. A compound according to claim 5, wherein:

X is selected from the group consisting of: O, S and $CH_2$;

$R^1$ is selected from the group consisting of: phenyl, 2-methylphenyl, 3-methylphenyl, 4-methylphenyl, 2-fluorophenyl, 4-chlorophenyl, 3-bromophenyl, 2-trifluoromethylphenyl, 2-trifluoromethoxyphenyl, 3-trifluoromethoxyphenyl, 4-phenoxyphenyl, 4-benzoxyphenyl, 3-(2-fluorophenyl)phenyl, 4-(2-fluorobenzoxy)phenyl, 2,3-dimethylphenyl, 2,4-dimethylphenyl, 2,6-dimethylphenyl, 2,6-difluorophenyl, 2,4-dichlorophenyl, 3,5-dichlorophenyl, 2-methyl-4-methoxy-phenyl, 2-methyl-3-chloro-phenyl, 2-methyl-4-chloro-phenyl, 2-methyl-4-benzoxy-phenyl, 3-cyano-4-trifluoromethyl-phenyl, 2-chloro-4-trifluoromethyl-phenyl, 2-methyl-3-(2-fluoro-5-methoxy-phenyl)-phenyl, 2-methylbenzyl, 2-chlorobenzyl, 2-trifluoromethylbenzyl, 2-trifluoromethoxybenzyl, 2-trifluoromethylthiobenzyl, 2-phenylbenzyl, 3-(2-fluorophenoxy)benzyl, 2,3-dichlorobenzyl, 2,4-dichlorobenzyl, 3,4-dichlorobenzyl, 2-methyl-4-chloro-benzyl, 2-methyl-3-trifluoromethyl-benzyl, and (2-(isopropylthio)-pyrid-3-yl)methyl; and $R^3$ is selected from the group consisting of: H, F, $CH_3$, $CH_2CH_3$, and $CF_3$.

8. A compound according to claim 5, wherein the compound is of Formula (III):

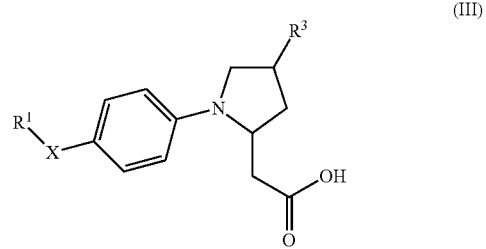

(III)

or a stereoisomer or a pharmaceutically acceptable salt thereof, wherein:

X, $R^1$ and $R^3$ are selected in concert from the group consisting of:

| X | $R^1$ | $R^3$ |
|---|---|---|
| O | 2-methyl-4-methoxy-phenyl | $CF_3$ |
| O | 2-methylphenyl | $CF_3$ |
| $CH_2$ | 2-methylphenyl | $CF_3$ |
| O | 2-trifluoromethoxybenzyl | H |
| O | 2-methylphenyl | H |
| O | 2,3-dimethylphenyl | $CF_3$ |
| $CH_2$ | 2-methylphenyl | F |
| O | 2-methyl-3-chloro-phenyl | $CF_3$ |
| O | 2-fluorophenyl | $CF_3$ |
| O | 2,6-dimethylphenyl | H |
| O | 2,4-dimethylphenyl | H |
| O | 2-methylphenyl | F |
| O | 2-fluorophenyl | F |
| O | 2-methylbenzyl | $CF_3$ |
| O | 2-trifluoromethylthiobenzyl | H |
| O | 2,3-dimethylphenyl | H |
| O | 2-methylphenyl | F |
| O | 2-methyl-4-benzoxy-phenyl | $CF_3$ |
| $CH_2$ | 2-methylphenyl | H |
| O | 2-methyl-4-methoxy-phenyl | H |
| $CH_2$ | 2-methylphenyl | $CH_3$ |
| O | 2-fluorophenyl | H |
| O | 2-methylbenzyl | F |
| O | 4-benzoxyphenyl | H |
| O | 2-trifluoromethoxybenzyl | $CF_3$ |
| O | 2-trifluoromethoxyphenyl | $CF_3$ |
| O | 2-methylphenyl | $CH_3$ |
| O | 2-methylbenzyl | H |
| O | 2-trifluoromethylbenzyl | H |
| O | 2-trifluoromethylbenzyl | $CH_3$ |
| O | 3-trifluoromethoxyphenyl | H |
| O | 4-benzoxyphenyl | H |
| O | 2,4-dichlorobenzyl | H |
| $CH_2$ | 4-chlorophenyl | H |
| $CH_2$ | 3-methylphenyl | H |
| O | 3,4-dichlorobenzyl | H |
| O | 3-methylphenyl | H |
| O | (2-(isopropylthio)-pyrid-3-yl)methyl | H |
| $CH_2$ | 2-fluorophenyl | H |
| $CH_2$ | 2,6-difluorophenyl | H |
| O | 4-chlorophenyl | H |
| O | 2-phenylbenzyl | H |
| O | 2-chloro-4-trifluoromethyl-phenyl | $CF_3$ |
| O | 2-trifluoromethylphenyl | $CF_3$ |

| X | R¹ | R³ |
|---|---|---|
| CH₂ | 4-methylphenyl | H |
| O | 3,5-dichlorophenyl | H |
| O | 2-methyl-3-(2-fluoro-5-methoxy-phenyl)-phenyl | H |
| O | 3-(2-fluorophenyl)phenyl | H |
| O | 4-phenoxyphenyl | H |
| CH₂ | 2-trifluoromethylphenyl | H |
| O | 3-bromophenyl | H |
| CH₂ | 4-benzoxyphenyl | H |
| O | 3-(2-fluorophenoxy)benzyl | H |
| O | 2,3-dichlorobenzyl | H |
| S | 2-methylphenyl | H |
| O | 2-trifluoromethylbenzyl | H |
| O | 2-methylphenyl | Et |
| O | 2,4-dichlorophenyl | H |
| CH₂ | 2,4-dimethylphenyl | H |
| CH₂ | 2-methyl-4-chloro-phenyl | H |
| O | 3-cyano-4-trifluoromethyl-phenyl | H |
| O | 4-methylphenyl | H |
| CH₂ | 3-fluoro-4-methyl-phenyl | H |
| O | 4-methoxyphenyl | H |
| CH₂ | 2-naphthyl | H |
| O | 4-methylthiobenzyl | H |
| O | (2-methyl-6-trifluoromethylpyrid-3-yl)methyl | H |
| O | phenyl | H |
| O | 4-methylbenzyl | H |
| CH₂ | 2,4-difluorophenyl | H |
| O | 2-chloro-4-cyano-phenyl | H |
| O | 2-trifluoromethyl-4-cyano-phenyl | H |
| CH₂ | 2-chlorophenyl | H |
| CH₂ | 2-fluoro-4-chloro-phenyl | H |
| O | 2-fluoro-3-methyl-benzyl | H |
| O | 3-(2-fluorobenzyl)phenyl | H |
| O | 3-chlorophenyl | H |
| CH₂ | phenyl | H |
| O | 2-fluorobenzyl | H |
| O | 3-trifluoromethyl-4-cyano-phenyl | H |
| CH₂ | 2-chloro-3-trifluoromethyl-phenyl | H |
| O | 2-benzylphenyl | H |
| O | 3-(5,5-dimethylcyclopent-1-enyl)-4-(2-fluoro-5-methoxy-phenyl)benzyl | H |
| O | benzyl | H |
| O | 3-fluorobenzyl | H |
| CH₂ | 3,5-difluorophenyl | H |
| O | 3-benzoxyphenyl | H |
| CH₂ | 4-trifluoromethylphenyl | H |
| CH₂ | 2,4-ditrifluoromethylphenyl | H |
| O | 3-(2-fluoro-5-methoxy-phenyl)phenyl | H |
| CH₂ | 3-trifluoromethylphenyl | H |
| O | 3-methyl-4-bromo-benzyl | H |
| O | 4-phenylbenzyl | H |
| O | 3-trifluoromethoxybenzyl | H |
| O | 2-cyanobenzyl | H |

9. A compound according to claim 1, wherein the compound is selected from the group consisting of:

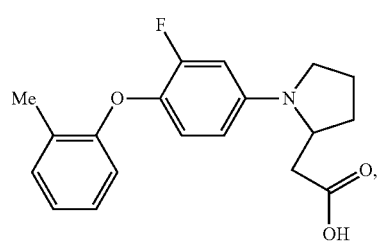

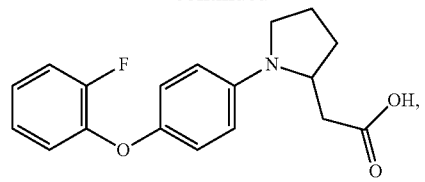

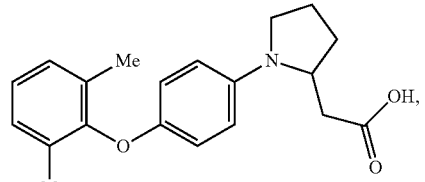

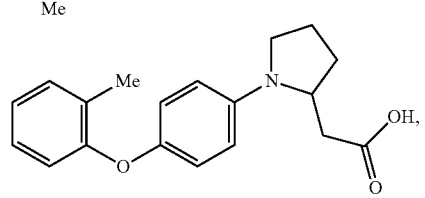

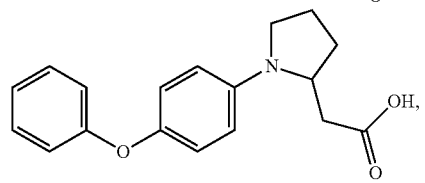

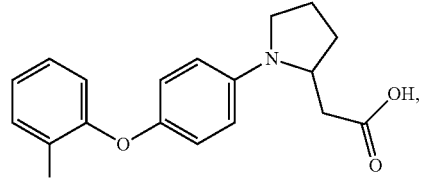

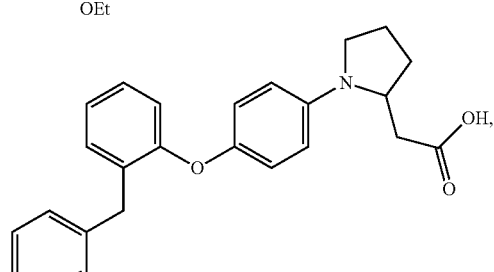

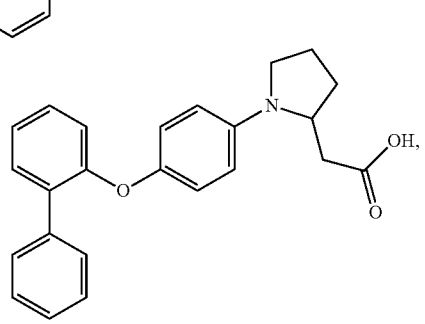

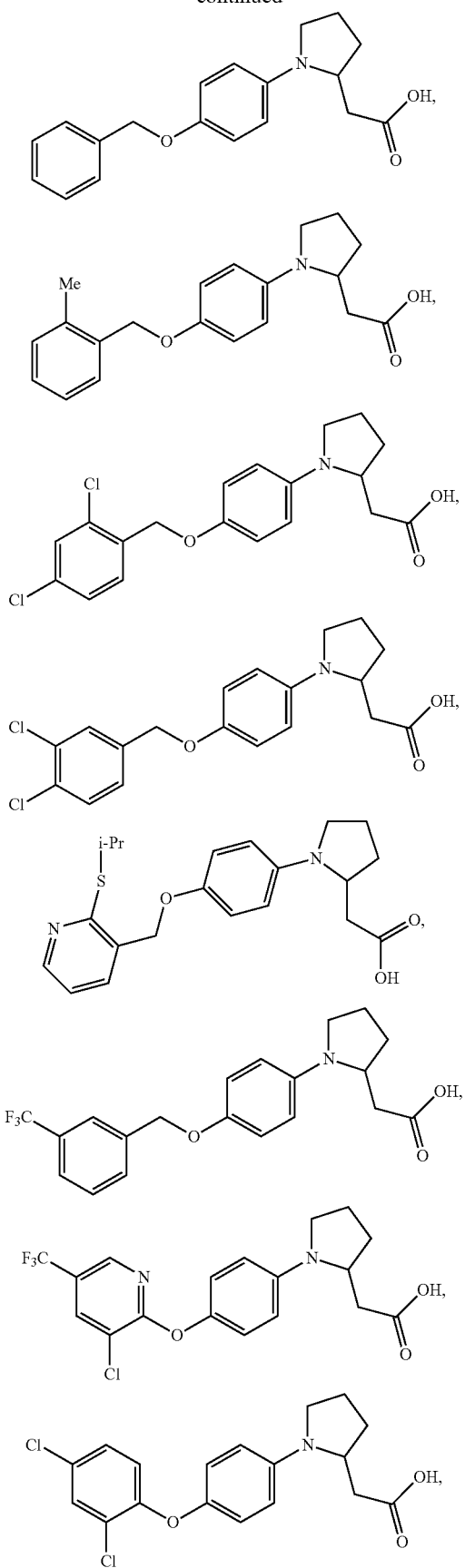
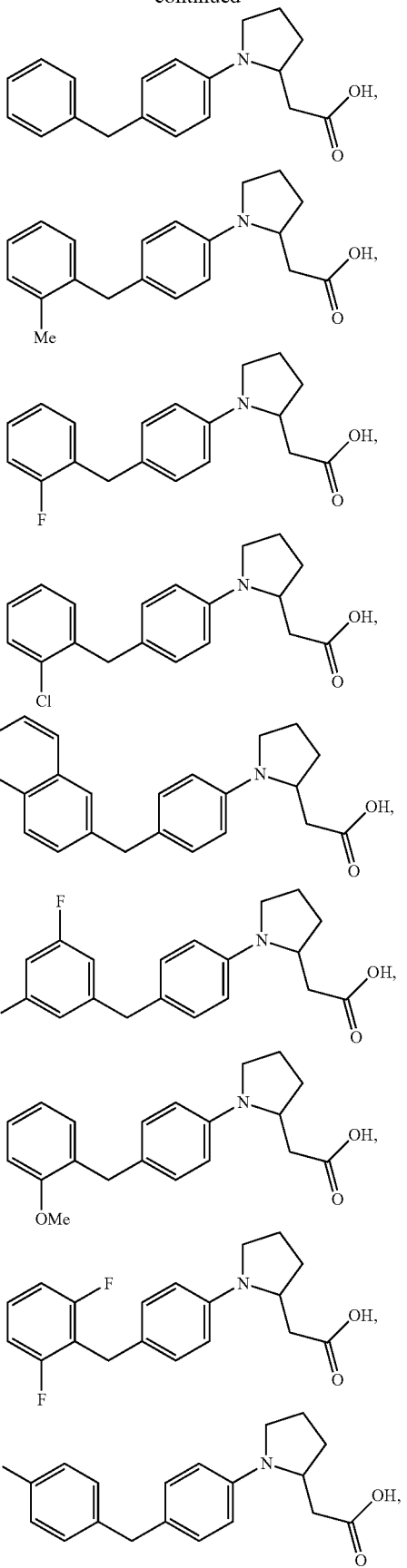

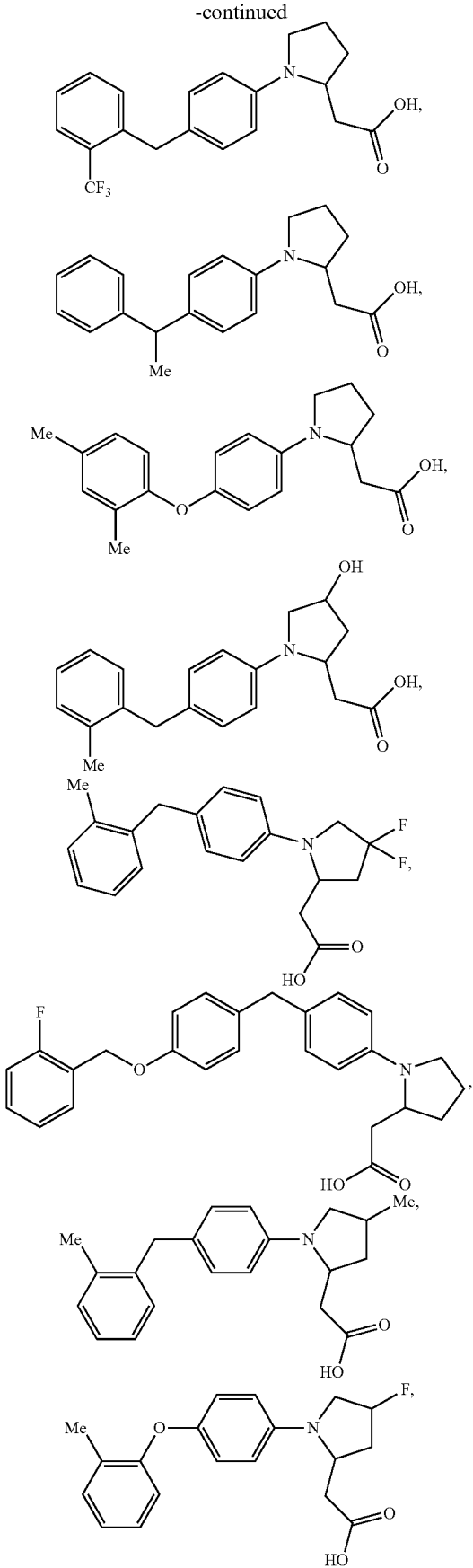
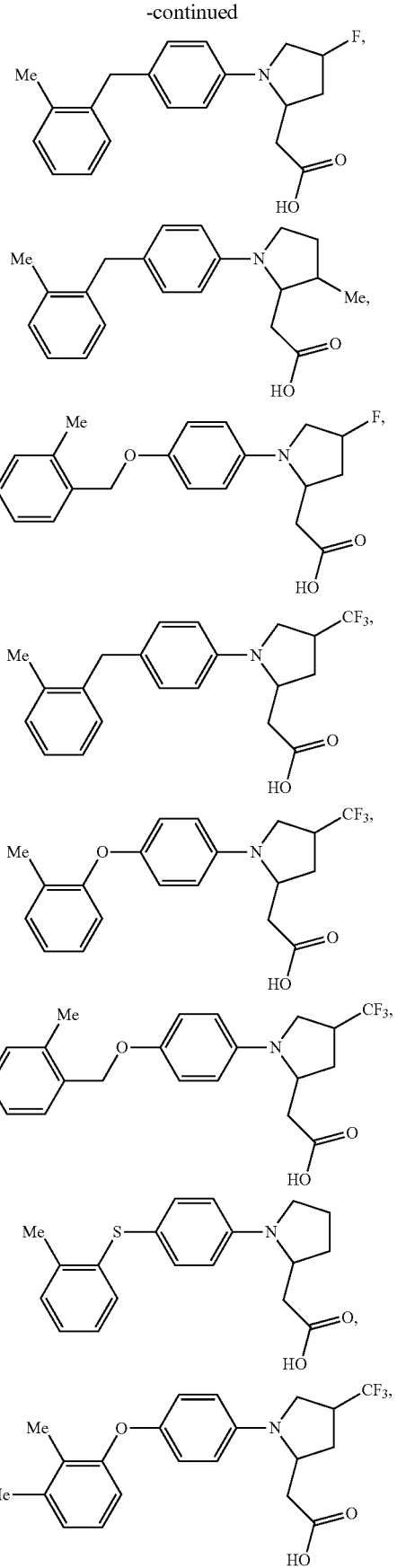

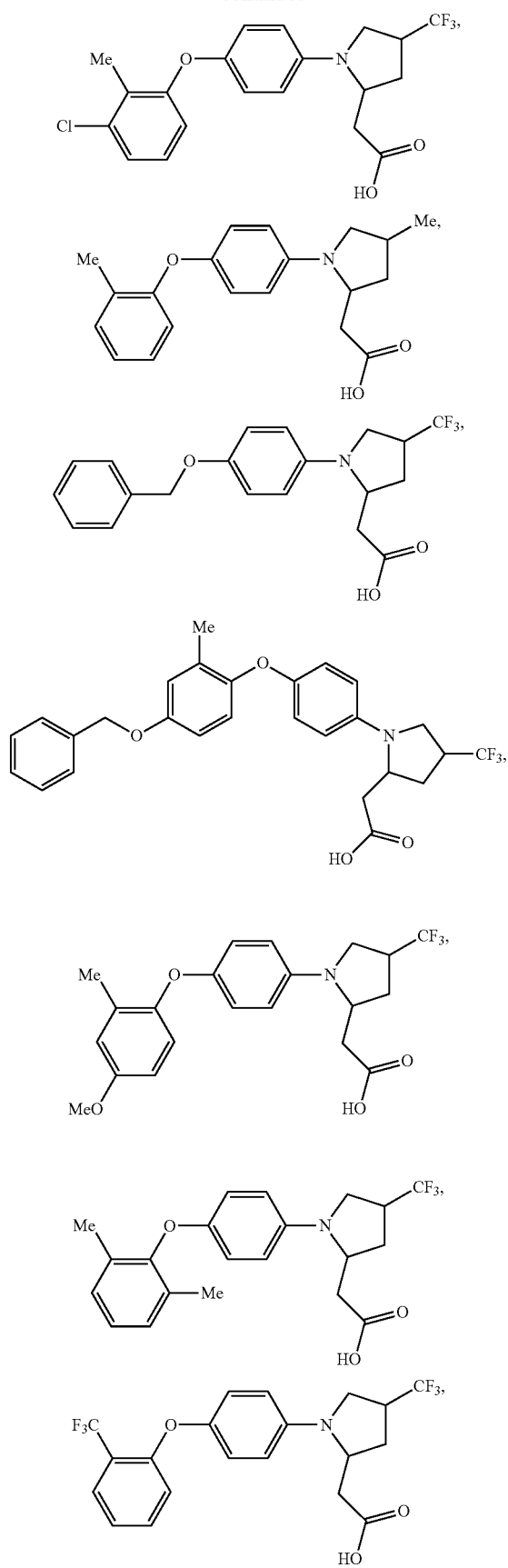
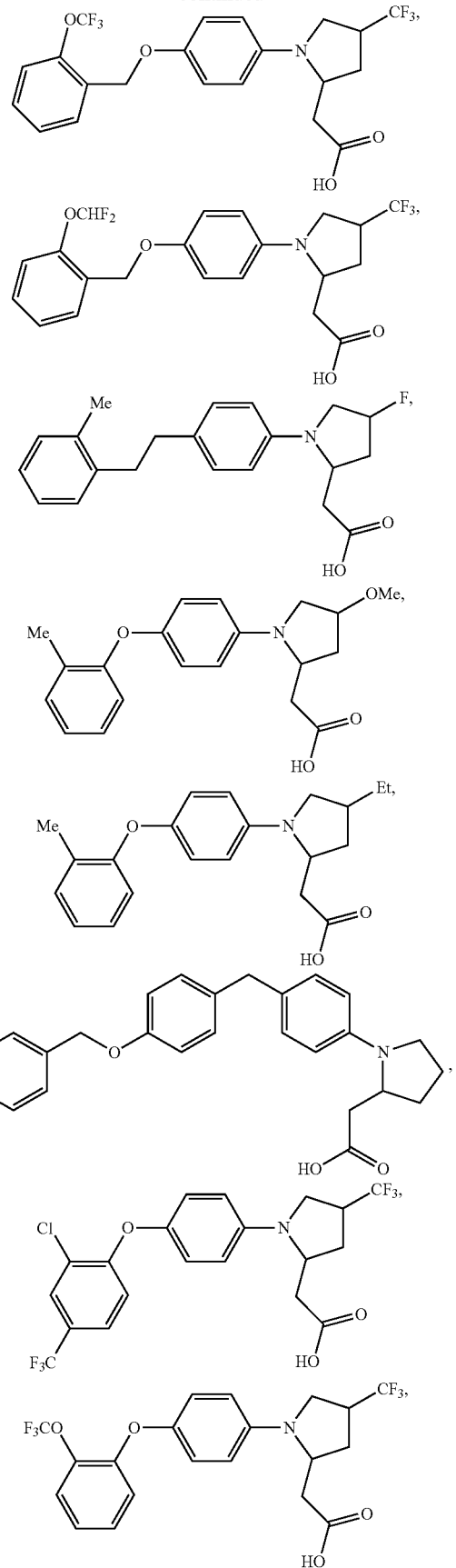

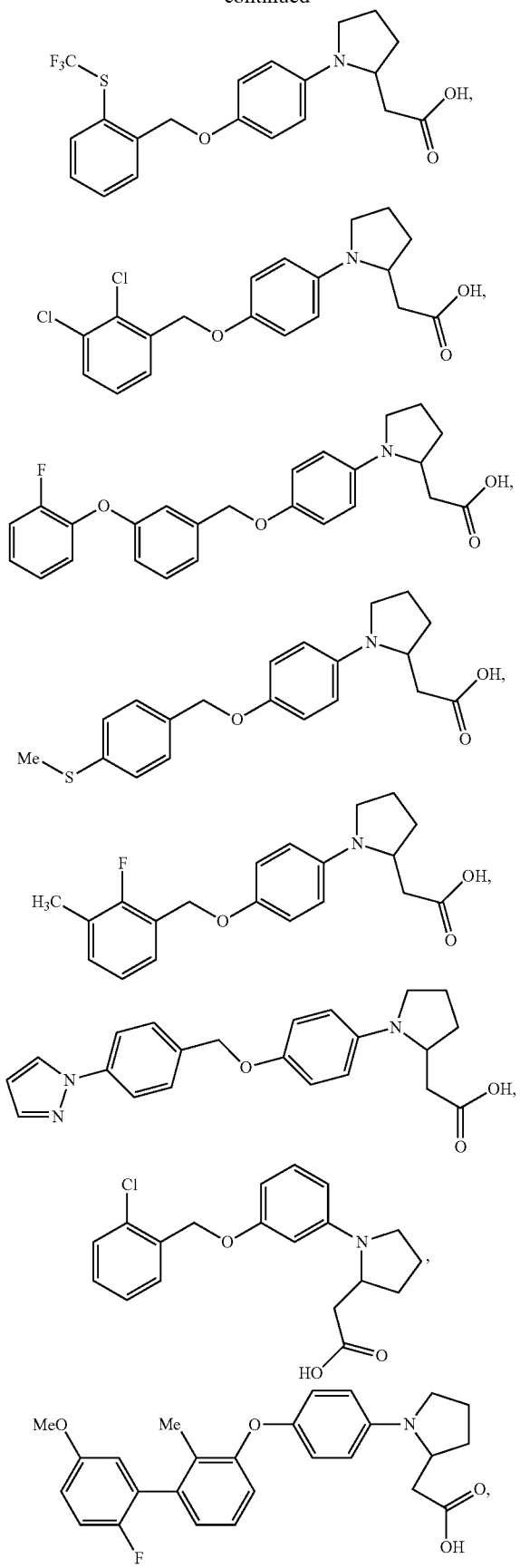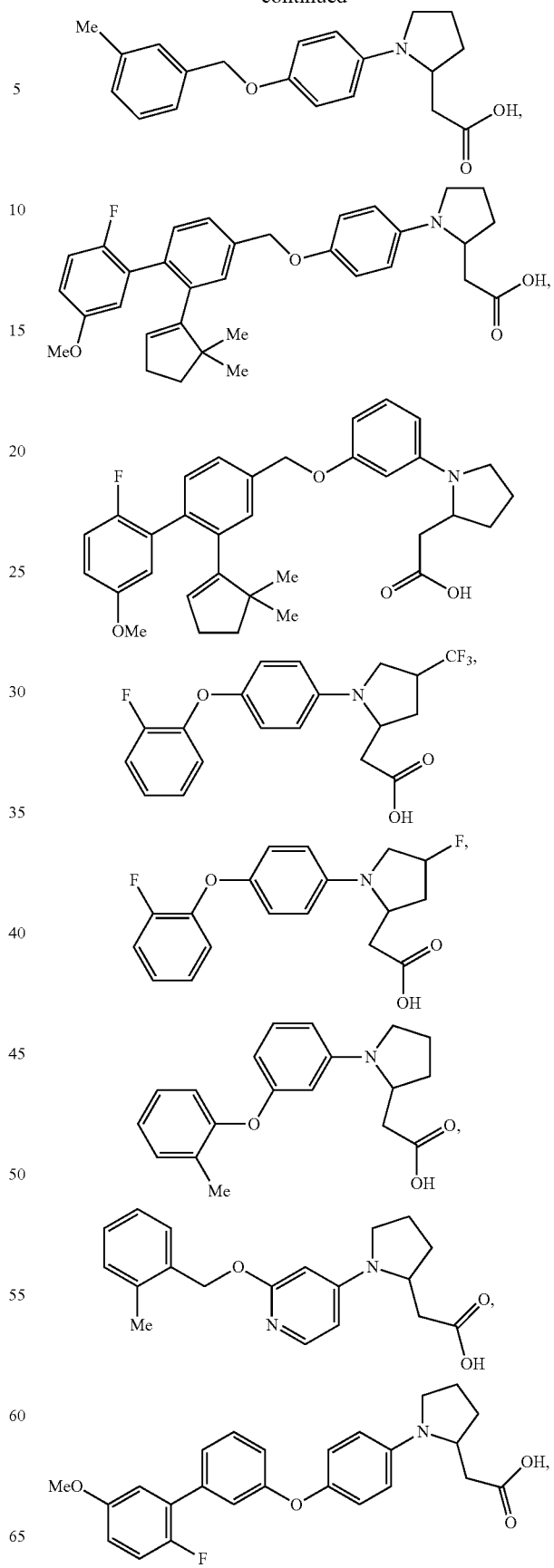

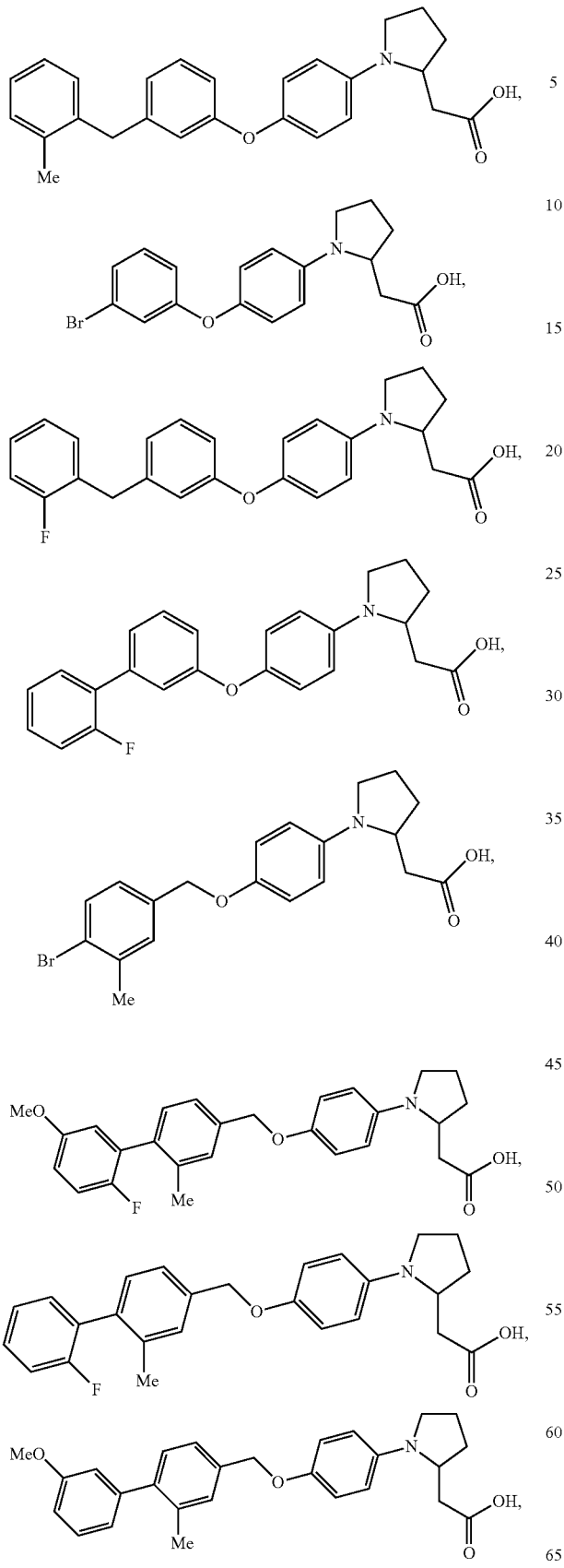
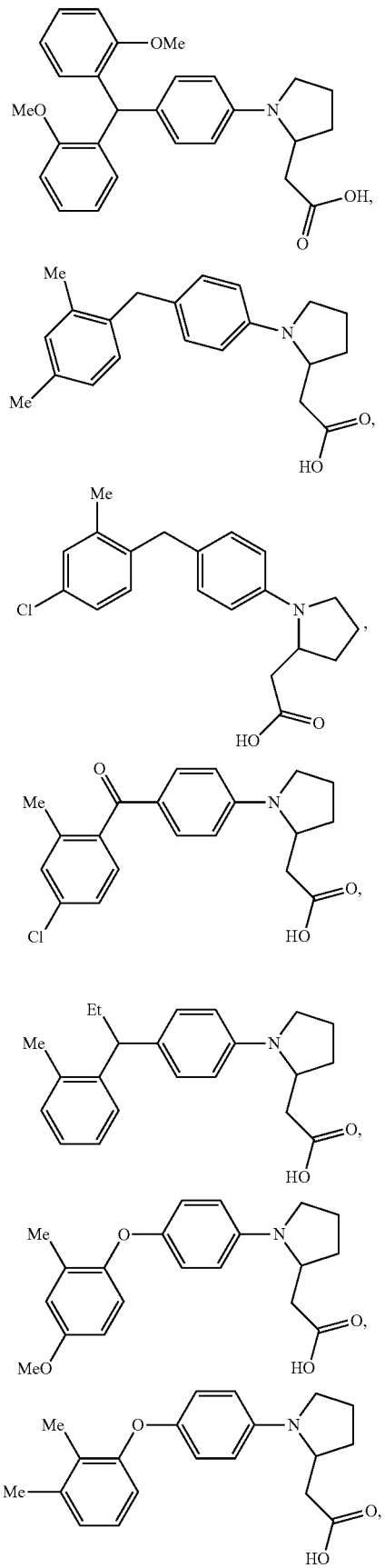

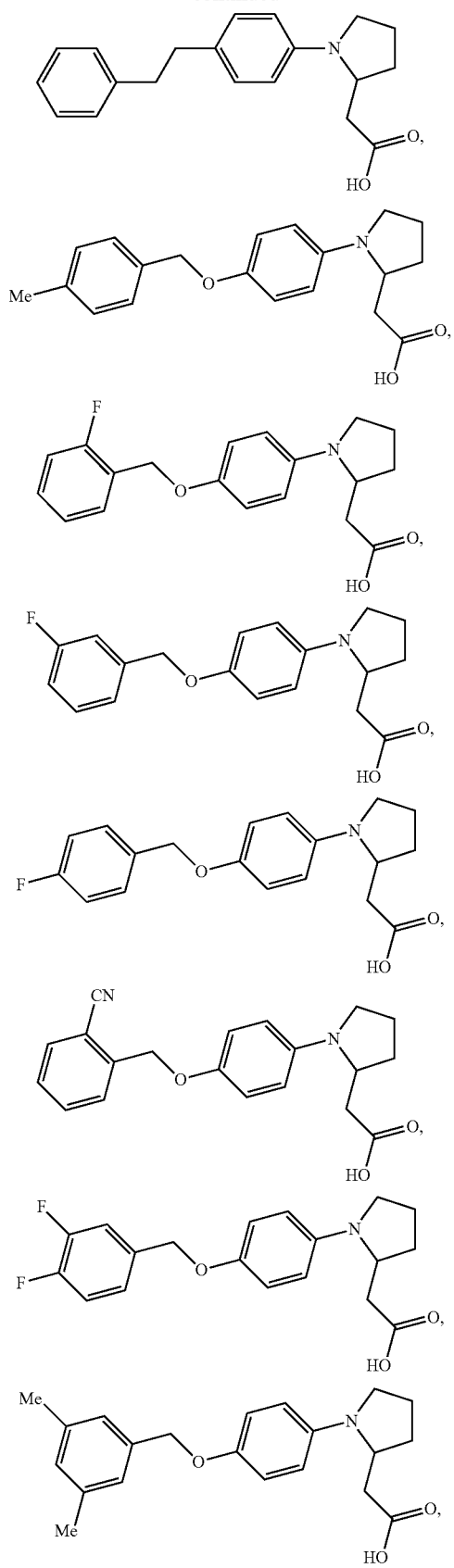
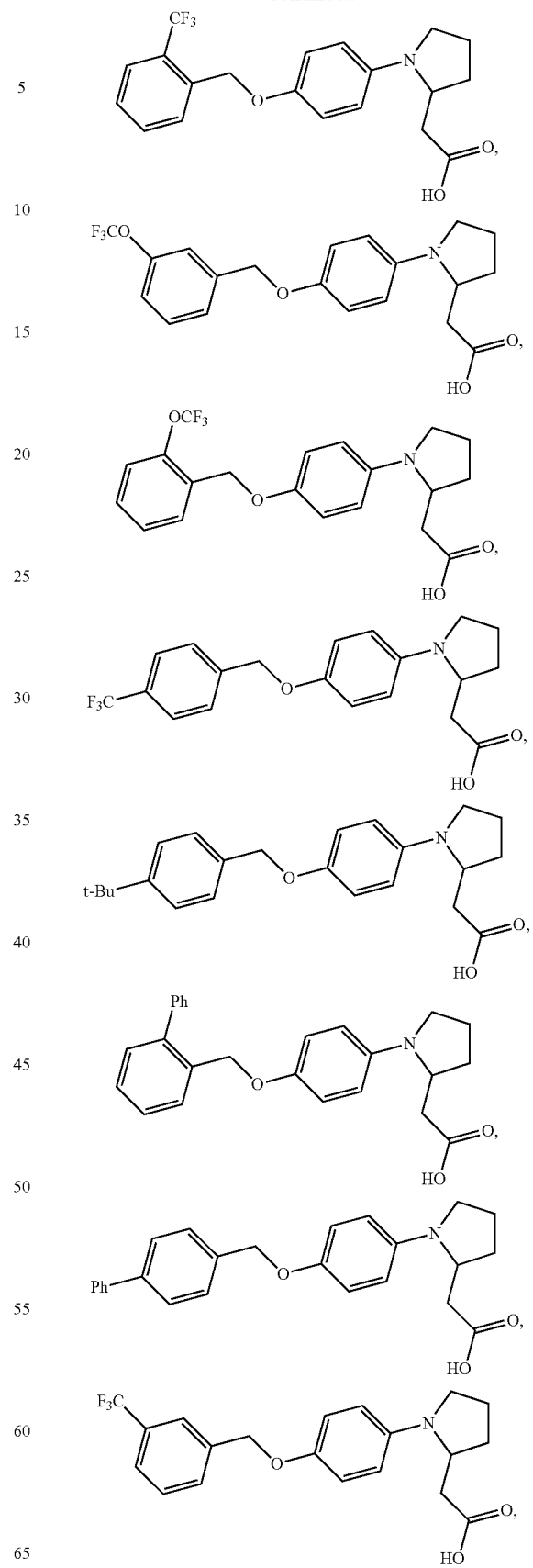

-continued
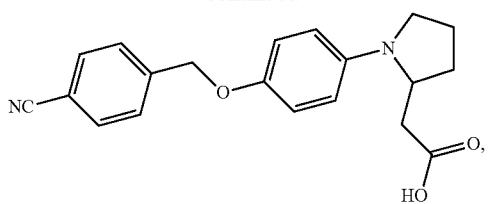
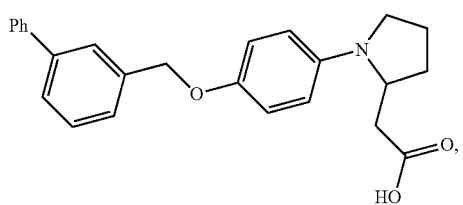
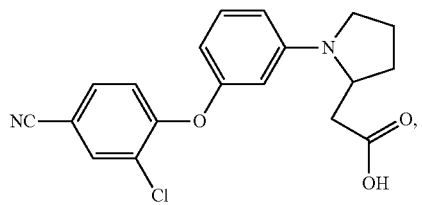
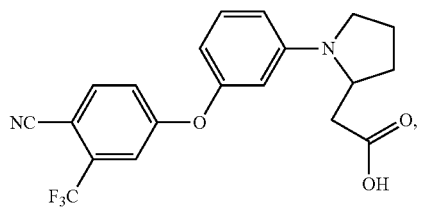
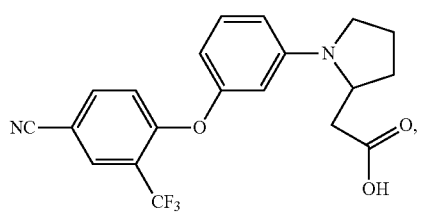
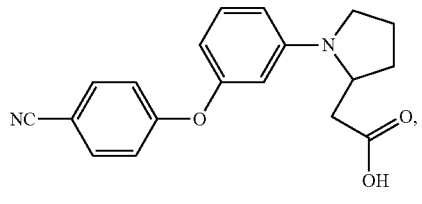
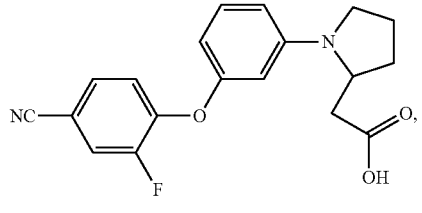
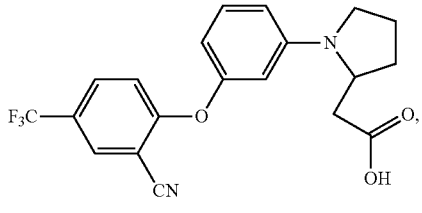
-continued
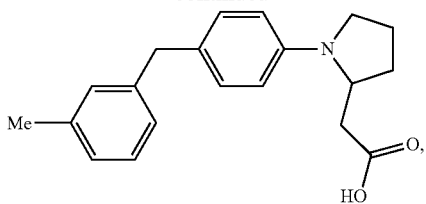
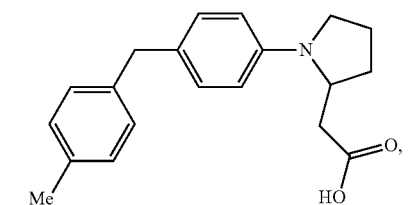
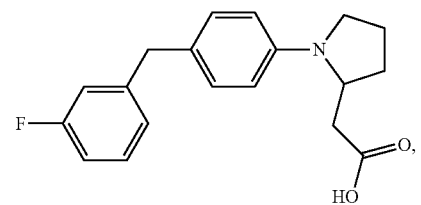
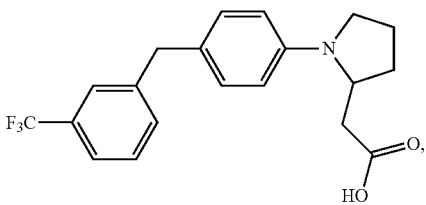
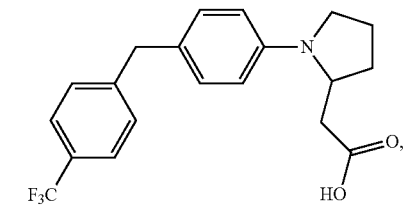
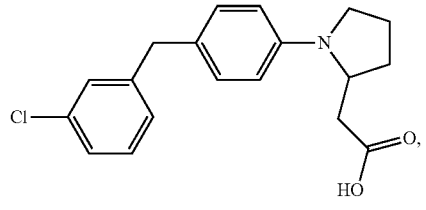
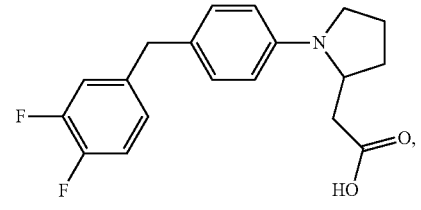
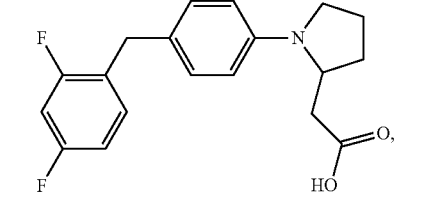

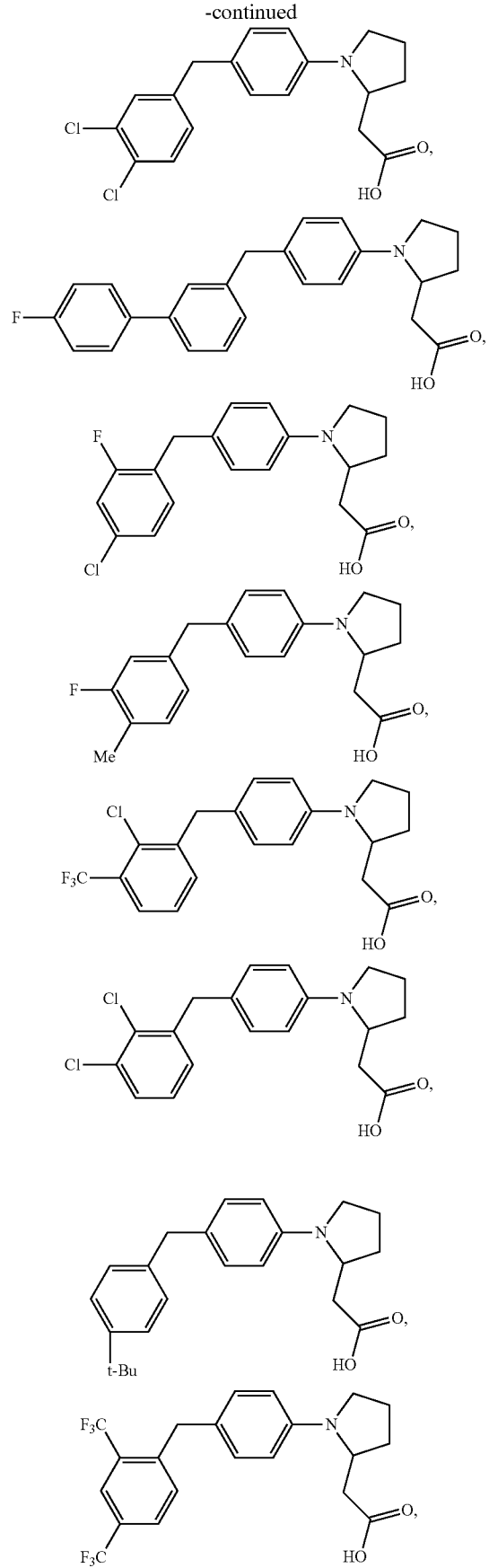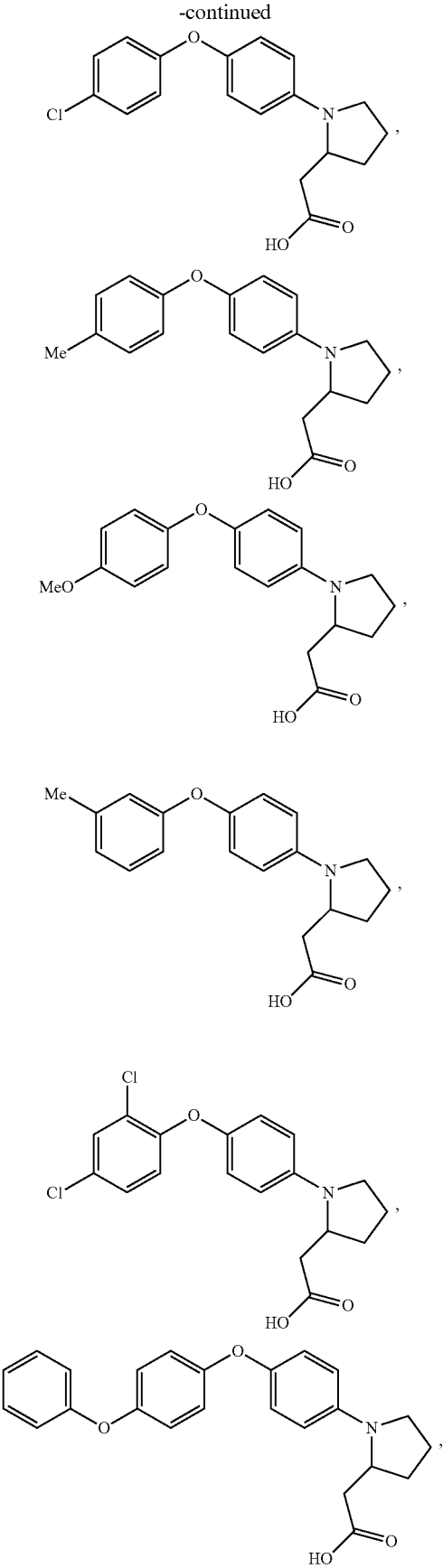

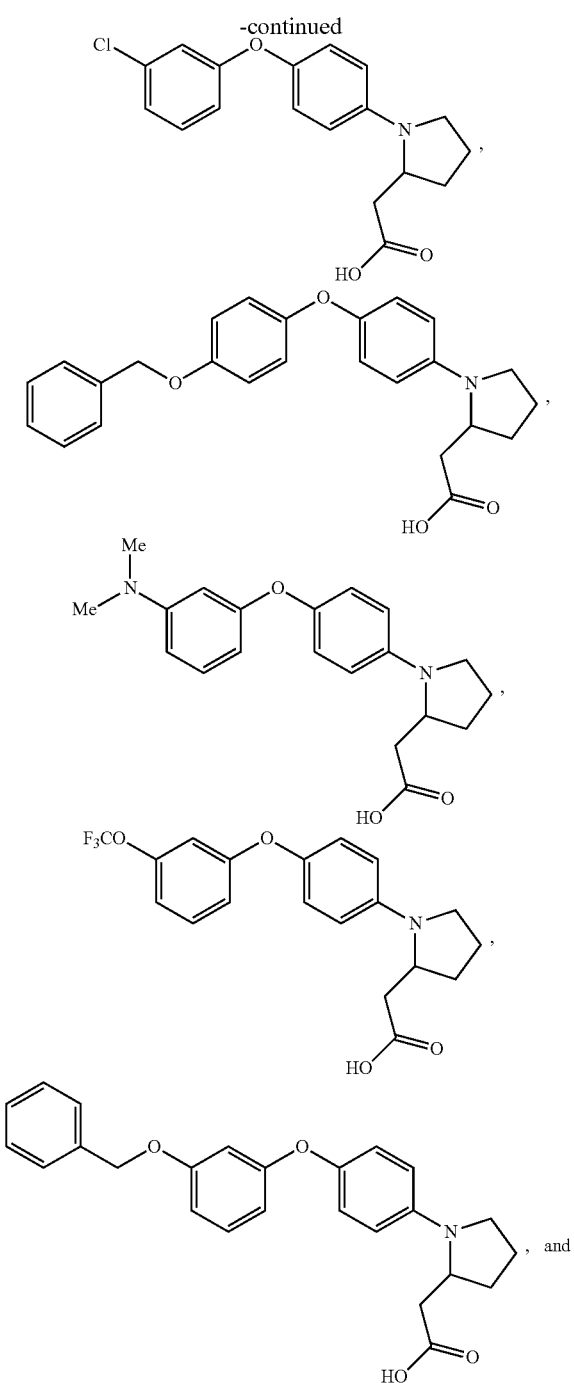

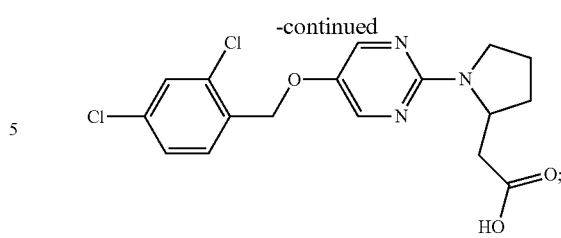

or a stereoisomer or a pharmaceutically acceptable salt thereof.

10. A pharmaceutical composition, comprising: a pharmaceutically acceptable carrier and a compound of claim 1, or a stereoisomer, a tautomer, or a pharmaceutically acceptable salt thereof.

11. A pharmaceutical composition, comprising: a pharmaceutically acceptable carrier and a compound of claim 2, or a stereoisomer, a tautomer, or a pharmaceutically acceptable salt thereof.

12. A pharmaceutical composition, comprising: a pharmaceutically acceptable carrier and a compound of claim 3, or a stereoisomer, a tautomer, or a pharmaceutically acceptable salt thereof.

13. A pharmaceutical composition, comprising: a pharmaceutically acceptable carrier and a compound of claim 4, or a stereoisomer, a tautomer, or a pharmaceutically acceptable salt thereof.

14. A pharmaceutical composition, comprising: a pharmaceutically acceptable carrier and a compound of claim 5, or a stereoisomer, a tautomer, or a pharmaceutically acceptable salt thereof.

15. A pharmaceutical composition, comprising: a pharmaceutically acceptable carrier and a compound of claim 6, or a stereoisomer, a tautomer, or a pharmaceutically acceptable salt thereof.

16. A pharmaceutical composition, comprising: a pharmaceutically acceptable carrier and a compound of claim 7, or a stereoisomer, a tautomer, or a pharmaceutically acceptable salt thereof.

17. A pharmaceutical composition, comprising: a pharmaceutically acceptable carrier and a compound of claim 8, or a stereoisomer, a tautomer, or a pharmaceutically acceptable salt thereof.

18. A pharmaceutical composition, comprising: a pharmaceutically acceptable carrier and a compound of claim 9, or a stereoisomer, a tautomer, or a pharmaceutically acceptable salt thereof.

* * * * *